(12) United States Patent
Komuro et al.

(10) Patent No.: US 11,820,736 B2
(45) Date of Patent: Nov. 21, 2023

(54) SALT, ACID GENERATOR, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Katsuhiro Komuro, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 17/718,748

(22) Filed: Apr. 12, 2022

(65) Prior Publication Data
US 2022/0348541 A1  Nov. 3, 2022

(30) Foreign Application Priority Data
Apr. 15, 2021 (JP) ................. 2021-069314

(51) Int. Cl.
  *C07C 381/12* (2006.01)
  *G03F 7/004* (2006.01)
  *G03F 7/16* (2006.01)

(52) U.S. Cl.
  CPC .......... *C07C 381/12* (2013.01); *G03F 7/0045* (2013.01); *G03F 7/162* (2013.01)

(58) Field of Classification Search
  CPC ........ G03F 7/0045; G03F 7/039; G03F 7/038; G03F 7/0397; G03F 7/0382; G03F 7/0392; G03F 7/20; G03F 7/26; C07C 2603/74; C07C 323/20; C07C 309/17; C07C 323/62; C07C 323/65; C07C 2601/08; H01L 21/0274; C07D 209/94; C07D 307/30; C07D 317/72; C07D 327/04;

(Continued)

(56) References Cited

U.S. PATENT DOCUMENTS

| | | | |
|---|---|---|---|
| 2009/0280433 A1 | 11/2009 | Matsumura et al. | |
| 2010/0304296 A1 | 12/2010 | Ichikawa et al. | |
| 2011/0217654 A1* | 9/2011 | Yamato .................. | C07C 69/753 430/326 |
| 2013/0108962 A1 | 5/2013 | Matsumura et al. | |
| 2018/0364571 A1* | 12/2018 | Nishio ................... | G03F 7/039 |
| 2020/0089111 A1 | 3/2020 | Hatakeyama et al. | |
| 2020/0089112 A1 | 3/2020 | Hatakeyama et al. | |

FOREIGN PATENT DOCUMENTS

| | | |
|---|---|---|
| EP | 2060949 A1 | 5/2009 |
| JP | 2011006400 A | 1/2011 |

(Continued)

OTHER PUBLICATIONS

Search Report issued by the BE Patent Office in corresponding BE application No. 202205275 dated Nov. 21, 2022. (4 pages).

(Continued)

*Primary Examiner* — Mark F. Huff
*Assistant Examiner* — Andrew Preston Traywick
(74) *Attorney, Agent, or Firm* — BUCHANAN INGERSOLL & ROONEY PC

(57) ABSTRACT

Disclosed are a salt represented by formula (I), an acid generator, and a resist composition including the same:

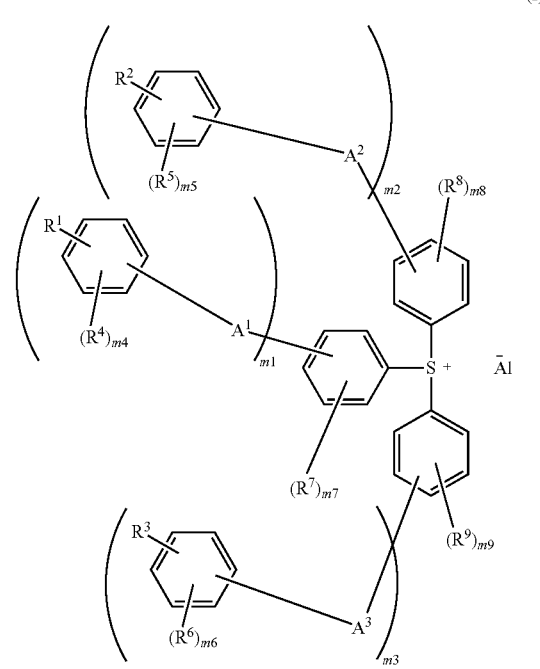

(I)

wherein $R^1$, $R^2$ and $R^3$ each represent a hydroxy group, *—O—$R^{10}$, *—O—CO—O—$R^{10}$, etc.; $L^{10}$ represents an alkanediyl group; $R^{10}$ represents an acid-labile group; $R^4$, $R^5$, $R^6$, $R^7$, $R^8$ and $R^9$ each represent a halogen atom, a haloalkyl group or a hydrocarbon group; $A^1$, $A^2$ and $A^3$ each represent a hydrocarbon group which may have a substituent, and —$CH_2$— included in the hydrocarbon group may be replaced by —O—, —CO—, —S— or —$SO_2$—; m1 represents an integer of 1 to 5, m2, m3, m8 and m9 represent an integer of 0 to 5, m4 to m7 represent an integer of 0 to 4, $1 \le m1+m7 \le 5$, $0 \le m2+m8 \le 5$, $0 \le m3+m9 \le 5$; and $Al^-$ represents an organic anion.

18 Claims, No Drawings

(58) Field of Classification Search
CPC .. C07D 493/04; C07D 493/14; C07D 319/08; C08F 2/48; C08F 212/12; C08F 220/18
See application file for complete search history.

(56) References Cited

FOREIGN PATENT DOCUMENTS

| | | |
|---|---|---|
| JP | 2020015713 A | 1/2020 |
| JP | 2020046661 A | 3/2020 |

OTHER PUBLICATIONS

Written Opinion issued by the BE Patent Office in corresponding BE application No. 202205275 dated Nov. 21, 2022, with an English translation of the Written Opinion. (13 pages).

* cited by examiner

SALT, ACID GENERATOR, RESIST COMPOSITION AND METHOD FOR PRODUCING RESIST PATTERN

BACKGROUND OF THE INVENTION

Field of the Invention

The present invention relates to a salt, an acid generator, a resist composition and a method for producing a resist pattern.

Description of the Related Art

JP 2011-006400 A mentions a salt represented by the following formula and a resist composition comprising the salt as an acid generator.

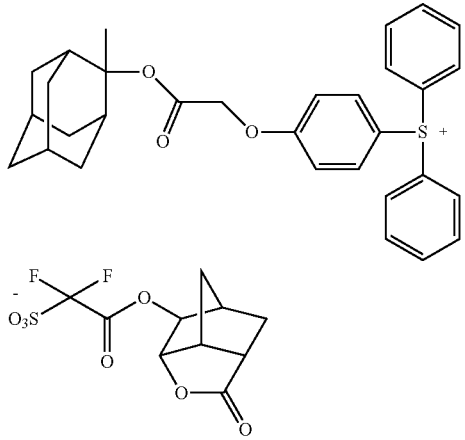

JP 2020-015713 A mentions a salt represented by the following formula and a resist composition comprising the salt as an acid generator.

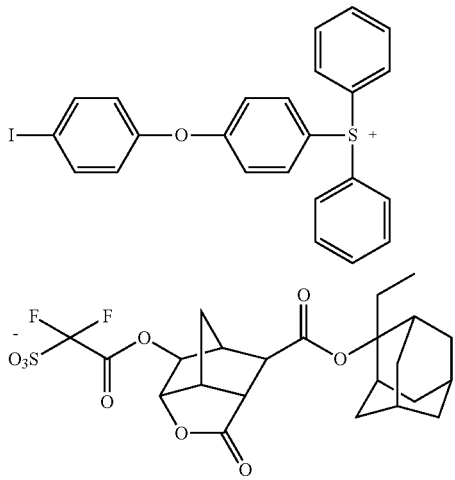

JP 2020-046661 A mentions salts represented by the following formulas and resist compositions comprising the salts as acid generators, respectively.

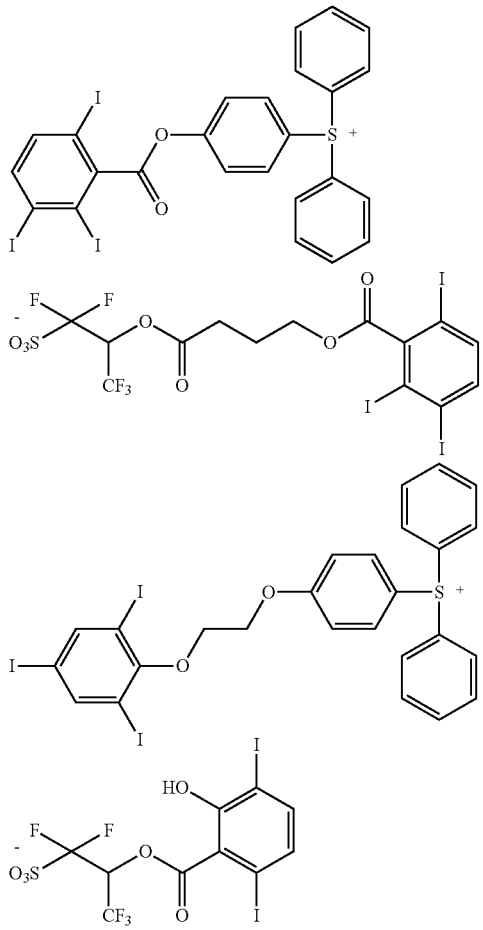

SUMMARY OF THE INVENTION

The present invention provides a salt capable of forming a resist pattern with CD Uniformity (CDU) which is better than that of a resist pattern formed from the resist compositions comprising the salts mentioned above.

The present invention includes the following inventions.

[1] A salt represented by formula (I):

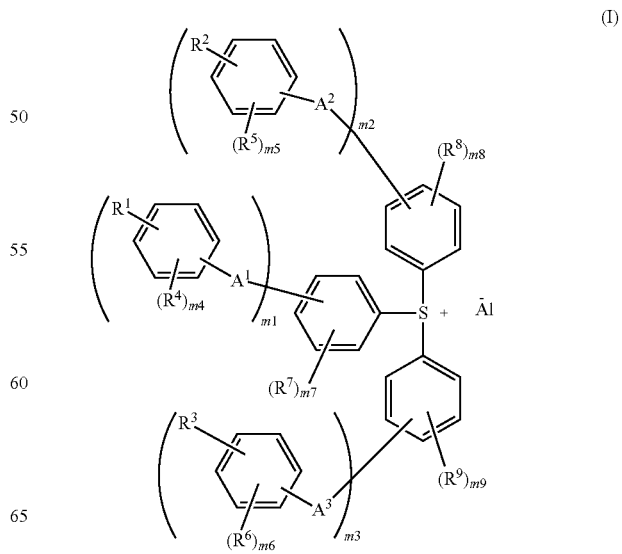

(I)

wherein, in formula (I), $R^1$, $R^2$ and $R^3$ each independently represent a hydroxy group, *—O—$R^{10}$, *—O—CO—O—$R^{10}$ or *—O-$L^{10}$-CO—O—$R^{10}$, and * represents a bonding site to the benzene ring, $L^{10}$ represents an alkanediyl group having 1 to 6 carbon atoms, $R^{10}$ represents an acid-labile group, $R^4$, $R^5$, $R^6$, $R^7$, $R^8$ and $R^9$ each independently represent a halogen atom, a haloalkyl group having 1 to 12 carbon atoms or a hydrocarbon group having 1 to 18 carbon atoms, the hydrocarbon group may have a substituent, and —$CH_2$— included in the haloalkyl group and the hydrocarbon group may be replaced by —O—, —S—, —CO— or —$SO_2$—, $A^1$, $A^2$ and $A^3$ each independently represent a hydrocarbon group having 2 to 20 carbon atoms, the hydrocarbon group may have a substituent, and —$CH_2$— included in the hydrocarbon group may be replaced by —O—, —CO—, —S— or —$SO_2$—, m1 represents an integer of 1 to 5, and when m1 is 2 or more, a plurality of groups in parentheses may be the same or different from each other, m2 represents an integer of 0 to 5, and when m2 is 2 or more, a plurality of groups in parentheses may be the same or different from each other, m3 represents an integer of 0 to 5, and when m3 is 2 or more, a plurality of groups in parentheses may be the same or different from each other, m4 represents an integer of 0 to 4, and when m4 is 2 or more, a plurality of $R^4$ may be the same or different from each other, m5 represents an integer of 0 to 4, and when m5 is 2 or more, a plurality of $R^5$ may be the same or different from each other, m6 represents an integer of 0 to 4, and when m6 is 2 or more, a plurality of $R^6$ may be the same or different from each other, m7 represents an integer of 0 to 4, and when m7 is 2 or more, a plurality of $R^7$ may be the same or different from each other, m8 represents an integer of 0 to 5, and when m8 is 2 or more, a plurality of $R^8$ may be the same or different from each other, m9 represents an integer of 0 to 5, and when m9 is 2 or more, a plurality of $R^9$ may be the same or different from each other, in which $1 \le m1+m7 \le 5$, $0 \le m2+m8 \le 5$, $0 \le m3+m9 \le 5$, and $Al^-$ represents an organic anion.

[2] The salt according to [1], wherein $A^1$ is *—$X^{01}$-$L^{01}$- or *-$L^{01}$-$X^{01}$—, $A^2$ is *—$X^{02}$-$L^{02}$- or *-$L^{02}$-$X^{02}$—, and $A^3$ is *—$X^{03}$-$L^{03}$- or *-$L^{03}$-$X^{03}$— ($X^{01}$, $X^{02}$ and $X^{03}$ each independently represent —O—, —CO—, —S— or —$SO_2$—, $L^{01}$, $L^{02}$ and $L^{03}$ each independently represent a hydrocarbon group having 1 to 19 carbon atoms, the hydrocarbon group may have a substituent, —$CH_2$— included in the hydrocarbon group may be replaced by —O—, —CO—, —S— or —$SO_2$—, and * represents a bonding site to the benzene ring to which $R^1$, $R^2$ or $R^3$ is bonded).

[3] The salt according to [2], wherein $X^{01}$, $X^{02}$ and $X^{03}$ are each independently —O— or —S—.

[4] The salt according to [2] or [3], wherein $L^{01}$, $L^{02}$ and $L^{03}$ are each independently an alkanediyl group having 1 to 6 carbon atoms (—$CH_2$— included in the alkanediyl group may be replaced by —O— or —CO—).

[5] The salt according to any one of [1] to [4], wherein $R^1$, $R^2$ and $R^3$ are each independently a hydroxy group, *—O—$R^{11}$ or *—O-$L^{10}$-CO—O—$R^{10}$ (* represents a bonding site to the benzene ring).

[6] The salt according to any one of [1] to [5], wherein the acid-labile group as for $R^{10}$ is a group represented by formula (1a) or a group represented by formula (2a):

wherein, in formula (1a), $R^{aa1}$, $R^{aa2}$ and $R^{aa3}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or a group obtained by combining these groups, or $R^{aa1}$ and $R^{aa2}$ may be bonded to each other to form an alicyclic hydrocarbon group having 3 to 20 carbon atoms together with carbon atoms to which $R^{aa1}$ and $R^{aa2}$ are bonded, and

* represents a bonding site:

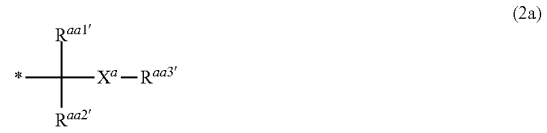

wherein, in formula (2a), $R^{aa1'}$ and $R^{aa2'}$ each independently represent a hydrogen atom or a hydrocarbon group having 1 to 12 carbon atoms, $R^{aa3'}$ represents a hydrocarbon group having 1 to 20 carbon atoms, or $R^{aa2'}$ and $R^{aa3'}$ may be bonded to each other to form a heterocyclic group having 3 to 20 carbon atoms together with —C—$X^a$— to which $R^{aa2'}$ and $R^{aa3'}$ are bonded, and —$CH_2$— included in the hydrocarbon group and the heterocyclic group may be replaced by —O— or —S—, $X^a$ represents an oxygen atom or a sulfur atom, and

* represents a bonding site.

[7] The salt according to any one of [1] to [6], wherein when m4, m5 or m6 is an integer of 1 or more, $R^4$, $R^5$ and $R^6$ are each independently a fluorine atom, an iodine atom, a perfluoroalkyl group having 1 to 4 carbon atoms or an alkyl group having 1 to 4 carbon atoms (—$CH_2$— included in the alkyl group may be replaced by —O— or —CO—).

[8] The salt according to any one of [1] to [7], wherein when m7, m8 or m9 is an integer of 1 or more, $R^7$, $R^8$ and $R^9$ are each independently a fluorine atom, an iodine atom, a perfluoroalkyl group having 1 to 4 carbon atoms or an alkyl group having 1 to 4 carbon atoms (—$CH_2$— included in the alkyl group may be replaced by —O— or —CO—).

[9] The salt according to any one of [1] to [8], wherein $Al^-$ is a sulfonic acid anion, a sulfonylimide anion, a sulfonylmethide anion or a carboxylic acid anion.

[10] The salt according to any one of [1] to [9], wherein $Al^-$ is a sulfonic acid anion and the sulfonic acid anion is an anion represented by formula (I-A):

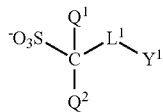

(I-A)

wherein, in formula (I-A),

Q$^1$ and Q$^2$ each independently represent a hydrogen atom, a fluorine atom, an alkyl group having 1 to 6 carbon atoms or a perfluoroalkyl group having 1 to 6 carbon atoms, L$^1$ represents a saturated hydrocarbon group having 1 to 24 carbon atoms, —CH$_2$— included in the saturated hydrocarbon group may be replaced by —O— or —CO—, and a hydrogen atom included in the saturated hydrocarbon group may be substituted with a fluorine atom or a hydroxy group, and Y$^1$ represents a methyl group which may have a substituent, or an alicyclic hydrocarbon group having 3 to 24 carbon atoms which may have a substituent, and —CH$_2$— included in the alicyclic hydrocarbon group may be replaced by —O—, —S—, —SO$_2$— or —CO—.

[11] An acid generator comprising the salt according to any one of [1] to [10].

[12] A resist composition comprising the acid generator according to [11] and a resin having an acid-labile group.

[13] The resist composition according to [12], wherein the resin having an acid-labile group includes at least one selected from the group consisting of a structural unit represented by formula (a1-0), a structural unit represented by formula (a1-1) and a structural unit represented by formula (a1-2):

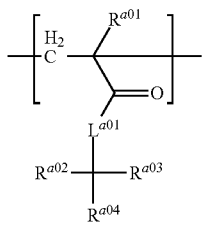

(a1-0)

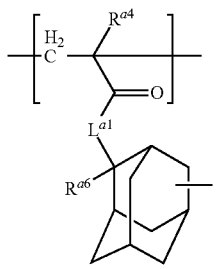

(a1-1)

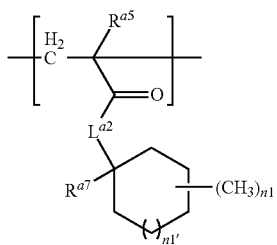

(a1-2)

wherein, in formula (a1-0), formula (a1-1) and formula (a1-2),

L$^{a01}$, L$^{a1}$ and L$^{a2}$ each independently represent —O— or *—O—(CH$_2$)$_{k1}$—CO—O—, k1 represents an integer of 1 to 7, and * represents a bonding site to —CO—, R$^{a01}$, R$^{a4}$ and R$^{a5}$ each independently represent a hydrogen atom, a halogen atom, or an alkyl group having 1 to 6 carbon atoms which may have a halogen atom, R$^{a02}$, R$^{a03}$ and R$^{a04}$ each independently represent an alkyl group having 1 to 8 carbon atoms, an alicyclic hydrocarbon group having 3 to 18 carbon atoms, an aromatic hydrocarbon group having 6 to 18 carbon atoms, or a group obtained by combining these groups, R$^{a6}$ and R$^{a7}$ each independently represent an alkyl group having 1 to 8 carbon atoms, an alkenyl group having 2 to 8 carbon atoms, an alicyclic hydrocarbon group having 3 to 18 carbon atoms, an aromatic hydrocarbon group having 6 to 18 carbon atoms, or a group formed by combining these groups, m1 represents an integer of 0 to 14, n1 represents an integer of 0 to 10, and n1' represents an integer of 0 to 3.

[14] The resist composition according to [12] or [13], wherein the resin having an acid-labile group includes a structural unit represented by formula (a2-A):

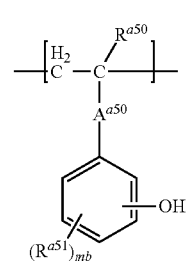

(a2-A)

wherein, in formula (a2-A),

R$^{a50}$ represents a hydrogen atom, a halogen atom, or an alkyl group having 1 to 6 carbon atoms which may have a halogen atom, R$^{a51}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group, A$^{a50}$ represents a single bond or *—X$^{a51}$-(A$^{a52}$-X$^{a52}$) and * represents a bonding site to carbon atoms to which —R$^{a50}$ is bonded, A$^{a52}$ represents an alkanediyl group having 1 to 6 carbon atoms, X$^{a51}$ and X$^{a52}$ each independently represent —O—, —CO—O— or —O—CO—, nb represents 0 or 1, and mb represents an integer of 0 to 4, and when mb is an integer of 2 or more, a plurality of R$^{a51}$ may be the same or different from each other.

[15] The resist composition according to any one of [12] to [14], further comprising a salt generating an acid having an acidity lower than that of an acid generated from the acid generator.

[16] A method for producing a resist pattern, which comprises:

(1) a step of applying the resist composition according to any one of [12] to [15] on a substrate, (2) a step of drying the applied resist composition to form a composition layer, (3) a step of exposing the composition layer, (4) a step of heating the exposed composition layer, and (5) a step of developing the heated composition layer.

It is possible to produce a resist pattern with satisfactory CD Uniformity (CDU) by using a resist composition comprising a salt of the present invention.

DETAILED DESCRIPTION OF THE PREFERRED EMBODIMENTS

In the present specification, "(meth)acrylic monomer" means "at least one of acrylic monomer and methacrylic monomer". Notations such as "(meth)acrylate" and "(meth) acrylic acid" mean the same thing. In groups mentioned in the present specification, regarding groups capable of having both a linear structure and a branched structure, they may have either the linear or branched structure. When —$CH_2$— included in the hydrocarbon group or the like is replaced by —O—, —S—, —CO— or —$SO_2$—, the same examples shall apply for each group. "Combined group" means a group in which two or more exemplified groups are bonded, and valences of those groups may be appropriately varied by bonding forms. "Derived" or "Induced" means that a polymerizable C=C bond included in the molecule becomes a —C—C— group (single bond) by polymerization. When stereoisomers exist, all stereoisomers are included.

[Salt Represented by Formula (I)]

The present invention relates to a salt represented by formula (I) (hereinafter sometimes referred to as "salt (I)").

Of the salt (I), the side having negative charge is sometimes referred to as "anion (I)", and the side having positive charge is sometimes referred to as "cation (I)":

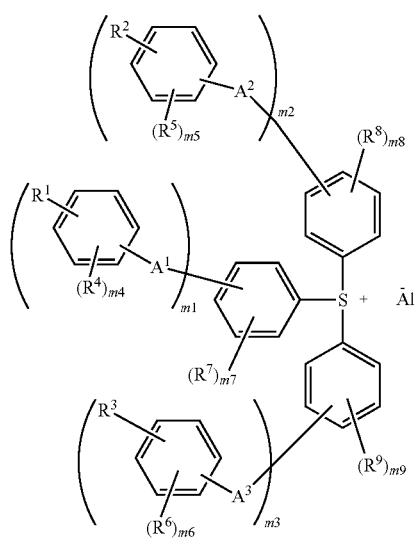

(I)

wherein all symbols are the same as defined above.

[Cation (I)]

The cation (I) of the salt represented by formula (I) is a cation represented by formula (I-C).

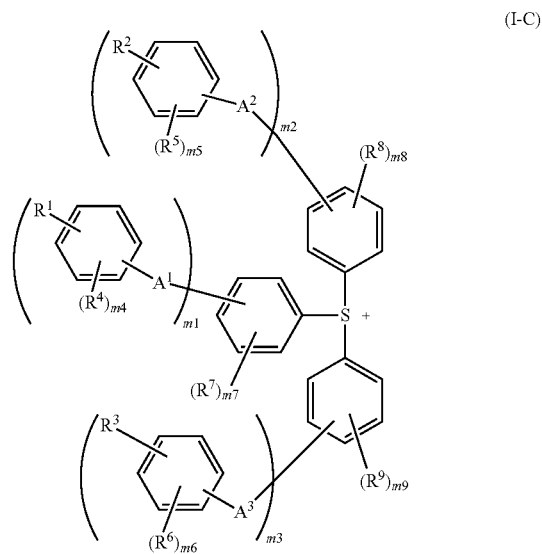

(I-C)

wherein, in formula (I-C), all symbols are the same as defined in formula (I).

Examples of the alkanediyl group in $L^{10}$ included in $R^1$, $R^2$ and $R^3$ in formula (I) include linear alkanediyl groups such as a methylene group, an ethylene group, a propane-1,3-diyl group, a butane-1,4-diyl group, a pentane-1,5-diyl group and a hexane-1,6-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group.

$L^{10}$ is preferably an alkanediyl group having 1 to 3 carbon atoms, and more preferably a methylene group.

The "acid-labile group" as for $R^{10}$ included in $R^1$, $R^2$ and $R^3$ means a group in which a leaving group including a group represented by $R^{10}$ is eliminated by contact with an acid (e.g., trifluoromethanesulfonic acid), thus forming a carboxy group or a hydroxy group.

The acid-labile group is preferably a group represented by formula (1a) (hereinafter sometimes referred to as "acid-labile group (1a)") or a group represented by formula (2a) (hereinafter sometimes referred to as "acid-labile group (2a)"):

(1a)

wherein, in formula (1a), $R^{aa1}$, $R^{aa2}$ and $R^{aa3}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or a group obtained by combining these groups, or $R^{aa1}$ and $R^{aa2}$ are bonded to each other to form an alicyclic hydrocarbon group having 3 to 20 carbon atoms together with carbon atoms to which $R^{aa1}$ and $R^{aa2}$ are bonded, and

* represents a bonding site:

(2a)

wherein, in formula (2a), $R^{aa1'}$ and $R^{aa2'}$ each independently represent a hydrogen atom or a hydrocarbon group having 1 to 12 carbon atoms, $R^{aa3'}$ represents a hydrocarbon group having 1 to 20 carbon atoms, or $R^{aa2'}$ and $R^{aa3'}$ are bonded to each other to form a heterocyclic group having 3 to 20 carbon atoms together with —C—$X^a$— to which $R^{aa2'}$ and $R^{aa3'}$ are bonded, and —CH$_2$— included in the hydrocarbon group and the heterocyclic group may be replaced by —O— or —S—, $X^a$ represents an oxygen atom or a sulfur atom, and
* represents a bonding site.

Examples of the alkyl group as for $R^{aa1}$, $R^{aa2}$ and $R^{aa3}$ include a methyl group, an ethyl group, a propyl group, an n-butyl group, an n-pentyl group, an n-hexyl group, an n-heptyl group, an n-octyl group and the like. The number of carbon atoms of the alkyl group as for $R^{aa1}$, $R^{aa2}$ and $R^{aa3}$ is preferably 1 to 6, and more preferably 1 to 4, and still more preferably 1 to 3.

Examples of the alkenyl group as for $R^{aa1}$, $R^{aa2}$ and $R^{aa3}$ include an ethenyl group, a propenyl group, an isopropenyl group, a butenyl group, an isobutenyl group, a tert-butenyl group, a pentenyl group, a hexenyl group, a heptenyl group, an octenyl group, an isooctenyl group and a nonenyl group.

The alicyclic hydrocarbon group as for $R^{aa1}$, $R^{aa2}$ and $R^{aa3}$ may be either monocyclic or polycyclic. Examples of the monocyclic alicyclic hydrocarbon group include cycloalkyl groups such as a cyclopentyl group, a cyclohexyl group, a cycloheptyl group, a cyclooctyl group and the like. Examples of the polycyclic alicyclic hydrocarbon group include a decahydronaphthyl group, an adamantyl group, a norbornyl group, and the following groups (* represents a bonding site). The number of carbon atoms of the alicyclic hydrocarbon group as for $R^{aa1}$, $R^{aa2}$ and $R^{aa3}$ is preferably 3 to 16, and more preferably 3 to 12.

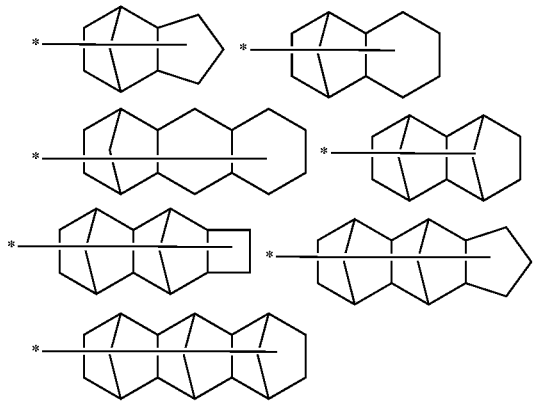

Examples of the aromatic hydrocarbon group as for $R^{aa1}$, $R^{aa2}$ and $R^{aa3}$ include aryl groups such as a phenyl group, a naphthyl group, an anthryl group, a biphenyl group and a phenanthryl group. The number of carbon atoms of the aromatic hydrocarbon group as for $R^{aa1}$, $R^{aa2}$ and $R^{aa3}$ is preferably 6 to 14, and more preferably 6 to 10.

Examples of the combined group include groups obtained by combining the above-mentioned alkyl group and alicyclic hydrocarbon group (alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups such as an alicyclic hydrocarbon group (a p-cyclohexylphenyl group, a p-adamantylphenyl group, etc.), aryl-cycloalkyl groups such as a phenylcyclohexyl group, and the like.

When $R^{aa1}$ and $R^{aa2}$ are bonded to each other to form an alicyclic hydrocarbon group together with carbon atoms to which $R^{aa1}$ and $R^{aa2}$ are bonded, examples of —C($R^{aa1}$)($R^{aa2}$)($R^{aa3}$) include the following groups. The alicyclic hydrocarbon group preferably has 3 to 16 carbon atoms, and more preferably 3 to 12 carbon atoms. * represents a bonding site to —O—.

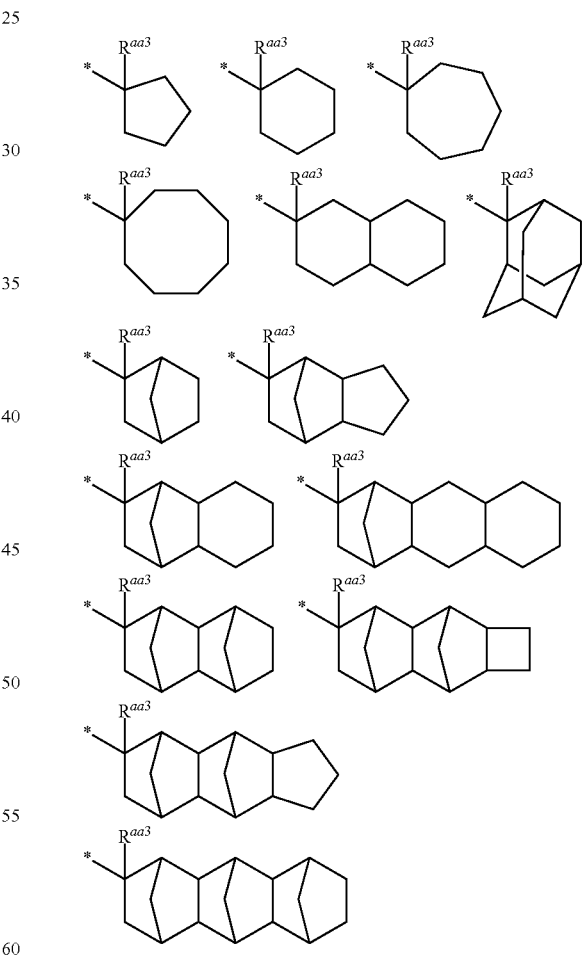

Examples of the group represented by formula (1a) include a 1,1,1-trialkyl group (a group in which $R^{aa1}$, $R^{aa2}$ and $R^{aa3}$ are an alkyl group, and preferably a tert-butyl group in formula (1a)), a 2-alkyladamantan-2-yl group (a group in which $R^{aa1}$, $R^{aa2}$ and carbon atoms to which $R^{aa1}$ and $R^{aa2}$ are bonded to form an adamantyl group, and $R^{aa3}$ is an alkyl group in formula (1a)) and a 1-(adamantan-1-yl)-1,1-dialkyl group (a group in which $R^{aa1}$ and $R^{aa2}$ are an alkyl group and $R^{aa3}$ is an adamantyl group in formula (1a)).

Examples of the hydrocarbon group as for $R^{aa1'}$, $R^{aa2'}$ and $R^{aa3'}$ include an alkyl group, an alicyclic hydrocarbon group, an aromatic hydrocarbon group, and groups formed by combining these groups.

Examples of the alkyl group and alicyclic hydrocarbon group include those which are the same as mentioned in $R^{aa1}$, $R^{aa2}$ and $R^{aa3}$.

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., cycloalkylalkyl groups or alkylcycloalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group, and the like.

When $R^{aa2'}$ and $R^{aa3'}$ are bonded to each other to form a heterocyclic group together with carbon atoms and $X^a$ to which $R^{aa2'}$ and $R^{aa3'}$ are bonded, examples of —C($R^{aa1'}$)($R^{aa2'}$)—$X^a$—($R^{aa3'}$) include the following groups. * represents a bonding site.

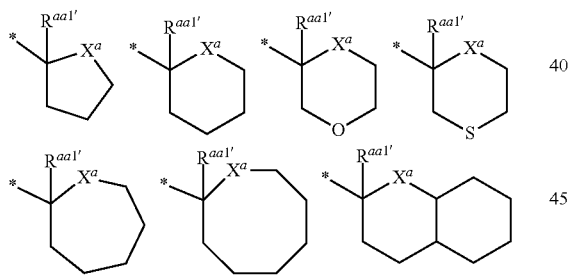

At least one of $R^{aa1'}$ and $R^{aa2'}$ is preferably a hydrogen atom.

Specific examples of the acid-labile group (1a) include the following groups. * represents a bonding site.

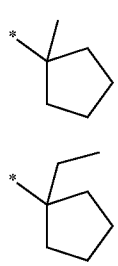

(I-R²-1-1)

(I-R²-1-2)

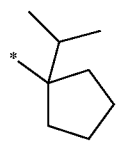

(I-R²-1-3)

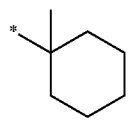

(I-R²-1-4)

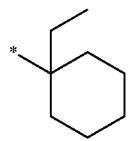

(I-R²-1-5)

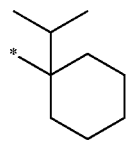

(I-R²-1-6)

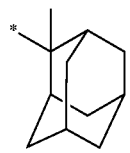

(I-R²-1-7)

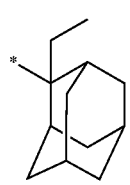

(I-R²-1-8)

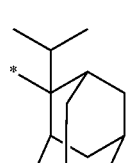

(I-R²-1-9)

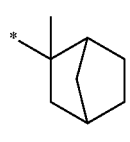

(I-R²-1-10)

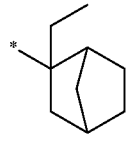

(I-R²-1-11)

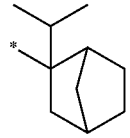

(I-R²-1-12)

-continued
(I-R²-1-13)
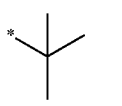
(I-R²-1-14)
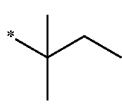
(I-R²-1-15)
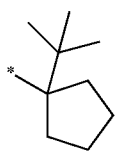
(I-R²-1-16)
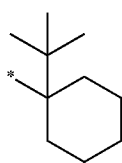
(I-R²-1-17)
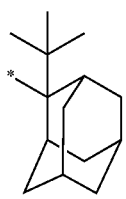
(I-R²-1-18)
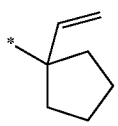
(I-R²-1-19)
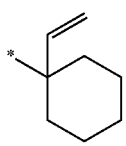
(I-R²-1-20)
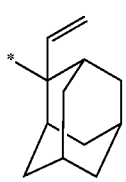
(I-R²-1-21)
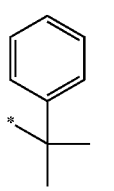
(I-R²-1-22)
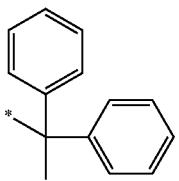
Specific examples of the acid-labile group (2a) include the following groups. * represents a bonding site.
(I-R²-2-1)
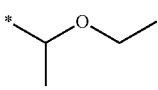
(I-R²-2-2)
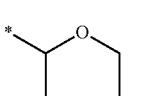
(I-R²-2-3)
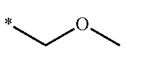
(I-R²-2-4)
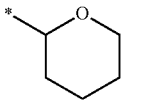
(I-R²-2-5)
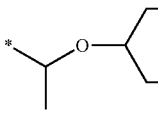
(I-R²-2-6)
(I-R²-2-7)
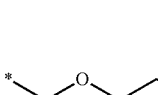
(I-R²-2-8)
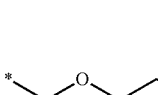
(I-R²-2-9)
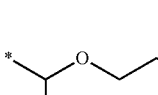
(I-R²-2-10)
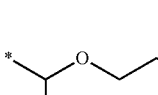
(I-R²-2-11)
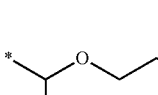

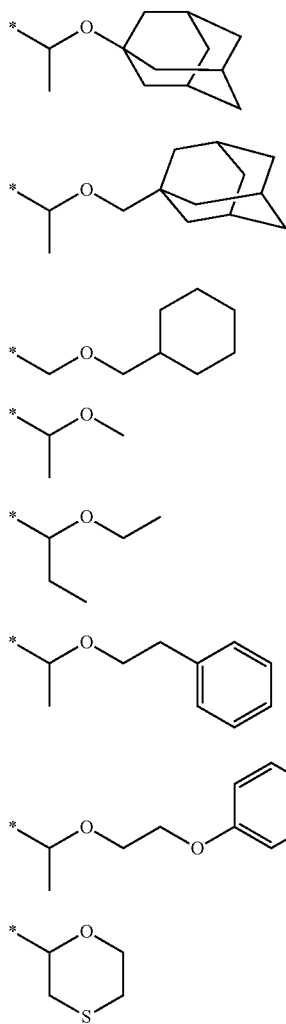

(I-R²-2-12)
(I-R²-2-13)
(I-R²-2-14)
(I-R²-2-15)
(I-R²-2-16)
(I-R²-2-17)
(I-R²-2-18)
(I-R²-2-19)

Each bonding site of $R^1$, $R^2$ and $R^3$ to the benzene ring may be each independently the o-position, the m-position or the p-position, with respect to the bonding site of $A^1$, $A^2$ and $A^3$, respectively. Particularly, $R^1$, $R^2$ and $R^3$ are each independently bonded preferably at the p-position or the m-position, and more preferably at the p-position, with respect to the bonding site of $A^1$, $A^2$ and $A^3$, respectively.

Preferably, $R^1$, $R^2$ and $R^3$ are each independently a hydroxy group, *—O—$R^{10}$ or *—O-$L^{10}$-CO—O—$R^{10}$, and more preferably *—O—$R^{10}$ or *—O-$L^{10}$-CO—O—$R^{10}$. * represents a bonding site to the benzene ring.

Examples of the halogen atom as for $R^4$, $R^5$, $R^6$, $R^7$, $R^8$ and $R^9$ include a fluorine atom, a chlorine atom, a bromine atom and an iodine atom.

The haloalkyl group having 1 to 12 carbon atoms as for $R^4$, $R^5$, $R^6$, $R^7$, $R^8$ and $R^9$ represents an alkyl group having 1 to 12 carbon atoms which has a halogen atom, and examples thereof include an alkyl fluoride group having 1 to 12 carbon atoms, an alkyl chloride group having 1 to 12 carbon atoms, an alkyl bromide group having 1 to 12 carbon atoms, an alkyl iodide group having 1 to 12 carbon atoms and the like. Examples of the haloalkyl group include a perfluoroalkyl group having 1 to 12 carbon atoms (a trifluoromethyl group, a pentafluoroethyl group, a heptafluoropropyl group, a nonafluorobutyl group, etc.), a 2,2,2-trifluoroethyl group, a 3,3,3-trifluoropropyl group, a 4,4,4-trifluorobutyl group, a 3,3,4,4,4-pentafluorobutyl group, a chloromethyl group, a bromomethyl group, an iodomethyl group and the like. The number of carbon atoms of the haloalkyl group is preferably 1 to 9, more preferably 1 to 6, still more preferably 1 to 4, and yet more preferably 1 to 3.

Examples of the hydrocarbon group having 1 to 18 carbon atoms as for $R^4$, $R^5$, $R^6$, $R^7$, $R^8$ and $R^9$ include a chain hydrocarbon group such as an alkyl group, an alicyclic hydrocarbon group, an aromatic hydrocarbon group, and groups formed by combining these groups.

Examples of the alkyl group include a methyl group, an ethyl group, an n-propyl group, an isopropyl group, an n-butyl group, a sec-butyl group, a tert-butyl group, a pentyl group, a hexyl group, a heptyl group, a 2-ethylhexyl group, an octyl group, a nonyl group, a decyl group, an undecyl group and a dodecyl group.

The number of carbon atoms of the chain hydrocarbon group is preferably 1 to 12, more preferably 1 to 9, still more preferably 1 to 6, yet more preferably 1 to 4, and further preferably 1 to 3.

The alicyclic hydrocarbon group may be either monocyclic or polycyclic, and examples thereof include groups shown below. The bonding site can be any position.

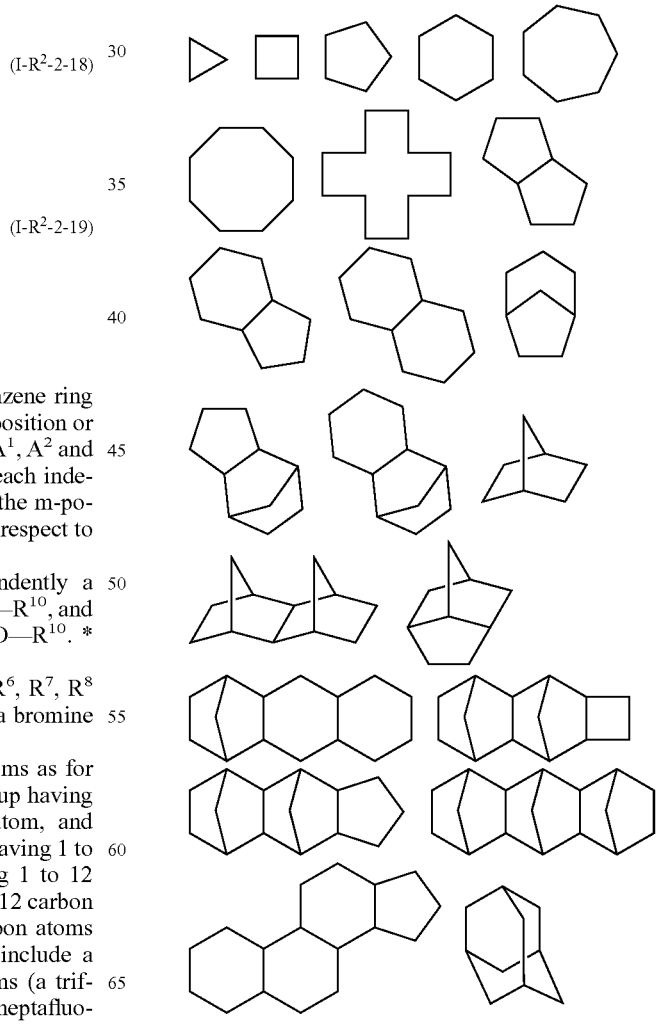

-continued

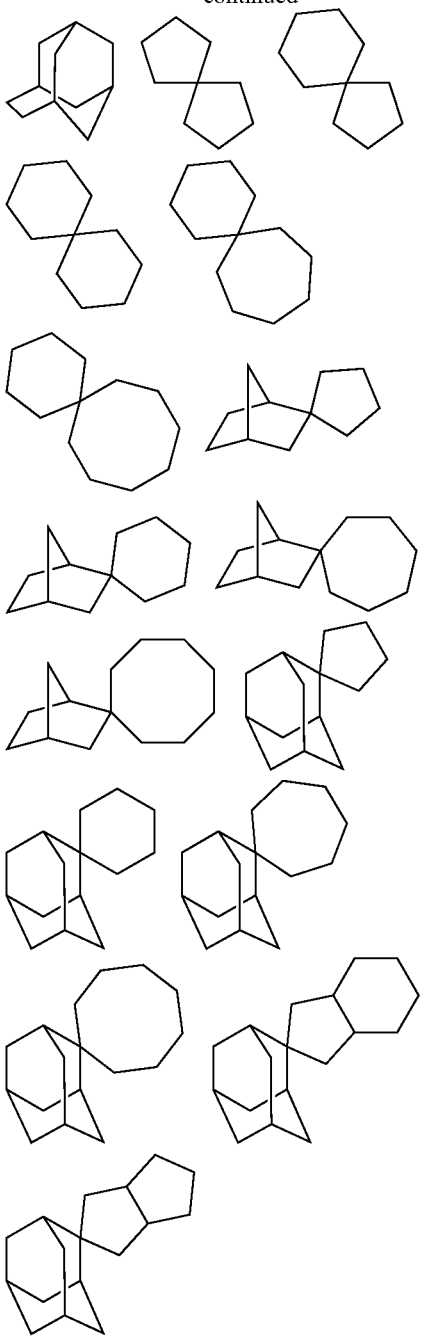

Specific examples of the monocyclic alicyclic hydrocarbon group include monocyclic cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include polycyclic cycloalkyl groups such as a decahydronaphthyl group, an adamantyl group and a norbornyl group. The number of carbon atoms of the alicyclic hydrocarbon group is preferably 3 to 18, more preferably 3 to 16, and still more preferably 3 to 12.

Examples of the aromatic hydrocarbon group include a phenyl group, a naphthyl group, a biphenyl group, an anthryl group, a phenanthryl group, a binaphthyl group and the like. The number of carbon atoms of the aromatic hydrocarbon group is preferably 6 to 18, more preferably 6 to 14, and still more preferably 6 to 10.

Examples of the group formed by combination include groups formed by combining an aromatic hydrocarbon group with a chain hydrocarbon group (e.g., an aromatic hydrocarbon group-alkanediyl group-*, an alkyl group-aromatic hydrocarbon group-*), groups formed by combining an alicyclic hydrocarbon group with a chain hydrocarbon group (e.g., an alicyclic hydrocarbon group-alkanediyl group-*, an alkyl group-alicyclic hydrocarbon group-*) and groups formed by combining an aromatic hydrocarbon group with an alicyclic hydrocarbon group (e.g., an aromatic hydrocarbon group-alicyclic hydrocarbon group-*, an alicyclic hydrocarbon group-aromatic hydrocarbon group-*). * represents a bonding site.

Examples of the aromatic hydrocarbon group-alkanediyl group-* include aralkyl groups such as a benzyl group and a phenethyl group.

Examples of the alkyl group-aromatic hydrocarbon group-* include a tolyl group, a xylyl group, a cumenyl group and the like.

Examples of the alicyclic hydrocarbon group-alkanediyl group-* include cycloalkylalkyl groups such as a cyclohexylmethyl group, a cyclohexylethyl group, a 1-(adamantan-1-yl)methyl group and a 1-(adamantan-1-yl)-1-methylethyl group.

Examples of the alkyl group-alicyclic hydrocarbon group-* include cycloalkyl groups having an alkyl group, such as a methylcyclohexyl group, a dimethylcyclohexyl group and a 2-alkyladamantan-2-yl group.

Examples of the aromatic hydrocarbon group-alicyclic hydrocarbon group-* include a phenylcyclohexyl group and the like.

Examples of the alicyclic hydrocarbon group-aromatic hydrocarbon group-* include a cyclohexylphenyl group and the like.

In combination, two or more of alicyclic hydrocarbon groups, aromatic hydrocarbon groups and chain hydrocarbon groups may be respectively combined. Any group may be bonded to the benzene ring.

Examples of the group in which —CH$_2$— included in the haloalkyl group and the hydrocarbon group is replaced by —O—, —S—, —CO— or —SO$_2$— include a hydroxy group (a group in which —CH$_2$— included in the methyl group is replaced by —O—), a thiol group (a group in which —CH$_2$— included in the methyl group is replaced by —S—), a carboxy group (a group in which —CH$_2$—CH$_2$— included in the ethyl group is replaced by —O—CO—), an alkoxy group (a group in which —CH$_2$— at any position included in the alkyl group is replaced by —O—), an alkylthio group (a group in which —CH$_2$— at any position included in the alkyl group is replaced by —S—), an alkoxycarbonyl group (a group in which —CH$_2$—CH$_2$— at any position included in the alkyl group is replaced by —O—CO—), an alkylcarbonyl group (a group in which —CH$_2$— at any position included in the alkyl group is replaced by —CO—), an alkylsulfonyl group (a group in which —CH$_2$— at any position included in the alkyl group is replaced by —SO$_2$—), an alkylcarbonyloxy group (a group in which —CH$_2$—CH$_2$— at any position included in the alkyl group is replaced by —CO—O—), an oxy group (a group in which —CH$_2$-included in the methylene group is replaced by —O—), a carbonyl group (a group in which —CH$_2$— included in the methylene group is replaced by —CO—), a thio group (a group in which —CH$_2$— included in the methylene group is replaced by —S—), a sulfonyl group (a group in which —CH$_2$— included in the methylene group is replaced by —SO$_2$—), an alkanediyloxy group (a group in which —CH$_2$— at any position included in the alkanediyl group is replaced by —O—), an alkanediyloxycarbonyl group (a group in which —CH$_2$—CH$_2$— at any position included in the alkanediyl group is replaced by —O—CO—), an alkanediylcarbonyl group (a group in which —CH$_2$— at any position included in the alkanediyl group is replaced by —CO—), an alkanediylcarbonyloxy group (a group in which —CH$_2$—CH$_2$— at any position included in the alkanediyl group is replaced by —CO—O—), an alkanediylthio group (a group in which —CH$_2$— at any position included in the alkanediyl group is replaced by —S—), an alkanediylsulfonyl group (a group in which —CH$_2$— at any position included in the alkanediyl group is replaced by —SO$_2$—), a cycloalkoxy group, a cycloalkylalkoxy group, an alkoxycarbonyloxy group, an aromatic hydrocarbon group-carbonyloxy group, an aromatic hydrocarbon group-carbonyl group, an aromatic hydrocarbon group-oxy group, a haloalkoxy group (a group in which —CH$_2$— at any position included in the haloalkyl group is replaced by —O—), a haloalkoxycarbonyl group (a group in which —CH$_2$—CH$_2$— at any position included in the haloalkyl group is replaced by —O—CO—), a haloalkylcarbonyl group (a group in which —CH$_2$— at any position included in the haloalkyl group is replaced by —CO—), a haloalkylcarbonyloxy group (a group in which —CH$_2$—CH$_2$— at any position included in the haloalkyl group is replaced by —CO—O—), and a group obtained by combining two or more of these groups.

Examples of the alkoxy group include alkoxy groups having 1 to 17 carbon atoms, for example, a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group and the like. The number of carbon atoms of the alkoxy group is preferably 1 to 11, more preferably 1 to 6, still more preferably 1 to 4, and yet more preferably 1 to 3.

Examples of the alkylthio group include alkylthio groups having 1 to 17 carbon atoms, for example, a methylthio group, an ethylthio group, a propylthio group, a butylthio group, a pentylthio group, a hexylthio group, an octylthio group, a 2-ethylhexylthio group, a nonylthio group, a decylthio group, an undecylthio group and the like. The number of carbon atoms of the alkylthio group is preferably 1 to 11, more preferably 1 to 6, still more preferably 1 to 4, and yet more preferably 1 to 3.

The alkoxycarbonyl group, the alkylcarbonyl group and the alkylcarbonyloxy group represent a group in which a carbonyl group or a carbonyloxy group is bonded to the above-mentioned alkyl group or alkoxy group.

Examples of the alkoxycarbonyl group include alkoxycarbonyl groups having 2 to 17 carbon atoms, for example, a methoxycarbonyl group, an ethoxycarbonyl group, a butoxycarbonyl group and the like. Examples of the alkylcarbonyl group include alkylcarbonyl groups having 2 to 18 carbon atoms, for example, an acetyl group, a propionyl group and a butyryl group. Examples of the alkylcarbonyloxy group include alkylcarbonyloxy groups having 2 to 17 carbon atoms, for example, an acetyloxy group, a propionyloxy group, a butyryloxy group and the like. The number of carbon atoms of the alkoxycarbonyl group is preferably 2 to 11, more preferably 2 to 6, still more preferably 2 to 4, and yet more preferably 2 or 3. The number of carbon atoms of the alkylcarbonyl group is preferably 2 to 12, more preferably 2 to 6, still more preferably 2 to 4, and yet more preferably 2 or 3. The number of carbon atoms of the alkylcarbonyloxy group is preferably 2 to 11, more preferably 2 to 6, still more preferably 2 to 4, and yet more preferably 2 or 3.

Examples of the alkylsulfonyl group include alkylsulfonyl groups having 1 to 17 carbon atoms, for example, a methylsulfonyl group, an ethylsulfonyl group, a propylsulfonyl group, a butylsulfonyl group, a pentylsulfonyl group, a hexylsulfonyl group, an octylsulfonyl group, a 2-ethylhexylsulfonyl group, a nonylsulfonyl group, a decylsulfonyl group, an undecylsulfonyl group and the like. The number of carbon atoms of the alkylsulfonyl group is preferably 1 to 11, more preferably 1 to 6, still more preferably 1 to 4, and yet more preferably 1 to 3.

Examples of the alkanediyloxy group include alkanediyloxy groups having 1 to 17 carbon atoms, for example, a methyleneoxy group, an ethyleneoxy group, a propanediyloxy group, a butanediyloxy group, a pentanediyloxy group and the like. The number of carbon atoms of the alkanediyloxy group is preferably 1 to 11, more preferably 1 to 6, still more preferably 1 to 4, and yet more preferably 1 to 3.

Examples of the alkanediyloxycarbonyl group include alkanediyloxycarbonyl groups having 2 to 17 carbon atoms, for example, a methyleneoxycarbonyl group, an ethyleneoxycarbonyl group, a propanediyloxycarbonyl group, a butanediyloxycarbonyl group and the like. Examples of the alkanediylcarbonyl group include alkanediylcarbonyl groups having 2 to 18 carbon atoms, for example, a methylenecarbonyl group, an ethylenecarbonyl group, a propanediylcarbonyl group, a butanediylcarbonyl group, a pentanediylcarbonyl group and the like. Examples of the alkanediylcarbonyloxy group include alkanediylcarbonyloxy groups having 2 to 17 carbon atoms, for example, a methylenecarbonyloxy group, an ethylenecarbonyloxy group, a propanediylcarbonyloxy group, a butanediylcarbonyloxy group and the like. The number of carbon atoms of the alkanediyloxycarbonyl group is preferably 2 to 11, more preferably 2 to 6, still more preferably 2 to 4, and yet more preferably 2 or 3. The number of carbon atoms of the alkanediylcarbonyl group is preferably 2 to 12, more preferably 2 to 6, still more preferably 2 to 4, and yet more preferably 2 or 3. The number of carbon atoms of the alkanediylcarbonyloxy group is preferably 2 to 11, more preferably 2 to 6, still more preferably 2 to 4, and yet more preferably 2 or 3.

Examples of the alkanediylthio group include alkanediylthio groups having 1 to 17 carbon atoms, for example, a methylenethio group, an ethylenethio group, a propylenethio group and the like. The number of carbon atoms of the alkanediylthio group is preferably 1 to 11, more preferably 1 to 6, still more preferably 1 to 4, and yet more preferably 1 to 3.

Examples of the alkanediylsulfonyl group include alkanediylsulfonyl groups having 1 to 17 carbon atoms, for example, a methylenesulfonyl group, an ethylenesulfonyl group, a propylenesulfonyl group and the like. The number of carbon atoms of the alkanediylsulfonyl group is preferably 1 to 11, more preferably 1 to 6, still more preferably 1 to 4, and yet more preferably 1 to 3.

Examples of the cycloalkoxy group include cycloalkoxy groups having 3 to 17 carbon atoms, for example, a cyclohexyloxy group and the like. Examples of the cycloalkylalkoxy group include cycloalkylalkoxy groups having 4 to 17 carbon atoms, for example, a cyclohexylmethoxy group and the like. Examples of the alkoxycarbonyloxy group include alkoxycarbonyloxy groups having 2 to 16 carbon atoms, for example, a butoxycarbonyloxy group and the like. Examples of the aromatic hydrocarbon group-carbonyloxy group include aromatic hydrocarbon group-carbonyloxy groups having 7 to 17 carbon atoms, for example, a benzoyloxy group and the like. Examples of the aromatic hydrocarbon group-carbonyl group include aromatic hydrocarbon group-carbonyl groups having 7 to 17 carbon atoms, for example, a benzoyl group and the like. Examples of the aromatic hydrocarbon group-oxy group include aromatic hydrocarbon group-oxy groups having 6 to 16 carbon atoms, for example, a phenyloxy group and the like.

Examples of the haloalkoxy group, the haloalkoxycarbonyl group, the haloalkylcarbonyl group and the haloalkylcarbonyloxy group include haloalkoxy groups having 1 to 11 carbon atoms, haloalkoxycarbonyl groups having 2 to 11 carbon atoms, haloalkylcarbonyl groups having 2 to 12 carbon atoms and haloalkylcarbonyloxy groups having 2 to 11 carbon atoms, for example, groups in which one or more hydrogen atoms of the above-mentioned groups are substituted with a halogen atom.

Examples of the group in which —CH$_2$— included in the alicyclic hydrocarbon group is replaced by —O—, —S—, —CO— or —SO$_2$— include groups shown below. —O— or —CO— of the groups shown below may be replaced by —S— or —SO$_2$—. The bonding site can be any position.

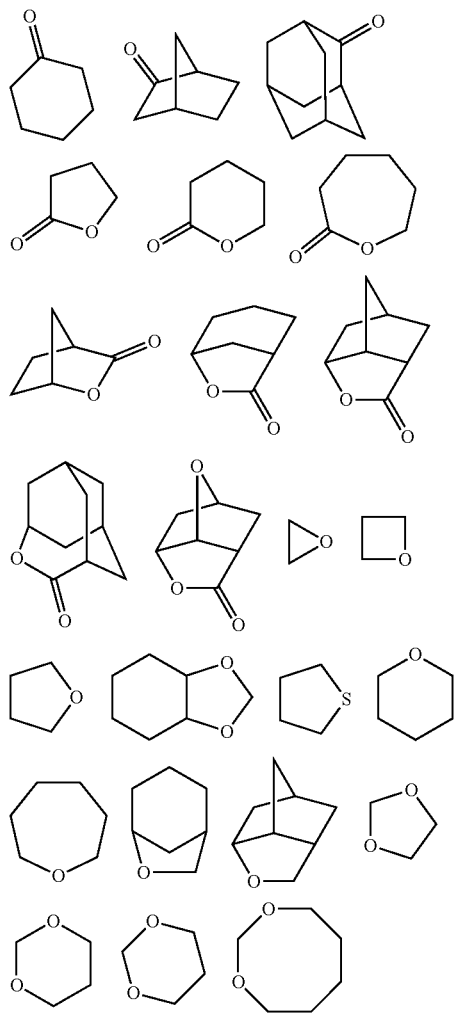

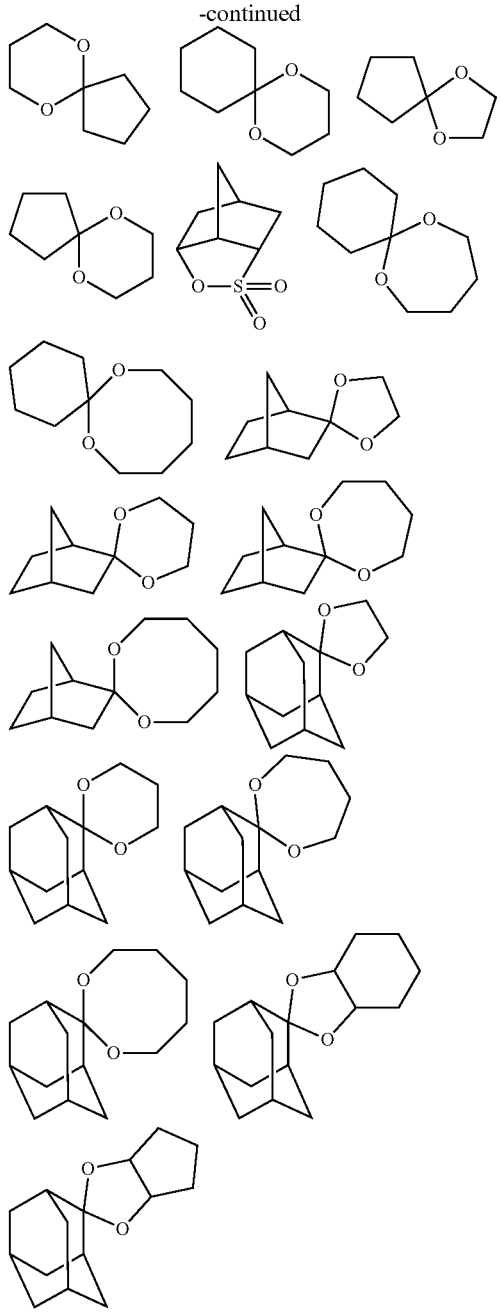

When —CH$_2$— included in the haloalkyl group and the hydrocarbon group is replaced by —O—, —S—, —CO— or —SO$_2$—, the number of carbon atoms before replacement is taken as the total number of the hydrocarbon group. The number may be 1, or 2 or more.

Examples of the substituent which may be possessed by the hydrocarbon group as for $R^4$, $R^5$, $R^6$, $R^7$, $R^8$ and $R^9$ include a halogen atom, a cyano group and an alkyl group having 1 to 12 carbon atoms (—CH$_2$— included in the alkyl group may be replaced by —O— or —CO—).

Examples of the halogen atom include the same groups as mentioned above.

Examples of the alkyl group having 1 to 12 carbon atoms include the same groups as mentioned above.

When —CH$_2$— included in the alkyl group as the substituent is replaced by —O— or —CO—, the number of carbon atoms before replacement is taken as the total number of the alkyl group. Examples of the replaced group include a hydroxy group, a carboxy group, an alkoxy group, an alkoxycarbonyl group, an alkylcarbonyl group, an alkylcarbonyloxy group and the like.

Examples of the alkoxy group, the alkoxycarbonyl group, the alkylcarbonyl group and the alkylcarbonyloxy group include alkoxy groups having 1 to 11 carbon atoms, alkoxycarbonyl groups having 2 to 11 carbon atoms, alkylcarbonyl group having 2 to 12 carbon atoms and alkylcarbonyloxy groups having 2 to 11 carbon atoms, for example, the same groups as mentioned above.

The hydrocarbon group may have one substituent or a plurality of substituents.

Examples of the hydrocarbon group as for $A^1$, $A^2$ and $A^3$ include chain hydrocarbon groups such as an alkanediyl group, alicyclic hydrocarbon groups, aromatic hydrocarbon groups, and groups formed by combining these groups. The number of carbon atoms of the hydrocarbon group is preferably 2 to 19, more preferably 2 to 18, still more preferably 2 to 16, yet more preferably 2 to 14, and further preferably 2 to 12.

Examples of the alkanediyl group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group.

The number of carbon atoms of the chain hydrocarbon group is preferably 2 to 18, more preferably 2 to 12, still more preferably 2 to 9, yet more preferably 2 to 6, further preferably 2 to 4, and still further preferably 2 or 3.

The alicyclic hydrocarbon group may be either monocyclic or polycyclic, and examples thereof include groups show below. The bonding site can be any position.

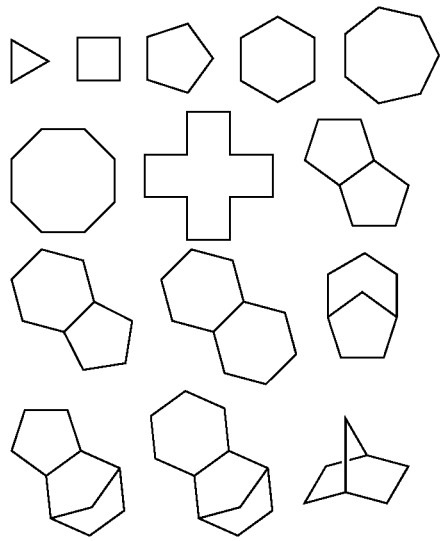

-continued

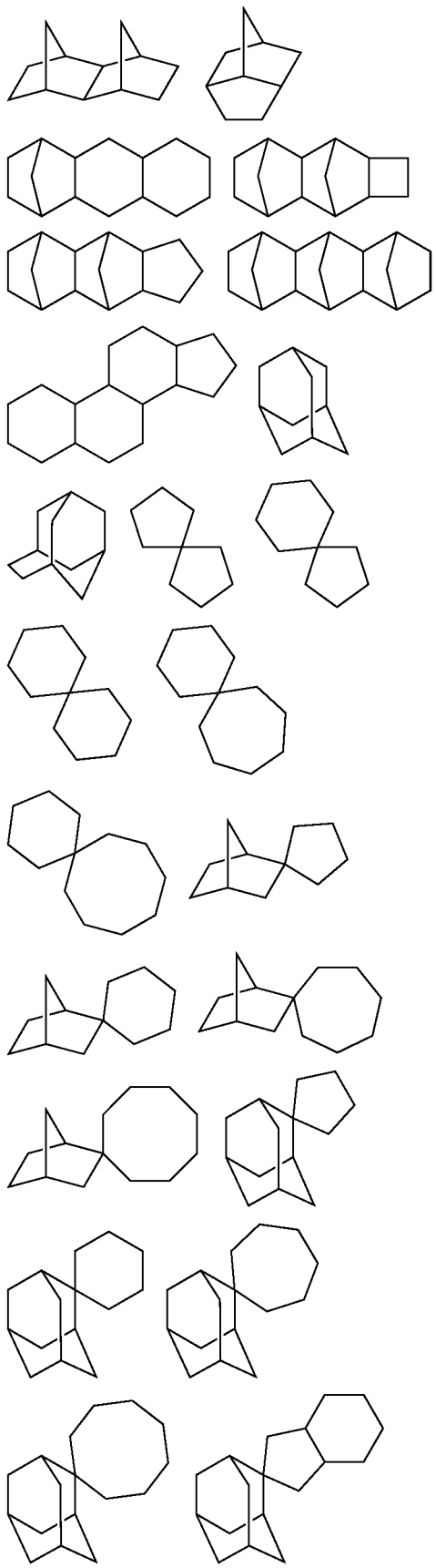

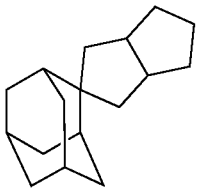

Specific examples thereof include monocyclic alicyclic hydrocarbon groups which are monocyclic cycloalkanediyl groups, such as a cyclobutane-1,3-diyl group, a cyclopentane-1,3-diyl group, a cyclohexane-1,4-diyl group and a cyclooctane-1,5-diyl group; and polycyclic alicyclic hydrocarbon groups which are polycyclic cycloalkanediyl groups, such as a norbornane-1,4-diyl group, a norbornane-2,5-diyl group, an adamantane-1,5-diyl group and an adamantane-2,6-diyl group.

The number of carbon atoms of the alicyclic hydrocarbon group is preferably 3 to 18, more preferably 3 to 16, still more preferably 3 to 12, and yet more preferably 3 to 10.

Examples of the aromatic hydrocarbon group include aromatic hydrocarbon groups, for example, arylene groups such as a phenylene group, a naphthylene group, an anthrylene group, a biphenylene group and a phenanthrylene group. The number of carbon atoms of the aromatic hydrocarbon group is preferably 6 to 18, more preferably 6 to 14, and still more preferably 6 to 10.

Examples of the group formed by combination include groups formed by combining an alicyclic hydrocarbon group with an alkanediyl group, groups formed by combining an aromatic hydrocarbon group with an alkanediyl group, and groups formed by combining an alicyclic hydrocarbon group with an aromatic hydrocarbon group. Here, the alkanediyl group in the combination with the alicyclic hydrocarbon group and/or the aromatic hydrocarbon group may include a methylene group. In combination, two or more of chain hydrocarbon groups, alicyclic hydrocarbon groups and aromatic hydrocarbon groups may be respectively combined. Any group may be bonded to the benzene ring to which $R^1$, $R^2$ or $R^3$ is bonded.

Examples of the group formed by combining an alicyclic hydrocarbon group with an alkanediyl group include a -divalent alicyclic hydrocarbon group-alkanediyl group-, an -alkanediyl group-divalent alicyclic hydrocarbon group-alkanediyl group-, an -alkanediyl group-divalent alicyclic hydrocarbon group- and the like.

Examples of the group formed by combining an aromatic hydrocarbon group with an alkanediyl group include a -divalent aromatic hydrocarbon group-alkanediyl group-, an -alkanediyl group-divalent aromatic hydrocarbon group-alkanediyl group-, an -alkanediyl group-divalent aromatic hydrocarbon group- and the like.

Examples of the group formed by combining an alicyclic hydrocarbon group with an aromatic hydrocarbon group include an -aromatic hydrocarbon group-alicyclic hydrocarbon group-, an -alicyclic hydrocarbon group-aromatic hydrocarbon group-, an -alicyclic hydrocarbon group-aromatic hydrocarbon group-an alicyclic hydrocarbon group- and the like.

When —$CH_2$— included in the hydrocarbon group is replaced by —O—, —CO—, —S— or —$SO_2$—, the number of carbon atoms before replacement is taken as the total number of the hydrocarbon group. The number may be either 1, or 2 or more.

Examples of the group in which —$CH_2$— included in the hydrocarbon group is replaced by —O—, —CO—, —S— or —$SO_2$— include a hydroxy group (a group in which —$CH_2$— included in the methyl group is replaced by —O—), a carboxy group (a group in which —$CH_2$—$CH_2$— included in the ethyl group is replaced by —O—CO—), a thiol group (a group in which —$CH_2$-included in the methyl group is replaced by —S—), an alkoxy group (a group in which —$CH_2$— at any position included in the alkyl group is replaced by —O—), an alkoxycarbonyl group (a group in which —$CH_2$—$CH_2$— at any position included in the alkyl group is replaced by —O—CO—), an alkylcarbonyl group (a group in which —$CH_2$— at any position included in the alkyl group is replaced by —CO—), an alkylcarbonyloxy group (a group in which —$CH_2$—$CH_2$— at any position included in the alkyl group is replaced by —CO—O—), an alkylthio group (a group in which —$CH_2$— at any position included in the alkyl group is replaced by —S—), an alkylsulfonyl group (a group in which —$CH_2$— at any position included in the alkyl group is replaced by —$SO_2$—), an oxy group (a group in which —$CH_2$— included in the methylene group is replaced by —O—), a carbonyl group (a group in which —$CH_2$— included in the methylene group is replaced by —CO—), a thio group (a group in which —$CH_2$— included in the methylene group is replaced by —S—), a sulfonyl group (a group in which —$CH_2$— included in the methylene group is replaced by —$SO_2$—), an alkanediyloxy group (a group in which —$CH_2$— at any position included in the alkanediyl group is replaced by —O—), an alkanediyloxycarbonyl group (a group in which —$CH_2$—$CH_2$— at any position included in the alkanediyl group is replaced by —O—CO—), an alkanediylcarbonyl group (a group in which —$CH_2$— at any position included in the alkanediyl group is replaced by —CO—), an alkanediylcarbonyloxy group (a group in which —$CH_2$—$CH_2$— at any position included in the alkanediyl group is replaced by —CO—O—), an alkanediylsulfonyl group (a group in which —$CH_2$— at any position included in the alkanediyl group is replaced by —$SO_2$—), an alkanediylthio group (a group in which —$CH_2$— at any position included in the alkanediyl group is replaced by —S—), a cycloalkoxy group, a cycloalkylalkoxy group, an alkoxycarbonyloxy group, an aromatic hydrocarbon group-carbonyloxy group, an aromatic hydrocarbon group-carbonyl group, an aromatic hydrocarbon group-oxy group, a group obtained by combining two or more groups of these groups, and the like.

Examples of the alkoxy group include alkoxy groups having 1 to 17 carbon atoms, for example, a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group and the like. The number of carbon atoms of the alkoxy group is preferably 1 to 11, more preferably 1 to 6, still more preferably 1 to 4, and yet more preferably 1 to 3.

The alkoxycarbonyl group, the alkylcarbonyl group and the alkylcarbonyloxy group represent a group in which a carbonyl group or a carbonyloxy group is bonded to the above-mentioned alkyl group or alkoxy group.

Examples of the alkoxycarbonyl group include alkoxycarbonyl groups having 2 to 17 carbon atoms, for example, a methoxycarbonyl group, an ethoxycarbonyl group, a butoxycarbonyl group and the like. Examples of the alkylcarbonyl group include alkylcarbonyl groups having 2 to 18 carbon atoms, for example, an acetyl group, a propionyl group and a butyryl group. Examples of the alkylcarbonyloxy group include alkylcarbonyloxy groups having 2 to 17 carbon atoms, for example, an acetyloxy group, a propionyloxy group, a butyryloxy group and the like. The number of carbon atoms of the alkoxycarbonyl group is preferably 2 to 11, more preferably 2 to 6, still more preferably 2 to 4, and yet more preferably 2 or 3. The number of carbon atoms of the alkylcarbonyl group is preferably 2 to 12, more preferably 2 to 6, still more preferably 2 to 4, and yet more preferably 2 or 3. The number of carbon atoms of the alkylcarbonyloxy group is preferably 2 to 11, more preferably 2 to 6, still more preferably 2 to 4, and yet more preferably 2 or 3.

Examples of the alkylthio group include alkylthio groups having 1 to 17 carbon atoms, for example, a methylthio group, an ethylthio group, a propylthio group, a butylthio group, a pentylthio group, a hexylthio group, an octylthio group, a 2-ethylhexylthio group, a nonylthio group, a decylthio group, an undecylthio group and the like. The number of carbon atoms of the alkylthio group is preferably 1 to 11, more preferably 1 to 6, still more preferably 1 to 4, and yet more preferably 1 to 3.

Examples of the alkylsulfonyl group include alkylsulfonyl groups having 1 to 17 carbon atoms, for example, a methylsulfonyl group, an ethylsulfonyl group, a propylsulfonyl group, a butylsulfonyl group, a pentylsulfonyl group, a hexylsulfonyl group, an octylsulfonyl group, a 2-ethylhexylsulfonyl group, a nonylsulfonyl group, a decylsulfonyl group, an undecylsulfonyl group and the like. The number of carbon atoms of the alkylsulfonyl group is preferably 1 to 11, more preferably 1 to 6, still more preferably 1 to 4, and yet more preferably 1 to 3.

Examples of the alkanediyloxy group include alkanediyloxy group having 1 to 17 carbon atoms, for example, a methyleneoxy group, an ethyleneoxy group, a propanediyloxy group, a butanediyloxy group, a pentanediyloxy group and the like. The number of carbon atoms of the alkanediyloxy group is preferably 1 to 11, more preferably 1 to 6, still more preferably 1 to 4, and yet more preferably 1 to 3.

Examples of the alkanediyloxycarbonyl group include alkanediyloxycarbonyl groups having 2 to 17 carbon atoms, for example, a methyleneoxycarbonyl group, an ethyleneoxycarbonyl group, a propanediyloxycarbonyl group, a butanediyloxycarbonyl group and the like. Examples of the alkanediylcarbonyl group include alkanediylcarbonyl groups having 2 to 18 carbon atoms, for example, a methylenecarbonyl group, an ethylenecarbonyl group, a propanediylcarbonyl group, a butanediylcarbonyl group, a pentanediylcarbonyl group and the like. Examples of the alkanediylcarbonyloxy group include alkanediylcarbonyloxy groups having 2 to 17 carbon atoms, for example, a methylenecarbonyloxy group, an ethylenecarbonyloxy group, a propanediylcarbonyloxy group, a butanediylcarbonyloxy group and the like. The number of carbon atoms of the alkanediyloxycarbonyl group is preferably 2 to 11, more preferably 2 to 6, still more preferably 2 to 4, and yet more preferably 2 or 3. The number of carbon atoms of the alkanediylcarbonyl group is preferably 2 to 12, more preferably 2 to 6, still more preferably 2 to 4, and yet more preferably 2 or 3. The number of carbon atoms of the alkanediylcarbonyloxy group is preferably 2 to 11, more preferably 2 to 6, still more preferably 2 to 4, and yet more preferably 2 or 3.

Examples of the alkanediylsulfonyl group include alkanediylsulfonyl groups having 1 to 17 carbon atoms, for example, a methylenesulfonyl group, an ethylenesulfonyl group, a propylenesulfonyl group and the like. The number of carbon atoms of the alkanediylsulfonyl group is preferably 1 to 11, more preferably 1 to 6, still more preferably 1 to 4, and yet more preferably 1 to 3.

Examples of the alkanediylthio group include alkanediylthio groups having 1 to 17 carbon atoms, for example, a methylenethio group, an ethylenethio group, a propylenethio group and the like. The number of carbon atoms of the alkanediylthio group is preferably 1 to 11, more preferably 1 to 6, still more preferably 1 to 4, and yet more preferably 1 to 3.

Examples of the cycloalkoxy group include cycloalkoxy groups having 3 to 17 carbon atoms, for example, a cyclohexyloxy group and the like. Examples of the cycloalkylalkoxy group include cycloalkylalkoxy groups having 4 to 17 carbon atoms, for example, a cyclohexylmethoxy group and the like. Examples of the alkoxycarbonyloxy group include alkoxycarbonyloxy groups having 2 to 16 carbon atoms, for example, a butoxycarbonyloxy group and the like. Examples of the aromatic hydrocarbon group-carbonyloxy group include aromatic hydrocarbon group-carbonyloxy groups having 7 to 17 carbon atoms, for example, a benzoyloxy group and the like. Examples of the aromatic hydrocarbon group-carbonyl group include aromatic hydrocarbon group-carbonyl groups having 7 to 17 carbon atoms, for example, a benzoyl group and the like. Examples of the aromatic hydrocarbon group-oxy group include aromatic hydrocarbon group-oxy groups having 6 to 16 carbon atoms, for example, a phenyloxy group and the like.

Examples of the group in which —CH$_2$— included in the alicyclic hydrocarbon group is replaced by —O—, —CO—, —S— or —SO$_2$— include groups shown below. —O— or —CO— of the groups shown below may be replaced by —S— or —SO$_2$—. The bonding site can be any position.

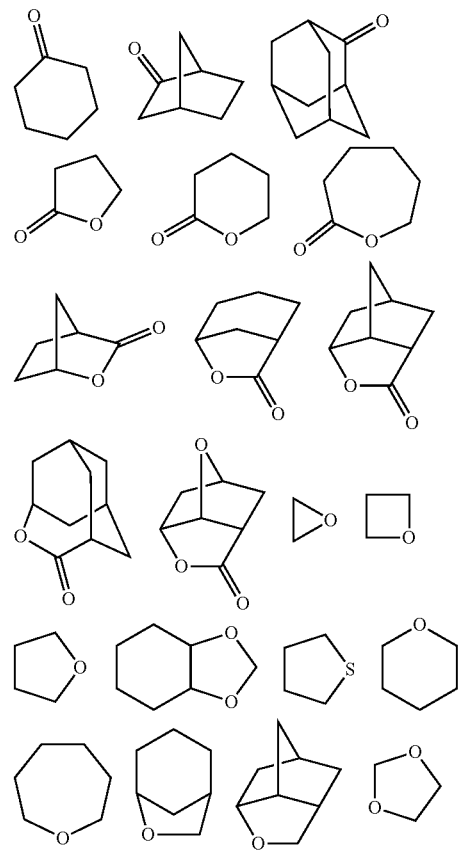

-continued

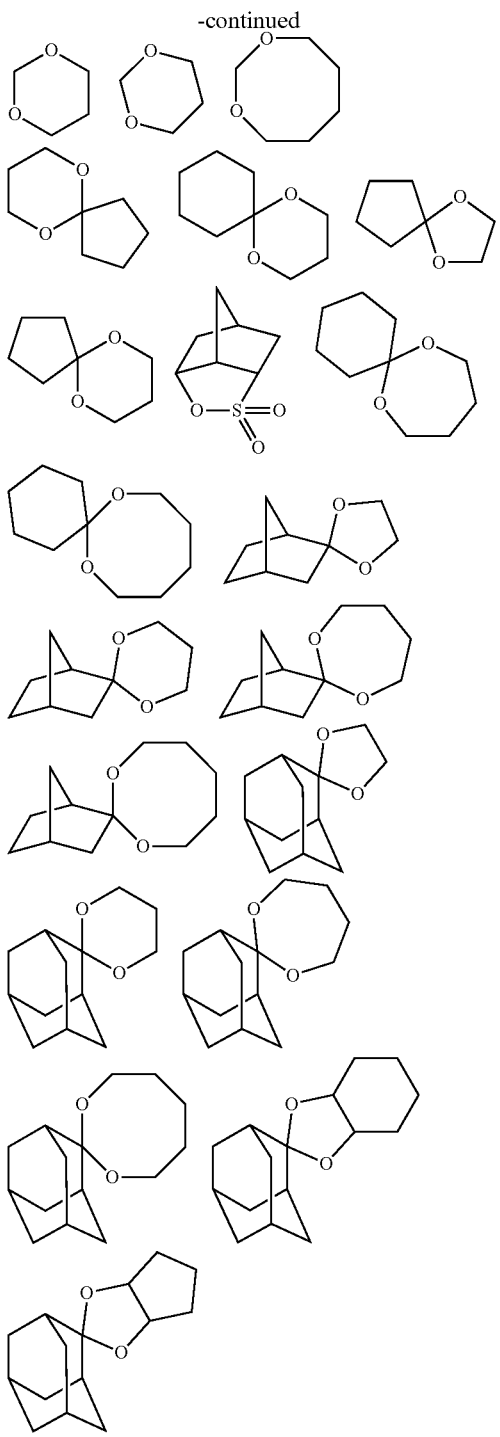

Examples of the substituent which may be possessed by the hydrocarbon group as for $A^1$, $A^2$ and $A^3$ include the same groups as mentioned for $R^4$ to $R^9$.

It is preferable that $A^1$, $A^2$ and $A^3$ are each independently a hydrocarbon group having 2 to 20 carbon atoms (the hydrocarbon group may have a substituent, —CH$_2$— included in the hydrocarbon group may be replaced by —O—, —CO—, —S— or —SO$_2$—, in which at least one of —CH$_2$— included in the hydrocarbon group is replaced by —O—, —CO—, —S— or —SO$_2$—). Specifically, it is more preferable that $A^1$ is *-$L^{011}$-$X^{01}$-$L^{012}$-, $A^2$ is *-$L^{021}$-$X^{02}$-$L^{022}$-, and $A^3$ is *-$L^{031}$-$X^{03}$-$L^{032}$-($X^{01}$, $X^{02}$ and $X^{03}$ each independently represent —O—, —CO—, —S— or —SO$_2$—, $L^{011}$, $L^{012}$, $L^{021}$, $L^{022}$, $L^{031}$ and $L^{032}$ each independently represent a single bond or a hydrocarbon group having 1 to 19 carbon atoms, the hydrocarbon group may have a substituent, —CH$_2$— included in the hydrocarbon group may be replaced by —O—, —CO—, —S— or —SO$_2$—, in which the total number of carbon atoms of $L^{011}$ and $L^{012}$ is 1 to 19, the total number of carbon atoms of $L^{021}$ and $L^{022}$ is 1 to 19, the total number of carbon atoms of $L^{031}$ and $L^{032}$ is 1 to 19, and * represents a bonding site to the benzene ring to which $R^1$, $R^2$ or $R^3$ is bonded), and it is still more preferable that $A^1$ is *—$X^{01}$-$L^{01}$- or *-$L^{01}$-$X^{01}$—, $A^2$ is *—$X^{02}$-$L^{02}$- or *-$L^{02}$-$X^{02}$—, and $A^3$ is *—$X^{03}$-$L^{03}$ or *-$L^{03}$-$X^{03}$ ($X^{01}$, $X^{02}$ and $X^{03}$ each independently represent —O—, —CO—, —S— or —SO$_2$—, $L^{01}$, $L^{02}$ and $L^{03}$ each independently represent a hydrocarbon group having 1 to 19 carbon atoms, the hydrocarbon group may have a substituent, —CH$_2$— included in the hydrocarbon group may be replaced by —O—, —CO—, —S— or —SO$_2$—, and * represents a bonding site to the benzene ring to which $R^1$, $R^2$ or $R^3$ is bonded).

Examples of the hydrocarbon group having 1 to 19 carbon atoms as for $L^{011}$, $L^{012}$, $L^{021}$, $L^{022}$, $L^{031}$, $L^{032}$, $L^{01}$, $L^{02}$ and $L^{03}$ (the hydrocarbon group may have a substituent, and —CH$_2$— included in the hydrocarbon group may be replaced by —O—, —CO—, —S— or —SO$_2$—) include the same groups as mentioned for $A^1$, $A^2$ and $A^3$ in the range of 1 to 19 carbon atoms.

Preferably, $X^{01}$, $X^{02}$ and $X^{03}$ are each independently —O— or —S—, and more preferably —O—.

Preferably, $L^{011}$, $L^{012}$, $L^{021}$, $L^{022}$, $L^{031}$ and $L^{032}$ are each independently a single bond or a hydrocarbon group having 1 to 18 carbon atoms (—CH$_2$— included in the hydrocarbon group may be replaced by —O—, —CO—, —S— or —SO$_2$—), more preferably a single bond or a hydrocarbon group having 1 to 14 carbon atoms (—CH$_2$— included in the hydrocarbon group may be replaced by —O—, —CO—, —S— or —SO$_2$—), still more preferably a single bond, a chain hydrocarbon group having 1 to 9 carbon atoms, an alicyclic hydrocarbon group having 3 to 12 carbon atoms, or a group obtained by combining a chain hydrocarbon group having 1 to 4 carbon atoms with an alicyclic hydrocarbon group having 3 to 10 carbon atoms (—CH$_2$— included in the chain hydrocarbon group and the alicyclic hydrocarbon group may be replaced by —O—, —CO—, —S— or —SO$_2$—), yet more preferably a single bond or an alkanediyl group having 1 to 6 carbon atoms (—CH$_2$- included in the alkanediyl group may be replaced by —O— or —CO—), further preferably a single bond or an alkanediyl group having 1 to 4 carbon atoms (—CH$_2$— included in the alkanediyl group may be replaced by —O— or —CO—), and still further preferably a single bond or an alkanediyl group having 1 to 3 carbon atoms (—CH$_2$— included in the alkanediyl group may be replaced by —O— or —CO—). Of these, a single bond, a methylene group, an ethane-1,1-diyl group, a propane-1,1-diyl group, a propane-2,2-diyl group, a carbonyl group, a carbonyloxy group, a carbonyloxymethylene group, an ethyleneoxy group, a methylenecarbonyloxymethylene group or an ethyleneoxycarbonyl group is preferable, and a single bond or a methylene group is more preferable. In which, the total number of carbon atoms of $L^{011}$ and $L^{012}$ is 1 to 19, the total number of carbon atoms of $L^{021}$ and $L^{022}$ is 1 to 19, and the total number of carbon atoms of $L^{031}$ and $L^{032}$ is 1 to 19.

Preferably, $L^{01}$, $L^{02}$ and $L^{03}$ are each independently a hydrocarbon group having 1 to 18 carbon atoms (—CH$_2$— included in the hydrocarbon group may be replaced by —O—, —CO—, —S— or —SO$_2$—), more preferably a hydrocarbon group having 1 to 14 carbon atoms (—CH$_2$— included in the hydrocarbon group may be replaced by —O—, —CO—, —S— or —SO$_2$—), still more preferably a chain hydrocarbon group having 1 to 9 carbon atoms, an alicyclic hydrocarbon group having 3 to 12 carbon atoms, or a group obtained by combining a chain hydrocarbon group having 1 to 4 carbon atoms with an alicyclic hydrocarbon group having 3 to 10 carbon atoms (—CH$_2$— included in the chain hydrocarbon group and the alicyclic hydrocarbon group may be replaced by —O—, —CO—, —S— or —SO$_2$—), yet more preferably an alkanediyl group having 1 to 6 carbon atoms (—CH$_2$— included in the alkanediyl group may be replaced by —O— or —CO—), further preferably an alkanediyl group having 1 to 4 carbon atoms (—CH$_2$— included in the alkanediyl group may be replaced by —O— or —CO—), and still further preferably an alkanediyl group having 1 to 3 carbon atoms (—CH$_2$— included in the alkanediyl group may be replaced by —O— or —CO—). Of these, a methylene group, an ethane-1,1-diyl group, a propane-1,1-diyl group, a propane-2,2-diyl group, a carbonyl group, a carbonyloxy group, a carbonyloxymethylene group, an ethyleneoxy group, a methylenecarbonyloxymethylene group or an ethyleneoxycarbonyl group is preferable, and a methylene group is more preferable.

The bonding site of A$^1$, A$^2$ and A$^3$ to the benzene ring to which S$^+$ is bonded may be each independently the o-position, the m-position or the p-position, with respect to the bonding site of S+, respectively. Particularly, when m1, m2 and m3 are 1, A$^1$, A$^2$ and A$^3$ are each independently bonded preferably at the p-position or the m-position, and more preferably at the p-position, with respect to the bonding site of S+, respectively. When m1, m2 and m3 are 2, it is preferable that one of A$^1$, one of A$^2$ and one of A$^3$ are each independently bonded at the o-position or the m-position and one of A$^1$, one of A$^2$ and one of A$^3$ are each independently bonded at the o-position or the m-position, and it is more preferable that two of A$^1$, two of A$^2$ and two of A$^3$ are each independently bonded at the m-position, with respect to the bonding site of S+, respectively. When m1, m2 and m3 are 3, it is preferable that two of A$^1$, two of A$^2$ and two of A$^3$ are each independently bonded at the o-position or the m-position and one of A$^1$, one of A$^2$ and one of A$^3$ are each independently bonded at the p-position or the m-position, and it is more preferable that two of A$^1$, two of A$^2$ and two of A$^3$ are each independently bonded at the m-position and one of A$^1$, one of A$^2$ and one of A$^3$ are each independently bonded at the p-position, with respect to the bonding site of S+, respectively. When m1, m2 and m3 are 4, it is preferable that two of A$^1$, two of A$^2$ and two of A$^3$ are each independently bonded at the o-position or the m-position and two of A$^1$, two of A$^2$ and two of A$^3$ are each independently bonded at the p-position or the m-position, and it is more preferable that two of A$^1$, two of A$^2$ and two of A$^3$ are each independently bonded at the o-position and two of A$^1$, two of A$^2$ and two of A$^3$ are each independently bonded at the m-position, with respect to the bonding site of S+, respectively.

m1 is preferably 1, 2, 3 or 4, more preferably 1, 2 or 3, still more preferably 1 or 2, and yet more preferably 1.

m2 is preferably 0, 1, 2, 3 or 4, more preferably 0, 1, 2 or 3, still more preferably 0, 1 or 2, and yet more preferably 0 or 1.

m3 is preferably 0, 1, 2, 3 or 4, more preferably 0, 1, 2 or 3, still more preferably 0, 1 or 2, and yet more preferably 0 or 1.

m4 is preferably 0, 1, 2 or 4, and more preferably 0, 1 or 2.

m5 is preferably 0, 1, 2 or 4, and more preferably 0, 1 or 2.

m6 is preferably 0, 1, 2 or 4, and more preferably 0, 1 or 2.

m7 is preferably 0, 1, 2 or 3, more preferably 0, 1 or 2, and still more preferably 0 or 1.

m8 is preferably 0, 1, 2 or 3, more preferably 0, 1 or 2, and still more preferably 0 or 1.

m9 is preferably 0, 1, 2 or 3, more preferably 0, 1 or 2, and still more preferably 0 or 1.

Particularly, at least one of m8 and m9 is preferably an integer of 1 or more.

Preferably, R$^4$, R$^5$ and R$^6$ are each independently a halogen atom, an alkyl fluoride group having 1 to 6 carbon atoms or an alkyl group having 1 to 6 carbon atoms (—CH$_2$- included in the alkyl group may be replaced by —O— or —CO—), more preferably a halogen atom, an alkyl fluoride group having 1 to 4 carbon atoms or an alkyl group having 1 to 4 carbon atoms (—CH$_2$— included in the alkyl group may be replaced by —O— or —CO—), still more preferably a fluorine atom, an iodine atom, a perfluoroalkyl group having 1 to 4 carbon atoms or an alkyl group having 1 to 4 carbon atoms (—CH$_2$— included in the alkyl group may be replaced by —O— or —CO—), and yet more preferably a fluorine atom, an iodine atom, a hydroxy group, a methoxy group or a trifluoromethyl group.

The bonding site of R$^4$, R$^5$ and R$^6$ to the benzene ring may be each independently the o-position, the m-position or the p-position, with respect to the bonding site of A$^1$, A$^2$ and A$^3$, respectively. Particularly, when m4, m5 and m6 are 1, R$^4$, R$^5$ and R$^6$ are each independently bonded preferably at the p-position or the m-position, and more preferably at the m-position, with respect to the bonding site of A$^1$, A$^2$ and A$^3$, respectively. When m4, m5 and m6 are 2, it is preferable that one of R$^4$, one of R$^5$ and one of R$^6$ are each independently bonded at the o-position or the m-position and one of R$^4$, one of R$^5$ and one of R$^6$ are each independently bonded at the p-position or the m-position, and it is more preferable that two of R$^4$, two of R$^5$ and two of R$^6$ are each independently bonded at the m-position, with respect to the bonding site of A$^1$, A$^2$ and A$^3$, respectively. When m4, m5 and m6 are 3, it is preferable that two of R$^4$, two of R$^5$ and two of R$^6$ are each independently bonded at the o-position or the m-position and one of R$^4$, one of R$^5$ and one of R$^6$ are each independently bonded at the p-position or the m-position, and it is more preferable that one of R$^4$, one of R$^5$ and one of R$^6$ are each independently bonded at the o-position and two of R$^4$, two of R$^5$ and two of R$^6$ are each independently bonded at the m-position, with respect to the bonding site of A$^1$, A$^2$ and A$^3$, respectively. When m4, m5 and m6 are 4, it is preferable that two of R$^4$, two of R$^5$ and two of R$^6$ are each independently bonded at the o-position or the m-position and two of R$^4$, two of R$^5$ and two of R$^6$ are each independently bonded at the p-position or the m-position, and it is more preferable that two of R$^4$, two of R$^5$ and two of R$^6$ are each indepen dently bonded at the o-position and two of $R^4$, two of $R^5$ and two of $R^6$ are each independently bonded at the m-position, with respect to the bonding site of $A^1$, $A^2$ and $A^3$, respectively.

Preferably, $R^7$, $R^8$ and $R^9$ are each independently a halogen atom, an alkyl fluoride group having 1 to 6 carbon atoms or an alkyl group having 1 to 6 carbon atoms (—CH$_2$— included in the alkyl group may be replaced by —O— or —CO—), more preferably a halogen atom, an alkyl fluoride group having 1 to 4 carbon atoms or an alkyl group having 1 to 4 carbon atoms (—CH$_2$— included in the alkyl group may be replaced by —O— or —CO—), still more preferably a fluorine atom, an iodine atom, a perfluoroalkyl group having 1 to 4 carbon atoms or an alkyl group having 1 to 4 carbon atoms (—CH$_2$— included in the alkyl group may be replaced by —O— or —CO—), and yet more preferably a fluorine atom, an iodine atom, a trifluoromethyl group, a hydroxy group, a methoxy group, a methyl group or a t-butyl group.

The bonding site of $R^7$, $R^8$ and $R^9$ to the benzene ring may be each independently the o-position, the m-position or the p-position with respect to the bonding site of S+, respectively. Particularly, when m7, m8 and m9 are 1, $R^7$, $R^8$ and $R^9$ are each independently bonded preferably at the p-position or the m-position, and more preferably at the p-position, with respect to the bonding site of $S^+$, respectively. When m7, m8 and m9 are 2, it is preferable that one of $R^7$, one of $R^8$ and one of $R^9$ are each independently bonded at the o-position or the m-position and one of $R^7$, one of $R^8$ and one of $R^9$ are each independently bonded at the p-position or the m-position, and it is more preferable that one of $R^7$, one of $R^8$ and one of $R^9$ are each independently bonded at the m-position and one of $R^7$, one of $R^8$ and one of $R^9$ are each independently bonded at the p-position or the m-position, with respect to the bonding site of $S^+$, respectively. When m7, m8 and m9 are 3, it is preferable that two of $R^7$, two of $R^8$ and two of $R^9$ are each independently bonded at the o-position or the m-position and one of $R^7$, one of $R^8$ and one of $R^9$ are each independently bonded at the p-position or the m-position, and it is more preferable that two of $R^7$, two of $R^8$ and two of $R^9$ are each independently bonded at the m-position and one of $R^7$, one of $R^8$ and one of $R^9$ are each independently bonded at the p-position, with respect to the bonding site of $S^+$, respectively. When m7, m8 and m9 are 4, it is preferable that two of $R^7$, two of $R^8$ and two of $R^9$ are each independently bonded at the o-position or the m-position and two of $R^7$, two of $R^8$ and two of $R^9$ are each independently bonded at the p-position or the m-position, and it is more preferable that two of $R^7$, two of $R^8$ and two of $R^9$ are each independently bonded at the m-position, one of $R^7$, one of $R^8$ and one of $R^9$ are each independently bonded at the o-position and one of $R^7$, one of $R^8$ and one of $R^9$ are each independently bonded at the p-position, with respect to the bonding site of $S^+$, respectively.

Examples of the cation (I) represented by formula (I-C) include a cation represented by formula (I-C-1) (hereinafter sometimes referred to as "cation (I-C-1)"):

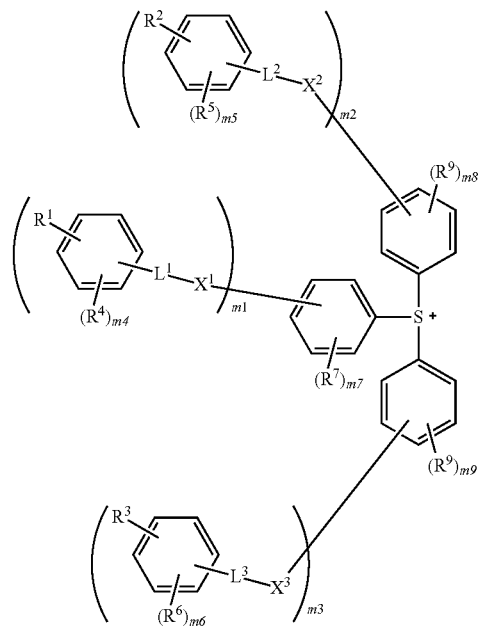

(I-C-1)

wherein, in formula (I-C-1),
$R^1$, $R^2$, $R^3$, $R^4$, $R^5$, $R^6$, $R^7$, $R^8$, $R^9$, m1, m2, m3, m4, m5, m6, m7, m8 and m9 are the same as defined in formula (I).

$L^1$, $L^2$ and $L^3$ each independently represent a hydrocarbon group having 1 to 18 carbon atoms, the hydrocarbon group may have a substituent, and —CH$_2$— included in the hydrocarbon group may be replaced by —O—, —CO—, —S— or —SO$_2$—, and $X^1$, $X^2$ and $X^3$ each independently represent —O— or —S—.

Examples of the hydrocarbon group having 1 to 18 carbon atoms (the hydrocarbon group may have a substituent, and —CH$_2$— included in the hydrocarbon group may be replaced by —O—, —CO—, —S— or —SO$_2$—) as for $L^1$, $L^2$ and $L^3$ include the same groups as mentioned for $A^1$, $A^2$ and $A^3$ in the range of 1 to 18 carbon atoms.

$X^1$ is preferably —O—.
$X^2$ is preferably —O—.
$X^3$ is preferably —O—.

The bonding site of $X^1$, $X^2$ and $X^3$ to the benzene ring may be each independently the o-position, the m-position or the p-position, with respect to the bonding site of S+, respectively. Particularly, when m1, m2 and m3 are 1, $X^1$, $X^2$ and $X^3$ are each independently bonded preferably at the p-position or the m-position, and more preferably at the p-position, with respect to the bonding site of S+, respectively. When m1, m2 and m3 are 2, it is preferable that one of $X^1$, one of $X^2$ and one of $X^3$ are each independently bonded at the o-position or the m-position and one of $X^1$, one of $X^2$ and one of $X^3$ are each independently bonded at the o-position or the m-position, and it is more preferable that two of $X^1$, two of $X^2$ and two of $X^3$ are each independently bonded at the m-position, with respect to the bonding site of $S^+$, respectively. When m1, m2 and m3 are 3, it is preferable that two of $X^1$, two of $X^2$ and two of $X^3$ are each independently bonded at the o-position or the m-position and one of $X^1$, one of $X^2$ and one of $X^3$ are each independently bonded at the p-position or the m-position, and it is more preferable that two of X¹, two of X² and two of X³ are each independently bonded at the m-position and one of X¹, one of X² and one of X³ are each independently bonded at the p-position, with respect to the bonding site of S⁺, respectively. When m1, m2 and m3 are 4, it is preferable that two of X¹, two of X² and two of X³ are each independently bonded at the o-position or the m-position and two of X¹, two of X² and two of X³ are each independently bonded at the p-position or the m-position, and it is more preferable that two of X¹, two of X² and two of X³ are each independently bonded at the o-position and two of X¹, two of X² and two of X3 are each independently bonded at the m-position, with respect to the bonding site of S⁺, respectively.

Preferably, $L^1$, $L^2$ and $L^3$ are each independently a hydrocarbon group having 1 to 16 carbon atoms (—CH₂— included in the hydrocarbon group may be replaced by —O—, —CO—, —S— or —SO₂—), more preferably a hydrocarbon group having 1 to 14 carbon atoms (—CH₂— included in the hydrocarbon group may be replaced by —O—, —CO—, —S— or —SO₂—), still more preferably a chain hydrocarbon group having 1 to 9 carbon atoms, an alicyclic hydrocarbon group having 3 to 12 carbon atoms, or a group obtained by combining a chain hydrocarbon group having 1 to 4 carbon atoms with an alicyclic hydrocarbon group having 3 to 10 carbon atoms (—CH₂— included in the chain hydrocarbon group and the alicyclic hydrocarbon group may be replaced by —O—, —CO—, —S— or —SO₂—), yet more preferably an alkanediyl group having 1 to 6 carbon atoms (—CH₂— included in the alkanediyl group may be replaced by —O— or —CO—), further preferably an alkanediyl group having 1 to 4 carbon atoms (—CH₂— included in the alkanediyl group may be replaced by —O— or —CO—), and still further preferably an alkanediyl group having 1 to 3 carbon atoms (—CH₂— included in the alkanediyl group may be replaced by —O— or —CO—). Of these, a methylene group, an ethane-1,1-diyl group, a propane-1,1-diyl group, a propane-2,2-diyl group, a carbonyl group, a carbonyloxy group, a carbonyloxymethylene group, an ethyleneoxy group, a methylenecarbonyloxymethylene group or an ethyleneoxycarbonyl group is preferable, and a methylene group is more preferable.

Examples of the cation (I) of the salt (I) include cations represented by the following formula (I-c-1) to formula (I-c-79).

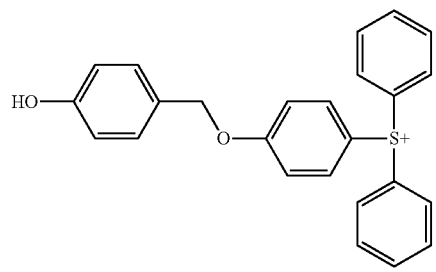
(I-c-1)

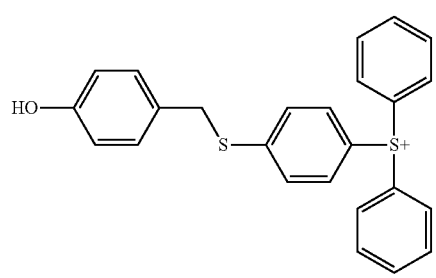
(I-c-2)

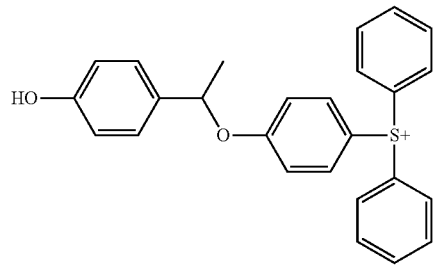
(I-c-3)

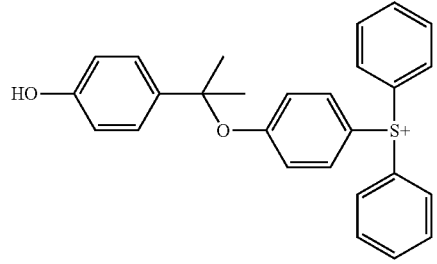
(I-c-4)

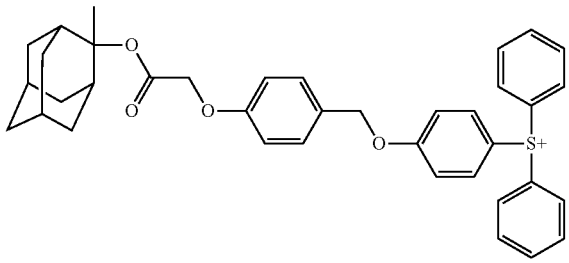
(I-c-5)

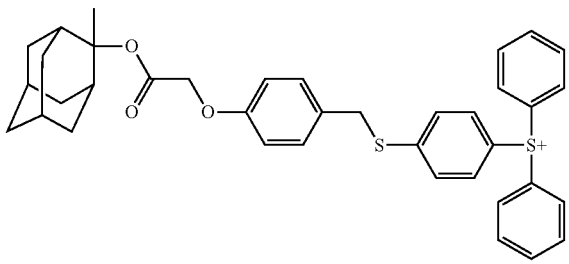
(I-c-6)

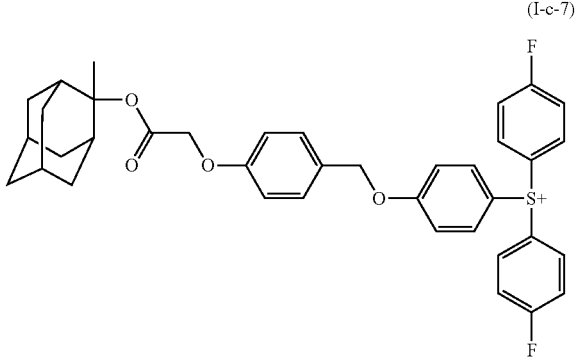
(I-c-7)

(I-c-8)
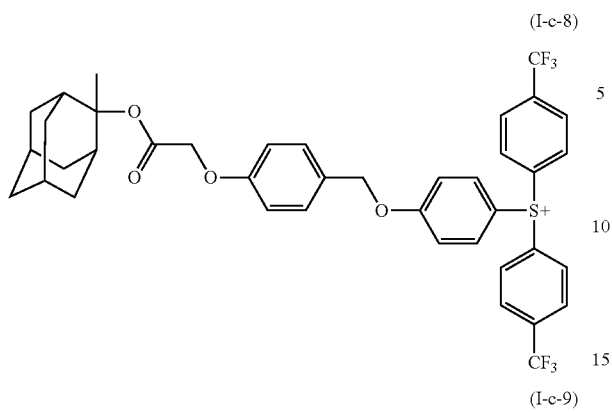
(I-c-9)
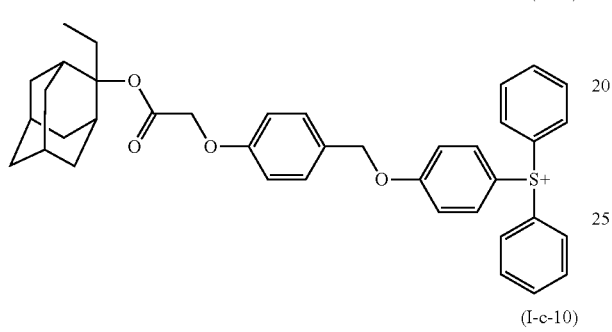
(I-c-10)
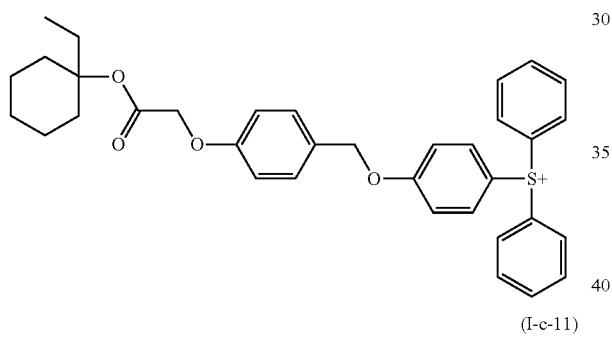
(I-c-11)
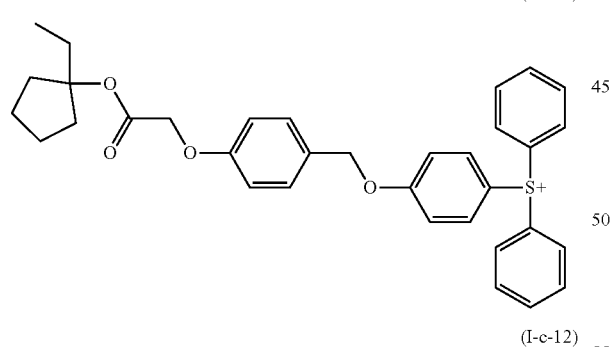
(I-c-12)
(I-c-13)
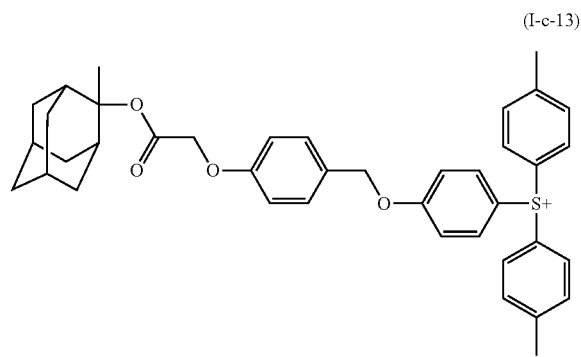
(I-c-14)
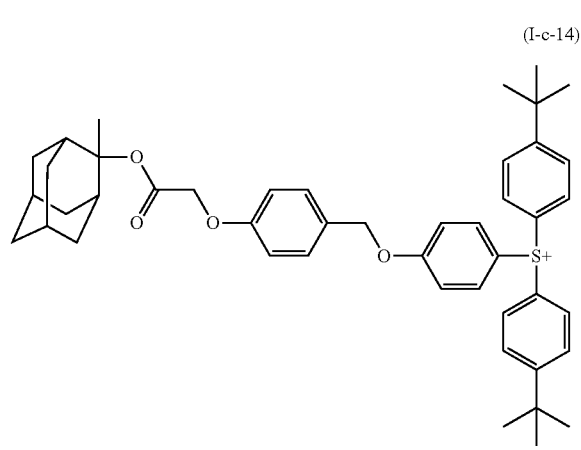
(I-c-15)
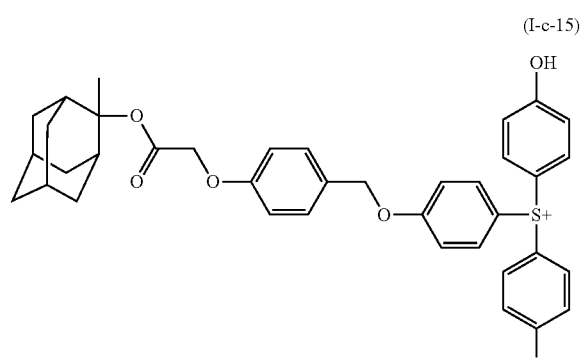
(I-c-16)
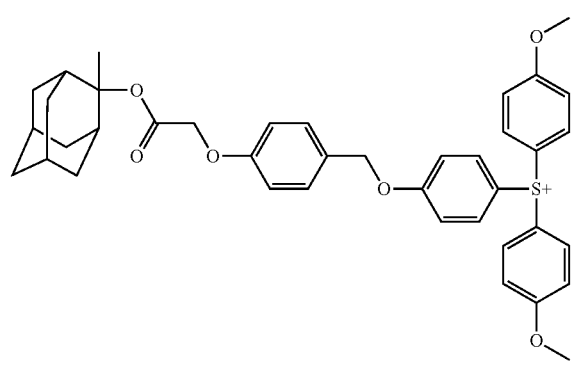

-continued
(I-c-17)
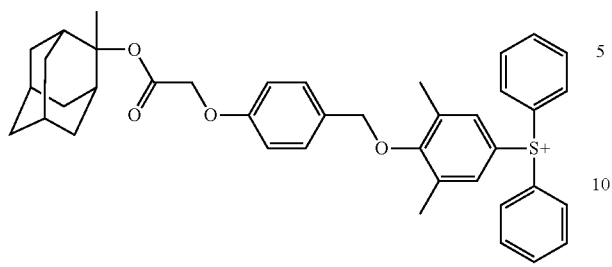
(I-c-18)
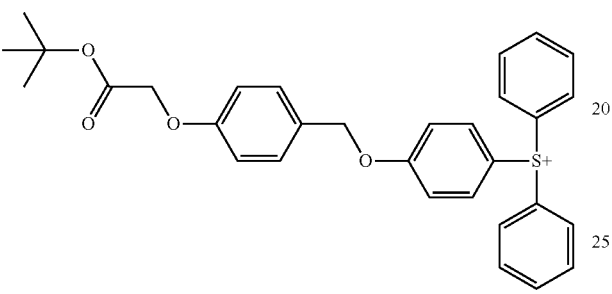
(I-c-19)
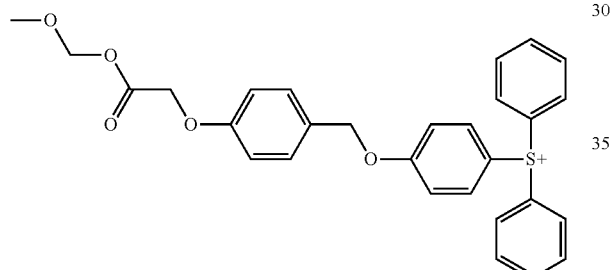
(I-c-20)
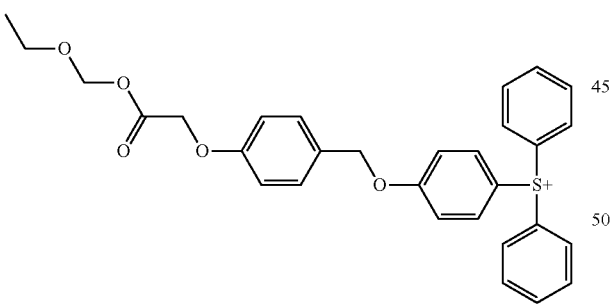
(I-c-21)
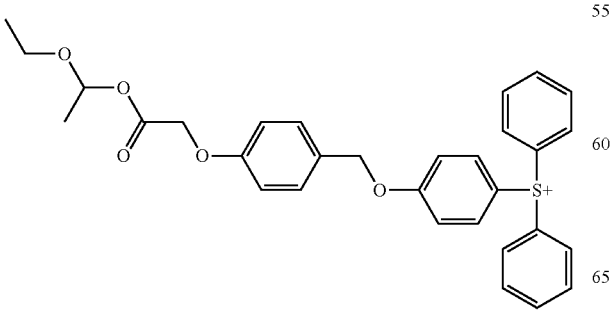
-continued
(I-c-22)
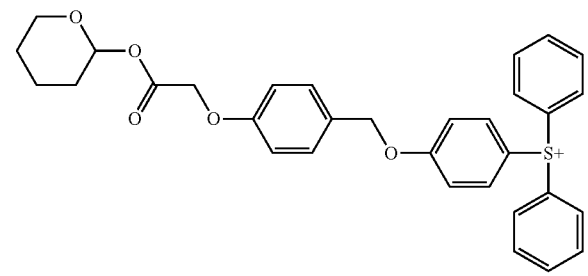
(I-c-23)
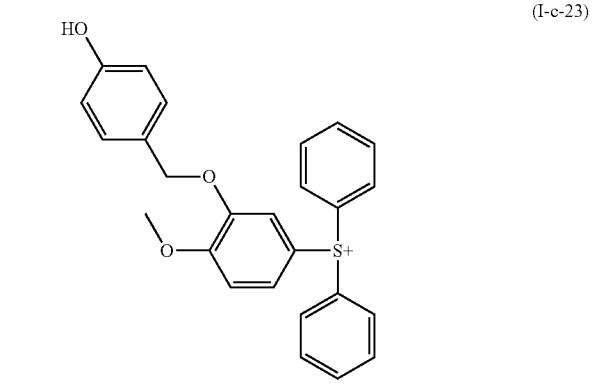
(I-c-24)
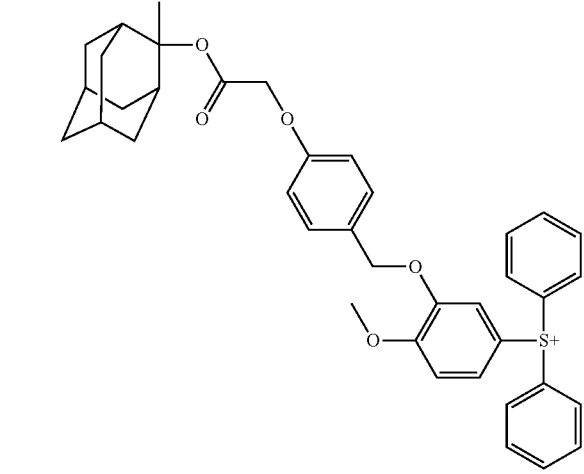
(I-c-25)
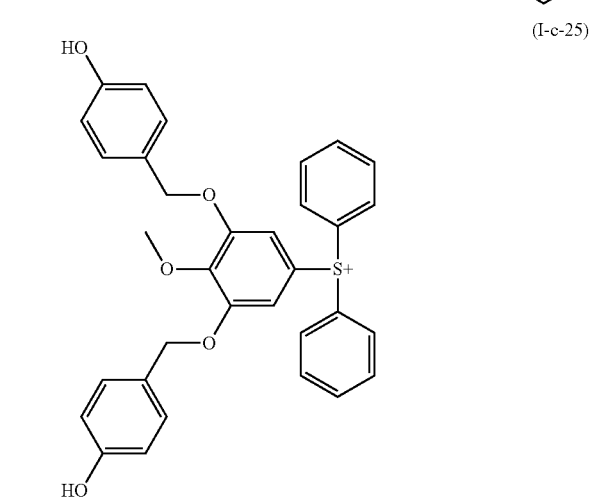

(I-c-26)
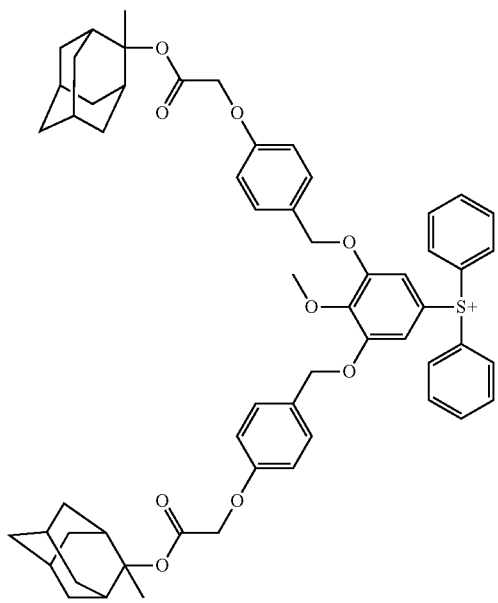
(I-c-28)
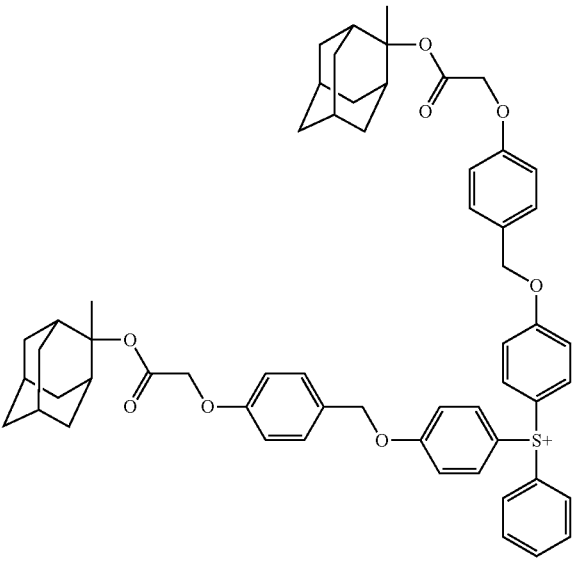
(I-c-27)
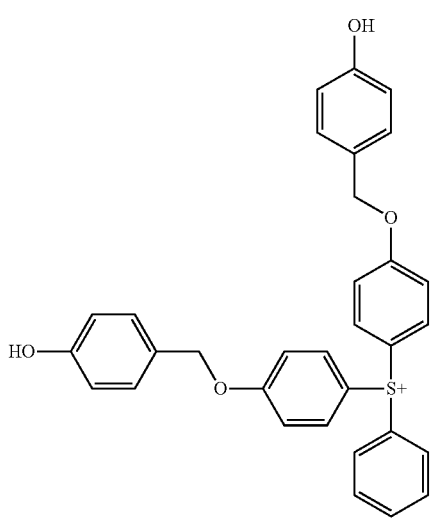
(I-c-29)

(I-c-30)
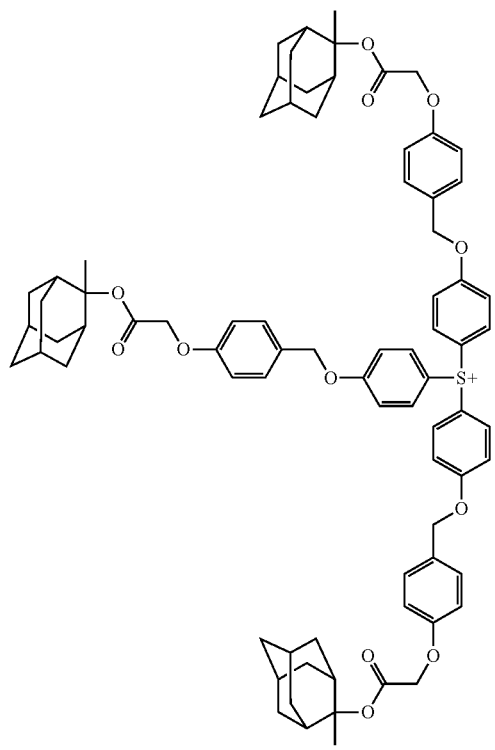
(I-c-31)
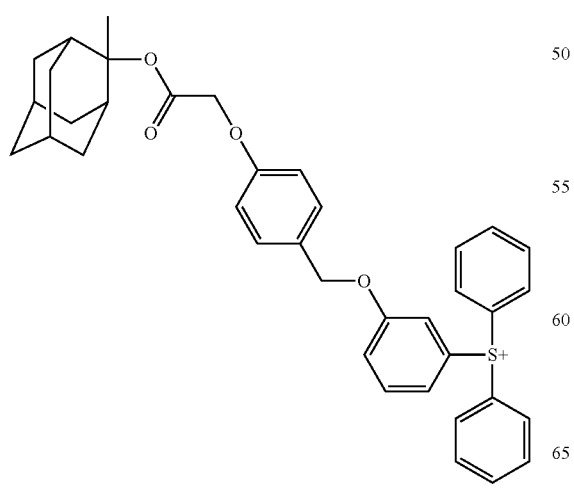
(I-c-32)
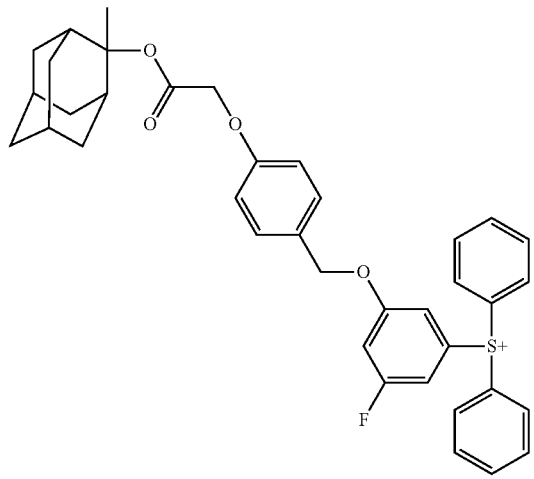
(I-c-33)
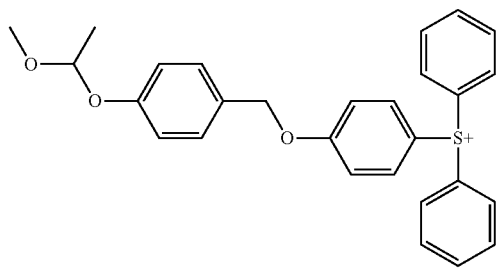
(I-c-34)
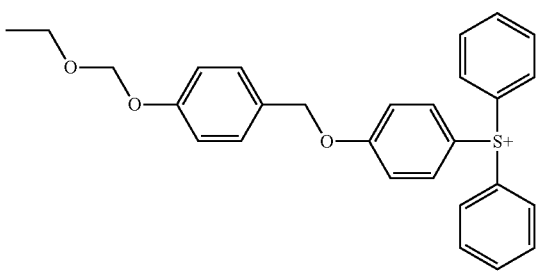
(I-c-35)

(I-c-36)
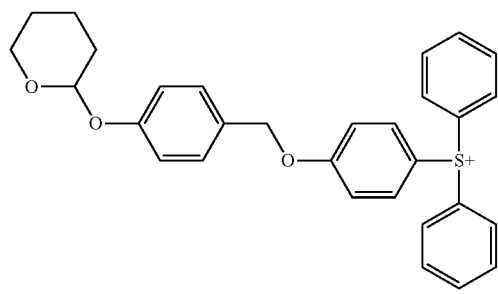
(I-c-37)
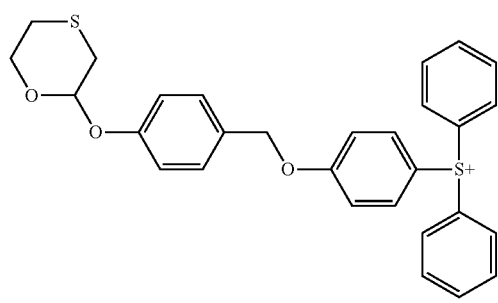
(I-c-38)
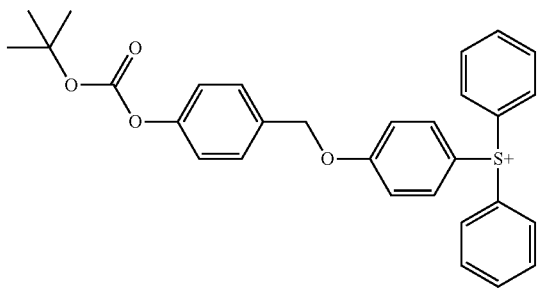
(I-c-39)
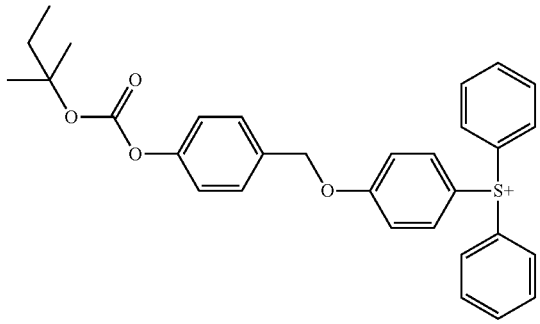
(I-c-40)
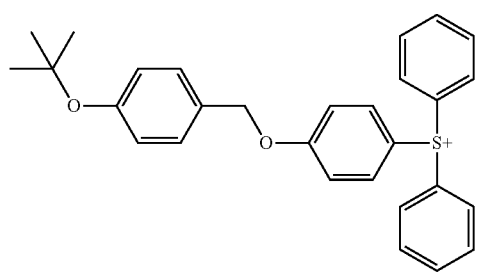
(I-c-41)
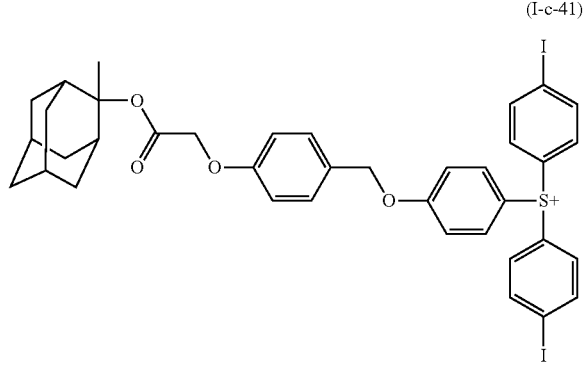
(I-c-42)
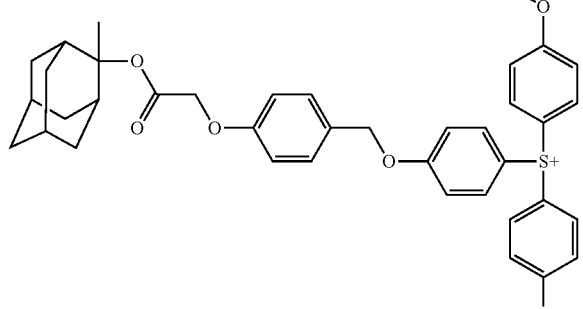
(I-c-43)
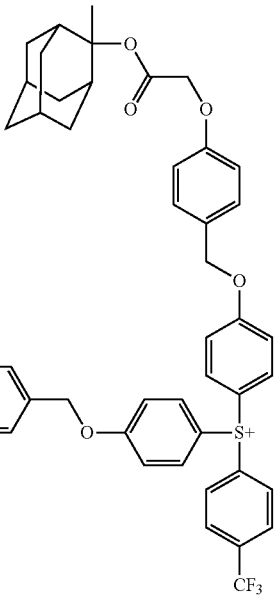

(I-c-44)
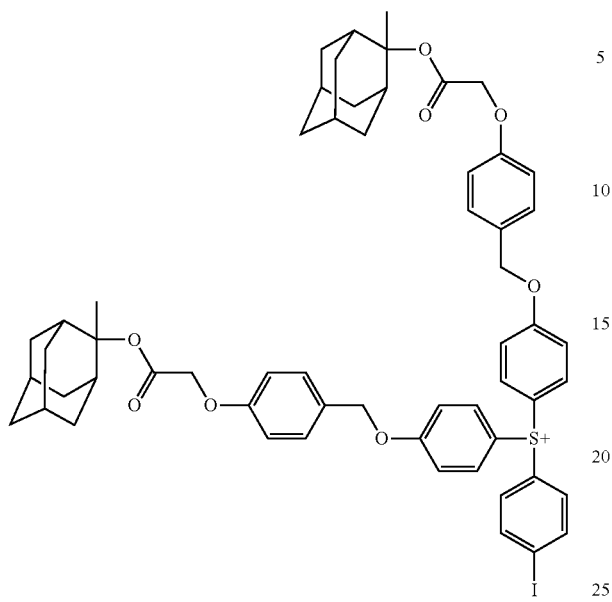
(I-c-47)
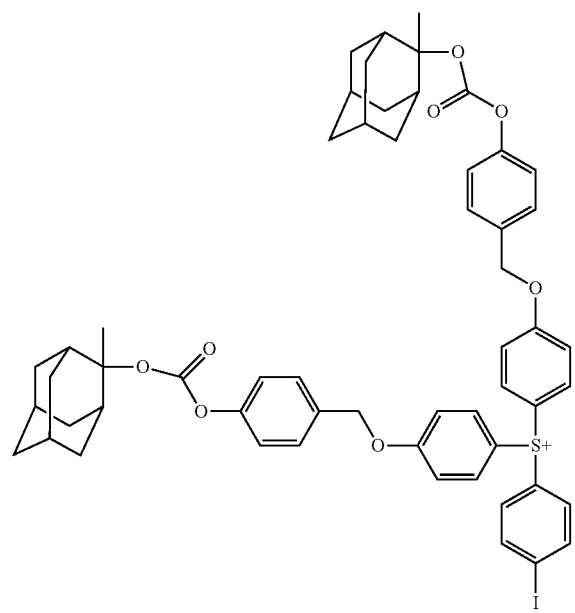
(I-c-45)
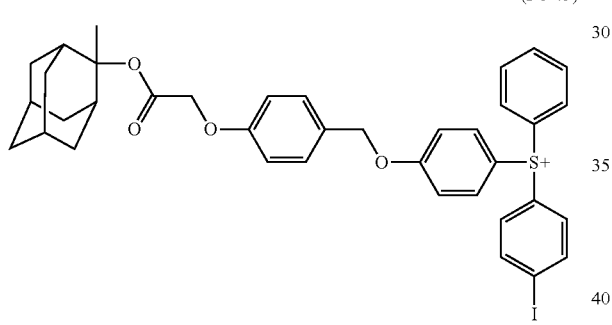
(I-c-48)
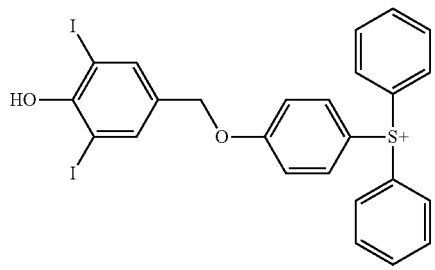
(I-c-46)
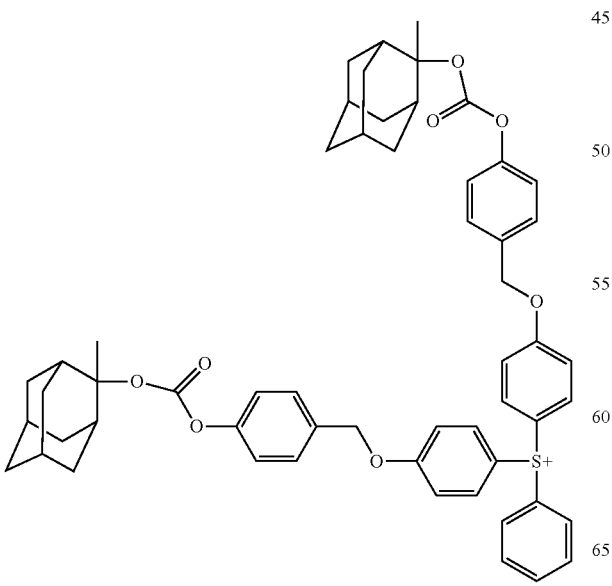
(I-c-49)
(I-c-50)
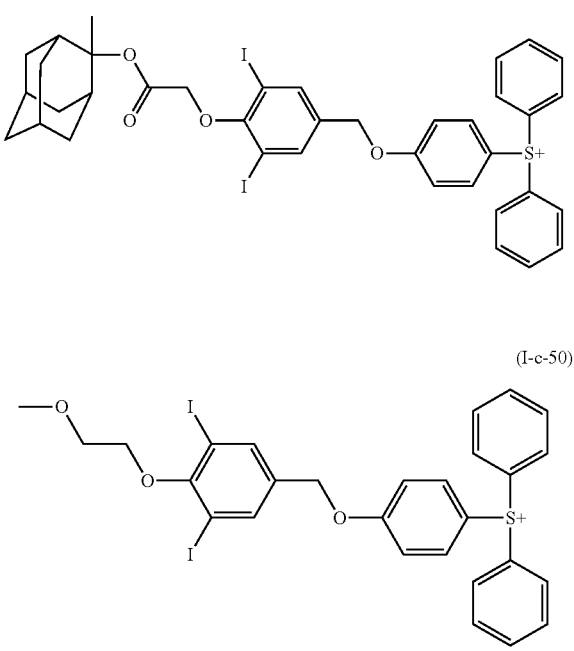

(I-c-51)
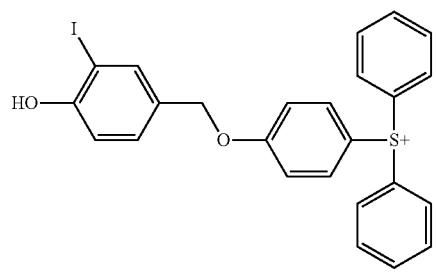
(I-c-56)
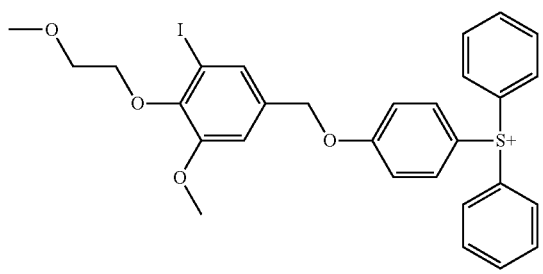
(I-c-52)
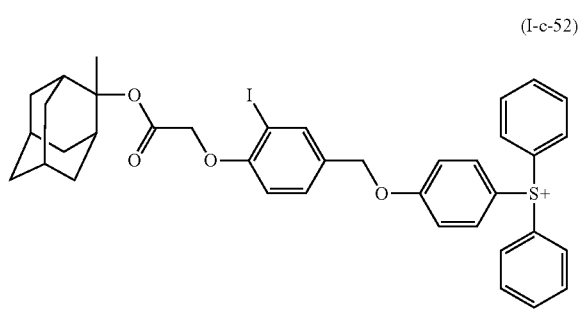
(I-c-57)
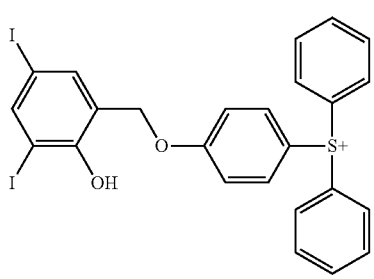
(I-c-53)
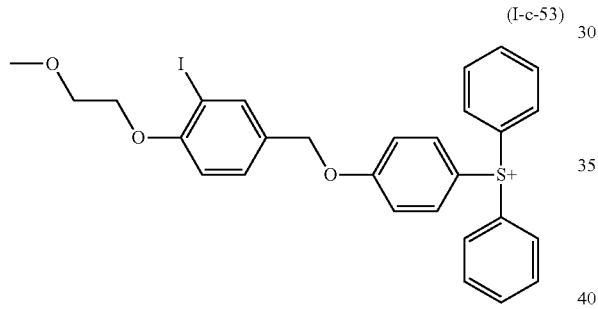
(I-c-58)
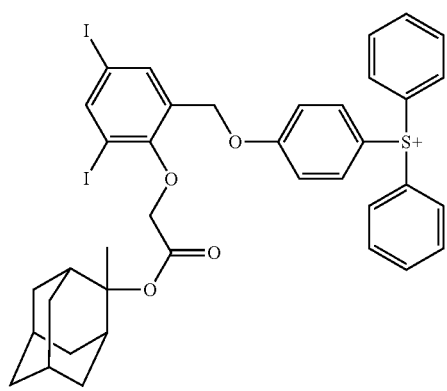
(I-c-54)
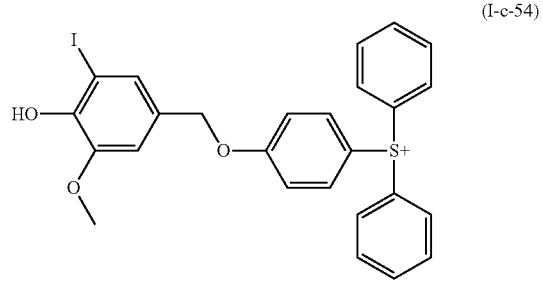
(I-c-59)
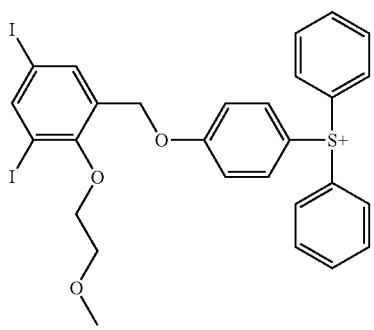
(I-c-55)
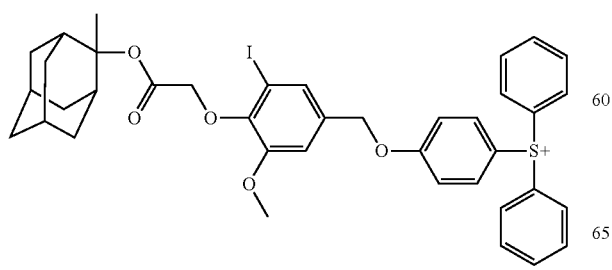
(I-c-60)
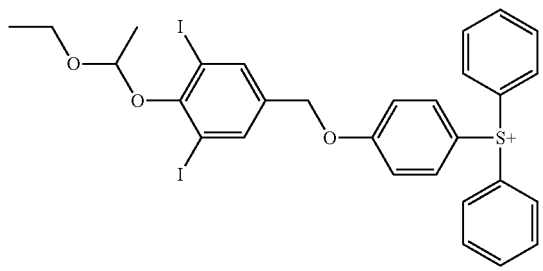

(I-c-61)
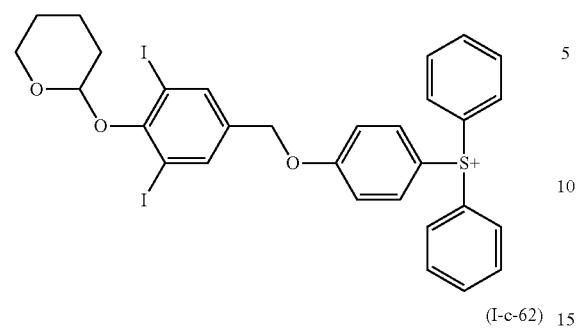
(I-c-62)
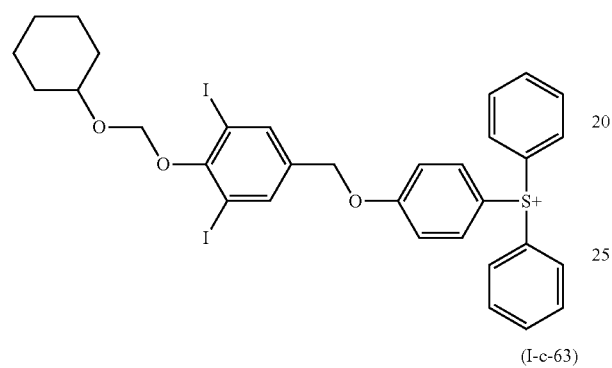
(I-c-63)
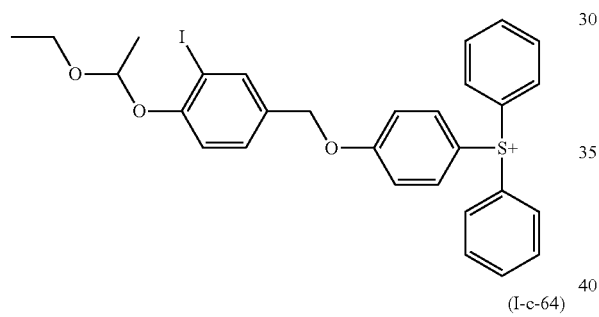
(I-c-64)
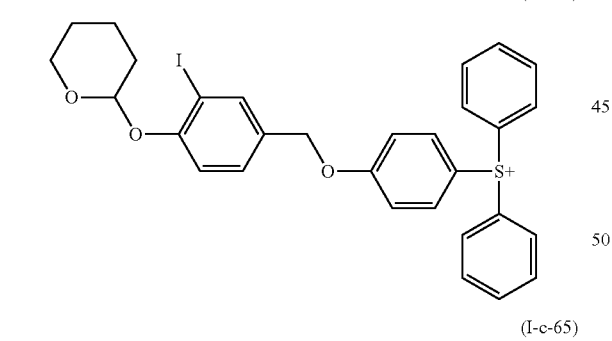
(I-c-65)
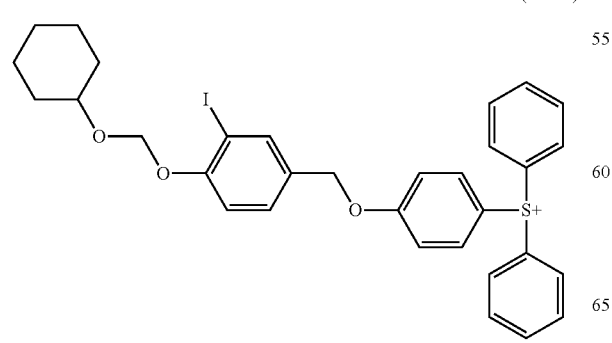
(I-c-66)
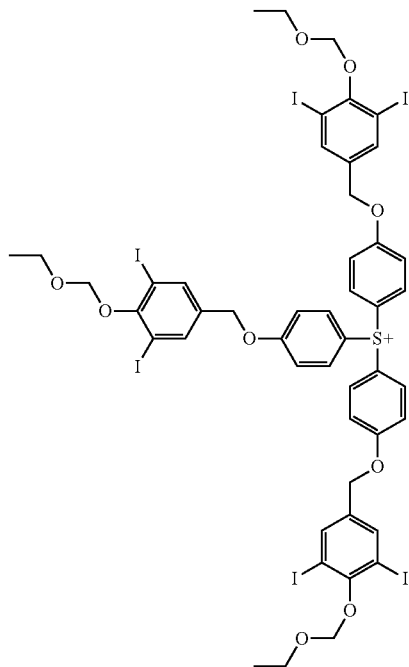
(I-c-67)
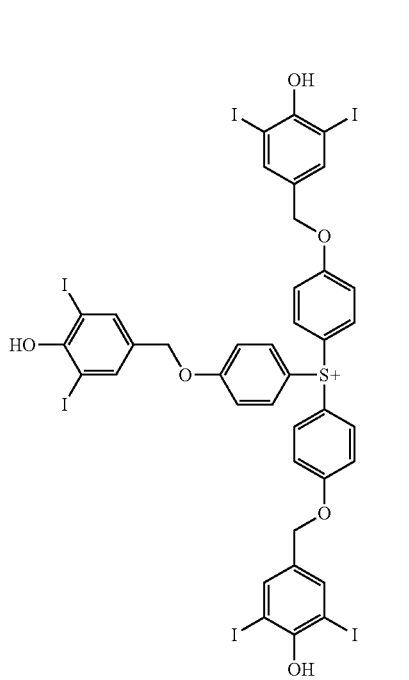

(I-c-68)
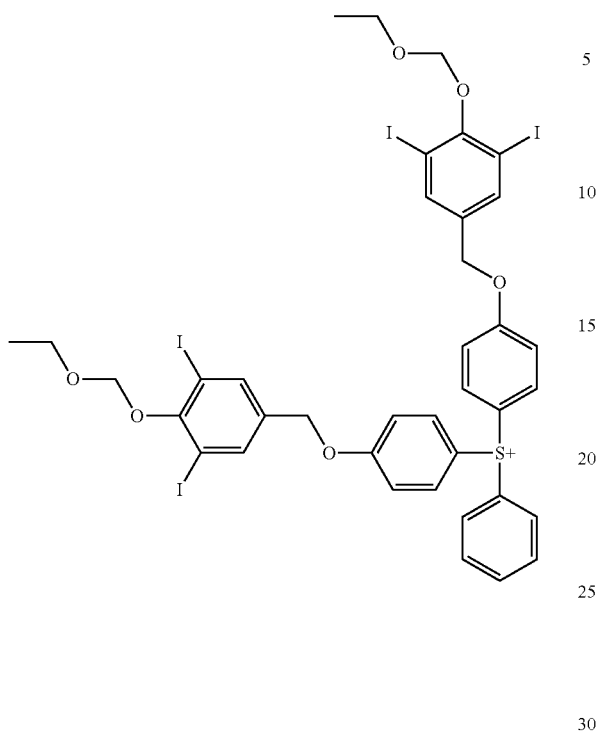
(I-c-69)
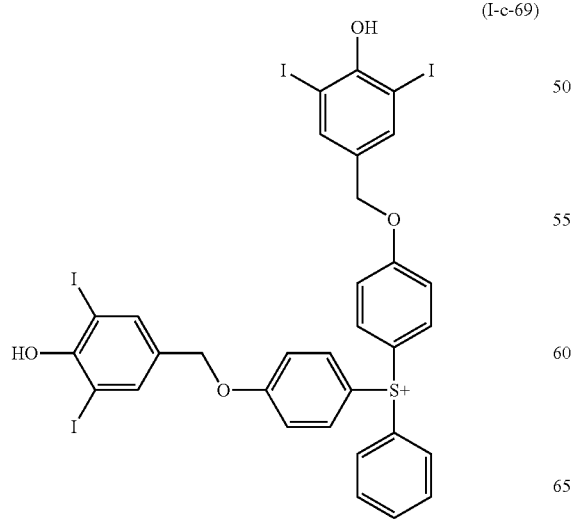
(I-c-70)
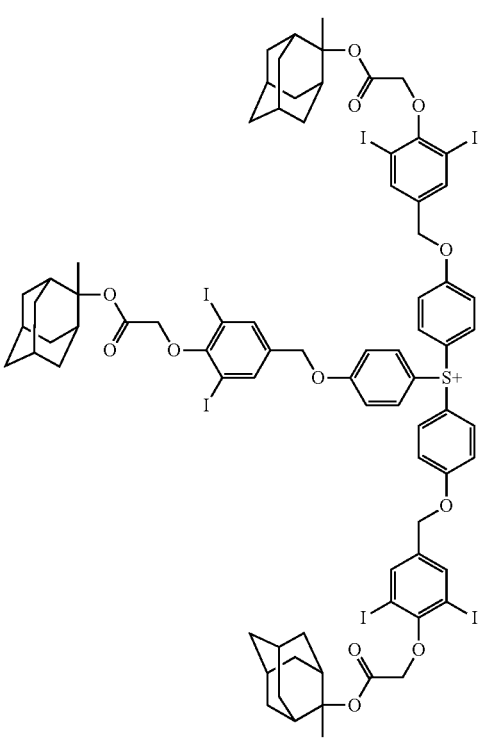
(I-c-71)
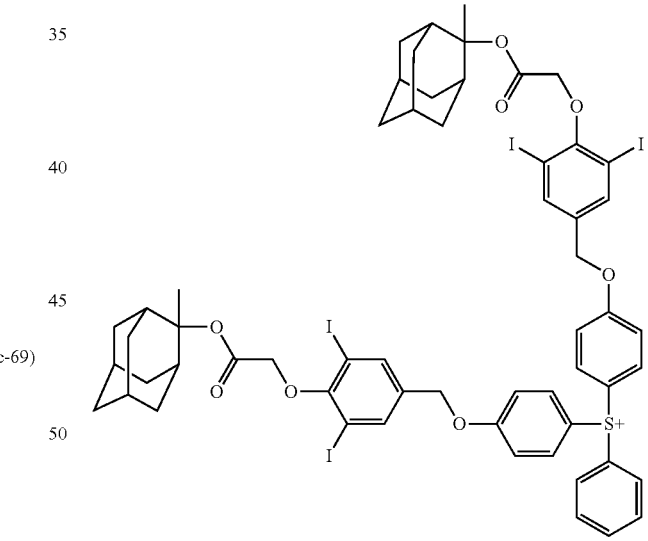
(I-c-72)
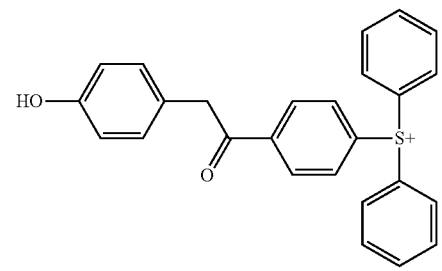

-continued (I-c-73)
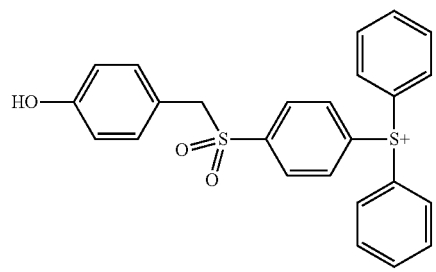

(I-c-74)
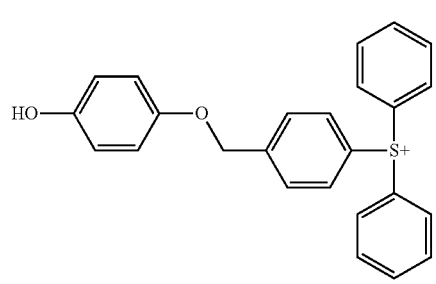

(I-c-75)
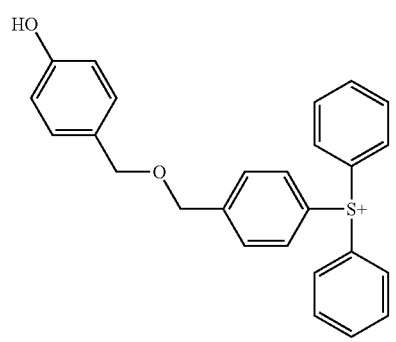

(I-c-76)
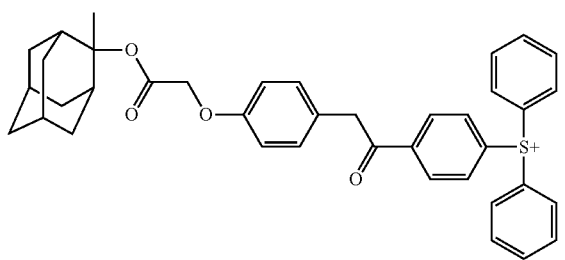

(I-c-77)
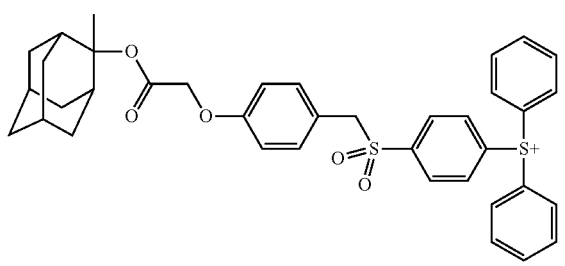

-continued (I-c-78)
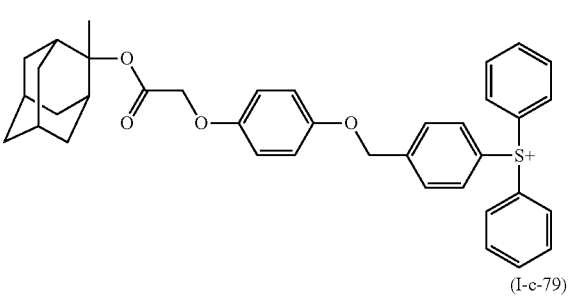

(I-c-79)
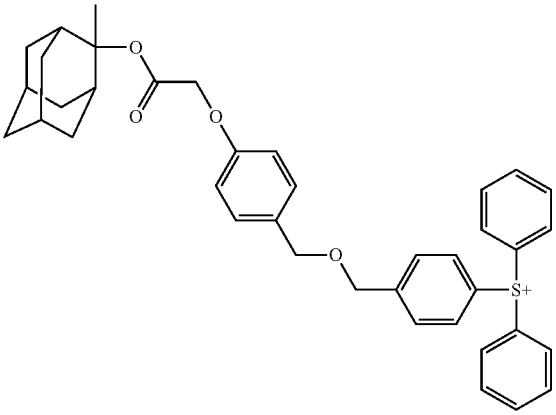

[Anion (I)]

The anion (I) of a salt represented by formula (I) is an organic anion represented by $Al^-$.

Examples of the organic anion represented by $Al^-$ include a sulfonic acid anion, a sulfonylimide anion, a sulfonylmethide anion and a carboxylic acid anion. The organic anion represented by $Al^-$ is preferably a sulfonic acid anion, and more preferably an anion represented by formula (I-A):

(I-A)
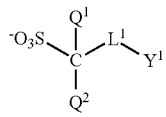

wherein, in formula (I-A), $Q^1$ and $Q^2$ each independently represent a hydrogen atom, a fluorine atom, an alkyl group having 1 to 6 carbon atoms or a perfluoroalkyl group having 1 to 6 carbon atoms, $L^1$ represents a saturated hydrocarbon group having 1 to 24 carbon atoms, —$CH_2$— included in the saturated hydrocarbon group may be replaced by —O— or —CO—, and a hydrogen atom included in the saturated hydrocarbon group may be substituted with a fluorine atom or a hydroxy group, and $Y^1$ represents a methyl group which may have a substituent, or an alicyclic hydrocarbon group having 3 to 24 carbon atoms which may have a substituent, and —$CH_2$— included in the alicyclic hydrocarbon group may be replaced by —O—, —S—, —$SO_2$— or —CO—.

In formula (I-A), when —$CH_2$— included in the saturated hydrocarbon group is replaced by —O— or —CO—, the number of carbon atoms before replacement is taken as the number of carbon atoms of the saturated hydrocarbon group. When —CH$_2$-included in the alicyclic hydrocarbon group is replaced by —O—, —S—, —SO$_2$— or —CO—, the number of carbon atoms before replacement is taken as the number of carbon atoms of the alicyclic hydrocarbon group.

Examples of the perfluoroalkyl group having 1 to 6 carbon atoms as for $Q^1$ and $Q^2$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group and a perfluorohexyl group.

Examples of the alkyl group as for $Q^1$ and $Q^2$ include a methyl group, an ethyl group, a propyl group, an isopropyl group, a butyl group, a sec-butyl group, a tert-butyl group, a pentyl group, a hexyl group and the like.

Preferably, at least one of $Q^1$ and $Q^2$ comprises a fluorine atom or a perfluoroalkyl group, more preferably at least one of $Q^1$ or $Q^2$ is a fluorine atom or a perfluoroalkyl group, still more preferably, $Q^1$ or $Q^2$ are each independently a fluorine atom or a trifluoromethyl group, and yet more preferably, both are fluorine atoms.

Examples of the divalent saturated hydrocarbon group in $L^1$ include a linear alkanediyl group, a branched alkanediyl group, a monocyclic or polycyclic divalent alicyclic saturated hydrocarbon group, or the divalent saturated hydrocarbon group may be a group formed by combining two or more of these groups.

Specific examples thereof include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group;
- branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group;
- monocyclic divalent alicyclic saturated hydrocarbon groups such as a cyclobutane-1,3-diyl group, a cyclopentane-1,3-diyl group, a cyclohexane-1,4-diyl group and a cyclooctane-1,5-diyl group; and
- polycyclic divalent alicyclic saturated hydrocarbon groups such as a norbornane-1,4-diyl group, a norbornane-2,5-diyl group, an adamantane-1,5-diyl group and an adamantane-2,6-diyl group.

The group in which —CH$_2$— included in the divalent saturated hydrocarbon group represented by $L^1$ is replaced by —O— or —CO— includes, for example, a group represented by any one of formula (b1-1) to formula (b1-3). In groups represented by formula (b1-1) to formula (b1-3) and groups represented by formula (b1-4) to formula (b1-11) which are specific examples thereof, * and ** represent a bonding site, and * represents a bonding site to —$Y^1$.

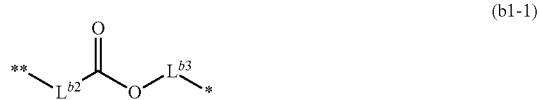
(b1-1)

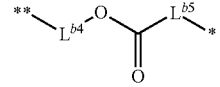
(b1-2)

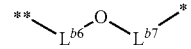
(b1-3)

In formula (b1-1),
$L^{b2}$ represents a single bond or a divalent saturated hydrocarbon group having 1 to 22 carbon atoms, and a hydrogen atom included in the saturated hydrocarbon group may be substituted with a fluorine atom,
$L^{b3}$ represents a single bond or a divalent saturated hydrocarbon group having 1 to 22 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and
the total number of carbon atoms of $L^{b2}$ and $L^{b3}$ is 22 or less.

In formula (b1-2),
$L^{b4}$ represents a single bond or a divalent saturated hydrocarbon group having 1 to 22 carbon atoms, and a hydrogen atom included in the saturated hydrocarbon group may be substituted with a fluorine atom,
$L^{b5}$ represents a single bond or a divalent saturated hydrocarbon group having 1 to 22 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and
the total number of carbon atoms of $L^{b4}$ and $L^{b5}$ is 22 or less.

In formula (b1-3),
$L^{b6}$ represents a single bond or a divalent saturated hydrocarbon group having 1 to 23 carbon atoms, a hydrogen atom included in the saturated hydrocarbon group may be substituted with a fluorine atom or a hydroxy group,
$L^{b7}$ represents a single bond or a divalent saturated hydrocarbon group having 1 to 23 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and
the total number of carbon atoms of $L^{b6}$ and $L^{b7}$ is 23 or less.

In groups represented by formula (b1-1) to formula (b1-3), when —CH$_2$— included in the saturated hydrocarbon group is replaced by —O— or —CO—, the number of carbon atoms before replacement is taken as the number of carbon atoms of the saturated hydrocarbon group.

Examples of the divalent saturated hydrocarbon group include those which are the same as the divalent saturated hydrocarbon group of $L^1$.

$L^{b2}$ is preferably a single bond, a methylene group, —CH(CF$_3$)— or —C(CF$_3$)$_2$—.
$L^{b3}$ is preferably a divalent saturated hydrocarbon group having 1 to 4 carbon atoms.
$L^{b4}$ is preferably a divalent saturated hydrocarbon group having 1 to 8 carbon atoms, and a hydrogen atom included in the divalent saturated hydrocarbon group may be substituted with a fluorine atom, and more preferably a methylene group, —CH(CF$_3$)— or —C(CF$_3$)$_2$—.

$L^{b5}$ is preferably a single bond or a divalent saturated hydrocarbon group having 1 to 8 carbon atoms.

$L^{b6}$ is preferably a single bond or a divalent saturated hydrocarbon group having 1 to 4 carbon atoms, and a hydrogen atom included in the saturated hydrocarbon group may be substituted with a fluorine atom.

$L^{b7}$ is preferably a single bond or a divalent saturated hydrocarbon group having 1 to 18 carbon atoms, a hydrogen atom included in the saturated hydrocarbon group may be substituted with a fluorine atom or a hydroxy group, and —CH$_2$— included in the divalent saturated hydrocarbon group may be replaced by —O— or —CO—.

The group in which —CH$_2$— included in the divalent saturated hydrocarbon group represented by $L^1$ is replaced by —O— or —CO— is preferably a group represented by formula (b1-1) or formula (b1-3).

Examples of the group represented by formula (b1-1) include groups represented by formula (b1-4) to formula (b1-8).

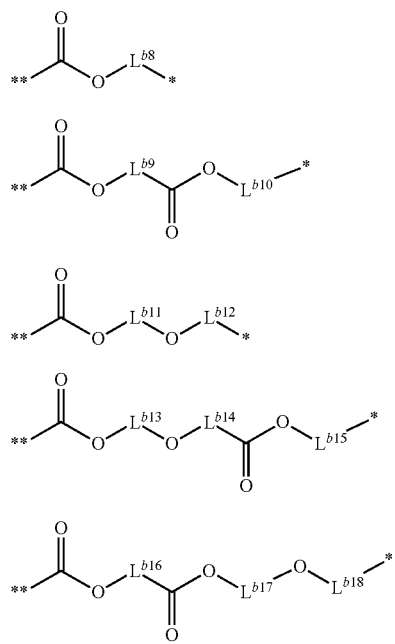

In formula (b1-4),
$L^{b8}$ represents a single bond or a divalent saturated hydrocarbon group having 1 to 22 carbon atoms, and a hydrogen atom included in the saturated hydrocarbon group may be substituted with a fluorine atom or a hydroxy group.

In formula (b1-5),
$L^{b9}$ represents a divalent saturated hydrocarbon group having 1 to 20 carbon atoms, and —CH$_2$— included in the divalent saturated hydrocarbon group may be replaced by —O— or —CO—.

$L^{b10}$ represents a single bond or a divalent saturated hydrocarbon group having 1 to 19 carbon atoms, and a hydrogen atom included in the divalent saturated hydrocarbon group may be substituted with a fluorine atom or a hydroxy group, and the total number of carbon atoms of $L^{b9}$ and $L^{b10}$ is 20 or less.

In formula (b1-6),
$L^{b11}$ represents a divalent saturated hydrocarbon group having 1 to 21 carbon atoms,
$L^{b12}$ represents a single bond or a divalent saturated hydrocarbon group having 1 to 20 carbon atoms, and a hydrogen atom included in the divalent saturated hydrocarbon group may be substituted with a fluorine atom or a hydroxy group, and the total number of carbon atoms of $L^{b11}$ and $L^{b12}$ is 21 or less.

In formula (b1-7),
$L^{b13}$ represents a divalent saturated hydrocarbon group having 1 to 19 carbon atoms,
$L^{b14}$ represents a single bond or a divalent saturated hydrocarbon group having 1 to 18 carbon atoms, and —CH$_2$— included in the divalent saturated hydrocarbon group may be replaced by —O— or —CO—,
$L^{b15}$ represents a single bond or a divalent saturated hydrocarbon group having 1 to 18 carbon atoms, and a hydrogen atom included in the divalent saturated hydrocarbon group may be substituted with a fluorine atom or a hydroxy group, and the total number of carbon atoms of $L^{b13}$ to $L^{b15}$ is 19 or less.

In formula (b1-8),
$L^{b16}$ represents a divalent saturated hydrocarbon group having 1 to 18 carbon atoms, and —CH$_2$— included in the divalent saturated hydrocarbon group may be replaced by —O— or —CO—,
$L^{b17}$ represents a divalent saturated hydrocarbon group having 1 to 18 carbon atoms,
$L^{b18}$ represents a single bond or a divalent saturated hydrocarbon group having 1 to 17 carbon atoms, and a hydrogen atom included in the divalent saturated hydrocarbon group may be substituted with a fluorine atom or a hydroxy group, and the total number of carbon atoms of $L^{b16}$ to $L^{b18}$ is 19 or less.

$L^{b8}$ is preferably a divalent saturated hydrocarbon group having 1 to 4 carbon atoms.

$L^{b9}$ is preferably a divalent saturated hydrocarbon group having 1 to 8 carbon atoms.

$L^{b10}$ is preferably a single bond or a divalent saturated hydrocarbon group having 1 to 19 carbon atoms, and more preferably a single bond or a divalent saturated hydrocarbon group having 1 to 8 carbon atoms.

$L^{b11}$ is preferably a divalent saturated hydrocarbon group having 1 to 8 carbon atoms.

$L^{b12}$ is preferably a single bond or a divalent saturated hydrocarbon group having 1 to 8 carbon atoms.

$L^{b13}$ is preferably a divalent saturated hydrocarbon group having 1 to 12 carbon atoms.

$L^{b14}$ is preferably a single bond or a divalent saturated hydrocarbon group having 1 to 6 carbon atoms.

$L^{b15}$ is preferably a single bond or a divalent saturated hydrocarbon group having 1 to 18 carbon atoms, and more preferably a single bond or a divalent saturated hydrocarbon group having 1 to 8 carbon atoms.

$L^{b16}$ is preferably a divalent saturated hydrocarbon group having 1 to 12 carbon atoms.

$L^{b17}$ is preferably a divalent saturated hydrocarbon group having 1 to 6 carbon atoms.

$L^{b18}$ is preferably a single bond or a divalent saturated hydrocarbon group having 1 to 17 carbon atoms, and more preferably a single bond or a divalent saturated hydrocarbon group having 1 to 4 carbon atoms.

Examples of the group represented by formula (b1-3) include groups represented by formula (b1-9) to formula (b1-11).

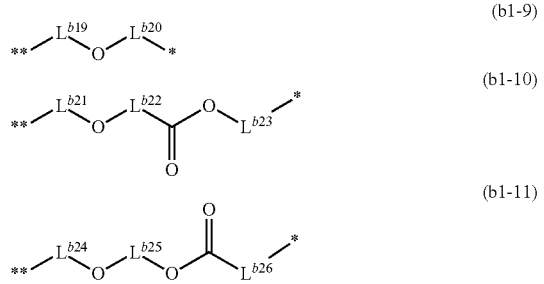

(b1-9)

(b1-10)

(b1-11)

In formula (b1-9),
$L^{b19}$ represents a single bond or a divalent saturated hydrocarbon group having 1 to 23 carbon atoms, and a hydrogen atom included in the saturated hydrocarbon group may be substituted with a fluorine atom,
$L^{b20}$ represents a single bond or a divalent saturated hydrocarbon group having 1 to 23 carbon atoms, and a hydrogen atom included in the saturated hydrocarbon group may be substituted with a fluorine atom, a hydroxy group or an alkylcarbonyloxy group, —$CH_2$— included in the alkylcarbonyloxy group may be replaced by —O— or —CO—, and a hydrogen atom included in the alkylcarbonyloxy group may be substituted with a hydroxy group, and the total number of carbon atoms of $L^{b19}$ and $L^{b20}$ is 23 or less.

In formula (b1-10),
$L^{b21}$ represents a single bond or a divalent saturated hydrocarbon group having 1 to 21 carbon atoms, and a hydrogen atom included in the saturated hydrocarbon group may be substituted with a fluorine atom,
$L^{b22}$ represents a single bond or a divalent saturated hydrocarbon group having 1 to 21 carbon atoms,
$L^{b23}$ represents a single bond or a divalent saturated hydrocarbon group having 1 to 21 carbon atoms, and a hydrogen atom included in the saturated hydrocarbon group may be substituted with a fluorine atom, a hydroxy group or an alkylcarbonyloxy group, —$CH_2$— included in the alkylcarbonyloxy group may be replaced by —O— or —CO—, and a hydrogen atom included in the alkylcarbonyloxy group may be substituted with a hydroxy group, and the total number of carbon atoms of $L^{b21}$, $L^{b22}$ and $L^{b23}$ is 21 or less.

In formula (b1-11),
$L^{b24}$ represents a single bond or a divalent saturated hydrocarbon group having 1 to 20 carbon atoms, and a hydrogen atom included in the saturated hydrocarbon group may be substituted with a fluorine atom,
$L^{b25}$ represents a divalent saturated hydrocarbon group having 1 to 21 carbon atoms,
$L^{b26}$ represents a single bond or a divalent saturated hydrocarbon group having 1 to 20 carbon atoms, a hydrogen atom included in the saturated hydrocarbon group may be substituted with a fluorine atom, a hydroxy group or an alkylcarbonyloxy group, —$CH_2$— included in the alkylcarbonyloxy group may be replaced by —O— or —CO—, and a hydrogen atom included in the alkylcarbonyloxy group may be substituted with a hydroxy group, and in which, the total number of carbon atoms of $L^{b24}$, $L^{b25}$ and $L^{b26}$ is 21 or less.

In the group represented by formula (b1-9) to the group represented by formula (b1-11), when a hydrogen atom included in the saturated hydrocarbon group is substituted with an alkylcarbonyloxy group, the number of carbon atoms before replacement is taken as the number of carbon atoms of the saturated hydrocarbon group.

Examples of the alkylcarbonyloxy group include an acetyloxy group, a propionyloxy group, a butyryloxy group, a cyclohexylcarbonyloxy group, an adamantylcarbonyloxy group and the like.

Examples of the group represented by formula (b1-4) include the followings.

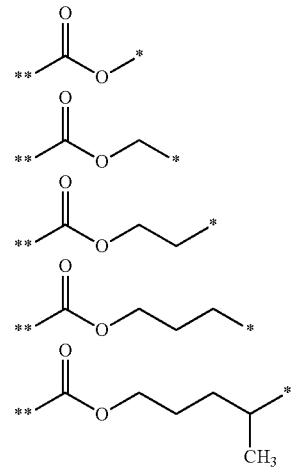

Examples of the group represented by formula (b1-5) include the followings.

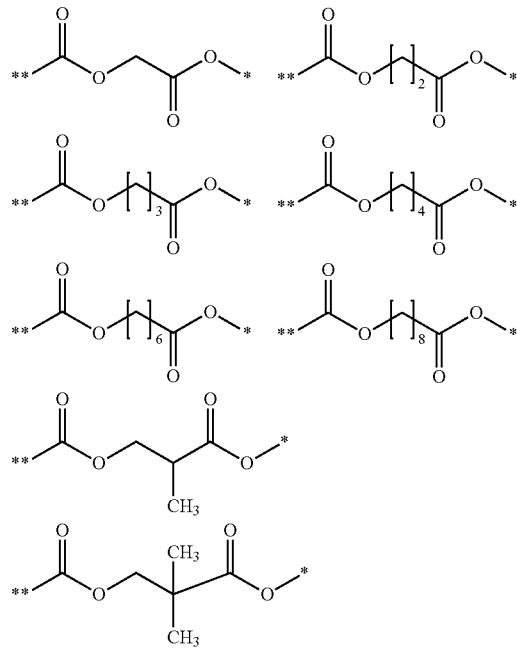

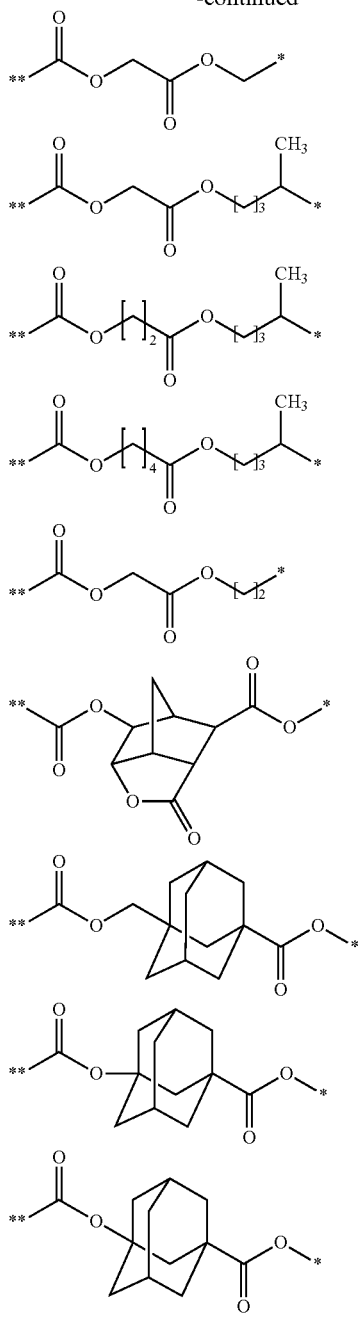
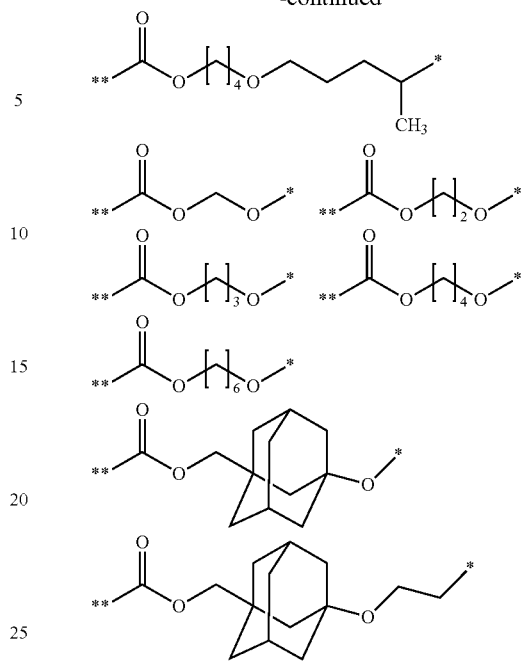
Examples of the group represented by formula (b1-6) include the followings.
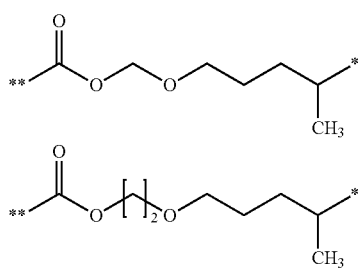
Examples of the group represented by formula (b1-7) include the followings.
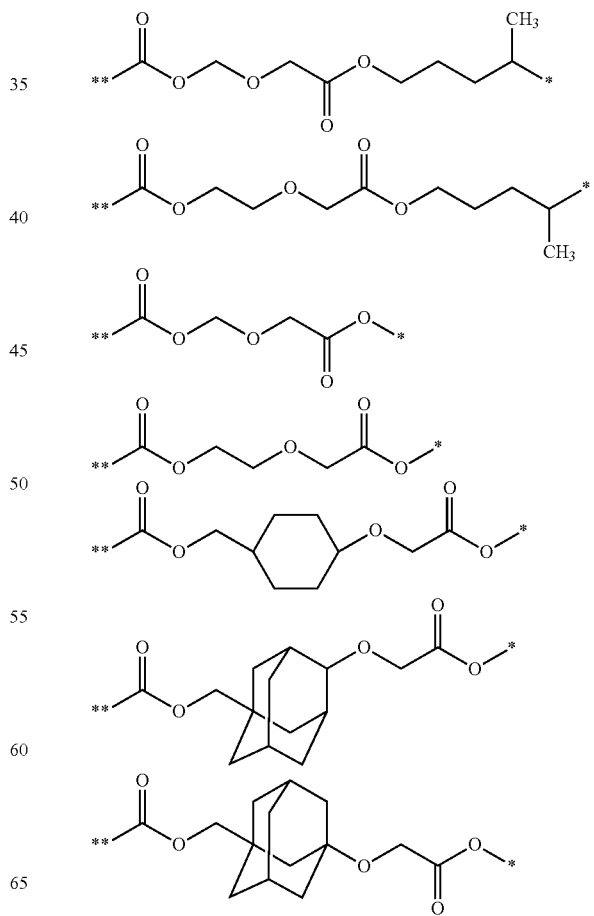

-continued
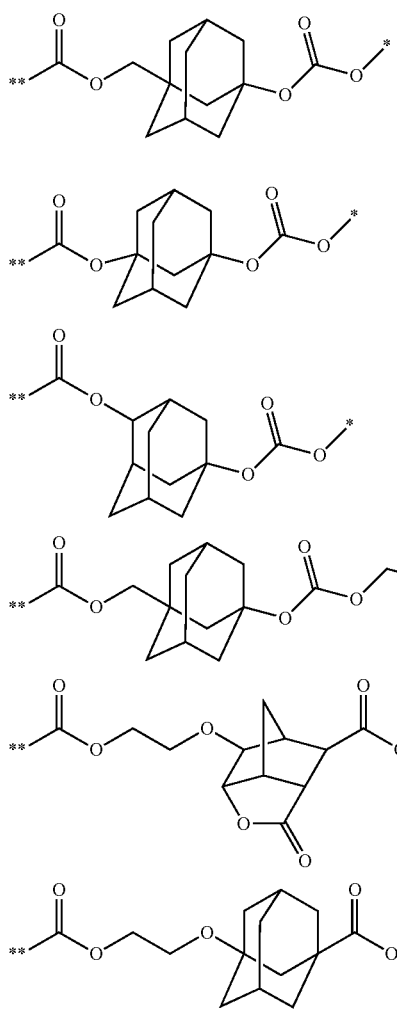
Examples of the group represented by formula (b1-8) include the followings.
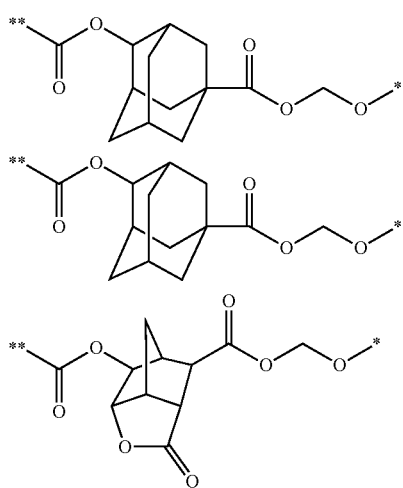
Examples of the group represented by formula (b1-2) include the followings.
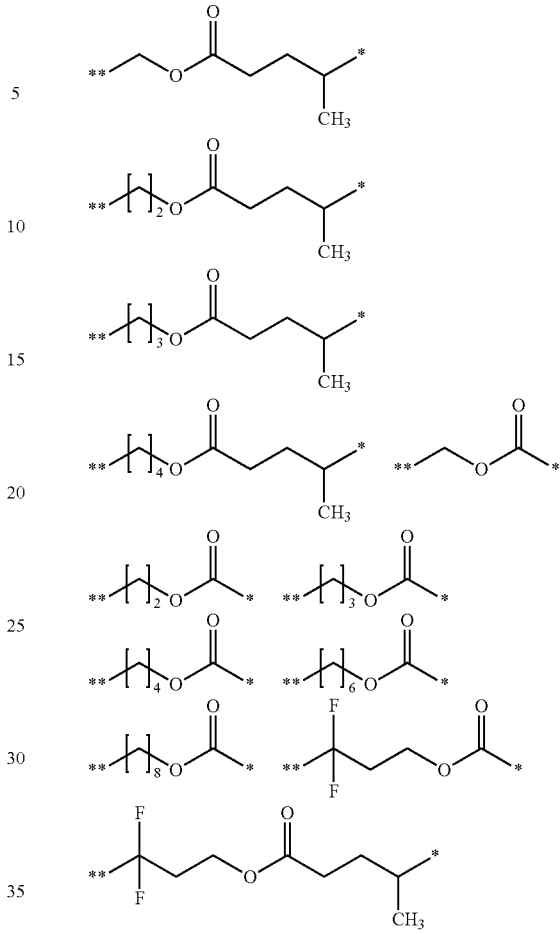
Examples of the group represented by formula (b1-9) include the followings.
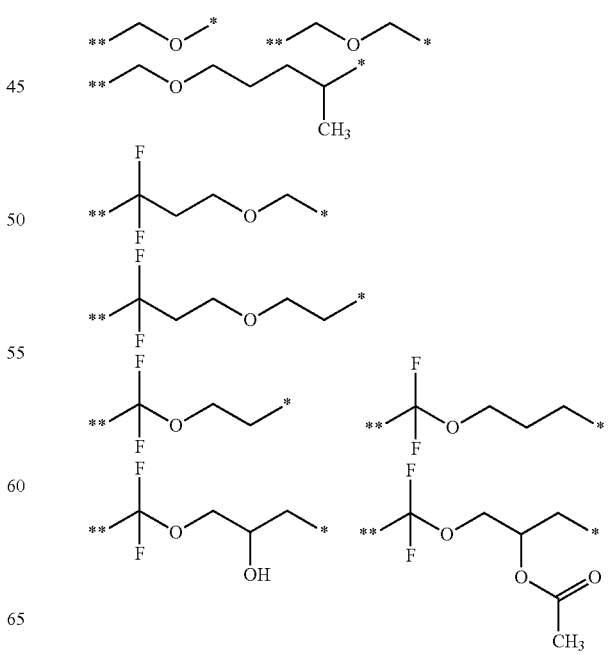

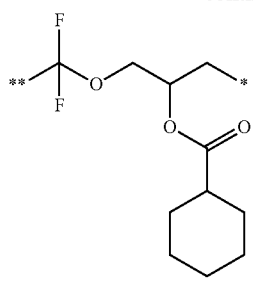
Examples of the group represented by formula (b1-10) include the followings.
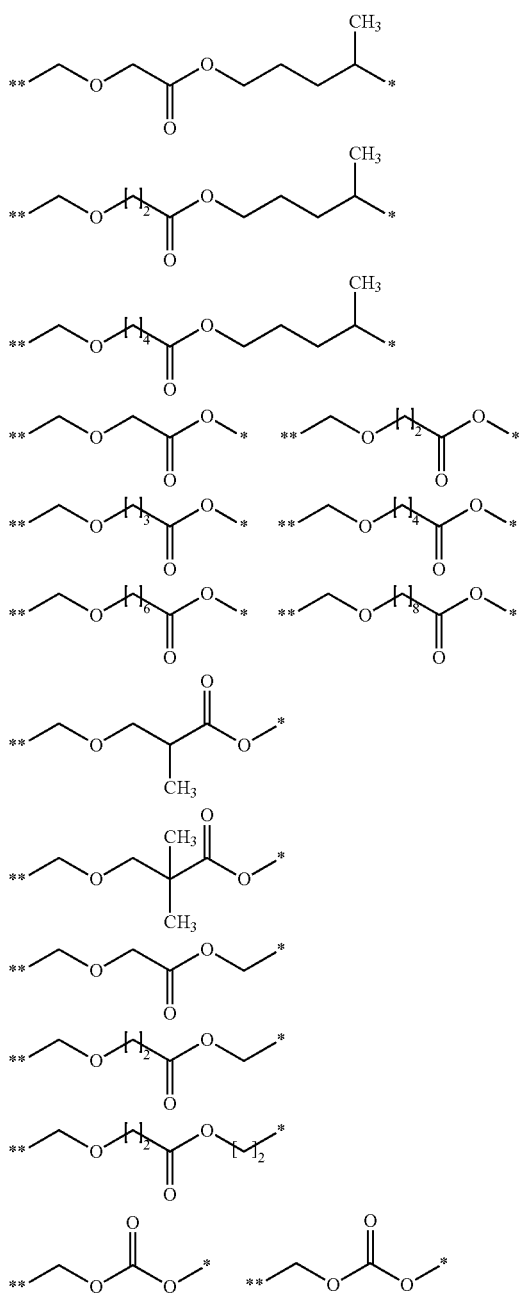
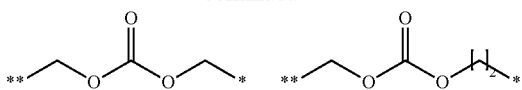
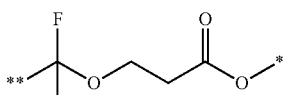
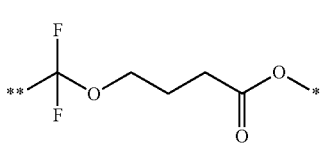
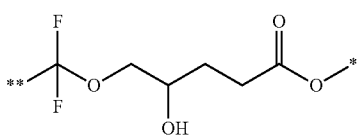
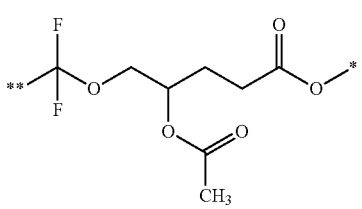
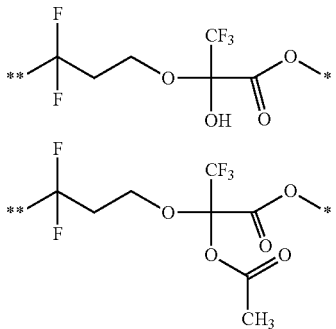
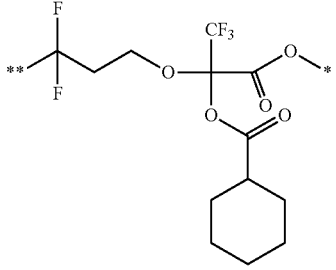
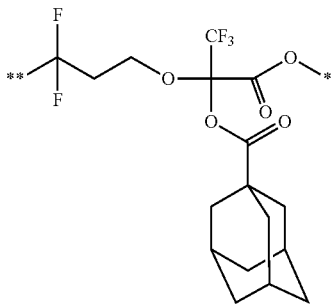

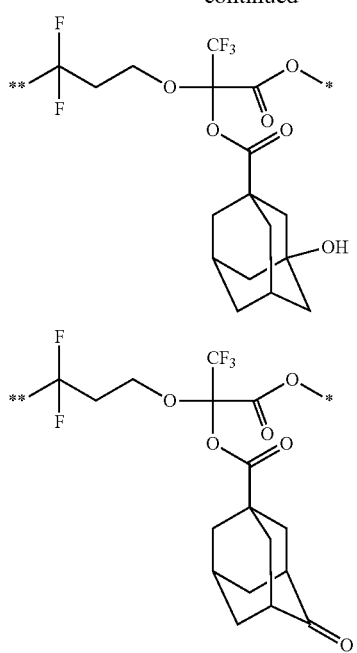
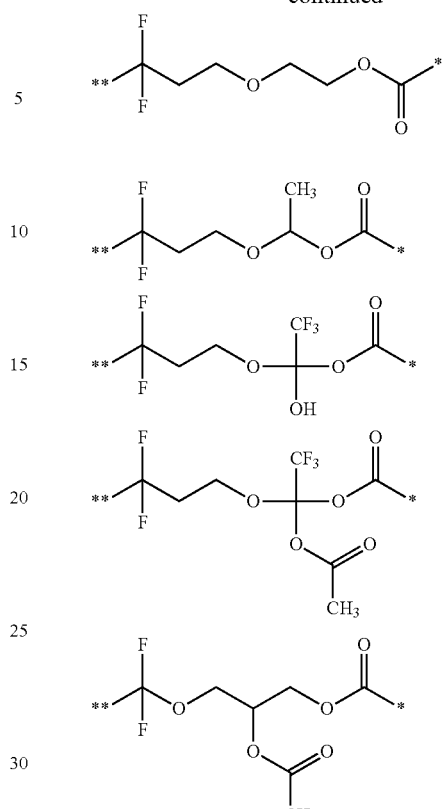
Examples of the group represented by formula (b1-1) include the followings.
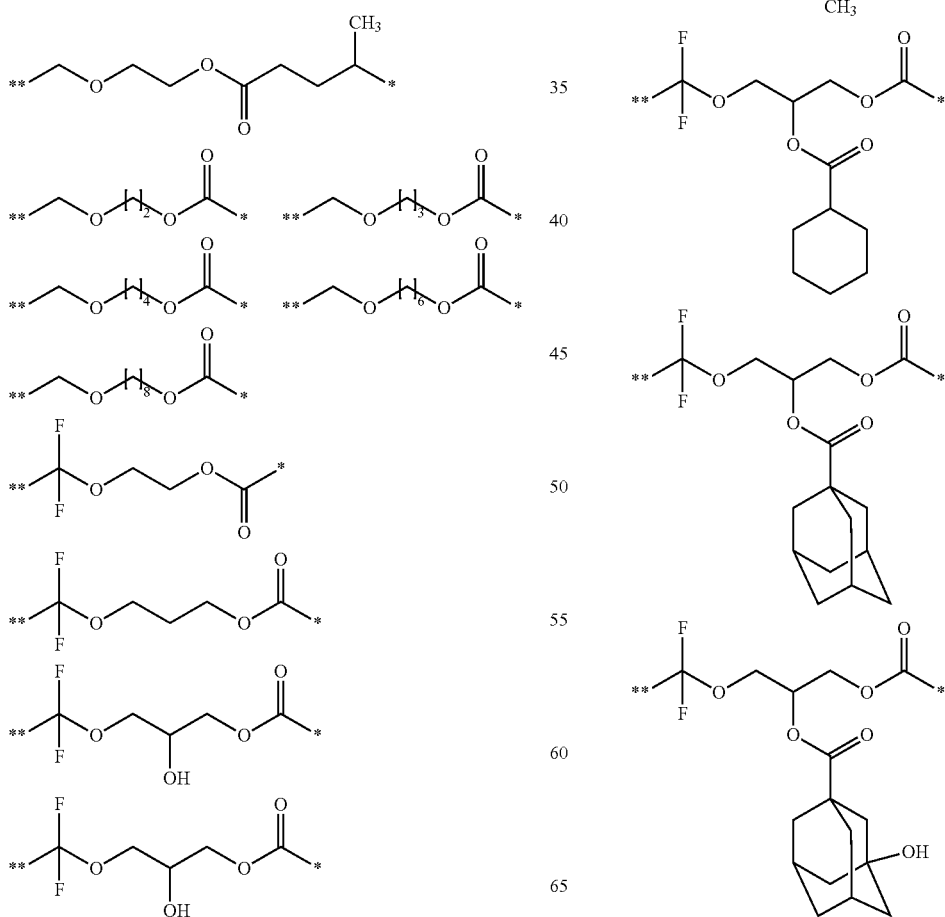

-continued

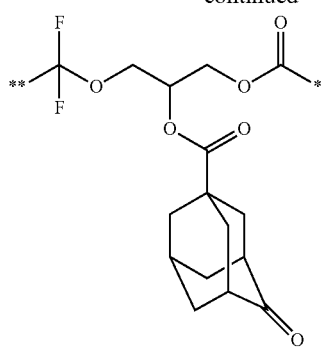

Examples of the alicyclic hydrocarbon group in which —CH$_2$— included in the alicyclic hydrocarbon group represented by Y$^1$ is not replaced by —O—, —S—, —SO$_2$— or —CO— include groups represented by formula (Y1) to formula (Y11) and formula (Y36) to formula (Y38).

When —CH$_2$— included in the alicyclic hydrocarbon group represented by Y1 is replaced by —O—, —S—, —SO$_2$— or —CO—, the number may be 1, or 2 or more. Examples of such group include groups represented by formula (Y12) to formula (Y35) and formula (Y39) to formula (Y43). —O— or —CO— of the groups represented by formula (Y12) to formula (Y35) and formula (Y39) to formula (Y43) may be replaced by —S— or —SO$_2$—. * represents a bonding site to L$^1$.

(Y1)

(Y2)

(Y3)

(Y4)

(Y5)

(Y6)

(Y7)

-continued (Y8)
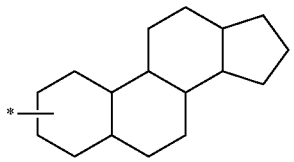

(Y9)

(Y10)

(Y11)
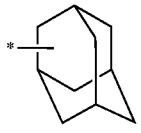

(Y12)
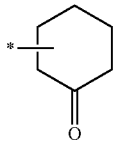

(Y13)
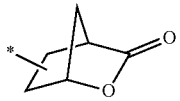

(Y14)
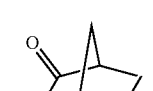

(Y15)
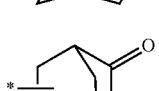

(Y16)
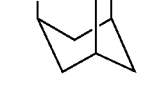

(Y17)
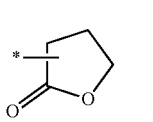

(Y18)
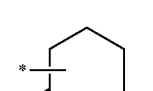

(Y19)
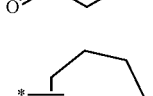

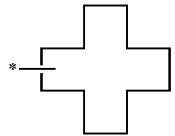
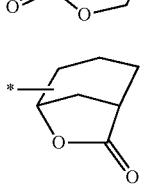

-continued
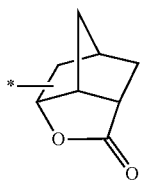 (Y20)
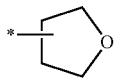 (Y21)
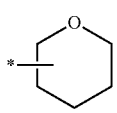 (Y22)
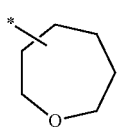 (Y23)
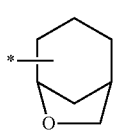 (Y24)
 (Y25)
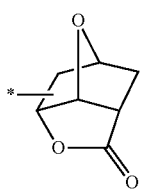 (Y26)
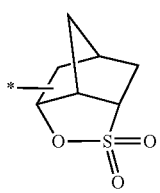 (Y27)
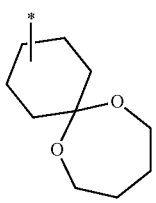 (Y28)
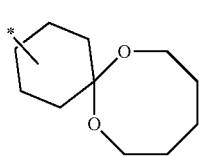 (Y29)
-continued
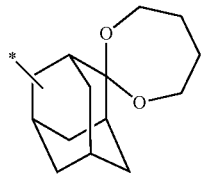 (Y30)
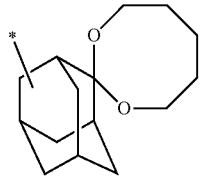 (Y31)
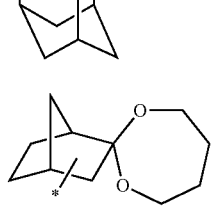 (Y32)
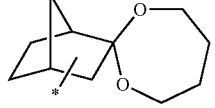 (Y33)
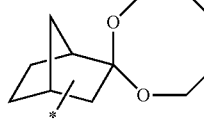 (Y34)
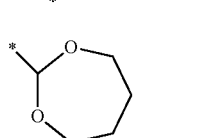 (Y35)
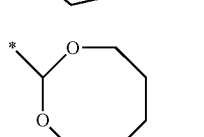 (Y36)
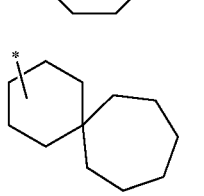 (Y37)
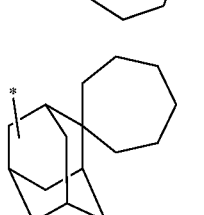 (Y38)
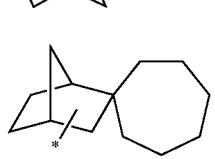 (Y39)

(Y40)
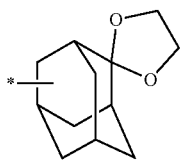

(Y41)
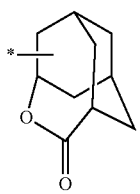

(Y42)
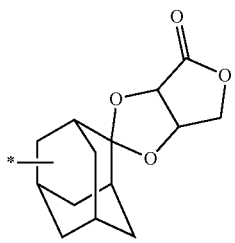

(Y43)
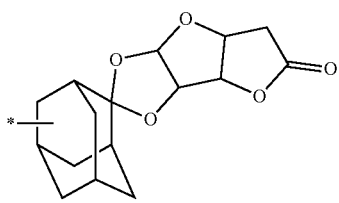

The alicyclic hydrocarbon group represented by $Y^1$ is preferably a group represented by any one of formula (Y1) to formula (Y20), formula (Y26), formula (Y27), formula (Y30), formula (Y31) and formula (Y39) to formula (Y43), more preferably a group represented by formula (Y11), formula (Y15), formula (Y16), formula (Y20), formula (Y26), formula (Y27), formula (Y30), formula (Y31), formula (Y39), formula (Y40), formula (Y42) or formula (Y43), and still more preferably a group represented by formula (Y11), formula (Y15), formula (Y20), formula (Y26), formula (Y27), formula (Y30), formula (Y31), formula (Y39), formula (Y40), formula (Y42) or formula (Y43).

When the alicyclic hydrocarbon group represented by Y1 is a spiro ring having an oxygen atom, such as formula (Y28) to formula (Y35), formula (Y39), formula (Y40), formula (Y42) or formula (Y43), the alkanediyl group between two oxygen atoms preferably has one or more fluorine atoms. Of alkanediyl groups included in a ketal structure, it is preferable that a methylene group adjacent to the oxygen atom is not substituted with a fluorine atom.

Examples of the substituent of the methyl group represented by $Y^1$ include a halogen atom, a hydroxy group, an alicyclic hydrocarbon group having 3 to 16 carbon atoms, an aromatic hydrocarbon group having 6 to 18 carbon atoms, a glycidyloxy group, a —$(CH_2)_{ja}$—CO—O—$R^{b1}$ group or a —$(CH_2)_{ja}$—O—CO—$R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms, or a group obtained by combining these groups. ja represents an integer of 0 to 4. —$CH_2$— included in the alkyl group and the alicyclic hydrocarbon group may be replaced by —O—, —$SO_2$— or —CO—, and a hydrogen atom included in the alkyl group, the alicyclic hydrocarbon group and the aromatic hydrocarbon group may be substituted with a hydroxy group or a fluorine atom).

Examples of the substituent of the alicyclic hydrocarbon group represented by Y1 include a halogen atom, a hydroxy group, an alkyl group having 1 to 16 carbon atoms which may be substituted with a hydroxy group (—$CH_2$— included in the alkyl group may be replaced by —O— or —CO—), an alicyclic hydrocarbon group having 3 to 16 carbon atoms, an aromatic hydrocarbon group having 6 to 18 carbon atoms, an aralkyl group having 7 to 21 carbon atoms, a glycidyloxy group, a —$(CH_2)_{ja}$—CO—O—$R^{b1}$ group or a —$(CH_2)_{ja}$—O—CO—$R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms, or a group obtained by combining these groups. ja represents an integer of 0 to 4. —$CH_2$— included in the alkyl group and the alicyclic hydrocarbon group may be replaced by —O—, —$SO_2$— or —CO—, and a hydrogen atom included in the alkyl group, the alicyclic hydrocarbon group and the aromatic hydrocarbon group may be substituted with a hydroxy group or a fluorine atom).

Examples of the halogen atom include a fluorine atom, a chlorine atom, a bromine atom and an iodine atom.

Examples of the alicyclic hydrocarbon group include a cyclopentyl group, a cyclohexyl group, a methylcyclohexyl group, a dimethylcyclohexyl group, a cycloheptyl group, a cyclooctyl group, a norbornyl group, an adamantyl group and the like. The alicyclic hydrocarbon group may have a chain hydrocarbon group, and examples thereof include a methylcyclohexyl group, a dimethylcyclohexyl group and the like. The number of carbon atoms of the alicyclic hydrocarbon group is preferably 3 to 12, and more preferably 3 to 10.

Examples of the aromatic hydrocarbon group include aryl groups such as a phenyl group, a naphthyl group, an anthryl group, a biphenyl group and a phenanthryl group. The aromatic hydrocarbon group may have a chain hydrocarbon group or an alicyclic hydrocarbon group, and it is possible to exemplify aromatic hydrocarbon groups which have a chain hydrocarbon group having 1 to 18 carbon atoms (a tolyl group, a xylyl group, a cumenyl group, a mesityl group, a p-methylphenyl group, a p-ethylphenyl group, a p-tert-butylphenyl group, a 2,6-diethylphenyl group, a 2-methyl-6-ethylphenyl group, etc.) and aromatic hydrocarbon groups which have an alicyclic hydrocarbon group having 3 to 18 carbon atoms (a p-cyclohexylphenyl group, a p-adamantylphenyl group, etc.). The number of carbon atoms of the aromatic hydrocarbon group is preferably 6 to 14, and more preferably 6 to 10.

Examples of the alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group, an octyl group, a nonyl group, a decyl group, an undecyl group, a dodecyl group and the like. The number of carbon atoms of the alkyl group is preferably 1 to 12, more preferably 1 to 6, and still more preferably 1 to 4.

Examples of the alkyl group substituted with a hydroxy group include hydroxyalkyl groups such as a hydroxymethyl group and a hydroxyethyl group.

Examples of the aralkyl group include a benzyl group, a phenethyl group, a phenylpropyl group, a naphthylmethyl group and a naphthylethyl group.

Examples of the group in which —CH$_2$— included in the alkyl group is replaced by —O—, —SO$_2$— or —CO— include an alkoxy group, an alkylsulfonyl group, an alkoxycarbonyl group, an alkylcarbonyl group, an alkylcarbonyloxy group, or a group obtained by combining these groups.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group. The number of carbon atoms of the alkoxy group is preferably 1 to 12, more preferably 1 to 6, and still more preferably 1 to 4.

Examples of the alkylsulfonyl group include a methylsulfonyl group, an ethylsulfonyl group, a propylsulfonyl group and the like. The number of carbon atoms of the alkylsulfonyl group is preferably 1 to 12, more preferably 1 to 6, and still more preferably 1 to 4.

Examples of the alkoxycarbonyl group include a methoxycarbonyl group, an ethoxycarbonyl group, a butoxycarbonyl group and the like. The number of carbon atoms of the alkoxycarbonyl group is preferably 2 to 12, more preferably 2 to 6, and still more preferably 2 to 4.

Examples of the alkylcarbonyl group include an acetyl group, a propionyl group and a butyryl group. The number of carbon atoms of the alkylcarbonyl group is preferably 2 to 12, more preferably 2 to 6, and still more preferably 2 to 4.

Examples of the alkylcarbonyloxy group include an acetyloxy group, a propionyloxy group, a butyryloxy group and the like. The number of carbon atoms of the alkylcarbonyloxy group is preferably 2 to 12, more preferably 2 to 6, and still more preferably 2 to 4.

Examples of the combined group include a group obtained by combining an alkoxy group with an alkyl group, a group obtained by combining an alkoxy group with an alkoxy group, a group obtained by combining an alkoxy group with an alkylcarbonyl group, a group obtained by combining an alkoxy group with an alkylcarbonyloxy group and the like.

Examples of the group obtained by combining an alkoxy group with an alkyl group include alkoxyalkyl groups such as a methoxymethyl group, a methoxyethyl group, an ethoxymethyl group, an ethoxyethyl group and the like. The number of carbon atoms of the alkoxyalkyl group is preferably 2 to 12, more preferably 2 to 6, and still more preferably 2 to 4.

Examples of the group obtained by combining an alkoxy group with an alkoxy group include alkoxyalkoxy groups such as a methoxymethoxy group, a methoxyethoxy group, an ethoxymethoxy group, an ethoxyethoxy group and the like. The number of carbon atoms of the alkoxyalkoxy group is preferably 2 to 12, more preferably 2 to 6, and still more preferably 2 to 4.

Examples of the group obtained by combining an alkoxy group with an alkylcarbonyl group include alkoxyalkylcarbonyl groups such as a methoxyacetyl group, a methoxypropionyl group, an ethoxyacetyl group, an ethoxypropionyl group and the like. The number of carbon atoms of the alkoxyalkylcarbonyl group is preferably 3 to 13, more preferably 3 to 7, and still more preferably 3 to 5.

Examples of the group obtained by combining an alkoxy group with an alkylcarbonyloxy group include alkoxyalkylcarbonyloxy groups such as a methoxyacetyloxy group, a methoxypropionyloxy group, an ethoxyacetyloxy group, an ethoxypropionyloxy group and the like. The number of carbon atoms of the alkoxyalkylcarbonyloxy group is preferably 3 to 13, more preferably 3 to 7, and still more preferably 3 to 5.

Examples of the group in which —CH$_2$— included in the alicyclic hydrocarbon group is replaced by —O—, —SO$_2$— or —CO— include groups represented by formula (Y12) to formula (Y35), formula (Y39) to formula (Y43) and the like.

Y$^1$ is preferably an alicyclic hydrocarbon group having 3 to 24 carbon atoms which may have a substituent, more preferably an alicyclic hydrocarbon group having 3 to 20 carbon atoms which may have a substituent, still more preferably an alicyclic hydrocarbon group having 3 to 18 carbon atoms which may have a substituent, yet more preferably an adamantyl group which may have a substituent or a norbornyl group which may have a substituent, and —CH$_2$— constituting the alicyclic hydrocarbon group, the adamantyl group or the norbornyl group may be replaced by —O—, —S—, —SO$_2$— or —CO—. Specific examples include the followings.

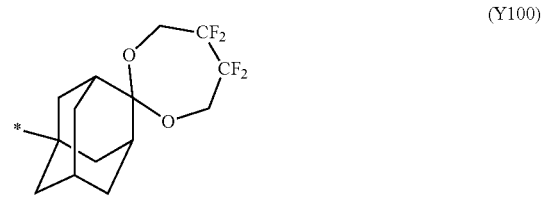

(Y100)

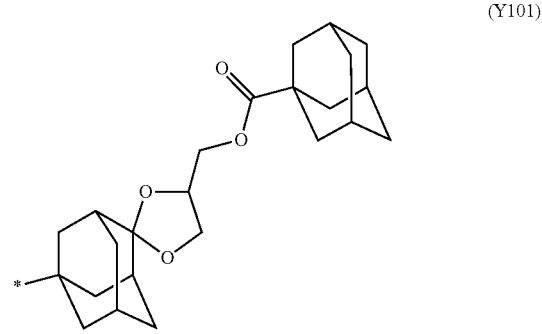

(Y101)

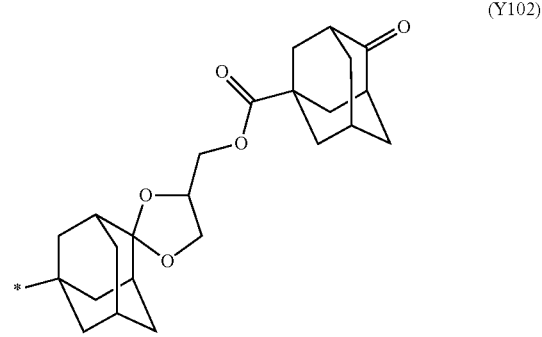

(Y102)

(Y103)
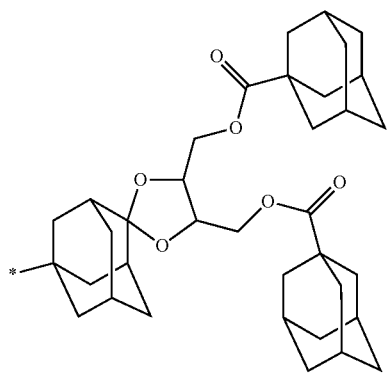
(Y104)
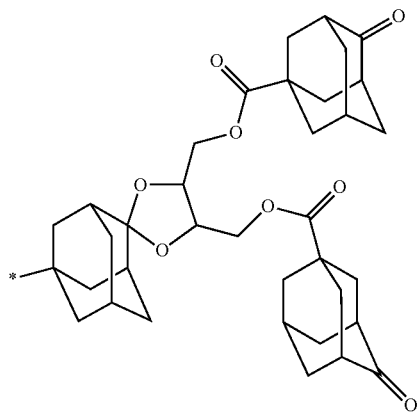
(Y105)
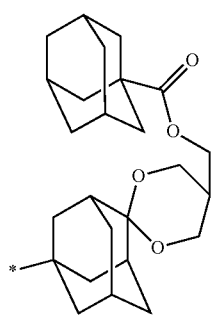
(Y-106)
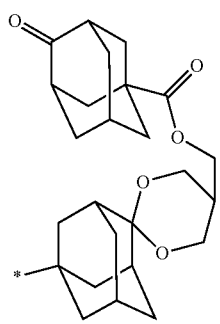
(Y107)
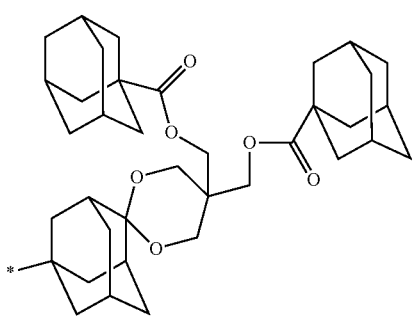
(Y108)
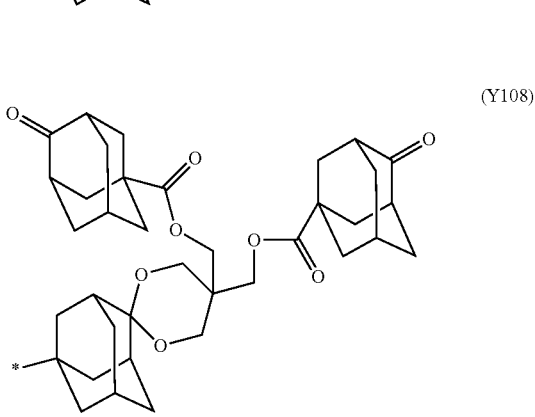
(Y109)
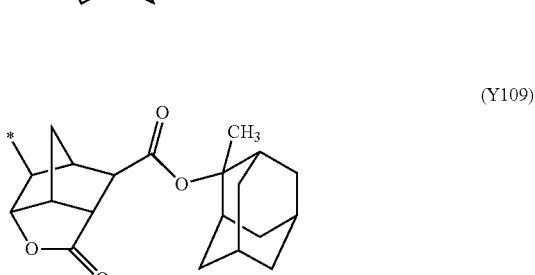
(Y110)
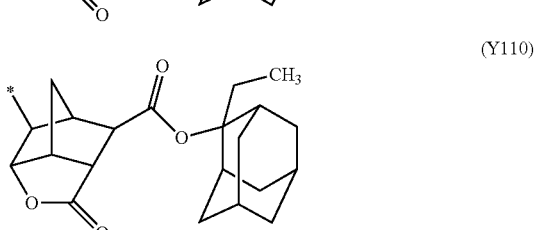
(Y111)
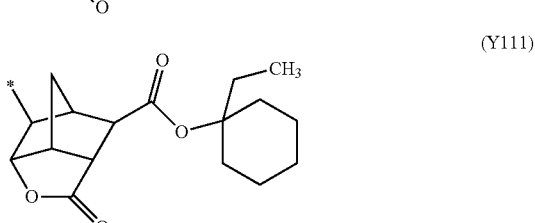
(Y42)
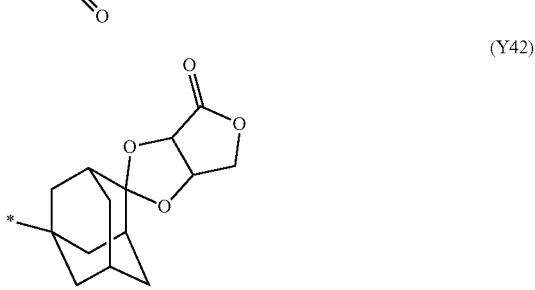

(Y112) 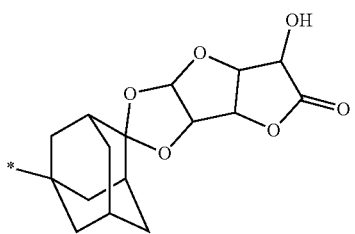
(Y113) 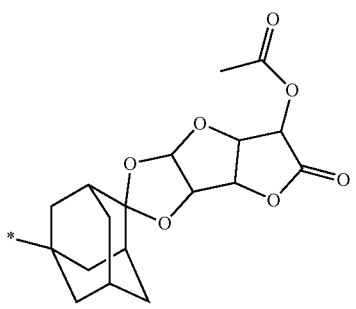
(Y114) 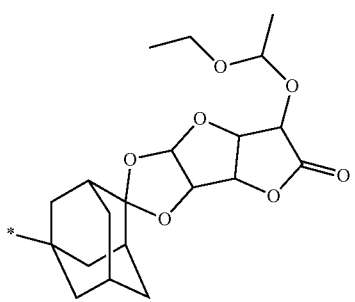
(Y115) 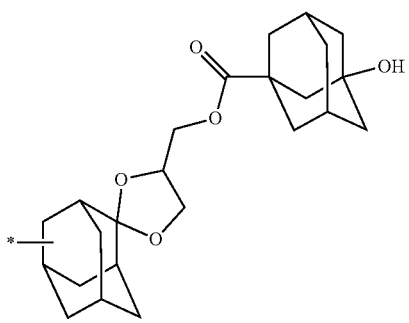
(Y116) 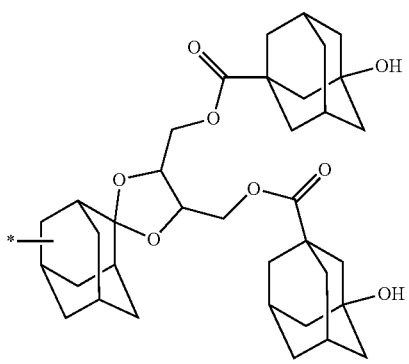
(Y11) 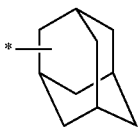
(Y4) 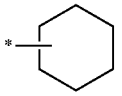
(Y117) 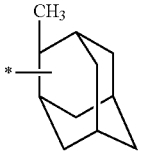
(Y118) 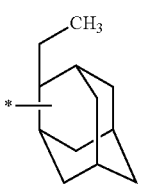
(Y119) 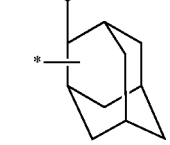
(Y120) 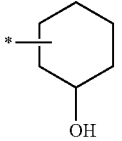
(Y121) 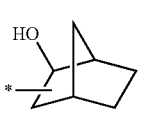
(Y122) 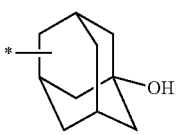
(Y123) 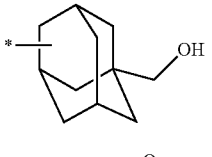
(Y15) 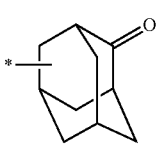
(Y124) 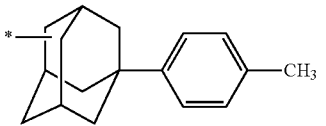

(Y125) 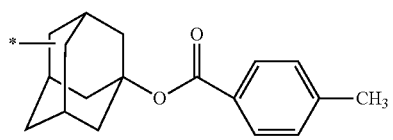
(Y126) 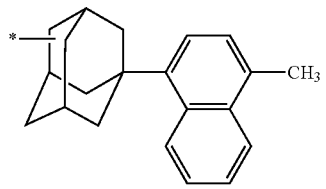
(Y127) 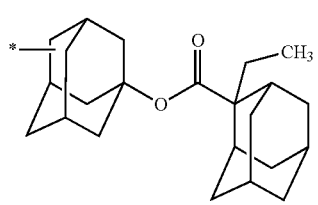
(Y128) 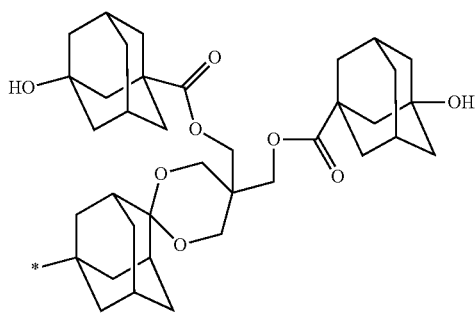
(Y129) 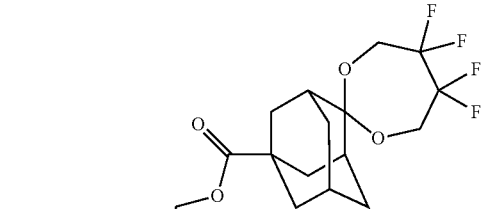
(Y130) 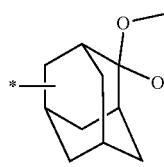
(Y131) 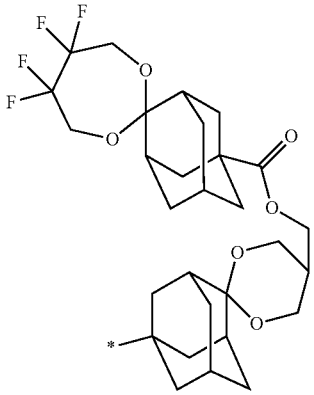
(Y132) 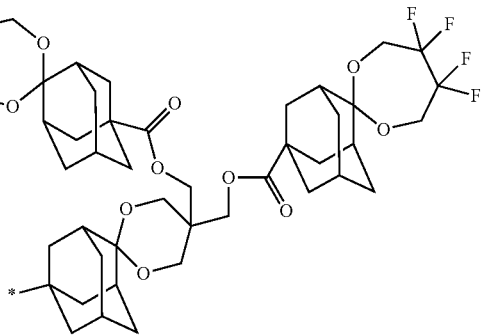
(Y133) 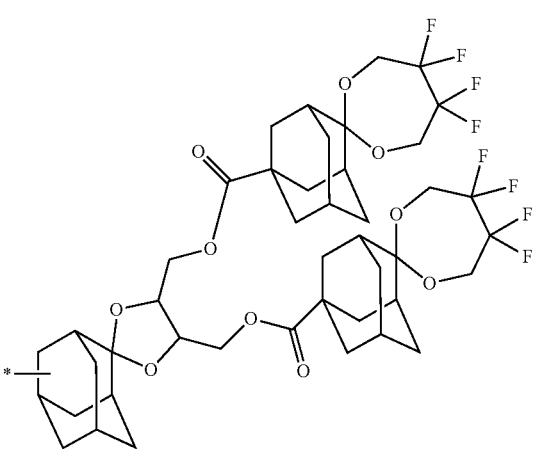
(Y134) 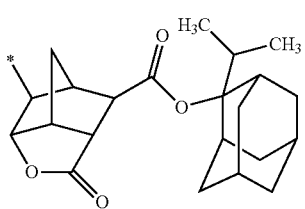

(Y135) 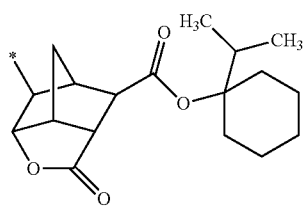

(Y136) 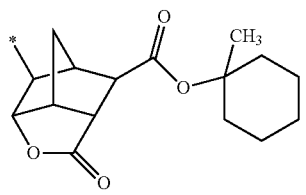

(Y137) 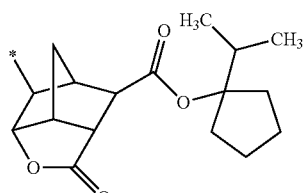

(Y138) 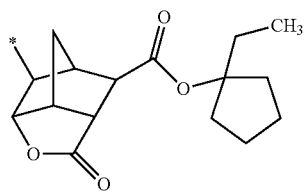

(Y139) 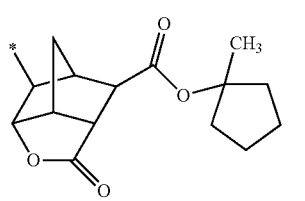

Of these, $Y^1$ is preferably an adamantyl group, a hydroxyadamantyl group, an oxoadamantyl group, a norbornanelactone group or a group represented by each of formula (Y42), formula (Y100) to formula (Y114) and formula (Y134) to formula (Y139), and particularly preferably a hydroxyadamantyl group, an oxoadamantyl group, a group including these groups, or a group represented by each of formula (Y42), formula (Y100) to formula (Y114) and formula (Y134) to formula (Y139).

The anion represented by formula (I-A) is preferably anions represented by formula (I-A-1) to formula (I-A-62) [hereinafter sometimes referred to as "anion (I-A-1)" according to the number of formula], and more preferably an anion represented by any one of formula (I-A-1) to formula (I-A-4), formula (I-A-9), formula (I-A-10), formula (I-A-24) to formula (I-A-33), formula (I-A-36) to formula (I-A-40) and formula (I-A-47) to formula (I-A-62)).

(I-A-1) 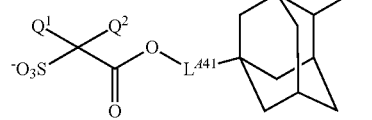

(I-A-2) 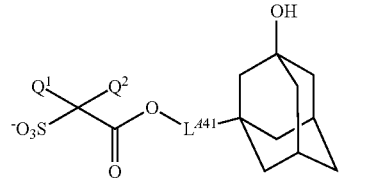

(I-A-3) 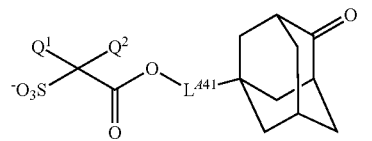

(I-A-4) 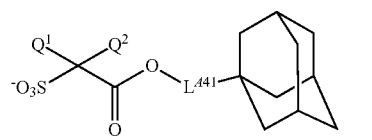

(I-A-5) 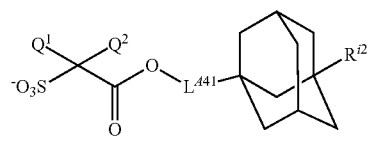

(I-A-6) 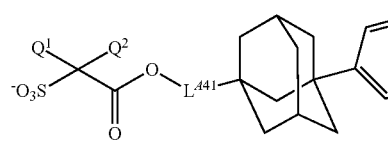

(I-A-7) 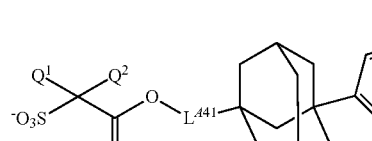

(I-A-8) 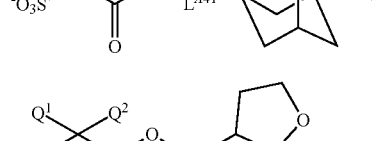

(I-A-9) 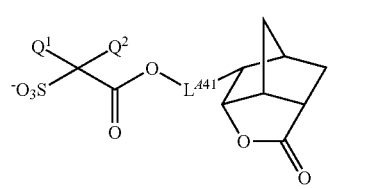

(I-A-10) 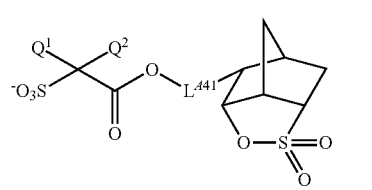

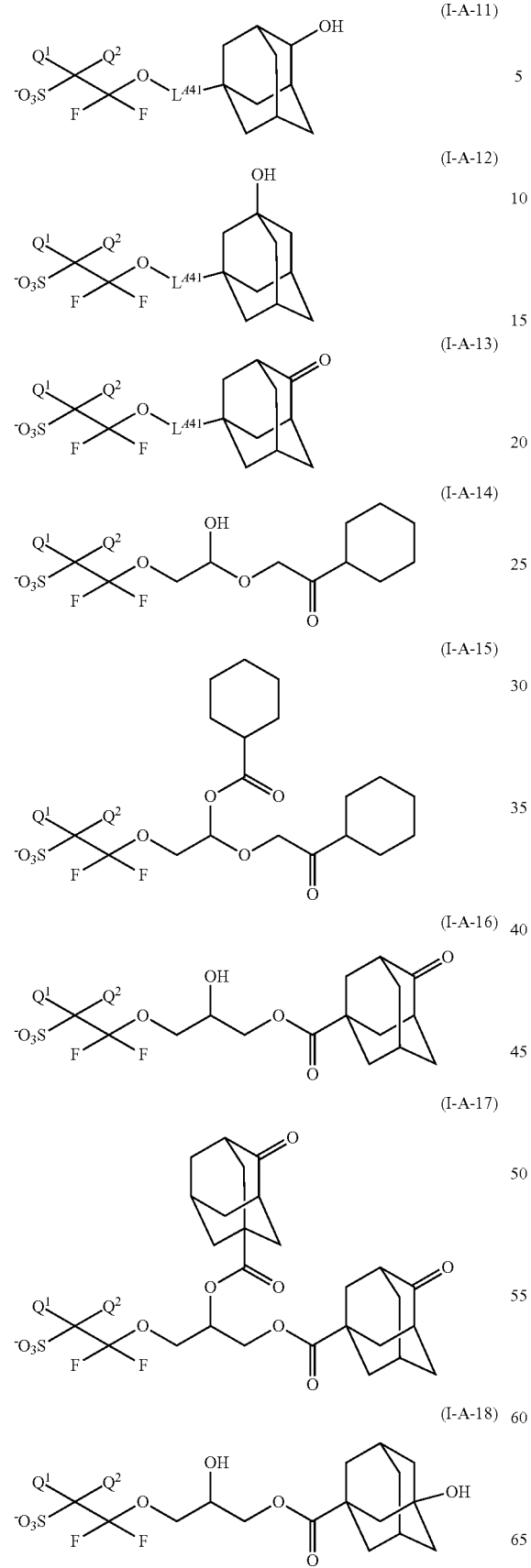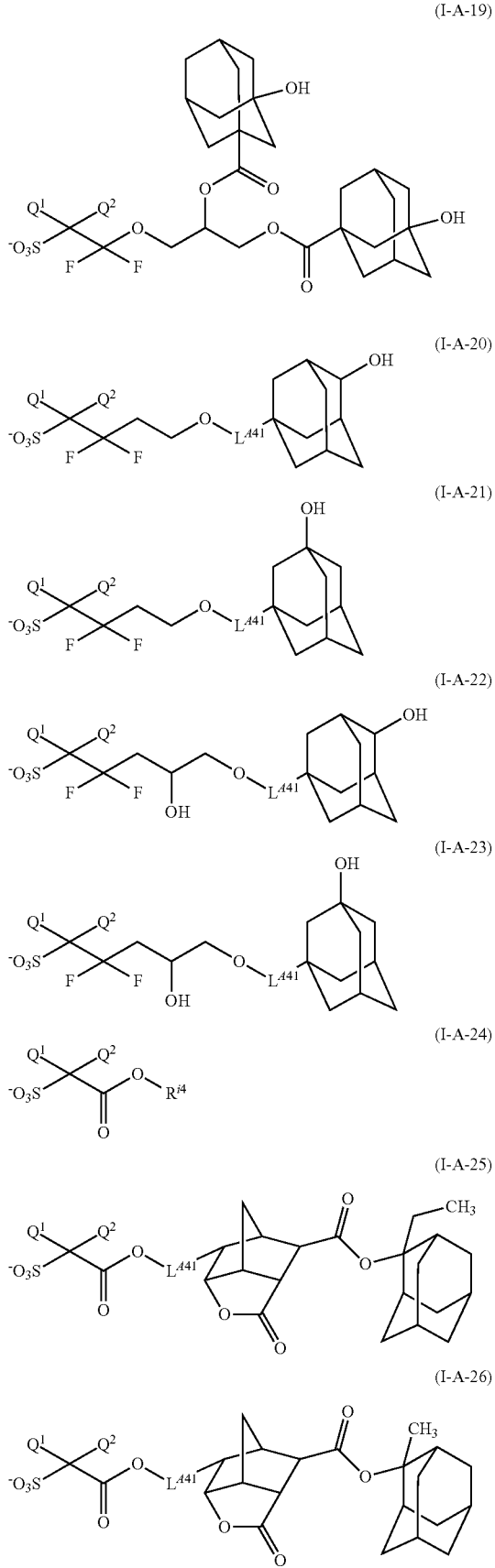

(I-A-27)
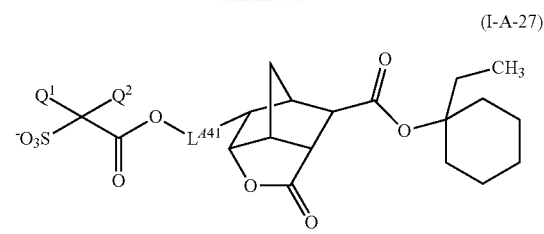
(I-A-28)
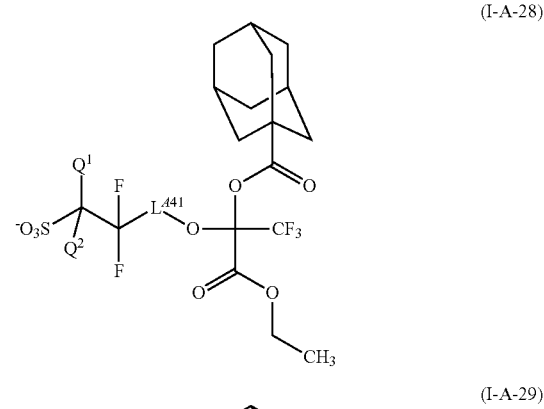
(I-A-29)
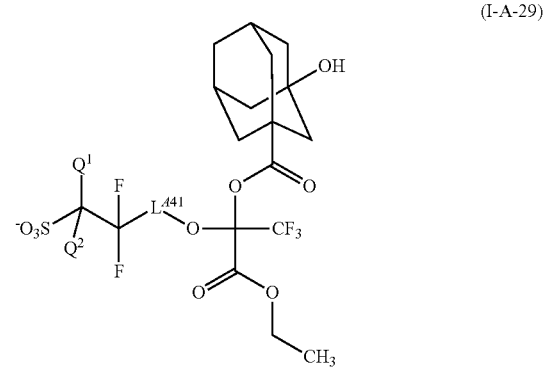
(I-A-30)
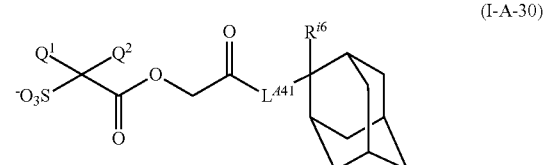
(I-A-31)
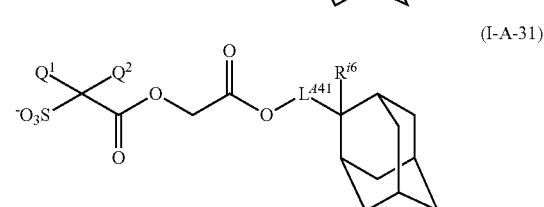
(I-A-32)
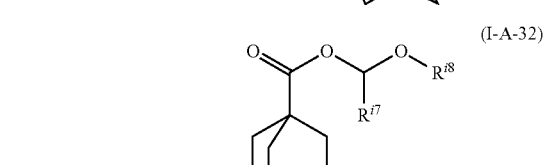
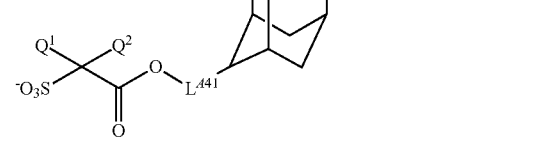
(I-A-33)
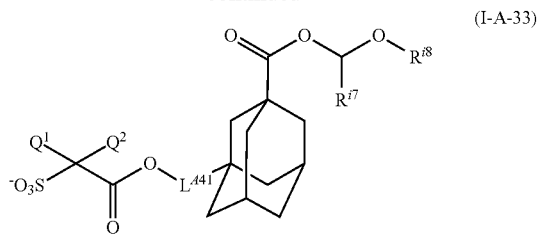
(I-A-34)
(I-A-35)
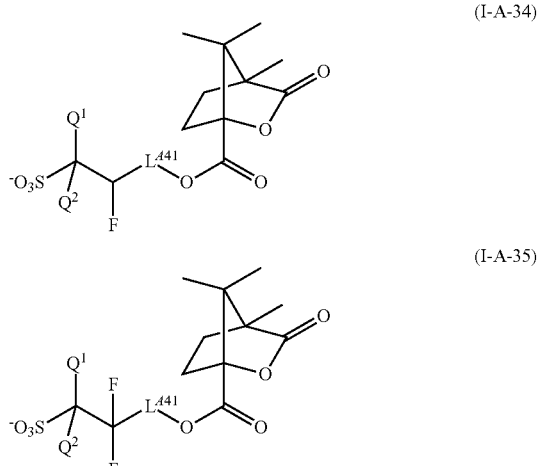
(I-A-36)
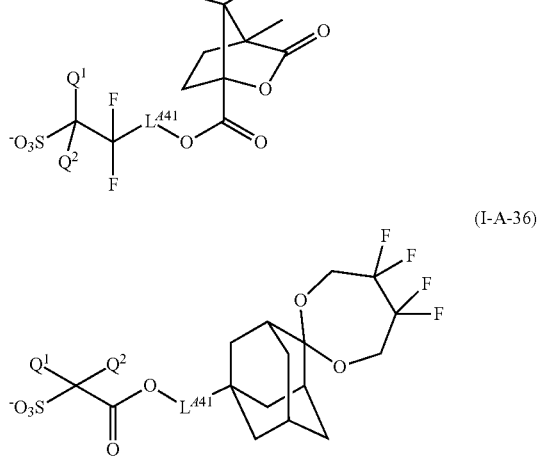
(I-A-37)
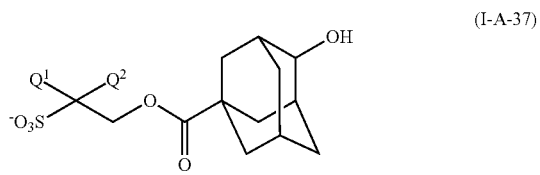
(I-A-38)
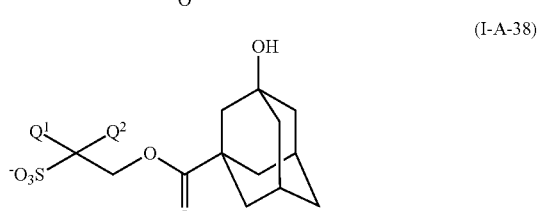
(I-A-39)
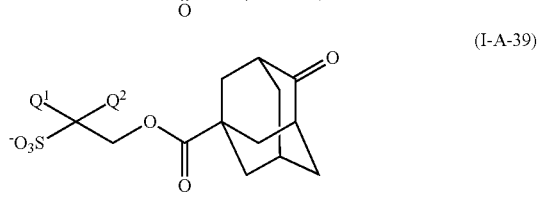
(I-A-40)
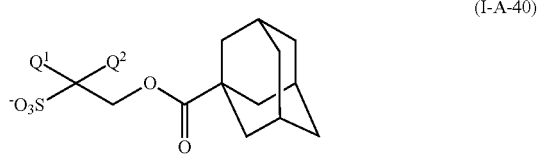

(I-A-41)
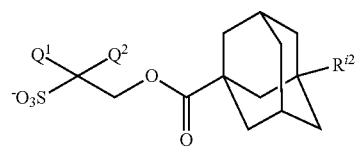
(I-A-42)
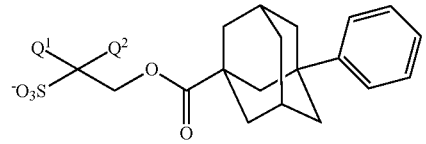
(I-A-43)
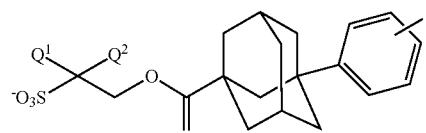
(I-A-44)
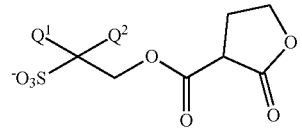
(I-A-45)
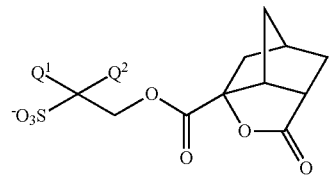
(I-A-46)
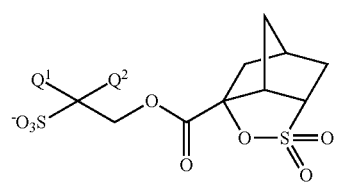
(I-A-47)
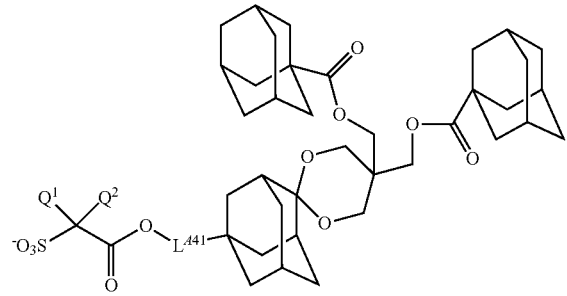
(I-A-48)
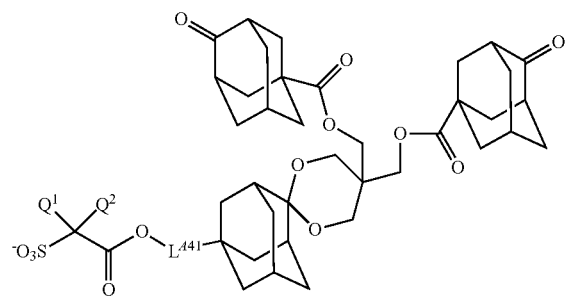
(I-A-49)
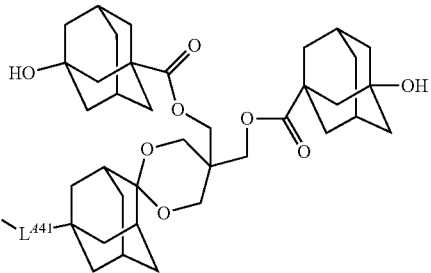
(I-A-50)
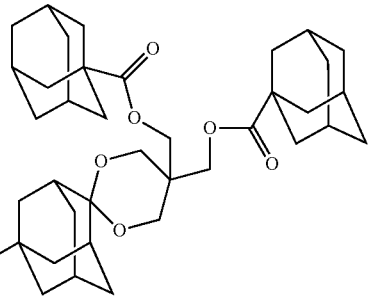
(I-A-51)
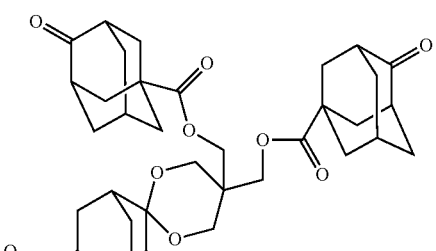
(I-A-52)
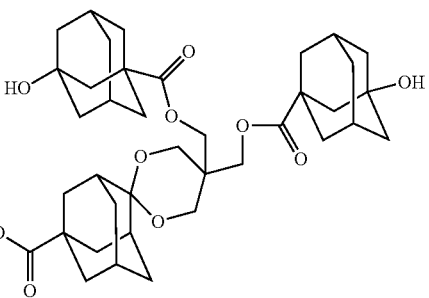

(I-A-53)
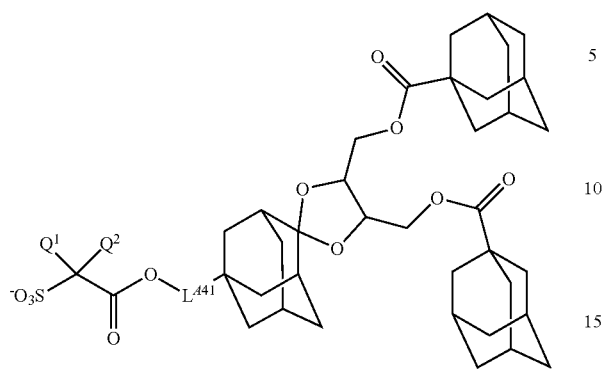

(I-A-54)
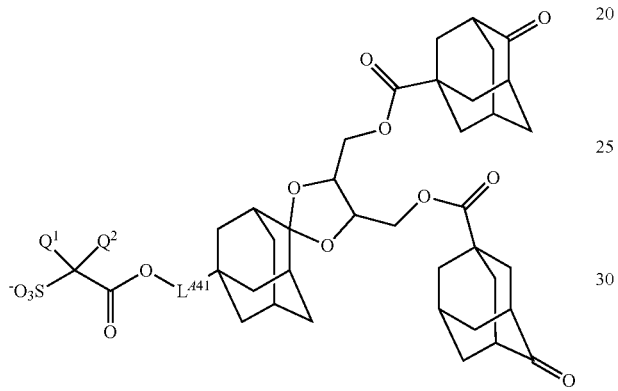

(I-A-55)
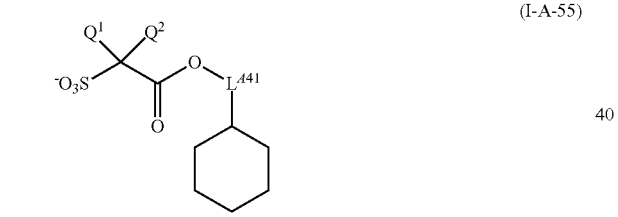

(I-A-56)
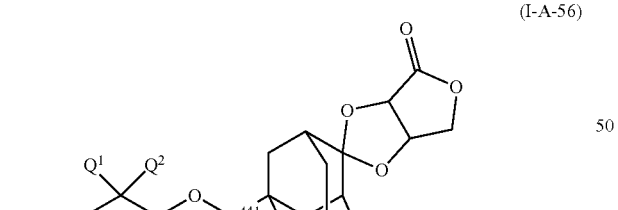

(I-A-57)
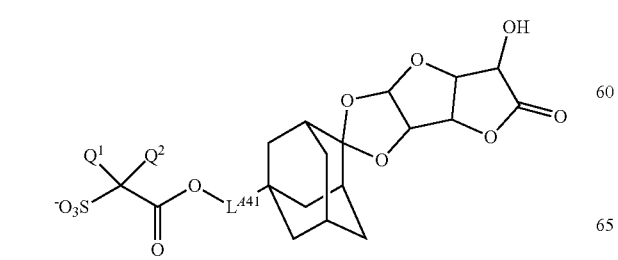

(I-A-58)
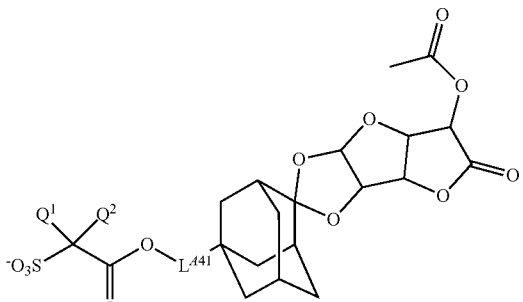

(I-A-59)
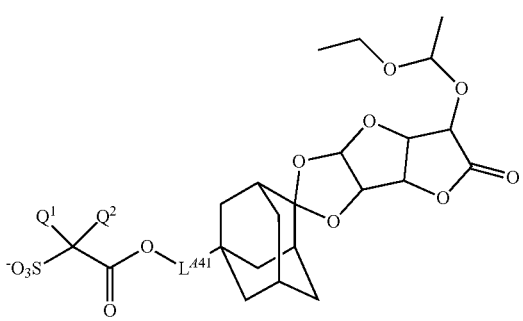

(I-A-60)
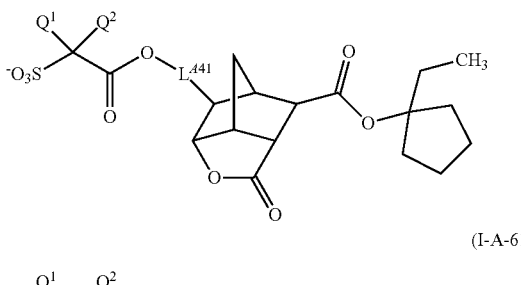

(I-A-61)
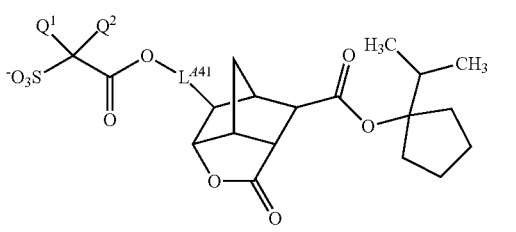

(I-A-62)
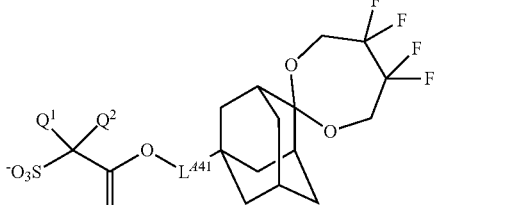

$R^{i2}$ to $R^{i7}$ each independently represent, for example, an alkyl group having 1 to 4 carbon atoms, and preferably a methyl group or an ethyl group. $R^{i8}$ is, for example, a chain hydrocarbon group having 1 to 12 carbon atoms, preferably an alkyl group having 1 to 4 carbon atoms, an alicyclic hydrocarbon group having 5 to 12 carbon atoms, or groups formed by combining these groups, and more preferably a methyl group, an ethyl group, a cyclohexyl group or an adamantyl group. $L^{441}$ is a single bond or an alkanediyl group having 1 to 4 carbon atoms. $Q^1$ and $Q^2$ are the same as defined above.
Specific examples of the anion represented by formula (I-A) include anions mentioned in JP 2010-204646 A.
Preferable anions represented by formula (I-A) are anions represented by formula (I-a-1) to formula (I-a-40).
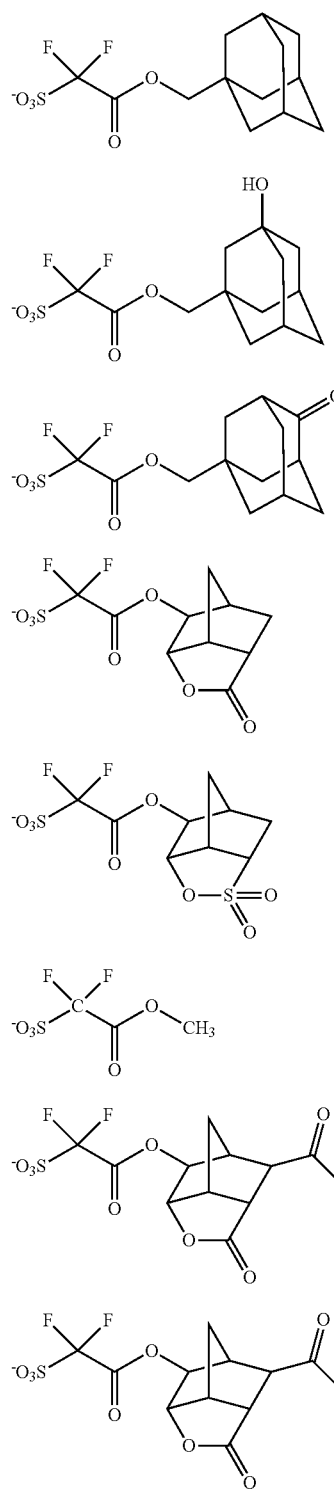
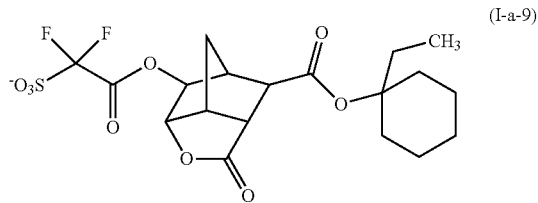
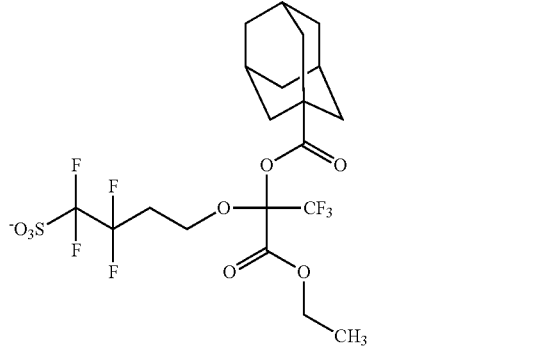
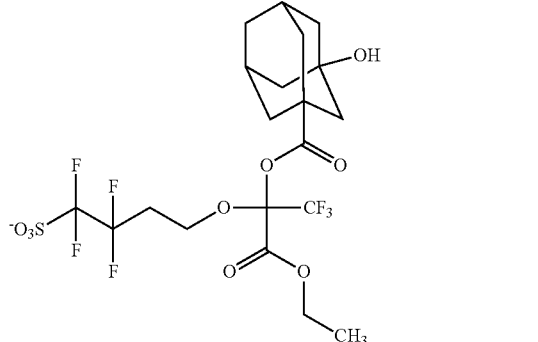
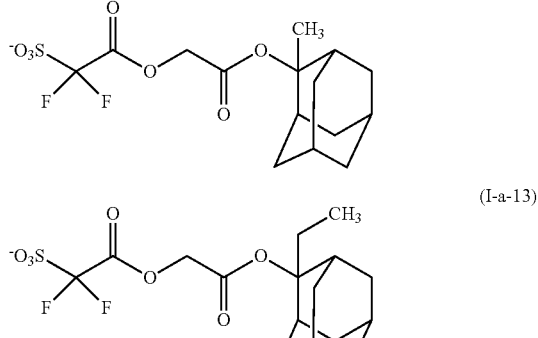
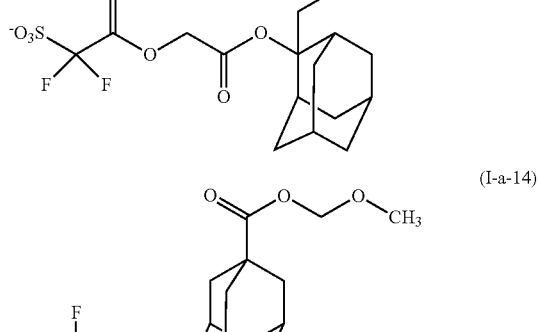
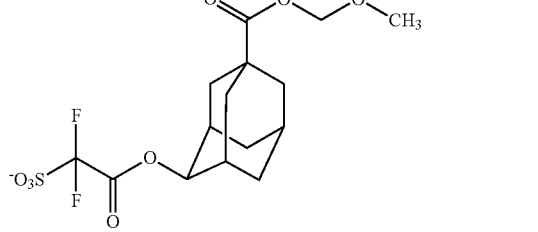

(I-a-15)
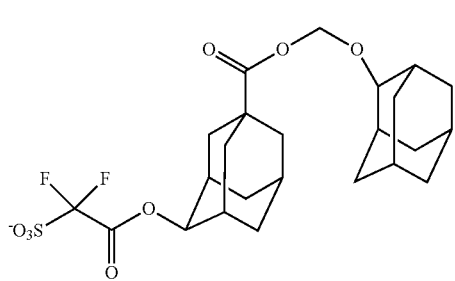
(I-a-22)
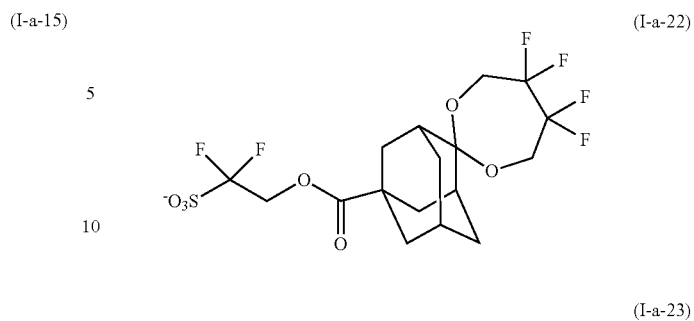
(I-a-16)
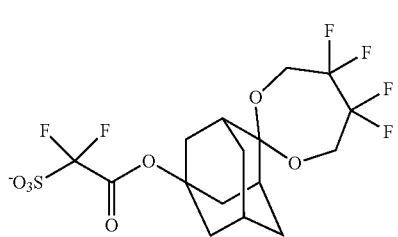
(I-a-23)
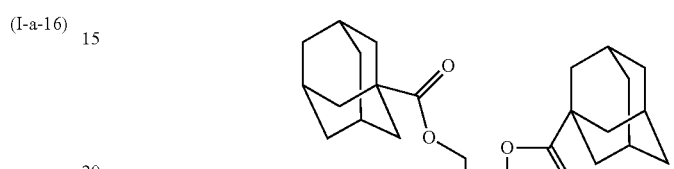
(I-a-17)
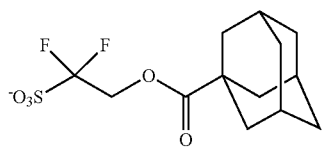
(I-a-18)
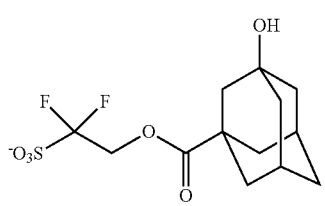
(I-a-24)
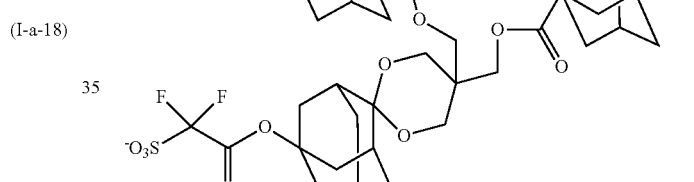
(I-a-19)
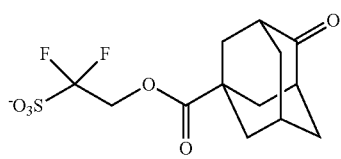
(I-a-25)
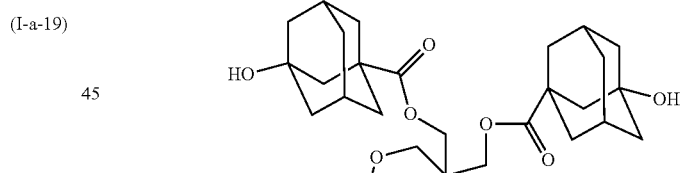
(I-a-20)
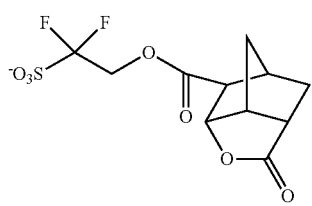
(I-a-26)
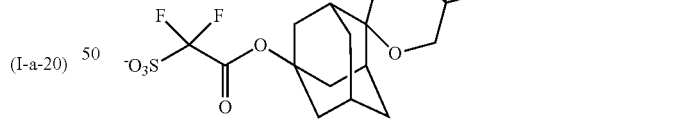
(I-a-21)
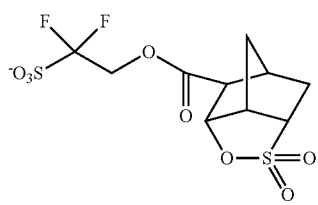
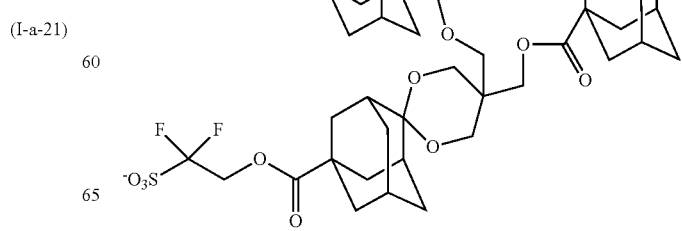

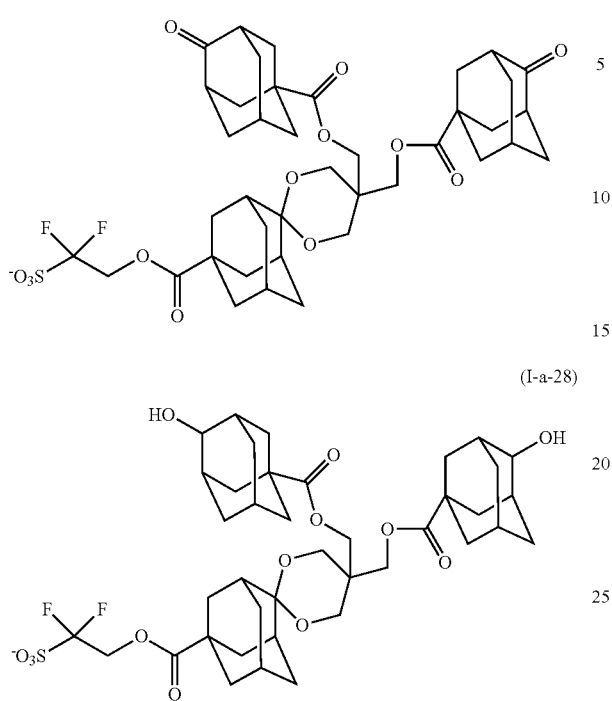
(I-a-27)
(I-a-28)
(I-a-29)
(I-a-30)
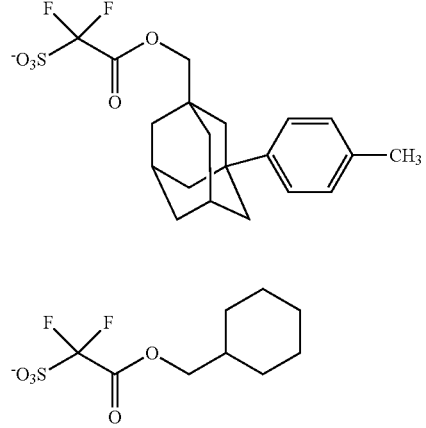
(I-a-31)
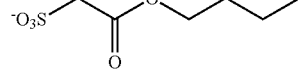
(I-a-32)
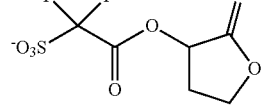
(I-a-33)
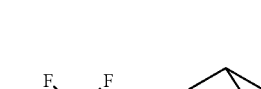
(I-a-34)
(I-a-35)
(I-a-36)
(I-a-37)
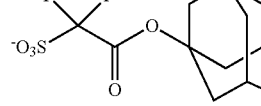

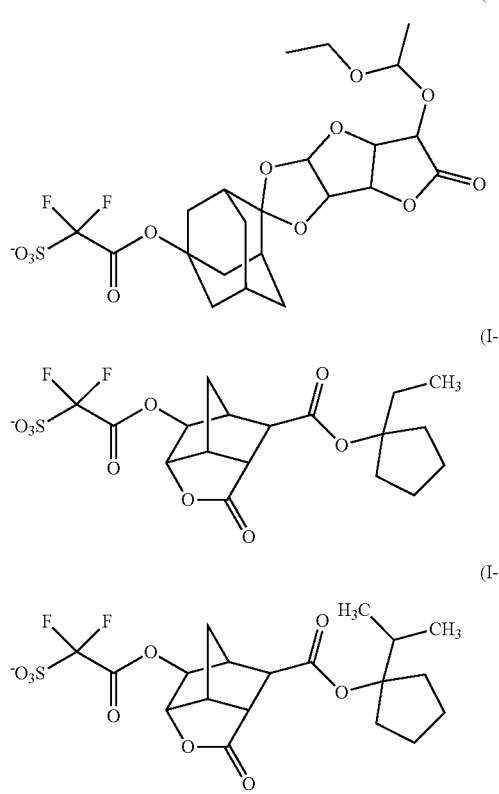

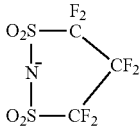

Of these, an anion represented by any one of formula (I-a-1) to formula (I-a-4), formula (I-a-7) to formula (I-a-11), formula (I-a-14) to formula (I-a-30) and formula (I-a-35) to formula (I-a-40) is preferable.

Examples of the sulfonylimide anion represented by Al⁻ include the followings.

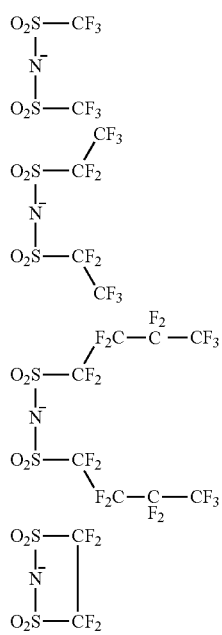

Examples of the sulfonylmethide anion represented by Al⁻ include the followings.

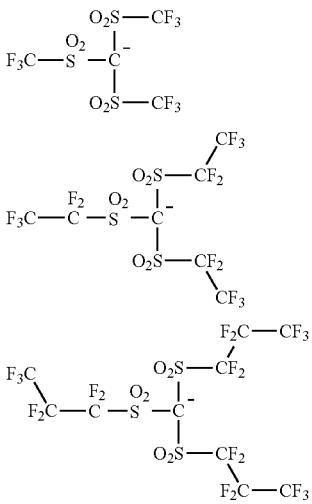

Examples of the carboxylic acid anion represented by Al⁻ include the followings.

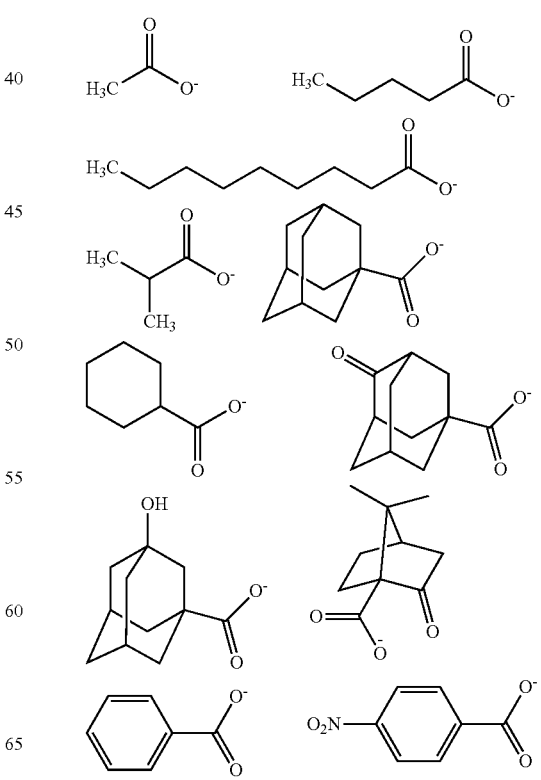

-continued

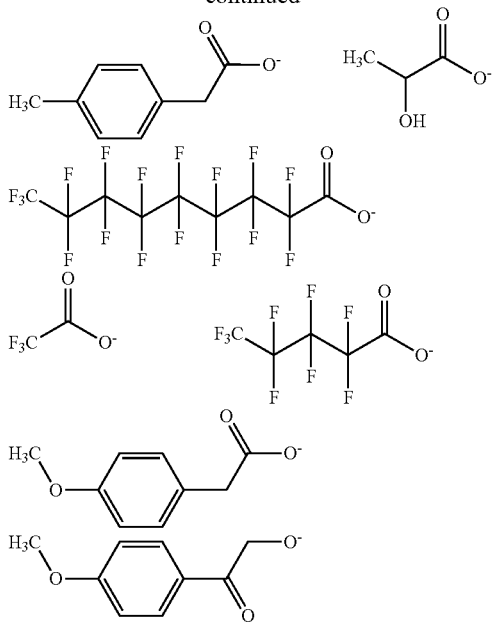

Specific examples of the salt (I) include salts obtained by optionally combining the above-mentioned cations and anions. Specific examples of the salt (I) are shown in the following table.

In the following table, the respective symbols represent symbols imparted to structures showing the above-mentioned anions and cations, and "to" indicates that each of the salt (I) and the anion (I) or the cation (I) corresponds to each other. For example, the salt (I-1) indicates a salt composed of an anion represented by formula (I-a-1) and a cation represented by formula (I-c-1), the salt (I-2) indicates a salt composed of an anion represented by formula (I-a-2) and a cation represented by formula (I-c-1), and the salt (I-39) indicates a salt composed of an anion represented by formula (I-a-1) and a cation represented by formula (I-c-2). The salt (I-3003) indicates a salt composed of an anion represented by formula (I-a-39) and a cation represented by formula (I-c-1), the salt (I-3004) indicates a salt composed of an anion represented by formula (I-a-39) and a cation represented by formula (I-c-2), and the salt (I-3082) indicates a salt composed of an anion represented by formula (I-a-40) and a cation represented by formula (I-c-1).

(I-1)

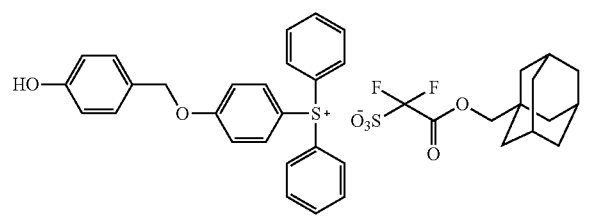

TABLE 1

| Salt (I) | Anion (I) | Cation (I) |
|---|---|---|
| (I-1) to (I-38) | (I-a-1) to (I-a-38) | (I-c-1) |
| (I-39) to (I-76) | (I-a-1) to (I-a-38) | (I-c-2) |

TABLE 1-continued

| Salt (I) | Anion (I) | Cation (I) |
|---|---|---|
| (I-77) to (I-114) | (I-a-1) to (I-a-38) | (I-c-3) |
| (I-115) to (I-152) | (I-a-1) to (I-a-38) | (I-c-4) |
| (I-153) to (I-190) | (I-a-1) to (I-a-38) | (I-c-5) |
| (I-191) to (I-228) | (I-a-1) to (I-a-38) | (I-c-6) |
| (I-229) to (I-266) | (I-a-1) to (I-a-38) | (I-c-7) |
| (I-267) to (I-304) | (I-a-1) to (I-a-38) | (I-c-8) |
| (I-305) to (I-342) | (I-a-1) to (I-a-38) | (I-c-9) |
| (I-343) to (I-380) | (I-a-1) to (I-a-38) | (I-c-10) |
| (I-381) to (I-418) | (I-a-1) to (I-a-38) | (I-c-11) |
| (I-419) to (I-456) | (I-a-1) to (I-a-38) | (I-c-12) |
| (I-457) to (I-494) | (I-a-1) to (I-a-38) | (I-c-13) |
| (I-495) to (I-532) | (I-a-1) to (I-a-38) | (I-c-14) |
| (I-533) to (I-570) | (I-a-1) to (I-a-38) | (I-c-15) |
| (I-571) to (I-608) | (I-a-1) to (I-a-38) | (I-c-16) |
| (I-609) to (I-646) | (I-a-1) to (I-a-38) | (I-c-17) |
| (I-647) to (I-684) | (I-a-1) to (I-a-38) | (I-c-18) |
| (I-685) to (I-722) | (I-a-1) to (I-a-38) | (I-c-19) |
| (I-723) to (I-760) | (I-a-1) to (I-a-38) | (I-c-20) |
| (I-761) to (I-798) | (I-a-1) to (I-a-38) | (I-c-21) |
| (I-799) to (I-836) | (I-a-1) to (I-a-38) | (I-c-22) |
| (I-837) to (I-874) | (I-a-1) to (I-a-38) | (I-c-23) |
| (I-875) to (I-912) | (I-a-1) to (I-a-38) | (I-c-24) |
| (I-913) to (I-950) | (I-a-1) to (I-a-38) | (I-c-25) |
| (I-951) to (I-988) | (I-a-1) to (I-a-38) | (I-c-26) |
| (I-989) to (I-1026) | (I-a-1) to (I-a-38) | (I-c-27) |
| (I-1027) to (I-1064) | (I-a-1) to (I-a-38) | (I-c-28) |
| (I-1065) to (I-1102) | (I-a-1) to (I-a-38) | (I-c-29) |
| (I-1103) to (I-1140) | (I-a-1) to (I-a-38) | (I-c-30) |
| (I-1141) to (I-1178) | (I-a-1) to (I-a-38) | (I-c-31) |
| (I-1179) to (I-1216) | (I-a-1) to (I-a-38) | (I-c-32) |
| (I-1217) to (I-1254) | (I-a-1) to (I-a-38) | (I-c-33) |
| (I-1255) to (I-1292) | (I-a-1) to (I-a-38) | (I-c-34) |
| (I-1293) to (I-1330) | (I-a-1) to (I-a-38) | (I-c-35) |
| (I-1331) to (I-1368) | (I-a-1) to (I-a-38) | (I-c-36) |
| (I-1369) to (I-1406) | (I-a-1) to (I-a-38) | (I-c-37) |
| (I-1407) to (I-1444) | (I-a-1) to (I-a-38) | (I-c-38) |
| (I-1445) to (I-1482) | (I-a-1) to (I-a-38) | (I-c-39) |
| (I-1483) to (I-1520) | (I-a-1) to (I-a-38) | (I-c-40) |
| (I-1521) to (I-1558) | (I-a-1) to (I-a-38) | (I-c-41) |
| (I-1559) to (I-1596) | (I-a-1) to (I-a-38) | (I-c-42) |
| (I-1597) to (I-1634) | (I-a-1) to (I-a-38) | (I-c-43) |
| (I-1635) to (I-1672) | (I-a-1) to (I-a-38) | (I-c-44) |
| (I-1673) to (I-1710) | (I-a-1) to (I-a-38) | (I-c-45) |
| (I-1711) to (I-1748) | (I-a-1) to (I-a-38) | (I-c-46) |
| (I-1749) to (I-1786) | (I-a-1) to (I-a-38) | (I-c-47) |
| (I-1787) to (I-1824) | (I-a-1) to (I-a-38) | (I-c-48) |
| (I-1825) to (I-1862) | (I-a-1) to (I-a-38) | (I-c-49) |
| (I-1863) to (I-1900) | (I-a-1) to (I-a-38) | (I-c-50) |
| (I-1901) to (I-1938) | (I-a-1) to (I-a-38) | (I-c-51) |
| (I-1939) to (I-1976) | (I-a-1) to (I-a-38) | (I-c-52) |
| (I-1977) to (I-2014) | (I-a-1) to (I-a-38) | (I-c-53) |
| (I-2015) to (I-2052) | (I-a-1) to (I-a-38) | (I-c-54) |
| (I-2053) to (I-2090) | (I-a-1) to (I-a-38) | (I-c-55) |
| (I-2091) to (I-2128) | (I-a-1) to (I-a-38) | (I-c-56) |
| (I-2129) to (I-2166) | (I-a-1) to (I-a-38) | (I-c-57) |
| (I-2167) to (I-2204) | (I-a-1) to (I-a-38) | (I-c-58) |
| (I-2205) to (I-2242) | (I-a-1) to (I-a-38) | (I-c-59) |
| (I-2243) to (I-2280) | (I-a-1) to (I-a-38) | (I-c-60) |
| (I-2281) to (I-2318) | (I-a-1) to (I-a-38) | (I-c-61) |
| (I-2319) to (I-2356) | (I-a-1) to (I-a-38) | (I-c-62) |
| (I-2357) to (I-2394) | (I-a-1) to (I-a-38) | (I-c-63) |
| (I-2395) to (I-2432) | (I-a-1) to (I-a-38) | (I-c-64) |
| (I-2433) to (I-2470) | (I-a-1) to (I-a-38) | (I-c-65) |
| (I-2471) to (I-2508) | (I-a-1) to (I-a-38) | (I-c-66) |
| (I-2509) to (I-2546) | (I-a-1) to (I-a-38) | (I-c-67) |
| (I-2547) to (I-2584) | (I-a-1) to (I-a-38) | (I-c-68) |
| (I-2585) to (I-2622) | (I-a-1) to (I-a-38) | (I-c-69) |
| (I-2623) to (I-2660) | (I-a-1) to (I-a-38) | (I-c-70) |
| (I-2661) to (I-2698) | (I-a-1) to (I-a-38) | (I-c-71) |
| (I-2699) to (I-2736) | (I-a-1) to (I-a-38) | (I-c-72) |
| (I-2737) to (I-2774) | (I-a-1) to (I-a-38) | (I-c-73) |
| (I-2775) to (I-2812) | (I-a-1) to (I-a-38) | (I-c-74) |
| (I-2813) to (I-2850) | (I-a-1) to (I-a-38) | (I-c-75) |
| (I-2851) to (I-2888) | (I-a-1) to (I-a-38) | (I-c-76) |
| (I-2889) to (I-2926) | (I-a-1) to (I-a-38) | (I-c-77) |
| (I-2927) to (I-2964) | (I-a-1) to (I-a-38) | (I-c-78) |
| (I-2965) to (I-3002) | (I-a-1) to (I-a-38) | (I-c-79) |

TABLE 1-continued

| Salt (I) | Anion (I) | Cation (I) |
| --- | --- | --- |
| (I-3003) to (I-3081) | (I-a-39) | (I-c-1) to (I-c-79) |
| (I-3082) to (I-3160) | (I-a-40) | (I-c-1) to (I-c-79) |

Of these, the salt (I) is preferably a salt obtained by combining an anion represented by any one of formula (I-a-1) to formula (I-a-4), formula (I-a-7) to formula (I-a-11), formula (I-a-14) to formula (I-a-30) and formula (I-a-35) to formula (I-a-40) with a cation represented by any one of formula (I-c-1) to formula (I-c-79), and specifically, the salt (I) preferably includes salt (I-1) to salt (I-4), salt (I-7) to salt (I-11), salt (I-14) to salt (I-30), salt (I-35) to salt (1-38), salt (I-39) to salt (1-42), salt (I-45) to salt (1-49), salt (I-52) to salt (1-68), salt (I-73) to salt (1-76), salt (I-77) to salt (1-80), salt (I-83) to salt (I-87), salt (I-90) to salt (1-106), salt (I-111) to salt (I-114), salt (I-115) to salt (I-118), salt (I-121) to salt (I-125), salt (I-128) to salt (I-144), salt (I-149) to salt (I-152), salt (I-153) to salt (1-156), salt (I-159) to salt (I-163), salt (I-166) to salt (I-182), salt (I-187) to salt (I-190), salt (I-191) to salt (I-194), salt (I-197) to salt (I-201), salt (I-204) to salt (I-220), salt (I-225) to salt (I-228), salt (I-229) to salt (I-232), salt (I-235) to salt (I-239), salt (I-242) to salt (I-258), salt (I-263) to salt (I-266), salt (I-267) to salt (I-270), salt (I-273) to salt (I-277), salt (I-280) to salt (I-296), salt (I-301) to salt (I-304), salt (I-305) to salt (I-308), salt (I-311) to salt (I-315), salt (I-318) to salt (I-334), salt (I-339) to salt (I-342), salt (I-343) to salt (1-346), salt (I-349) to salt (I-353), salt (I-356) to salt (1-372), salt (I-377) to salt (I-380), salt (I-381) to salt (I-384), salt (I-387) to salt (I-391), salt (I-394) to salt (I-410), salt (I-415) to salt (I-418), salt (I-419) to salt (1-422), salt (I-425) to salt (I-429), salt (I-432) to salt (1-448), salt (I-453) to salt (I-456), salt (I-457) to salt (I-460), salt (I-463) to salt (I-467), salt (I-470) to salt (I-486), salt (I-491) to salt (I-494), salt (I-495) to salt (I-498), salt (I-501) to salt (I-505), salt (I-508) to salt (I-524), salt (I-529) to salt (I-532), salt (I-533) to salt (I-536), salt (I-539) to salt (I-543), salt (I-546) to salt (I-562), salt (I-567) to salt (I-570), salt (I-571) to salt (I-574), salt (I-577) to salt (I-581), salt (I-584) to salt (I-600), salt (I-605) to salt (I-608), salt (I-609) to salt (I-612), salt (I-615) to salt (I-619), salt (I-622) to salt (I-638), salt (I-643) to salt (I-646), salt (I-647) to salt (I-650), salt (I-653) to salt (I-657), salt (I-660) to salt (I-676), salt (I-681) to salt (I-684), salt (I-685) to salt (I-688), salt (I-691) to salt (I-695), salt (I-698) to salt (I-714), salt (I-719) to salt (I-722), salt (I-723) to salt (I-726), salt (I-729) to salt (I-733), salt (I-736) to salt (I-752), salt (I-757) to salt (I-760), salt (I-761) to salt (I-764), salt (I-767) to salt (I-771), salt (I-774) to salt (I-790), salt (I-795) to salt (I-798), salt (I-799) to salt (I-802), salt (I-805) to salt (I-809), salt (I-812) to salt (I-828), salt (I-833) to salt (I-836), salt (I-837) to salt (I-840), salt (I-843) to salt (I-847), salt (I-850) to salt (I-866), salt (I-871) to salt (I-874), salt (I-875) to salt (I-878), salt (I-881) to salt (I-885), salt (I-888) to salt (I-904), salt (I-909) to salt (I-912), salt (I-913) to salt (I-916), salt (I-919) to salt (I-923), salt (I-926) to salt (1-942), salt (I-947) to salt (I-950), salt (I-951) to salt (I-954), salt (I-957) to salt (I-961), salt (I-964) to salt (I-980), salt (I-985) to salt (I-988), salt (I-989) to salt (1-992), salt (I-995) to salt (I-999), salt (I-1002) to salt (I-1018), salt (I-1023) to salt (I-1026), salt (I-1027) to salt (I-1030), salt (I-1033) to salt (I-1037), salt (I-1040) to salt (I-1056), salt (I-1061) to salt (I-1064), salt (I-1065) to salt (I-1068), salt (I-1071) to salt (I-1075), salt (I-1078) to salt (I-1094), salt (I-1099) to salt (I-1102), salt (I-1103) to salt (I-1106), salt (I-1109) to salt (I-1113), salt (I-1116) to salt (I-1132), salt (I-1137) to salt (I-1140), salt (I-1141) to salt (I-1144), salt (I-1147) to salt (I-1151), salt (I-1154) to salt (1-1170), salt (I-1175) to salt (1-1178), salt (I-1179) to salt (I-1182), salt (I-1185) to salt (I-1189), salt (I-1192) to salt (I-1208), salt (I-1213) to salt (I-1216), salt (I-1217) to salt (I-1220), salt (I-1223) to salt (I-1227), salt (I-1230) to salt (1-1246), salt (I-1251) to salt (I-1254), salt (I-1255) to salt (I-1258), salt (I-1261) to salt (I-1265), salt (I-1268) to salt (I-1284), salt (I-1289) to salt (I-1292), salt (I-1293) to salt (I-1296), salt (I-1299) to salt (I-1303), salt (I-1306) to salt (I-1322), salt (I-1327) to salt (I-1330), salt (I-1331) to salt (I-1334), salt (I-1337) to salt (I-1341), salt (I-1344) to salt (I-1360), salt (I-1365) to salt (1-1368), salt (I-1369) to salt (I-1372), salt (I-1375) to salt (I-1379), salt (I-1382) to salt (I-1398), salt (I-1403) to salt (I-1406), salt (I-1407) to salt (I-1410), salt (I-1413) to salt (I-1417), salt (I-1420) to salt (I-1436), salt (I-1441) to salt (I-1444), salt (I-1445) to salt (I-1448), salt (I-1451) to salt (I-1455), salt (I-1458) to salt (I-1474), salt (I-1479) to salt (I-1482), salt (I-1483) to salt (I-1486), salt (I-1489) to salt (I-1493), salt (I-1496) to salt (I-1512), salt (I-1517) to salt (I-1520), salt (I-1521) to salt (I-1524), salt (I-1527) to salt (I-1531), salt (I-1534) to salt (I-1550), salt (I-1555) to salt (I-1558), salt (I-1559) to salt (I-1562), salt (I-1565) to salt (I-1569), salt (I-1572) to salt (I-1588), salt (I-1593) to salt (I-1596), salt (I-1597) to salt (I-1600), salt (I-1603) to salt (I-1607), salt (I-1610) to salt (I-1626), salt (I-1631) to salt (I-1634), salt (I-1635) to salt (I-1638), salt (I-1641) to salt (I-1645), salt (I-1648) to salt (I-1664), salt (I-1669) to salt (I-1672), salt (I-1673) to salt (1-1676), salt (I-1679) to salt (1-1683), salt (I-1686) to salt (I-1702), salt (I-1707) to salt (I-1710), salt (I-1711) to salt (I-1714), salt (I-1717) to salt (I-1721), salt (I-1724) to salt (I-1740), salt (I-1745) to salt (I-1748), salt (I-1749) to salt (I-1752), salt (I-1755) to salt (I-1759), salt (I-1762) to salt (I-1778), salt (I-1783) to salt (I-1786), salt (I-1787) to salt (I-1790), salt (I-1793) to salt (I-1797), salt (I-1800) to salt (I-1816), salt (I-1821) to salt (I-1824), salt (I-1825) to salt (I-1828), salt (I-1831) to salt (I-1835), salt (I-1838) to salt (I-1854), salt (I-1859) to salt (1-1862), salt (I-1863) to salt (I-1866), salt (I-1869) to salt (I-1873), salt (I-1876) to salt (I-1892), salt (I-1897) to salt (I-1900), salt (I-1901) to salt (I-1904), salt (I-1907) to salt (I-1911), salt (I-1914) to salt (1-1930), salt (I-1935) to salt (1-1938), salt (I-1939) to salt (I-1942), salt (I-1945) to salt (I-1949), salt (I-1952) to salt (I-1968), salt (I-1973) to salt (I-1976), salt (I-1977) to salt (I-1980), salt (I-1983) to salt (I-1987), salt (I-1990) to salt (I-2006), salt (I-2011) to salt (I-2014), salt (I-2015) to salt (I-2018), salt (I-2021) to salt (I-2025), salt (I-2028) to salt (I-2044), salt (I-2049) to salt (I-2052), salt (I-2053) to salt (I-2056), salt (I-2059) to salt (I-2063), salt (I-2066) to salt (I-2082), salt (I-2087) to salt (I-2090), salt (I-2091) to salt (I-2094), salt (I-2097) to salt (I-2101), salt (I-2104) to salt (I-2120), salt (I-2125) to salt (I-2128), salt (I-2129) to salt (I-2132), salt (I-2135) to salt (I-2139), salt (I-2142) to salt (I-2158), salt (I-2163) to salt (I-2166), salt (I-2167) to salt (I-2170), salt (I-2173) to salt (I-2177), salt (I-2180) to salt (I-2196), salt (I-2201) to salt (I-2204), salt (I-2205) to salt (I-2208), salt (I-2211) to salt (1-2215), salt (I-2218) to salt (I-2234), salt (I-2239) to salt (I-2242), salt (I-2243) to salt (I-2246), salt (I-2249) to salt (I-2253), salt (I-2256) to salt (I-2272), salt (I-2277) to salt (I-2280), salt (I-2281) to salt (I-2284), salt (I-2287) to salt (I-2291), salt (I-2294) to salt (I-2310), salt (I-2315) to salt (I-2318), salt (I-2319) to salt (I-2322), salt (I-2325) to salt (I-2329), salt (I-2332) to salt (I-2348), salt (I-2353) to salt (I-2356), salt (I-2357) to salt (I-2360), salt (I-2363) to salt (I-2367), salt (I-2370) to salt (I-2386), salt (I-2391) to salt (I-2394), salt (I-2395) to salt (1-2398), salt (I-2401) to salt (1-2405), salt (I-2408) to salt (I-2424), salt (I-2429) to salt (I-2432), salt (I-2433) to salt (I-2436), salt (I-2439) to salt (I-2443), salt (I-2446) to salt (I-2462), salt (I-2467) to salt (I-2470), salt (I-2471) to salt (I-2474), salt (I-2477) to salt (I-2481), salt (I-2484) to salt (I-2500), salt (I-2505) to salt (I-2508), salt (I-2509) to salt (I-2512), salt (I-2515) to salt (I-2519), salt (I-2522) to salt (I-2538), salt (I-2543) to salt (I-2546), salt (I-2547) to salt (I-2550), salt (I-2553) to salt (I-2557), salt (I-2560) to salt (I-2576), salt (I-2581) to salt (I-2584), salt (I-2585) to salt (I-2588), salt (I-2591) to salt (I-2595), salt (I-2598) to salt (I-2614), salt (I-2619) to salt (I-2622), salt (I-2623) to salt (1-2626), salt (I-2629) to salt (1-2633), salt (I-2636) to salt (I-2652), salt (I-2657) to salt (I-2660), salt (I-2661) to salt (I-2664), salt (I-2667) to salt (I-2671), salt (I-2674) to salt (I-2690), salt (I-2695) to salt (I-2698), salt (I-2699) to salt (1-2702), salt (I-2705) to salt (1-2709), salt (I-2712) to salt (I-2728), salt (I-2733) to salt (I-2736), salt (I-2737) to salt (I-2740), salt (I-2743) to salt (I-2747), salt (I-2750) to salt (I-2766), salt (I-2771) to salt (I-2774), salt (I-2775) to salt (I-2778), salt (I-2781) to salt (I-2785), salt (I-2788) to salt (I-2804), salt (I-2809) to salt (I-2812), salt (I-2813) to salt (I-2816), salt (I-2819) to salt (1-2823), salt (I-2826) to salt (1-2842), salt (I-2847) to salt (I-2850), salt (I-2851) to salt (I-2854), salt (I-2857) to salt (I-2861), salt (I-2864) to salt (1-2880), salt (I-2885) to salt (1-2888), salt (I-2889) to salt (I-2892), salt (I-2895) to salt (I-2899), salt (I-2902) to salt (I-2918), salt (I-2923) to salt (I-2926), salt (I-2927) to salt (I-2930), salt (I-2933) to salt (I-2937), salt (I-2940) to salt (I-2956), salt (I-2961) to salt (I-2964), salt (I-2965) to salt (I-2968), salt (I-2971) to salt (I-2975), salt (I-2978) to salt (I-2994), salt (I-2999) to salt (I-3002) and salt (I-3003) to salt (I-3160).

<Method for Producing Salt (I)>

The salt (I) can be produced by reacting a salt represented by formula (I-a) with a salt represented by formula (I-b) in a solvent:

wherein all symbols are the same as defined above, $R^A$, $R^B$ and $R^C$ each independently represent a hydrocarbon group having 1 to 12 carbon atoms, or $R^A$, $R^B$ and $R^C$ may combine together to form an aromatic ring, and $R^D$ represents a hydrogen atom or a hydrocarbon group having 1 to 12 carbon atoms.

Examples of the solvent include chloroform, monochlorobenzene, acetonitrile, water and the like.

The reaction temperature is usually 15° C. to 80° C., and the reaction time is usually 0.5 to 24 hours.

Examples of the salt represented by formula (I-b) include salts represented by the following formulas. These salts can be easily produced by the methods mentioned in JP 2011-116747 A and JP 2016-047815 A, or a known production method.

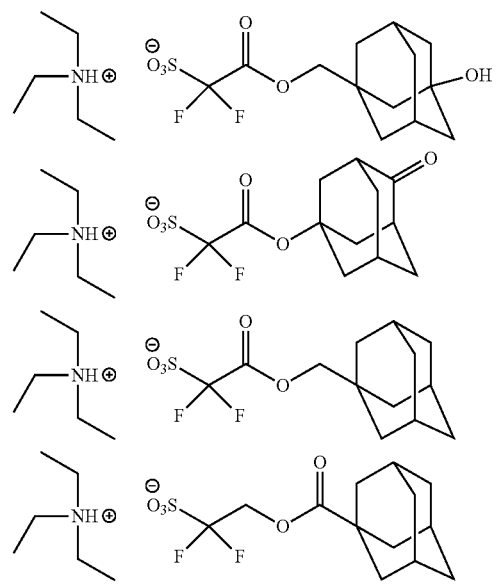

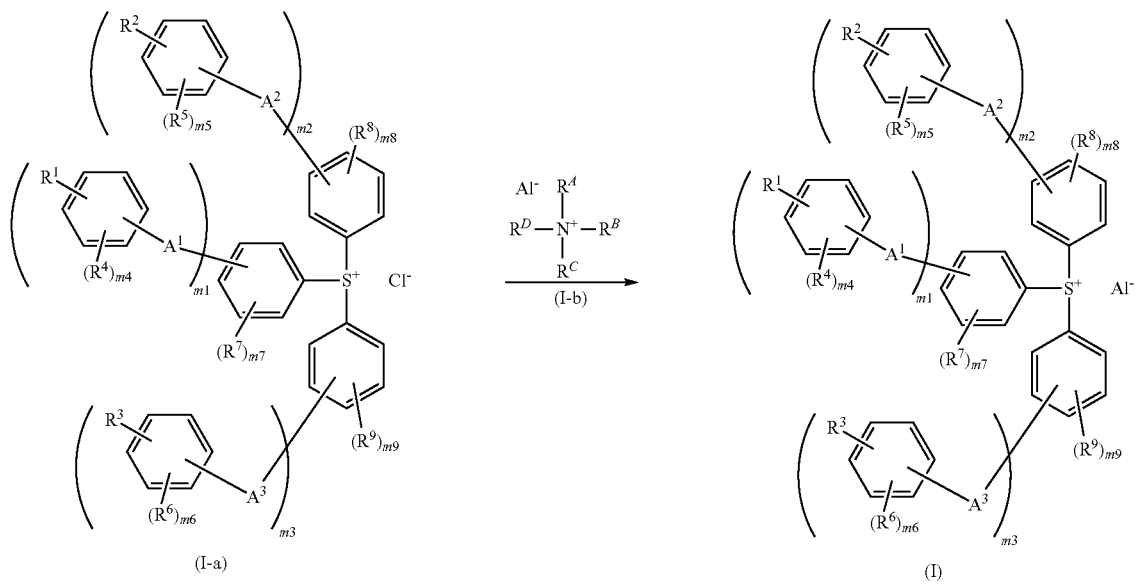

(I-a)

(I)

109
-continued
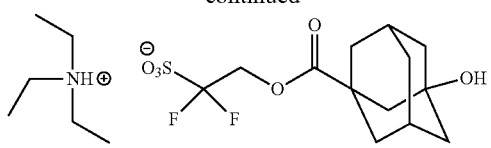
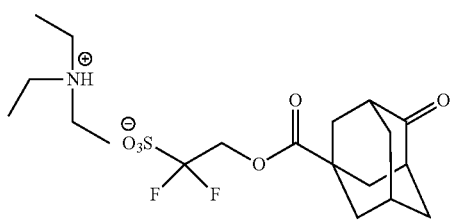
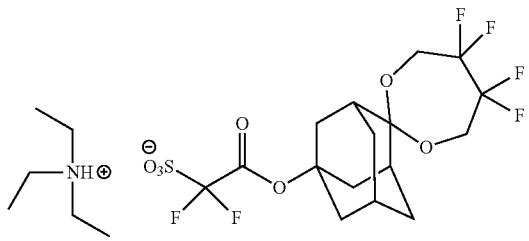
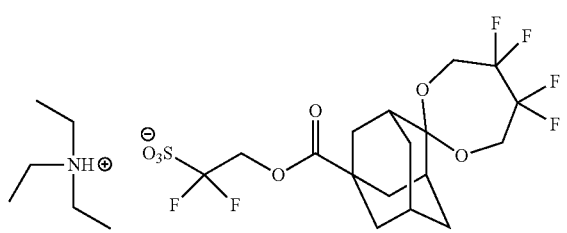
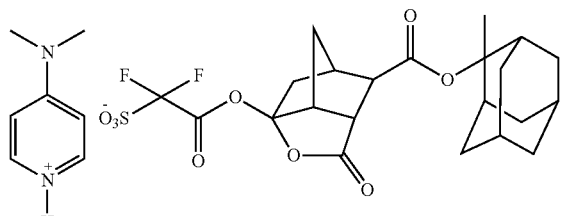
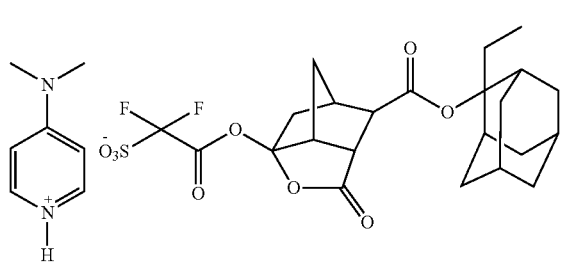
110
-continued
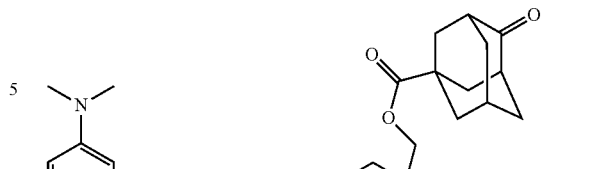
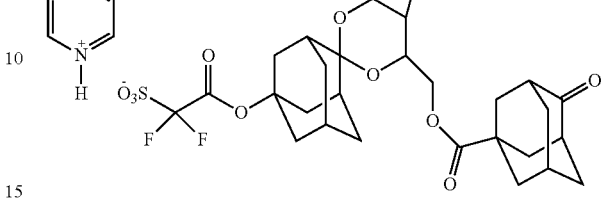
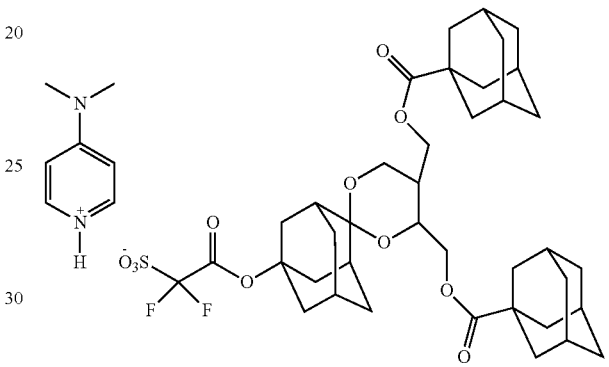
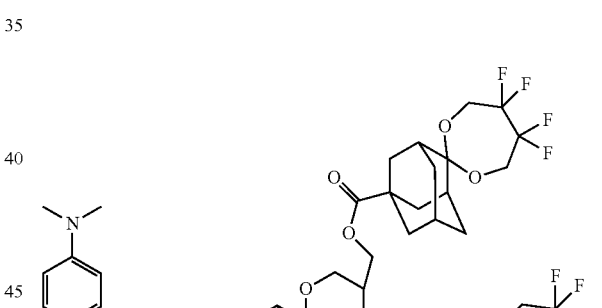
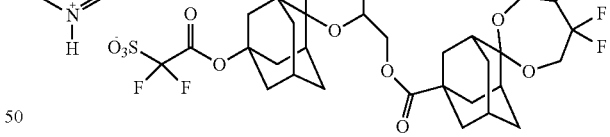
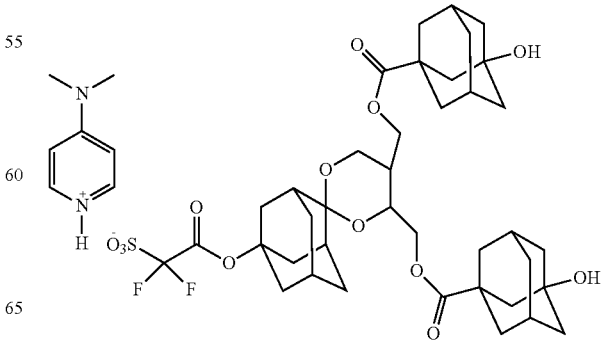

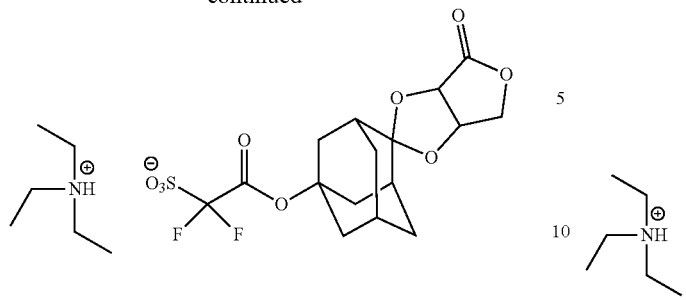
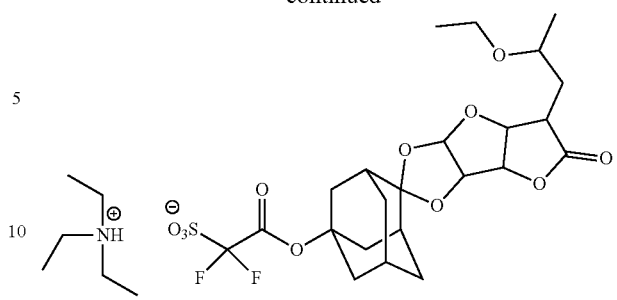
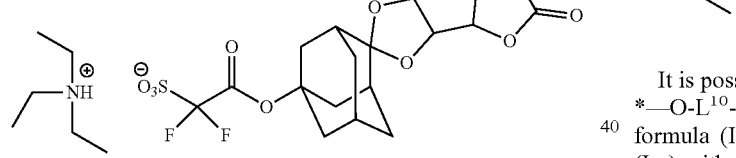
It is possible to produce a salt in which $R^1$, $R^2$ and $R^3$ are *—O-$L^{10}$-CO—O—$R^{10}$ in the salt (I-a) (salt represented by formula (I-a1)) by reacting a salt represented by formula (I-c) with a compound represented by formula (I-d) in the presence of a base catalyst in a solvent:
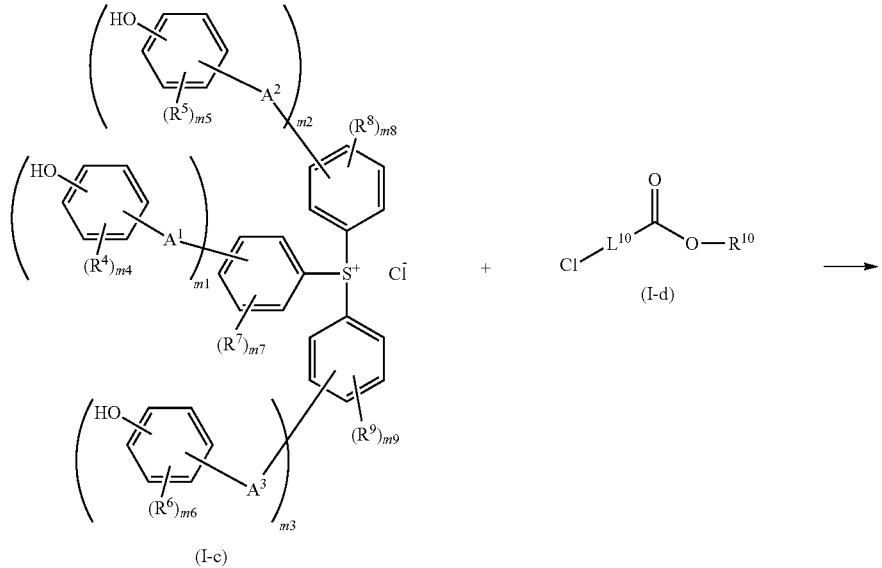

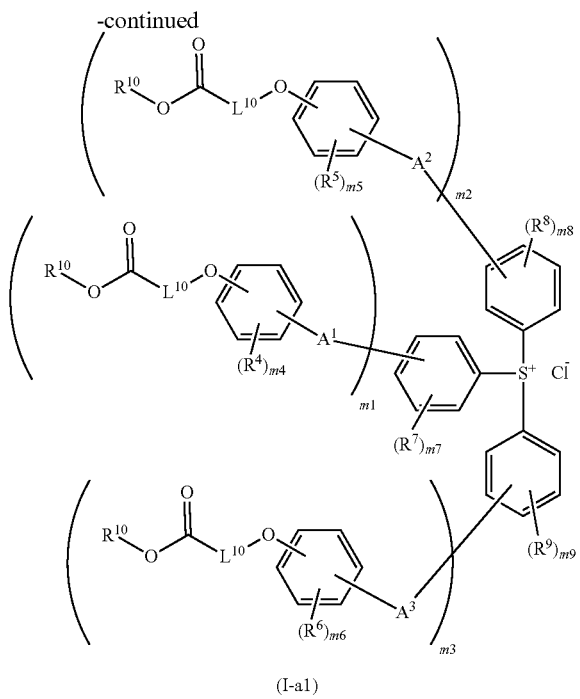

(I-a1)

wherein all symbols are the same as defined above.

Examples of the base include potassium carbonate, potassium iodide, pyridine, triethylamine and the like.

Examples of the solvent include chloroform, monochlorobenzene, dimethylformamide, acetonitrile, ethyl acetate, water and the like.

The reaction temperature is usually 15° C. to 80° C., and the reaction time is usually 0.5 to 24 hours.

Examples of the compound represented by formula (I-d) include compounds represented by the following formulas, which are easily available on the market and also can be easily produced by a known production method.

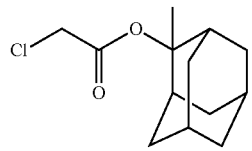

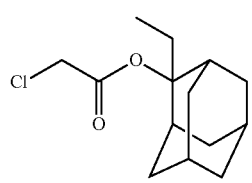

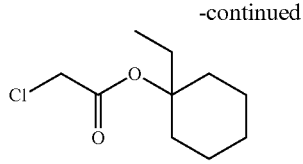

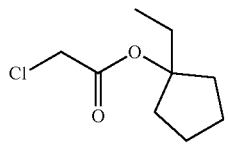

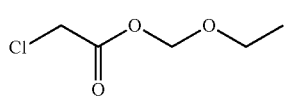

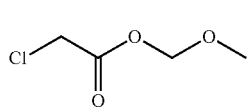

It is possible to produce a salt represented by formula (I-c) by reacting a salt represented by formula (I-e), a compound represented by formula (I-f1), a compound represented by formula (I-f2) and a compound represented by formula (I-f3) in the presence of a catalyst in a solvent:

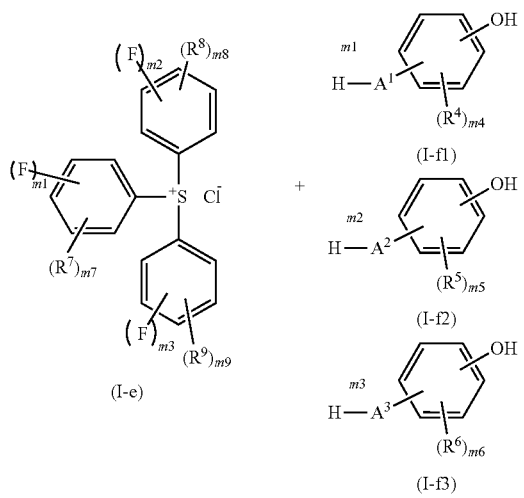

(I-e)  +  (I-f1) (I-f2) (I-f3)  →  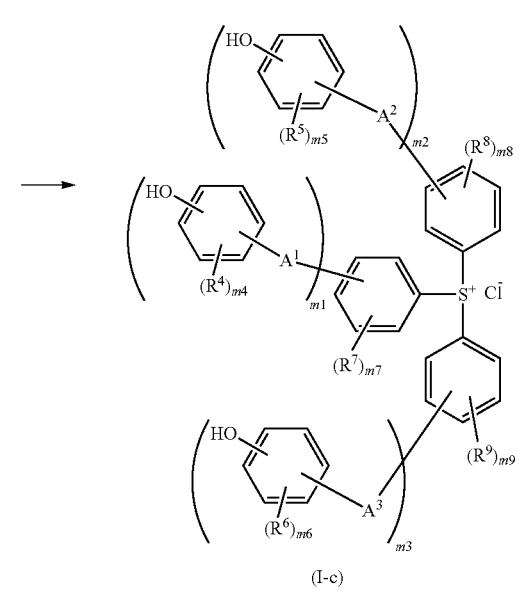

(I-c)

wherein all symbols are the same as defined above.

Examples of the catalyst include potassium carbonate, sodium hydride and the like.

Examples of the solvent include chloroform, monochlorobenzene, acetonitrile, water and the like.

The reaction temperature is usually 15° C. to 100° C., and the reaction time is usually 0.5 to 24 hours.

Examples of the salt represented by formula (I-e) include salts represented by the following formulas, which are easily available on the market.

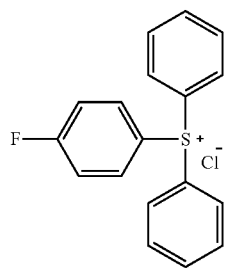

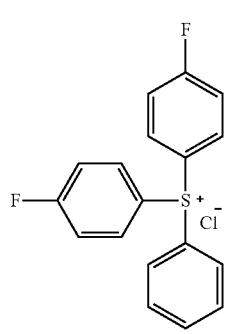

-continued

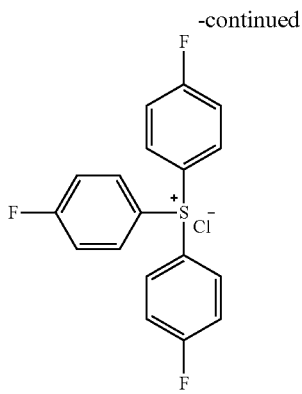

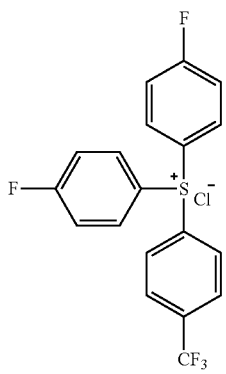

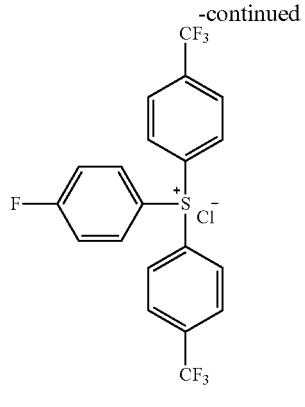

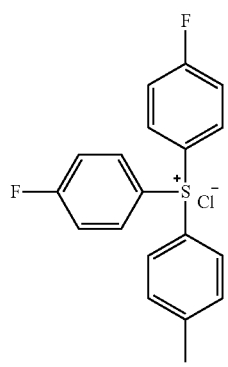

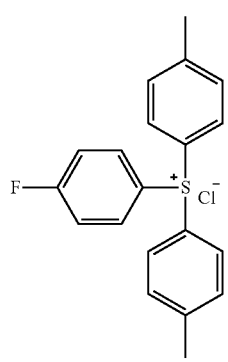

Examples of the compound represented by formula (I-f1), the compound represented by formula (I-f2) and the compound represented by formula (I-f3) include compounds represented by the following formulas, which are easily available on the market.

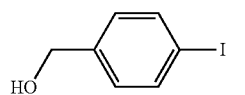 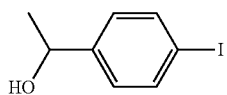

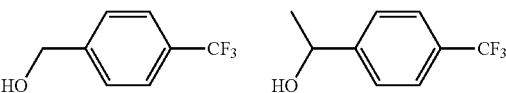

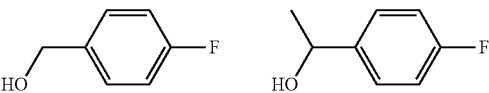

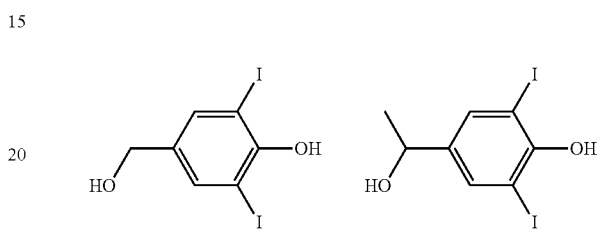

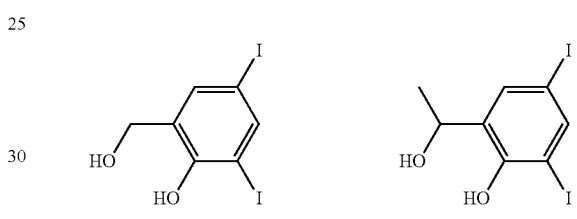

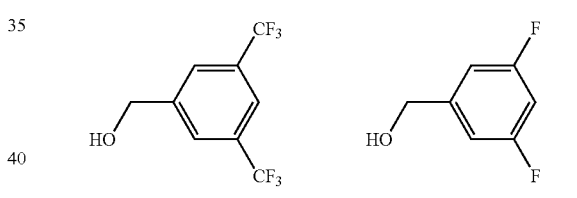

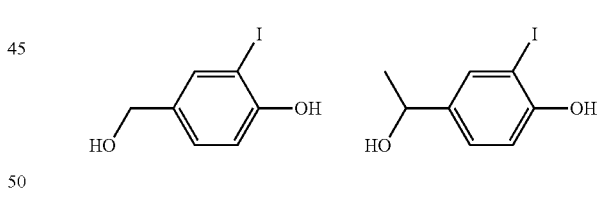

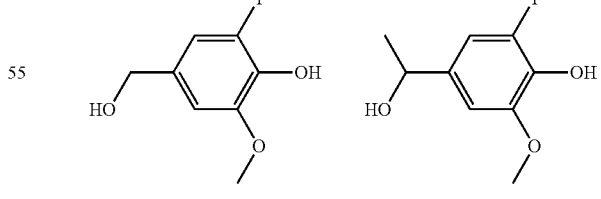

It is also possible to produce the salt represented by formula (I-c) by reacting a salt represented by formula (I-e), a compound represented by formula (I-f4), a compound represented by formula (I-f5) and a compound represented by formula (I-f6) in the presence of potassium carbonate in a solvent, followed by subjecting to an acid treatment:

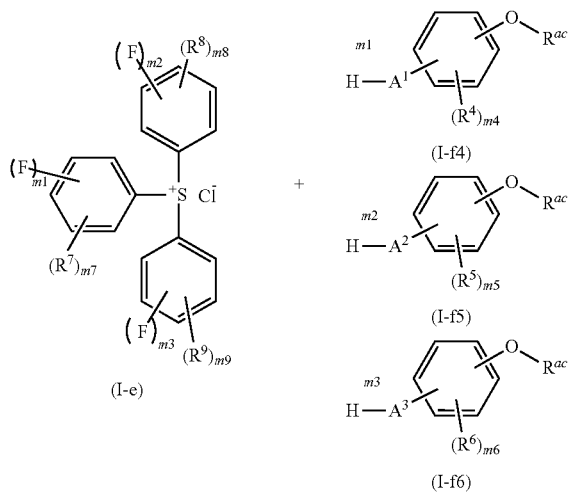

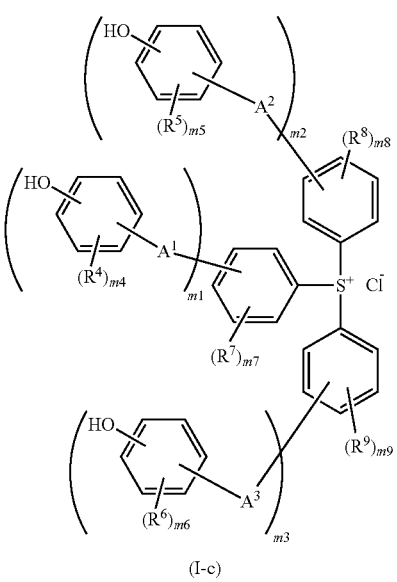

wherein all symbols are the same as defined above, and
$R^{ac}$ represents an acid-labile group.

Examples of the solvent include chloroform, monochlorobenzene, acetonitrile, water and the like.

The reaction temperature is usually 15° C. to 100° C., and the reaction time is usually 0.5 to 24 hours.

Examples of the acid include p-toluenesulfonic acid, hydrochloric acid and the like.

Examples of the compound represented by formula (I-f4), the compound represented by formula (I-f5) and the compound represented by formula (I-f6) include compounds represented by the following formulas, which are easily available on the market.

It is possible to produce a salt in which $R^1$, $R^2$ and $R^3$ are *—O—$R^{10}$ in the salt (I-a) (salt represented by formula (I-a2)) by reacting a salt represented by formula (I-c) with a compound represented by formula (I-d2) in the presence of a base catalyst in a solvent:

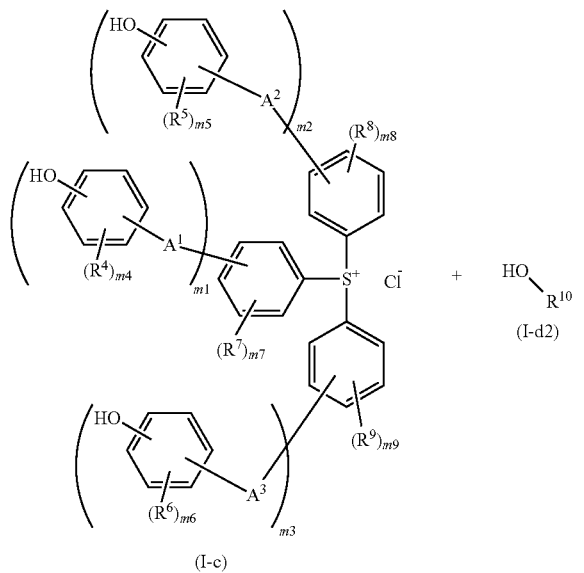

(I-c)

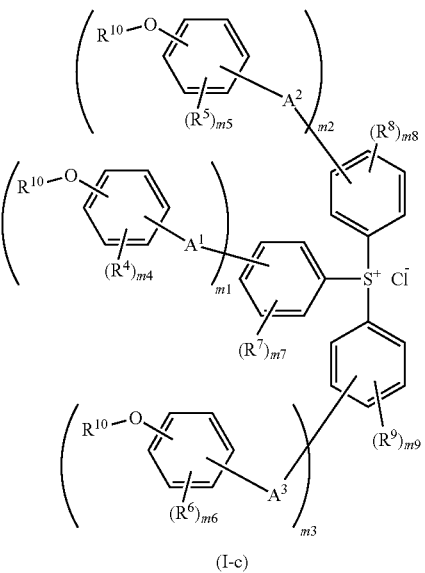

(I-c)

wherein all symbols are the same as defined above.

Examples of the base include sodium hydroxide, potassium hydroxide and the like.

Examples of the solvent include chloroform, monochlorobenzene, dimethylformamide, acetonitrile, ethyl acetate, water and the like.

The reaction temperature is usually 15° C. to 80° C., and the reaction time is usually 0.5 to 24 hours.

Examples of the compound represented by formula (I-d2) include compounds represented by the following formulas, which are easily available on the market and also can be easily produced by a known production method.

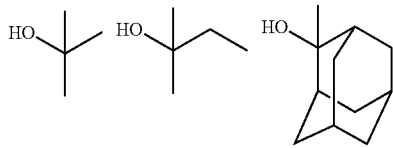

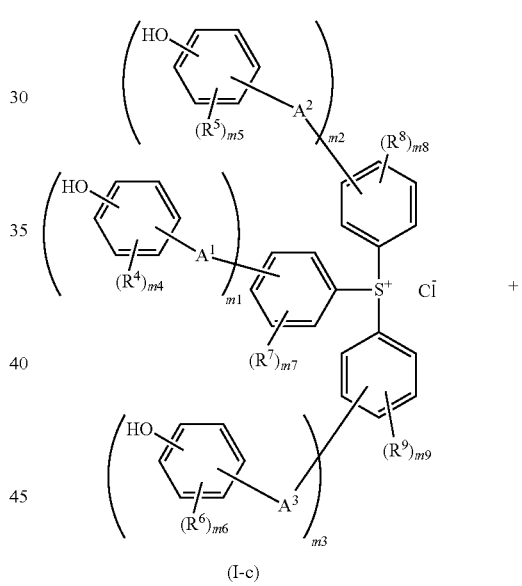

(I-c)

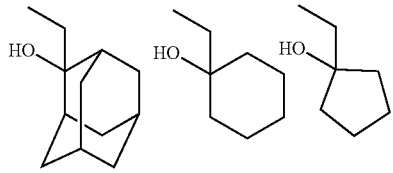

It is possible to produce a salt in which $R^1$, $R^2$ and $R^3$ are *—O—CO—O—$R^{10}$ in the salt (I-a) (salt represented by formula (I-a3)) by reacting a salt represented by formula (I-c) with a compound represented by formula (I-d2) in the presence of carbonyldiimidazole in a solvent:

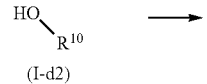

(I-d2)

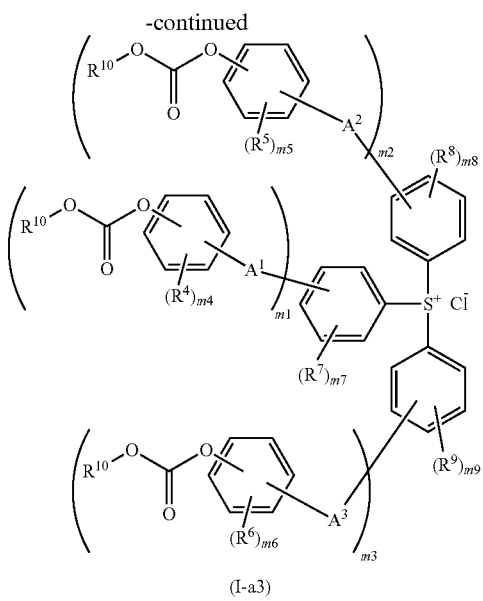

(I-a3)

wherein all symbols are the same as defined above.

Examples of the solvent include chloroform, monochlorobenzene, dimethylformamide, acetonitrile, ethyl acetate, water and the like.

The reaction temperature is usually 15° C. to 80° C., and the reaction time is usually 0.5 to 24 hours.

<Acid Generator>

The acid generator of the present invention is an acid generator comprising a salt (I). The acid generator may comprise the salt (I) alone, or two or more of the salts (I).

The acid generator of the present invention may comprise, in addition to the salt (I), an acid generator known in the resist field (hereinafter sometimes referred to as "acid generator (B)"). The acid generator (B) may be used alone, or two or more acid generators may be used in combination.

Either nonionic or ionic acid generator may be used as the acid generator (B). Examples of the nonionic acid generator include sulfonate esters (e.g., 2-nitrobenzyl ester, aromatic sulfonate, oxime sulfonate, N-sulfonyloxyimide, sulfonyloxyketone, diazonaphthoquinone 4-sulfonate), sulfones (e.g., disulfone, ketosulfone, sulfonyldiazomethane) and the like. Typical examples of the ionic acid generator include onium salts containing an onium cation (e.g., diazonium salt, phosphonium salt, sulfonium salt, iodonium salt). Examples of the anion of the onium salt include sulfonic acid anion, sulfonylimide anion, sulfonylmethide anion and the like.

Specific examples of the acid generator (B) include compounds generating an acid upon exposure to radiation mentioned in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712. Compounds produced by a known method may also be used. Two or more acid generators (B) may also be used in combination.

The acid generator (B) is preferably a salt represented by formula (B1) (hereinafter sometimes referred to as "acid generator (B1)", in which the salt (I) is excluded):

(B1)

wherein, in formula (B1), $Q^{b1}$ and $Q^{b2}$ each independently represent a hydrogen atom, a fluorine atom, an alkyl group having 1 to 6 carbon atoms or a perfluoroalkyl group having 1 to 6 carbon atoms, $L^{b1}$ represents a divalent saturated hydrocarbon group having 1 to 24 carbon atoms, —$CH_2$— included in the divalent saturated hydrocarbon group may be replaced by —O— or —CO—, and a hydrogen atom included in the divalent saturated hydrocarbon group may be substituted with a fluorine atom or a hydroxy group, Y represents a methyl group which may have a substituent, or an alicyclic hydrocarbon group having 3 to 24 carbon atoms which may have a substituent, and —$CH_2$— included in the alicyclic hydrocarbon group may be replaced by —O—, —S—, —$SO_2$— or —CO—, and Z1+ represents an organic cation.

Examples of $Q^{b1}$, $Q^{b2}$, $L^{b1}$ and Y in formula (B1) include those which are the same as the above-mentioned $Q^1$, $Q^2$, $L^1$ and $Y^1$ in formula (I-A).

Examples of the sulfonic acid anion in formula (B1) include those which are the same as the anion represented by formula (I-A).

Examples of the organic cation as for Z1+ include an organic onium cation, an organic sulfonium cation, an organic iodonium cation, an organic ammonium cation, a benzothiazolium cation and an organic phosphonium cation. Of these, an organic sulfonium cation and an organic iodonium cation are preferable, and an arylsulfonium cation is more preferable. Specific examples thereof include a cation represented by any one of formula (b2-1) to formula (b2-4) (hereinafter sometimes referred to as "cation (b2-1)" or the like according to the number of formula).

(b2-1)

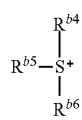

-continued

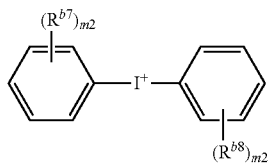

(b2-2)

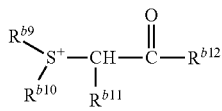

(b2-3)

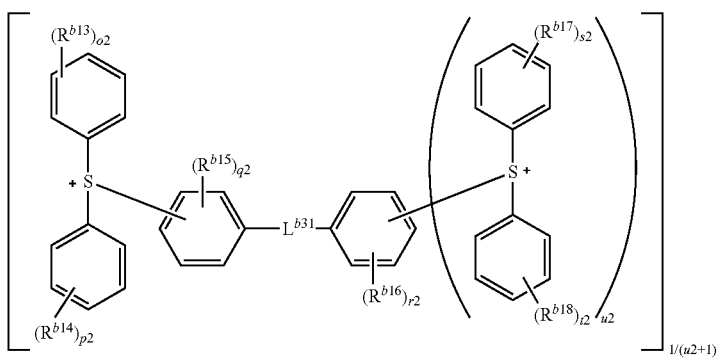

(b2-4)

In formula (b2-1) to formula (b2-4), $R^{b4}$ to $R^{b6}$ each independently represent a chain hydrocarbon group having 1 to 30 carbon atoms, an alicyclic hydrocarbon group having 3 to 36 carbon atoms or an aromatic hydrocarbon group having 6 to 36 carbon atoms, a hydrogen atom included in the chain hydrocarbon group may be substituted with a hydroxy group, an alkoxy group having 1 to 12 carbon atoms, an alicyclic hydrocarbon group having 3 to 12 carbon atoms or an aromatic hydrocarbon group having 6 to 18 carbon atoms, a hydrogen atom included in the alicyclic hydrocarbon group may be substituted with a halogen atom, an aliphatic hydrocarbon group having 1 to 18 carbon atoms, an alkylcarbonyl group having 2 to 4 carbon atoms or a glycidyloxy group, and a hydrogen atom included in the aromatic hydrocarbon group may be substituted with a halogen atom, a hydroxy group, an aliphatic hydrocarbon group having 1 to 18 carbon atoms, an alkyl fluoride group having 1 to 12 carbon atoms or an alkoxy group having 1 to 12 carbon atoms.

$R^{b4}$ and $R^{b5}$ may be bonded to each other to form a ring together with sulfur atoms to which $R^{b4}$ and $R^{b5}$ are bonded, and —CH$_2$— included in the ring may be replaced by —O—, —S— or —CO—, $R^{b7}$ and $R^{b8}$ each independently represent a halogen atom, a hydroxy group, an aliphatic hydrocarbon group having 1 to 12 carbon atoms, an alkyl fluoride group having 1 to 12 carbon atoms or an alkoxy group having 1 to 12 carbon atoms, m2 and n2 each independently represent an integer of 0 to 5, when m2 is 2 or more, a plurality of $R^{b7}$ may be the same or different, and when n2 is 2 or more, a plurality of $R^{b8}$ may be the same or different, $R^{b9}$ and $R^{b10}$ each independently represent a chain hydrocarbon group having 1 to 36 carbon atoms or an alicyclic hydrocarbon group having 3 to 36 carbon atoms, $R^{b9}$ and $R^{b10}$ may be bonded to each other to form a ring together with sulfur atoms to which $R^{b9}$ and $R^{b10}$ are bonded, and —CH$_2$— included in the ring may be replaced by —O—, —S— or —CO—, $R^{b11}$ represents a hydrogen atom, a chain hydrocarbon group having 1 to 36 carbon atoms, an alicyclic hydrocarbon group having 3 to 36 carbon atoms or an aromatic hydrocarbon group having 6 to 18 carbon atoms, $R^{b12}$ represents a chain hydrocarbon group having 1 to 12 carbon atoms, an alicyclic hydrocarbon group having 3 to 18 carbon atoms or an aromatic hydrocarbon group having 6 to 18 carbon atoms, a hydrogen atom included in the chain hydrocarbon group may be substituted with an aromatic hydrocarbon group having 6 to 18 carbon atoms, a hydrogen atom included in the aromatic hydrocarbon group may be substituted with an alkoxy group having 1 to 12 carbon atoms or an alkylcarbonyloxy group having 1 to 12 carbon atoms, $R^{b11}$ and $R^{b12}$ may be bonded to each other to form a ring, including —CH—CO— to which $R^{b11}$ and $R^{b12}$ are bonded, and —CH$_2$— included in the ring may be replaced by —O—, —S— or —CO—, $R^{b13}$ to $R^{b18}$ each independently represent a halogen atom, a hydroxy group, an aliphatic hydrocarbon group having 1 to 12 carbon atoms, an alkyl fluoride group having 1 to 12 carbon atoms or an alkoxy group having 1 to 12 carbon atoms, $R^{b13}$ and $R^{b14}$ may be bonded to each other to form a ring having a sulfur atom together with the benzene ring to which $R^{b13}$ and $R^{b14}$ are bonded, and —CH$_2$— included in the ring may be replaced by —O—, —S— or —CO—, $L^{b31}$ represents a sulfur atom or an oxygen atom, o2, p2, s2 and t2 each independently represent an integer of 0 to 5, q2 and r2 each independently represent an integer of 0 to 4, u2 represents 0 or 1, and when o2 is 2 or more, a plurality of $R^{b13}$ are the same or different, when p2 is 2 or more, a plurality of $R^{b14}$ are the same or different, when q2 is 2 or more, a plurality of $R^{b15}$ are the same or different, when r2 is 2 or more, a plurality of $R^{b16}$ are the same or different, when s2 is 2 or more, a plurality of $R^{b17}$ are the same or different, and when t2 is 2 or more, a plurality of $R^{b18}$ are the same or different.

When u2 is 0, any one of o2, p2, q2 and r2 is preferably 1 or more and at least one of $R^{b13}$ to $R^{b16}$ is preferably a halogen atom, and when u2 is 1, any one of o2, p2, s2, t2, q2 and r2 is preferably 1 or more and at least one of $R^{b13}$ to $R^{b18}$ is preferably a halogen atom.

Further, when u2 is 0, r2 is preferably 1 or more, and more preferably 1. When u2 is 0 and r2 is 1 or more, $R^{b16}$ is preferably a halogen atom.

The aliphatic hydrocarbon group represents a chain hydrocarbon group and an alicyclic hydrocarbon group.

Examples of the chain hydrocarbon group include alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Particularly, the chain hydrocarbon group of $R^{b9}$ to $R^{b12}$ preferably has 1 to 12 carbon atoms.

The alicyclic hydrocarbon group may be either monocyclic or polycyclic, and examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a decahydronaphthyl group, an adamantyl group, a norbornyl group and the following groups.

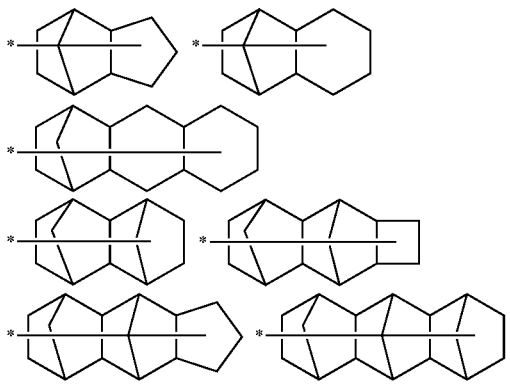

Particularly, the alicyclic hydrocarbon group of $R^{b9}$ to $R^{b12}$ preferably has 3 to 18 carbon atoms, and more preferably 4 to 12 carbon atoms.

Examples of the alicyclic hydrocarbon group in which a hydrogen atom is substituted with an aliphatic hydrocarbon group include a methylcyclohexyl group, a dimethylcyclohexyl group, a 2-methyladamantan-2-yl group, a 2-ethyladamantan-2-yl group, a 2-isopropyladamantan-2-yl group, a methylnorbornyl group, an isobornyl group and the like. In the alicyclic hydrocarbon group in which a hydrogen atom is substituted with an aliphatic hydrocarbon group, the total number of carbon atoms of the alicyclic hydrocarbon group and the aliphatic hydrocarbon group is preferably 20 or less.

The alkyl fluoride group represents an alkyl group having 1 to 12 carbon atoms which has a fluorine atom, and examples thereof include a fluoromethyl group, a difluoromethyl group, a trifluoromethyl group, a perfluorobutyl and the like. The number of carbon atoms of the alkyl fluoride group is preferably 1 to 9, more preferably 1 to 6, still more preferably 1 to 4.

Examples of the aromatic hydrocarbon group include aryl groups such as a phenyl group, a biphenyl group, a naphthyl group and a phenanthryl group. The aromatic hydrocarbon group may have a chain hydrocarbon group or an alicyclic hydrocarbon group, and it is possible to exemplify aromatic hydrocarbon groups which have a chain hydrocarbon group having 1 to 18 carbon atoms (a tolyl group, a xylyl group, a cumenyl group, a mesityl group, a p-ethylphenyl group, a p-tert-butylphenyl group, a 2,6-diethylphenyl group, a 2-methyl-6-ethylphenyl group, etc.) and aromatic hydrocarbon groups which have an alicyclic hydrocarbon group having 3 to 18 carbon atoms (a p-cyclohexylphenyl group, a p-adamantylphenyl group, etc.) and the like. When the aromatic hydrocarbon group has a chain hydrocarbon group or an alicyclic hydrocarbon group, a chain hydrocarbon group having 1 to 18 carbon atoms and an alicyclic hydrocarbon group having 3 to 18 carbon atoms are preferable.

Examples of the aromatic hydrocarbon group in which a hydrogen atom is substituted with an alkoxy group include a p-methoxyphenyl group and the like.

Examples of the chain hydrocarbon group in which a hydrogen atom is substituted with an aromatic hydrocarbon group include aralkyl groups such as a benzyl group, a phenethyl group, a phenylpropyl group, a trityl group, a naphthylmethyl group and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the alkylcarbonyl group include an acetyl group, a propionyl group and a butyryl group.

Examples of the halogen atom include a fluorine atom, a chlorine atom, a bromine atom and an iodine atom.

Examples of the alkylcarbonyloxy group include a methylcarbonyloxy group, an ethylcarbonyloxy group, a propylcarbonyloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

The ring formed by bonding $R^{b4}$ and $R^{b5}$ each other, together with sulfur atoms to which $R^{b4}$ and $R^{b5}$ are bonded, may be a monocyclic, polycyclic, aromatic, nonaromatic, saturated or unsaturated ring. This ring includes a ring having 3 to 18 carbon atoms and is preferably a ring having 4 to 18 carbon atoms. The ring having a sulfur atom includes a 3-membered to 12-membered ring and is preferably a 3-membered to 7-membered ring and includes, for example, the following rings and the like. * represents a bonding site.

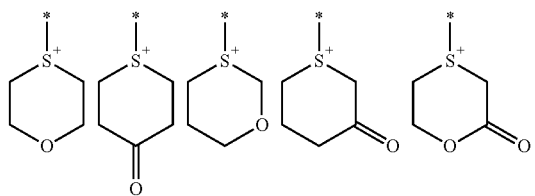

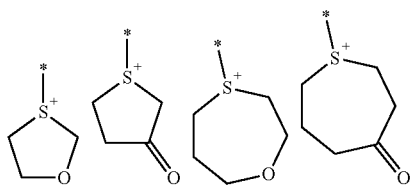

The ring formed by combining $R^{b9}$ and $R^{b10}$ together may be a monocyclic, polycyclic, aromatic, nonaromatic, saturated or unsaturated ring. This ring includes a 3-membered to 12-membered ring and is preferably a 3-membered to 7-membered ring. The ring includes, for example, a thiolan-1-ium ring (tetrahydrothiophenium ring), a thian-1-ium ring, a 1,4-oxathian-4-ium ring and the like.

The ring formed by combining $R^{b11}$ and $R^{b12}$ together may be a monocyclic, polycyclic, aromatic, nonaromatic, saturated or unsaturated ring. This ring includes a 3-membered to 12-membered ring and is preferably a 3-membered to 7-membered ring. Examples thereof include an oxocycloheptane ring, an oxocyclohexane ring, an oxonorbornane ring, an oxoadamantane ring and the like.

Of cation (b2-1) to cation (b2-4), a cation (b2-1) is preferable.

Examples of the cation (b2-1) include the following cations.

(b2-c-1)

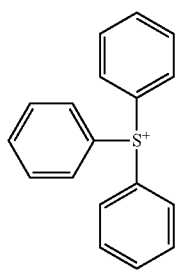

(b2-c-2)

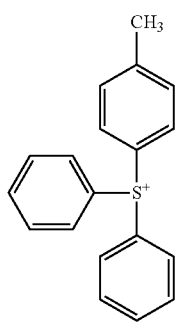

(b2-c-3)

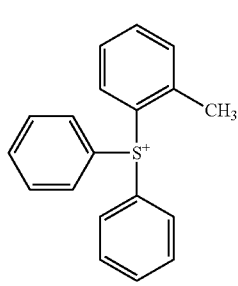

(b2-c-4)

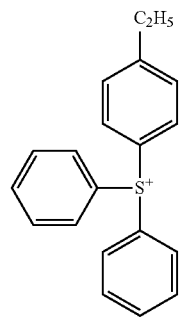

(b2-c-5)

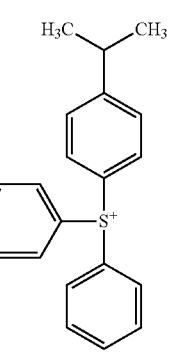

(b2-c-6)

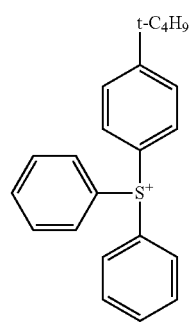

(b2-c-7)

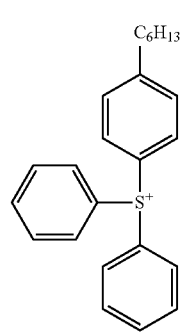

(b2-c-8)

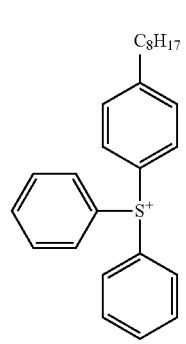

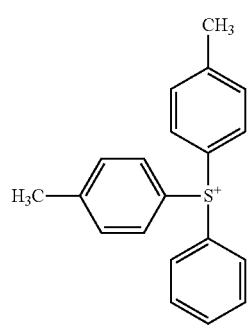
(b2-c-9)
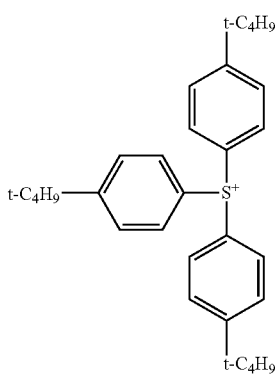
(b2-c-13)
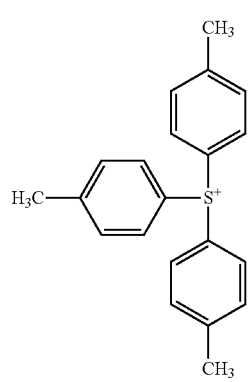
(b2-c-10)
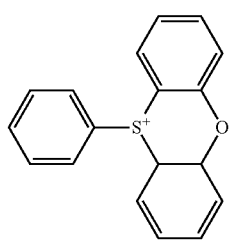
(b2-c-14)
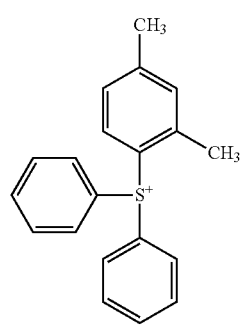
(b2-c-11)
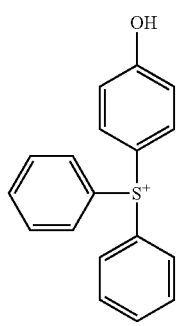
(b2-c-15)
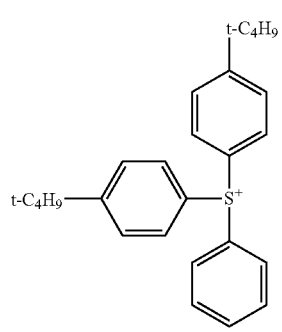
(b2-c-12)
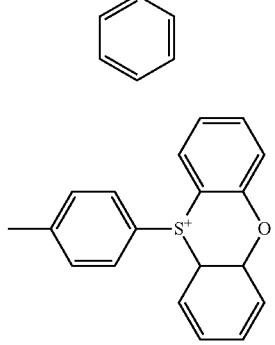
(b2-c-16)
(b2-c-17)

(b2-c-18)
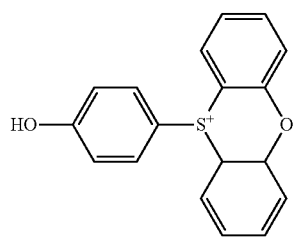
(b2-c-19)
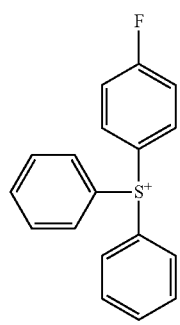
(b2-c-20)
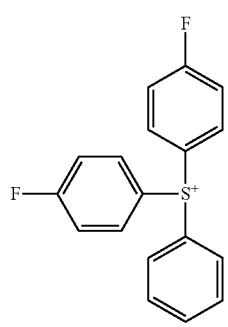
(b2-c-21)
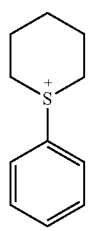
(b2-c-22)
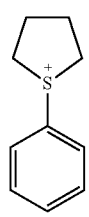
(b2-c-23)
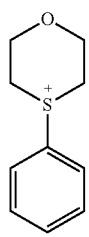
(b2-c-24)
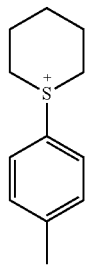
(b2-c-25)
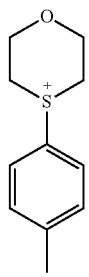
(b2-c-26)
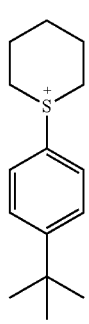
(b2-c-27)
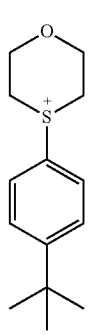
(b2-c-47)
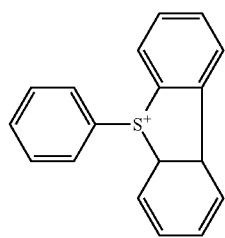

(b2-c-48)
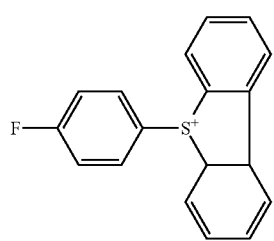
(b2-c-49)
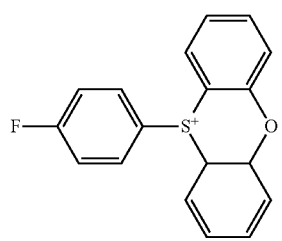
(b2-c-51)
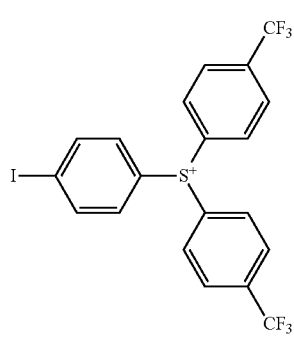
(b2-c-52)
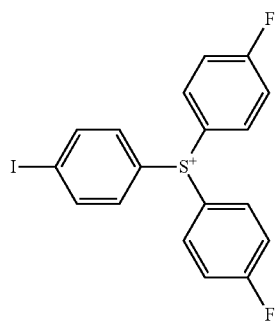
(b2-c-53)
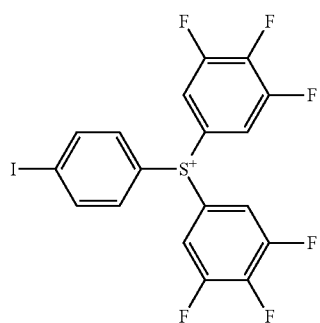
Examples of the cation (b2-2) include the following cations.
(b2-c-28)
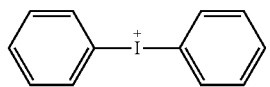
(b2-c-29)
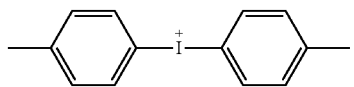
(b2-c-30)
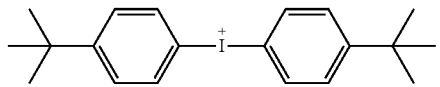
(b2-c-50)
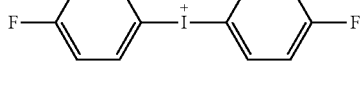
Examples of the cation (b2-3) include the following cations.
(b2-c-31)
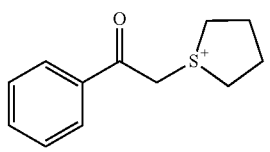
(b2-c-32)
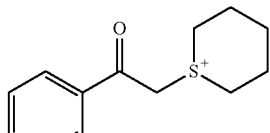
(b2-c-33)
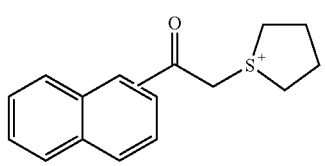
(b2-c-34)
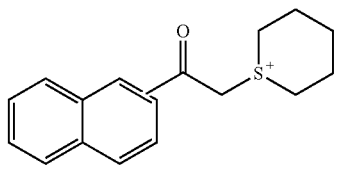
Examples of the cation (b2-4) include the following cations.
(b2-c-35)
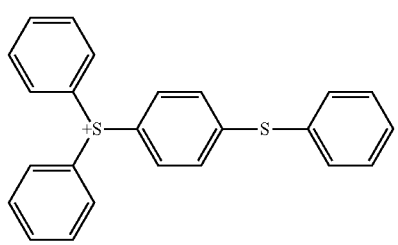

-continued
(c2-c-36)
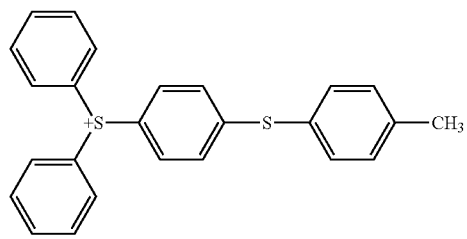
(b2-c-37)
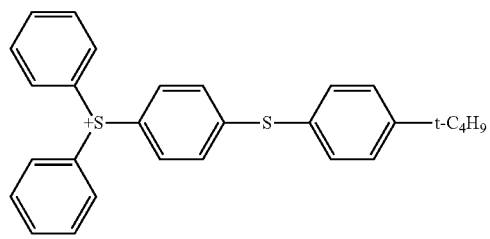
(b2-c-38)
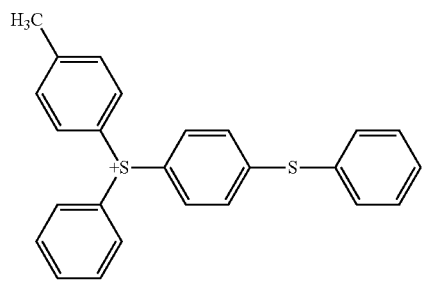
(b2-c-39)
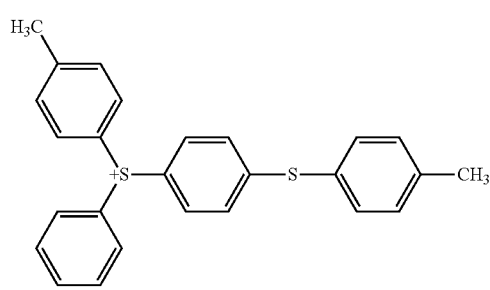
(b2-c-40)
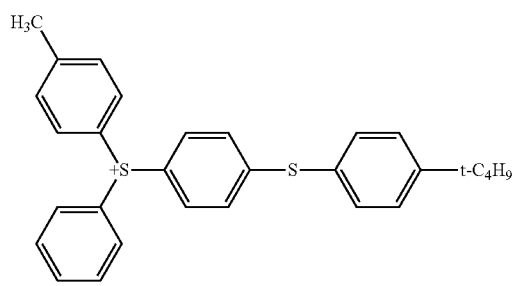
-continued
(b2-c-41)
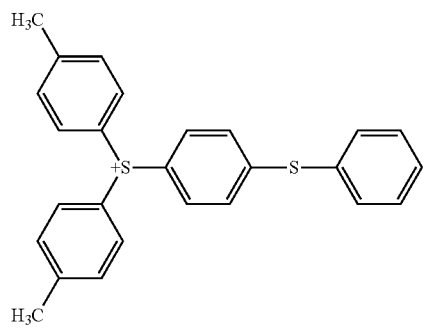
(b2-c-42)
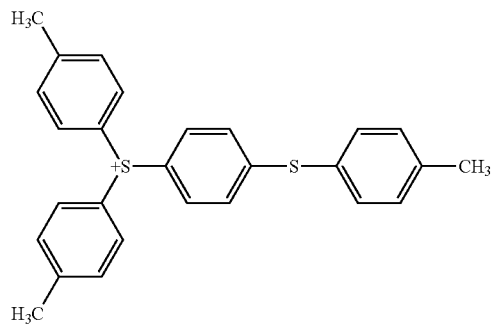
(b2-c-43)
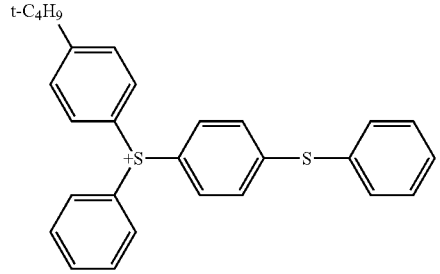
(b2-c-44)
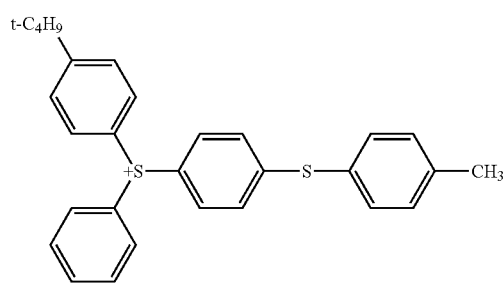
(b2-c-45)
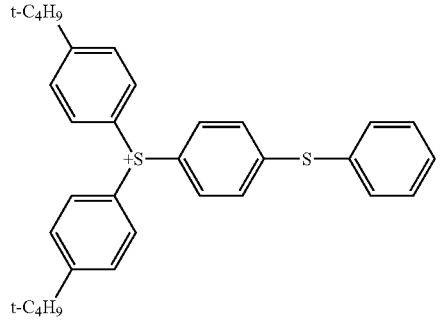

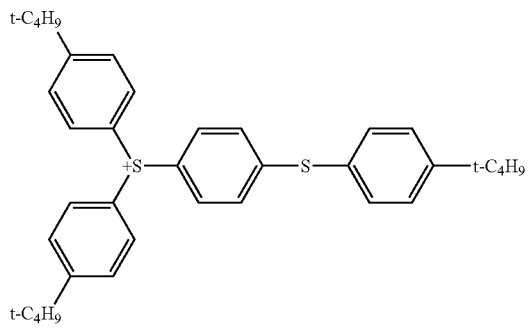
(b2-c-46)

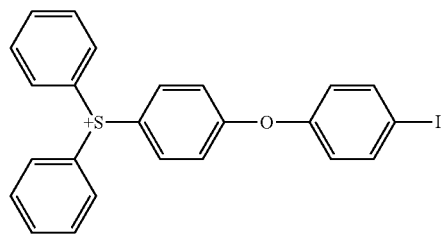
(b2-c-54)

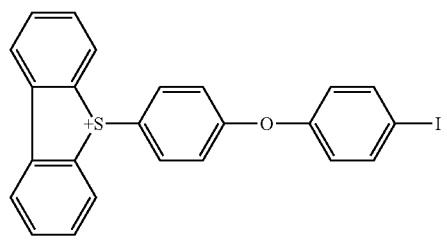
(b2-c-55)

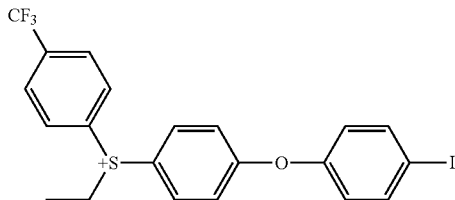
(b2-c-56)

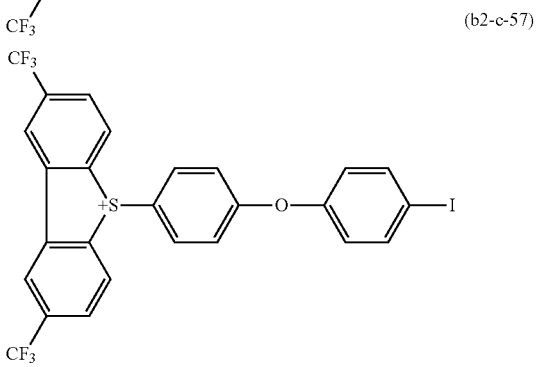
(b2-c-57)

The acid generator (B) is a combination of the anion mentioned above and the organic cation mentioned above, and these can be optionally combined. The acid generator (B) preferably includes a combination of an anion represented by any one of formula (I-a-1) to formula (I-a-3), formula (I-a-7) to formula (I-a-19) and formula (I-a-22) to formula (I-a-40) with a cation (b2-1), a cation (b2-2), a cation (b2-3) or a cation (b2-4).

The acid generator (B) preferably includes those represented by formula (B1-1) to formula (B1-60). Of these acid generators, those containing an arylsulfonium cation are preferable and those represented by formula (B1-1) to formula (B1-3), formula (B1-5) to formula (B1-7), formula (B1-11) to formula (B1-14), formula (B1-20) to formula (B1-26), formula (B1-29) and formula (B1-31) to formula (B1-60) are particularly preferable.

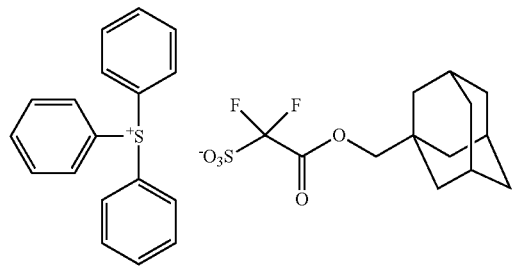
(B1-1)

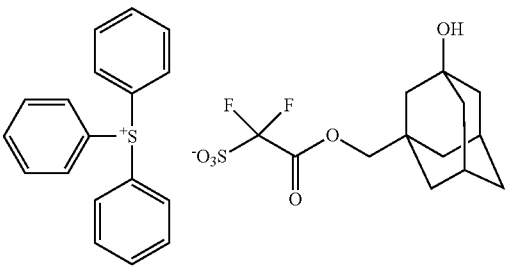
(B1-2)

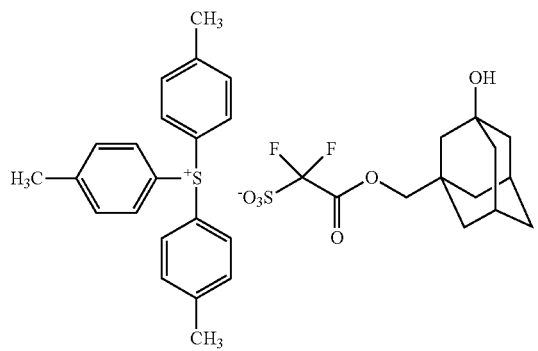
(B1-3)

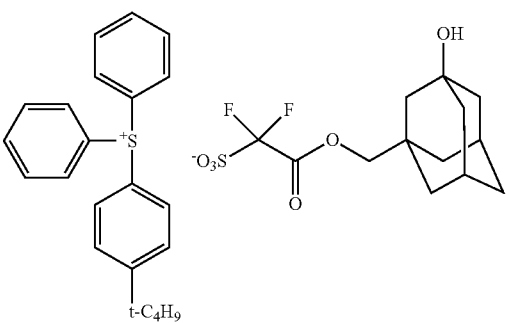
(B1-4)

-continued
(B1-5)
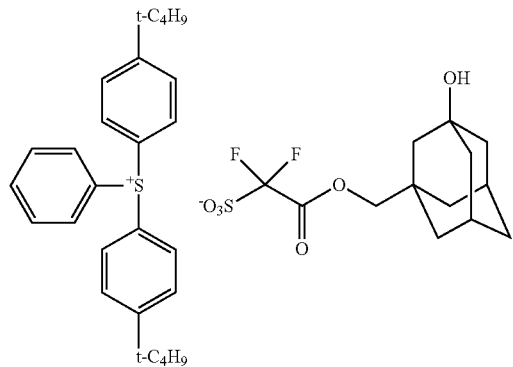
(B1-6)
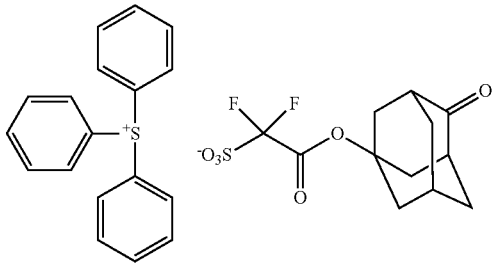
(B1-7)
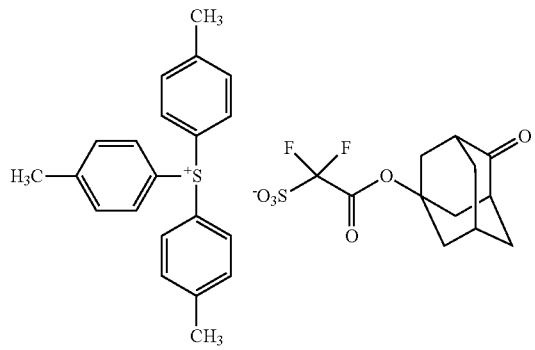
(B1-8)
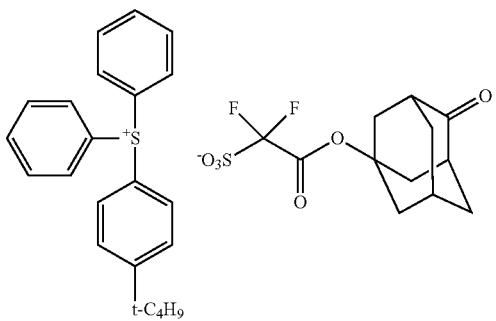
(B1-9)
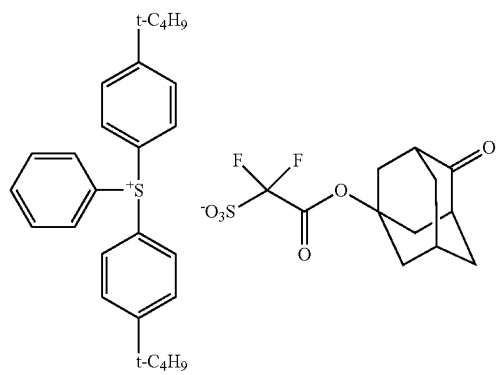
(B1-10)
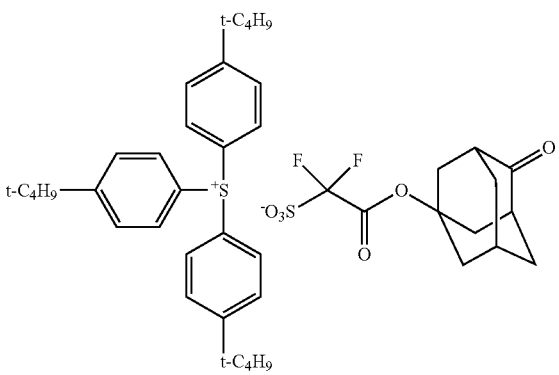
(B1-11)
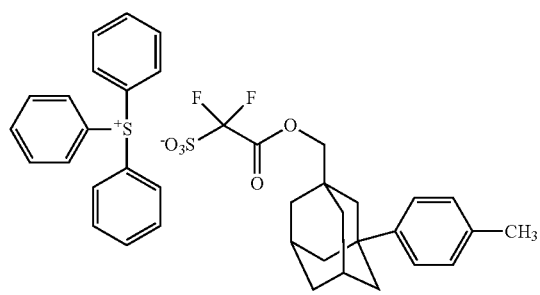
(B1-12)
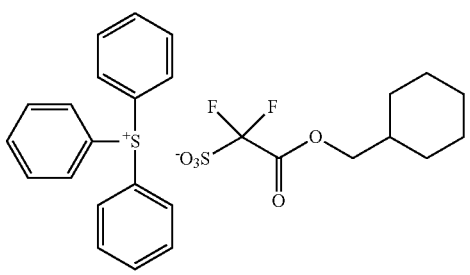

-continued
(B1-13)
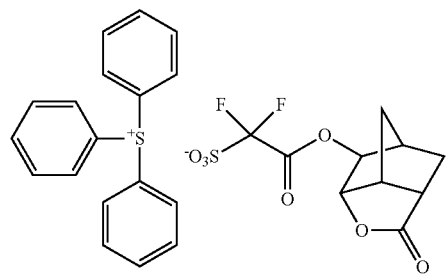
(B1-14)
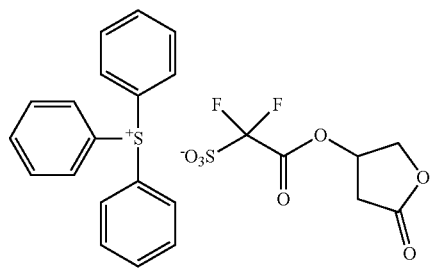
(B1-15)
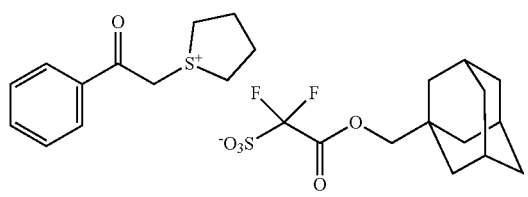
(B1-16)
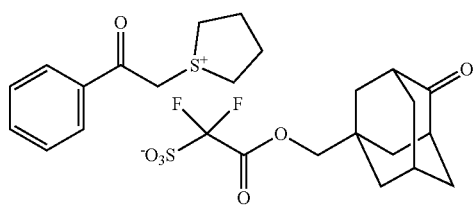
(B1-17)
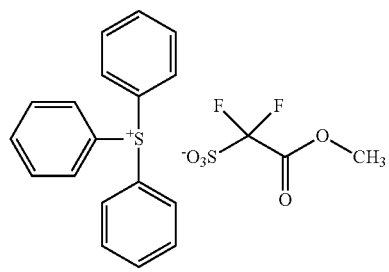
(B1-18)
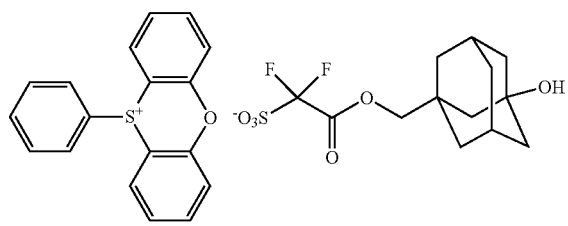
(B1-19)
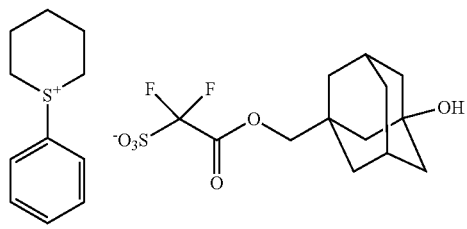
(B1-20)
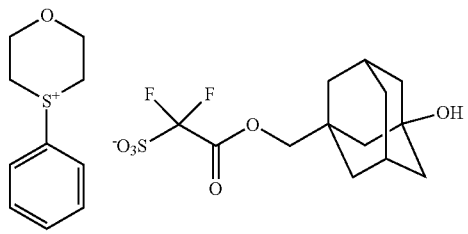
(B1-21)
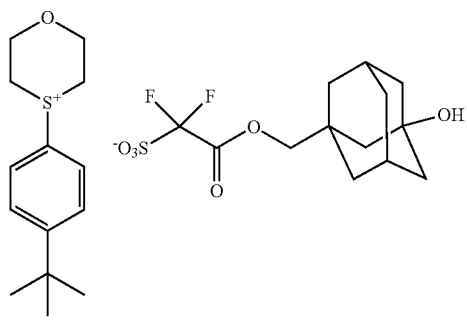
(B1-22)
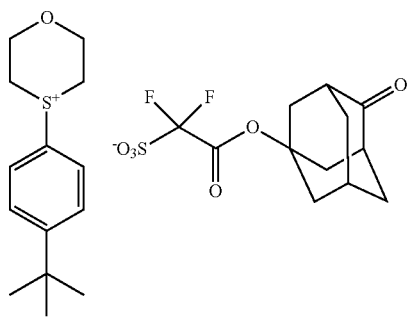

(B1-23) 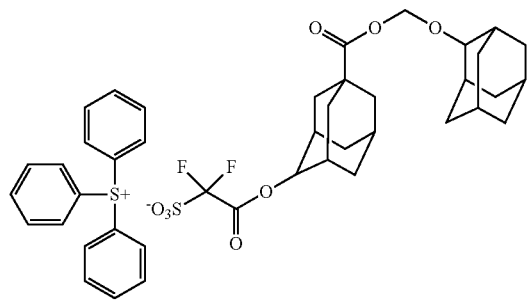
(B1-24) 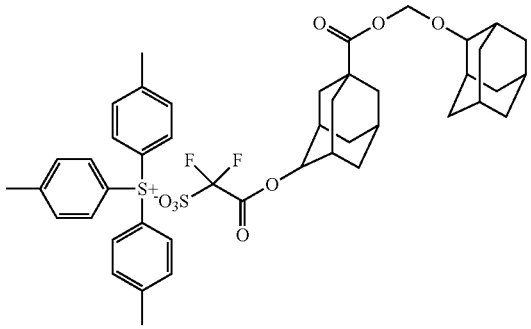
(B1-25) 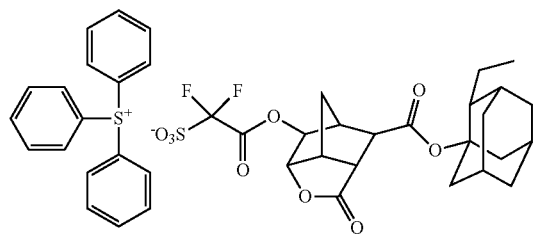
(B1-26) 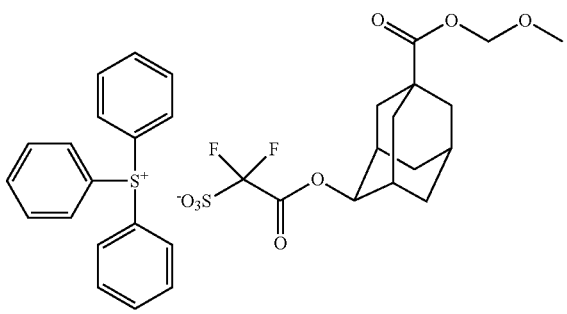
(B1-27) 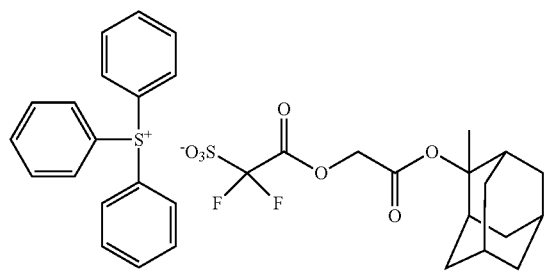
(B1-28) 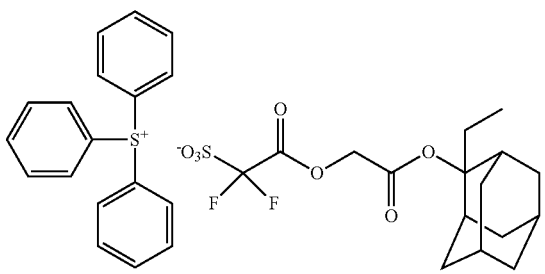
(B1-29) 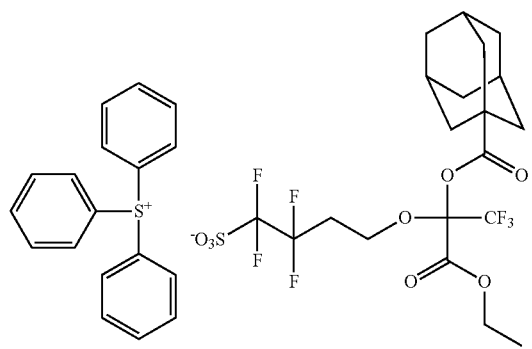
(B1-30) 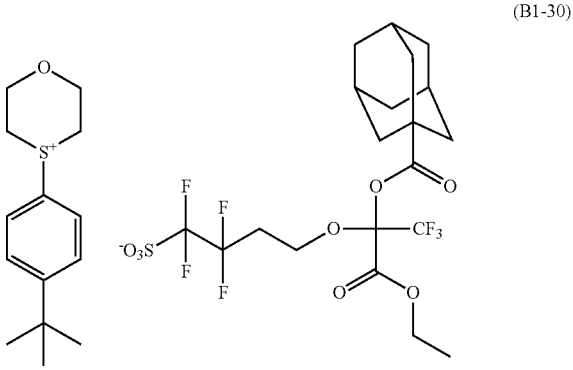

-continued
(B1-31)
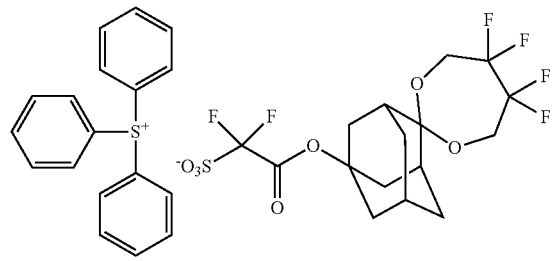
(B1-32)
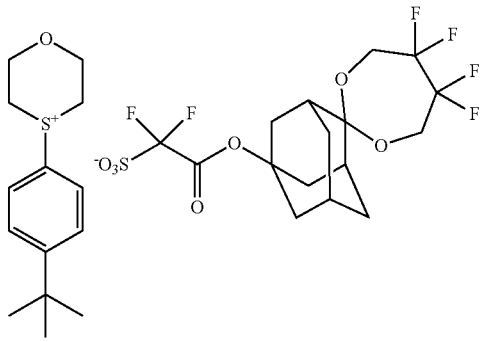
(B1-33)
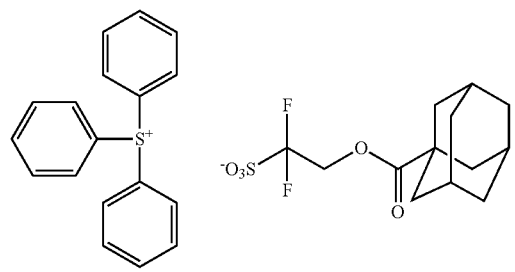
(B1-34)
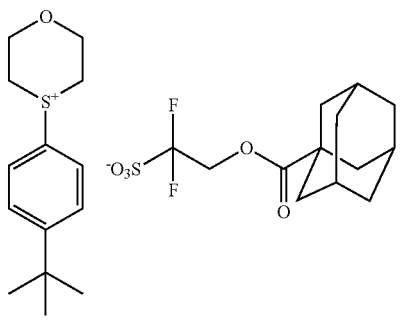
(B1-35)
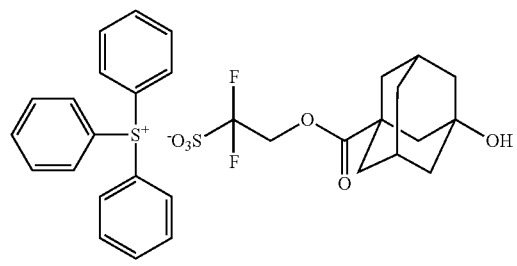
(B1-36)
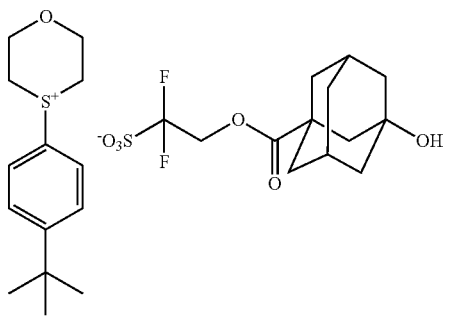
(B1-37)
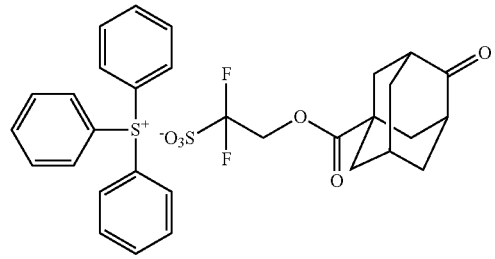
(B1-38)
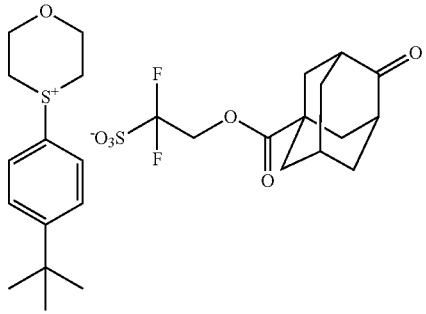

-continued
(B1-39)
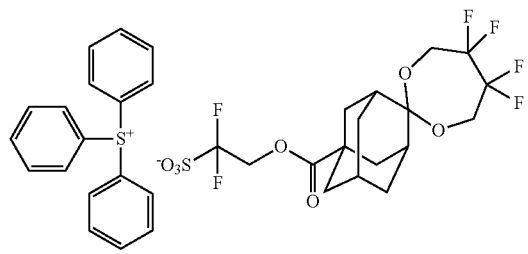
(B1-40)
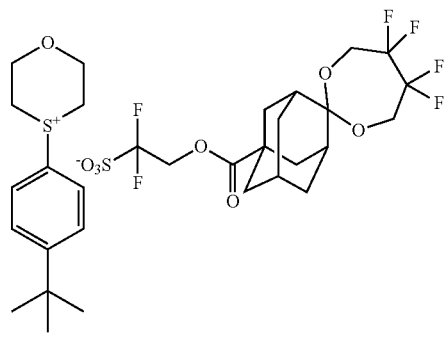
(B1-41)
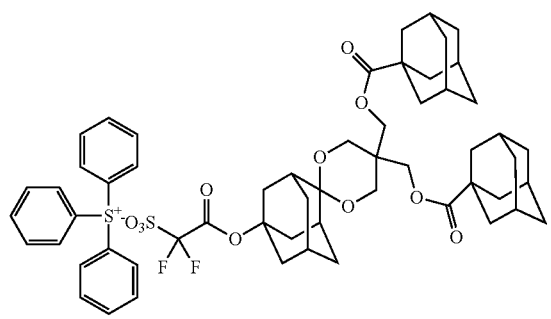
(B1-42)
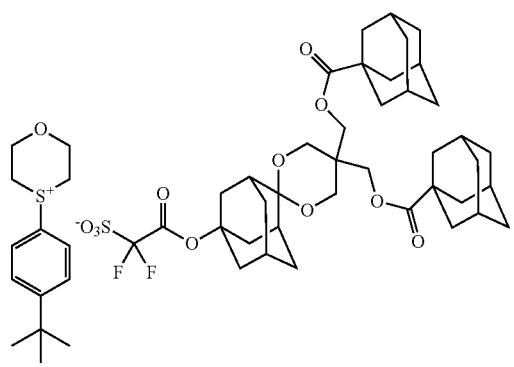
(B1-43)
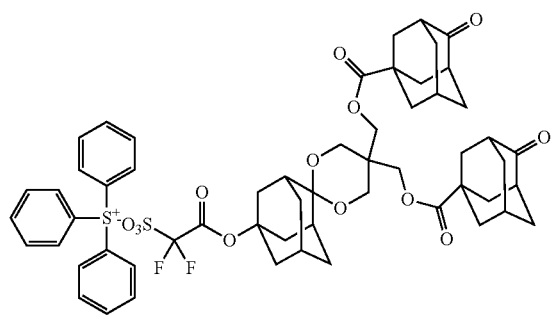
(B1-44)
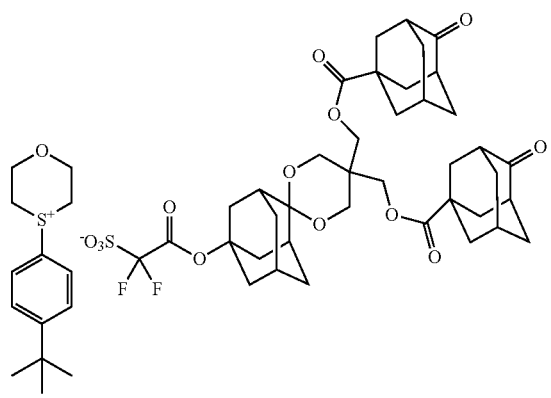
(B1-45)
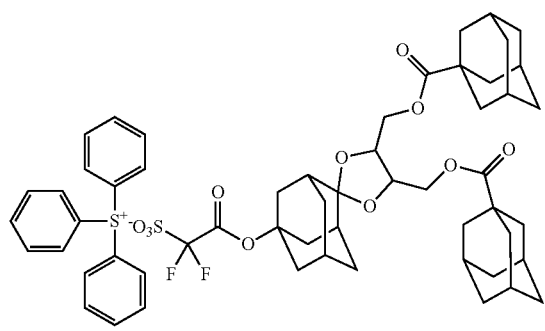
(B1-46)
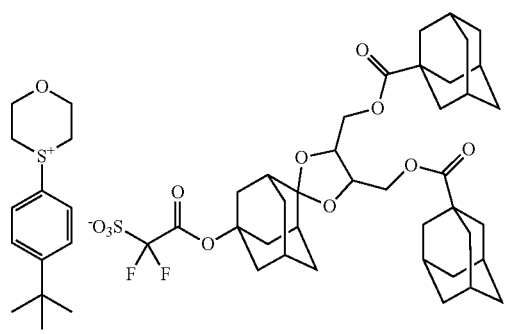

-continued
(B1-47)
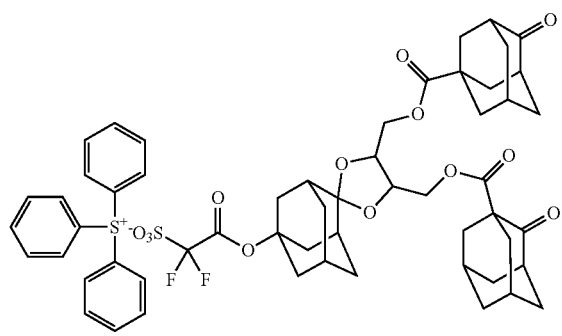
(B1-48)
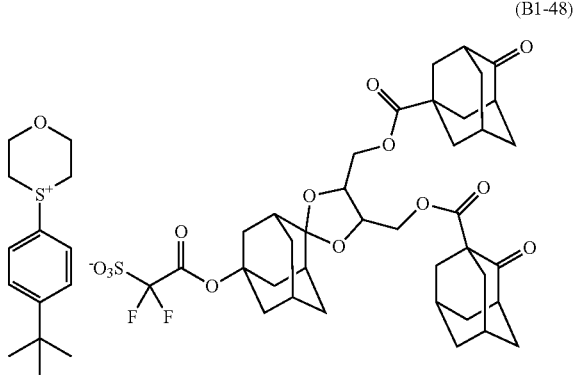
(B1-49)
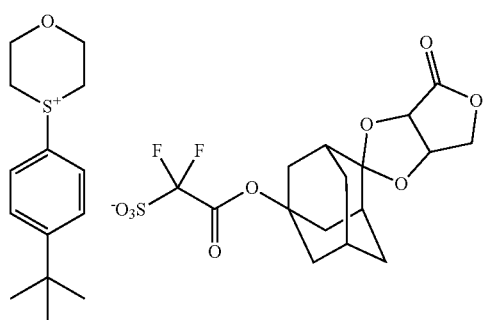
(B1-50)
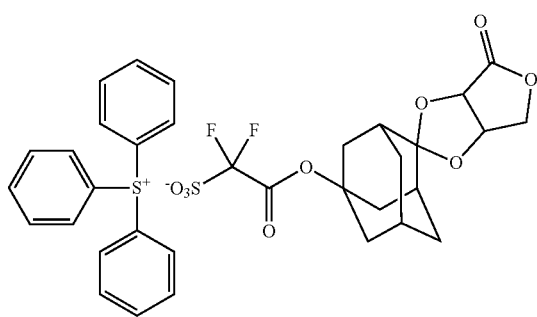
(B1-51)
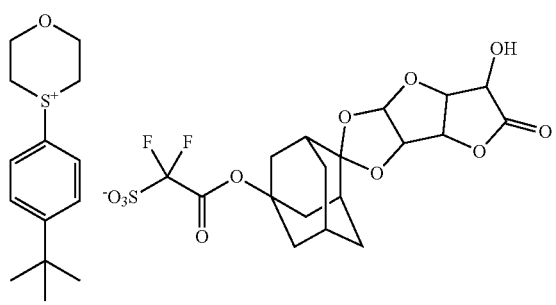
(B1-52)
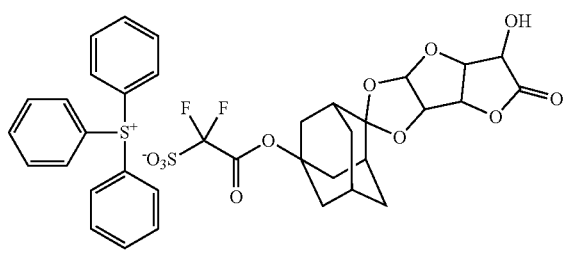
(B1-53)
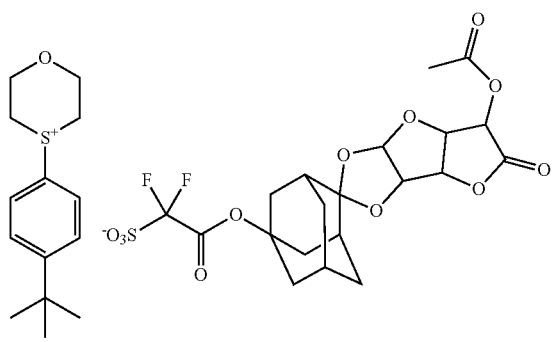
(B1-54)
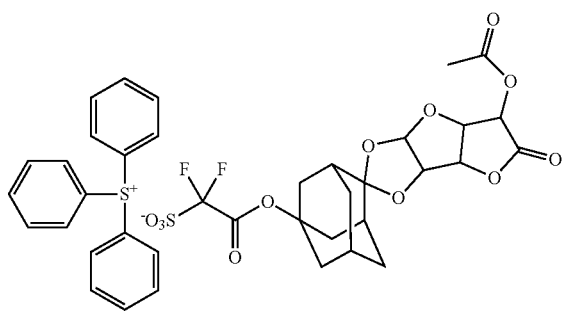

-continued (B1-55) 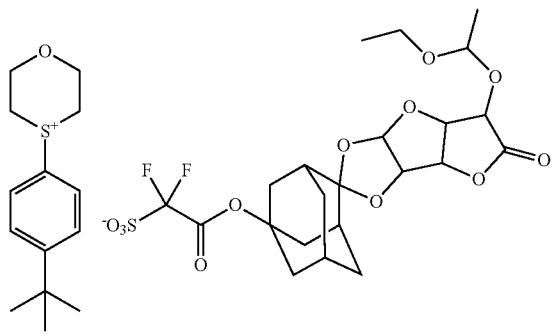

(B1-56) 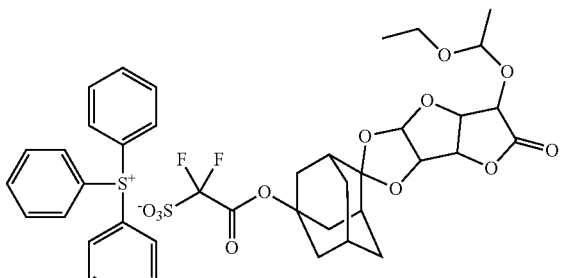

(B1-57) 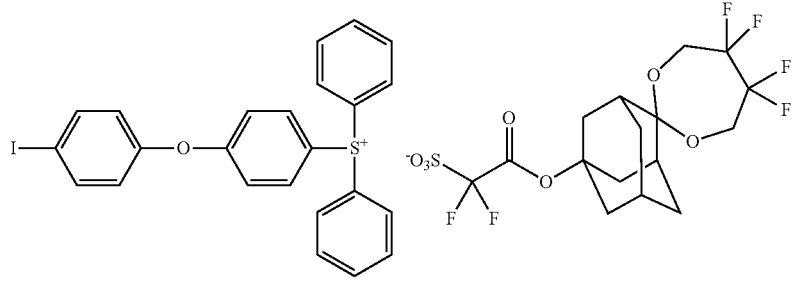

(B1-58) 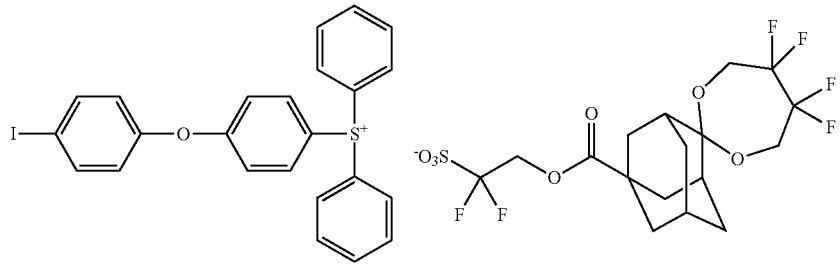

(B1-59) 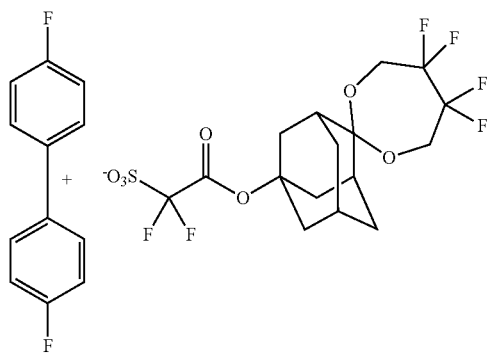

(B1-60) 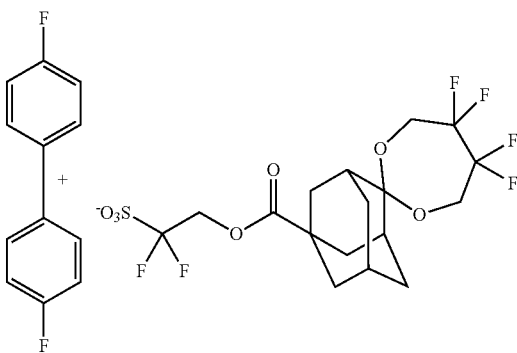

When the salt (I) and the acid generator (B) are included as the acid generator, a ratio of the content of the salt (I) to that of the acid generator (B) (mass ratio; salt (I):acid generator (B)) is usually 1:99 to 99:1, preferably 2:98 to 98:2, more preferably 5:95 to 95:5, still more preferably 10:90 to 90:10, and particularly preferably 15:85 to 85:15.

<Resist Composition>

The resist composition of the present invention comprises an acid generator comprising a salt (I) and a resin having an acid-labile group (hereinafter sometimes referred to as "resin (A)"). The "acid-labile group" means a group having a leaving group which is eliminated by contact with an acid, thus converting a constitutional unit into a constitutional unit having a hydrophilic group (e.g. a hydroxy group or a carboxy group).

The resist composition of the present invention preferably comprises a quencher such as a salt generating an acid having an acidity lower than that of an acid generated from the acid generator (hereinafter sometimes referred to as "quencher (C)"), and preferably comprises a solvent (hereinafter sometimes referred to as "solvent (E)").

<Acid Generator>

In the resist composition of the present invention, the total content of the acid generator is preferably 1 part by mass or more and 45 parts by mass or less, more preferably 1 part by mass or more and 40 parts by mass or less, and still more preferably 3 parts by mass or more and 40 parts by mass or less, based on 100 parts by mass of the below-mentioned resin (A).

<Resin (A)>

The resin (A) includes a structural unit having an acid-labile group (hereinafter sometimes referred to as "structural unit (a1)"). It is preferable that the resin (A) further includes a structural unit other than the structural unit (a1). Examples of the structural unit other than the structural unit (a1) include a structural unit having no acid-labile group (hereinafter sometimes referred to as "structural unit (s)"), a structural unit other than the structural unit (a1) and the structural unit (s) (e.g. a structural unit having a halogen atom mentioned later (hereinafter sometimes referred to as "structural unit (a4)"), a structural unit having a non-leaving hydrocarbon group mentioned later (hereinafter sometimes referred to as "structural unit (a5)") and other structural units derived from monomers known in the art.

<Structural Unit (a1)>

The structural unit (a1) is derived from a monomer having an acid-labile group (hereinafter sometimes referred to as "monomer (a1)").

The acid-labile group contained in the resin (A) is preferably a group represented by formula (1) (hereinafter also referred to as group (1)) and/or a group represented by formula (2) (hereinafter also referred to as group (2)):

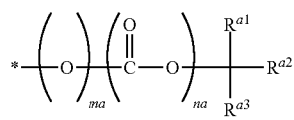

(1)

wherein, in formula (1), $R^{a1}$, $R^{a2}$ and $R^{a3}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or a group obtained by combining these groups, or $R^{a1}$ and $R^{a2}$ are bonded to each other to form an alicyclic hydrocarbon group having 3 to 20 carbon atoms together with carbon atoms to which $R^{a1}$ and $R^{a2}$ are bonded, ma and na each independently represent 0 or 1, and at least one of ma and na represents 1, and
represents a bonding site:

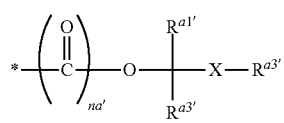

(2)

wherein, in formula (2), $R^{a1'}$ and $R^{a2'}$ each independently represent a hydrogen atom or a hydrocarbon group having 1 to 12 carbon atoms, $R^{a3'}$ represents a hydrocarbon group having 1 to 20 carbon atoms, or $R^{a2'}$ and $R^{a3'}$ are bonded to each other to form a heterocyclic ring group having 3 to 20 carbon atoms together with carbon atoms and X to which $R^{a2'}$ and $R^{a3'}$ are bonded, and —CH$_2$— included in the hydrocarbon group and the heterocyclic ring group may be replaced by —O— or —S—, X represents an oxygen atom or a sulfur atom,
na' represents 0 or 1, and
represents a bonding site.

Examples of the alkyl group in $R^{a1}$, $R^{a2}$ and $R^{a3}$ include a methyl group, an ethyl group, a propyl group, a butyl group, a pentyl group, a hexyl group, a heptyl group, an octyl group and the like.

Examples of the alkenyl group in $R^{a1}$, $R^{a2}$ and $R^{a3}$ include an ethenyl group, a propenyl group, an isopropenyl group, a butenyl group, an isobutenyl group, a tert-butenyl group, a pentenyl group, a hexenyl group, a heptenyl group, an octenyl group, an isooctenyl group and a nonenyl group.

The alicyclic hydrocarbon group in $R^{a1}$, $R^{a2}$ and $R^{a3}$ may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group and the following groups (* represents a bonding site). The number of carbon atoms of the alicyclic hydrocarbon group of $R^{a1}$, $R^{a2}$ and $R^{a3}$ is preferably 3 to 16.

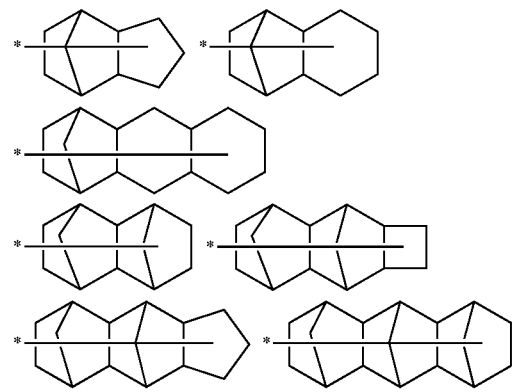

Examples of the aromatic hydrocarbon group in $R^{a1}$, $R^{a2}$ and $R^{a3}$ include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group, and the like.

Preferably, ma is 0 and na is 1.

When $R^{a1}$ and $R^{a2}$ are bonded to each other to form an alicyclic hydrocarbon group, examples of —C($R^{a1}$) ($R^{a2}$) ($R^{a3}$) include the following groups. The alicyclic hydrocarbon group preferably has 3 to 12 carbon atoms. * represents a bonding site to —O—.

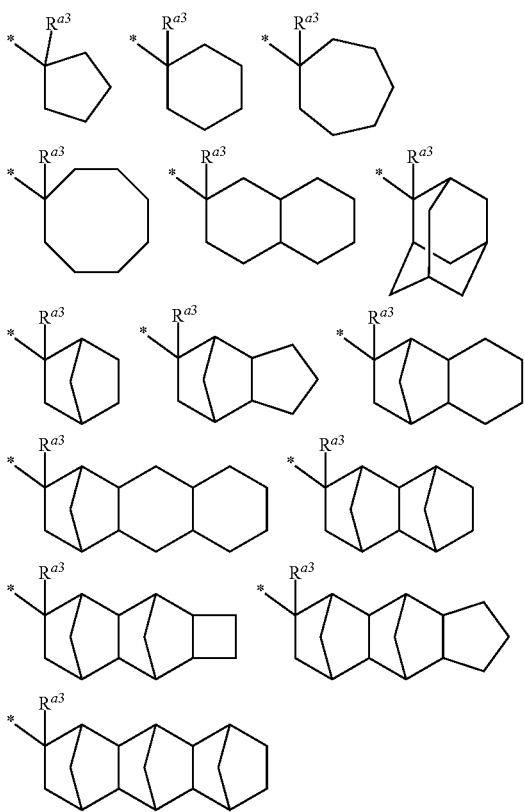

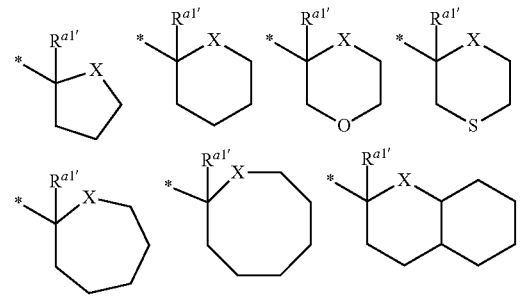

At least one of $R^{a1'}$ and $R^{a2'}$ is preferably a hydrogen atom.

na' is preferably 0.

Examples of the group (1) include the following groups.

A group wherein, in formula (1), $R^{a1}$, $R^{a2}$ and $R^{a3}$ are alkyl groups, ma=0 and na=1. The group is preferably a tert-butoxycarbonyl group.

A group wherein, in formula (1), $R^{a1}$ and $R^{a2}$ are bonded to each other to form an adamantyl group together with carbon atoms to which $R^{a1}$ and $R^{a2}$ are bonded, $R^{a3}$ is an alkyl group, ma=0 and na=1.

A group wherein, in formula (1), $R^{a1}$ and $R^{a2}$ are each independently an alkyl group, $R^{a3}$ is an adamantyl group, ma=0 and na=1.

Specific examples of the group (1) include the following groups. * represents a bonding site.

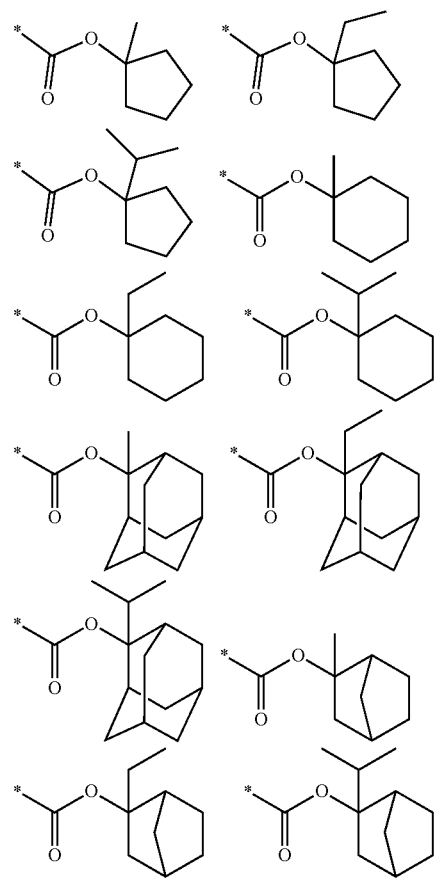

Examples of the hydrocarbon group in $R^{a1'}$, $R^{a2'}$ and $R^{a3'}$ include an alkyl group, an alicyclic hydrocarbon group, an aromatic hydrocarbon group, and groups formed by combining these groups.

Examples of the alkyl group and the alicyclic hydrocarbon group include those which are the same as mentioned in $R^{a1}$, $R^{a2}$ and $R^{a3}$.

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group, and the like.

When $R^{a2'}$ and $R^{a3'}$ are bonded to each other to form a heterocyclic ring group together with carbon atoms and X to which $R^{a2'}$ and $R^{a3'}$ are bonded, examples of —C($R^{a1'}$)($R^{a2'}$)—X—$R^{a3'}$ include the following groups. * represents a bonding site.

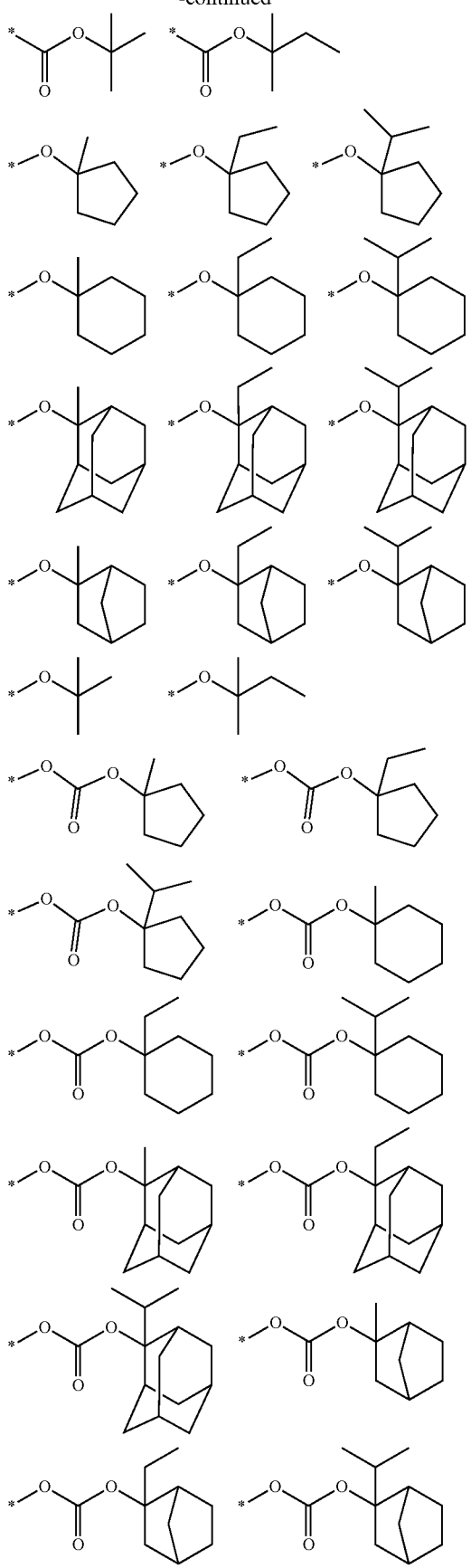
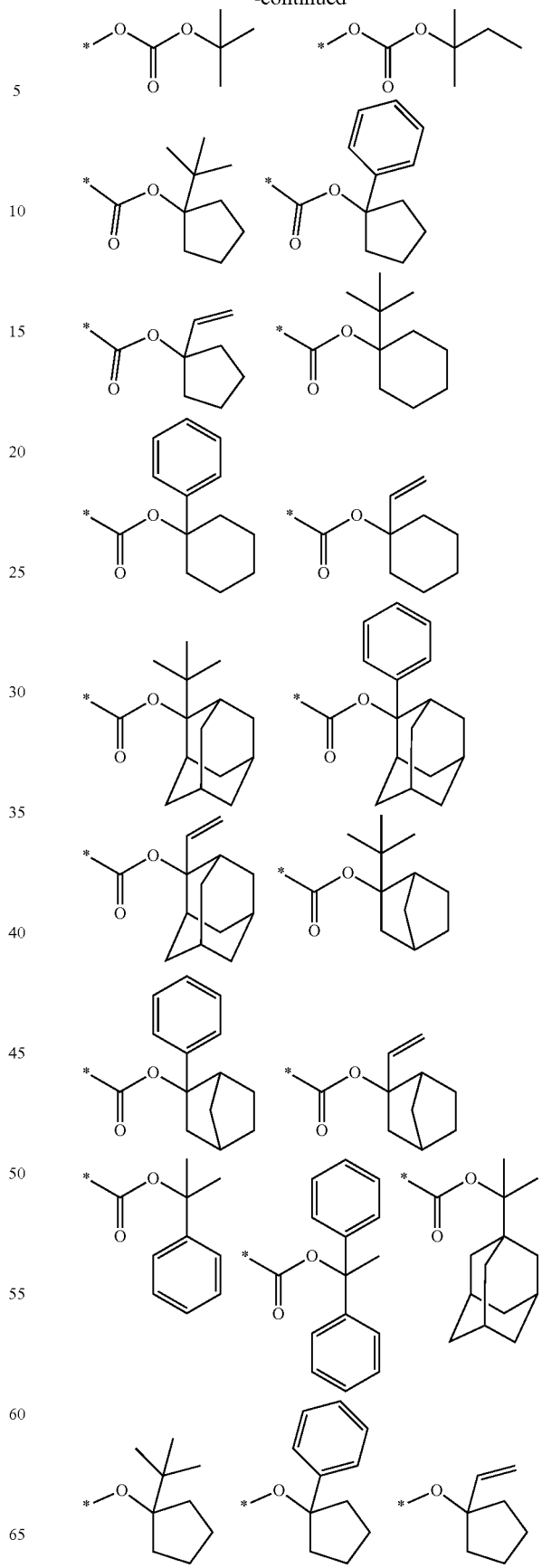

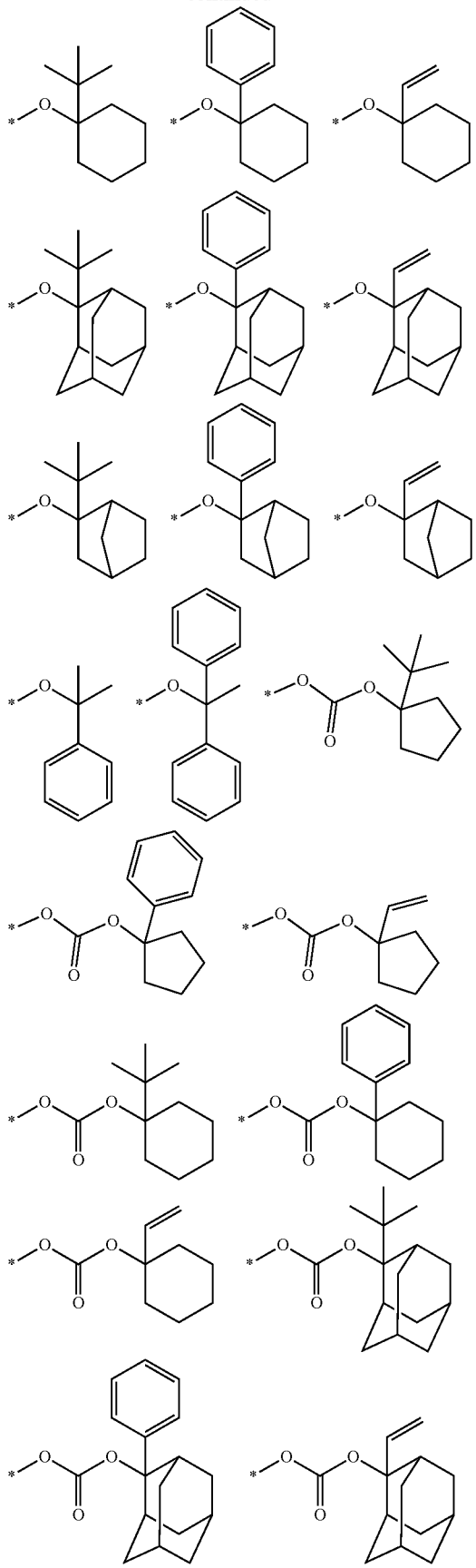
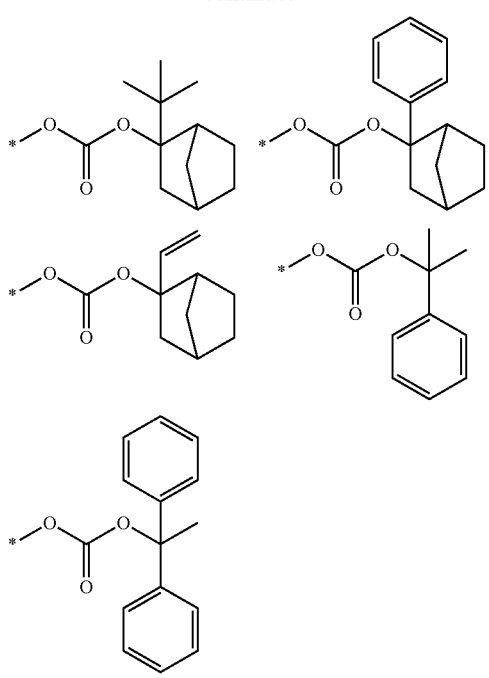
Specific examples of the group (2) include the following groups. * represents a bonding site.
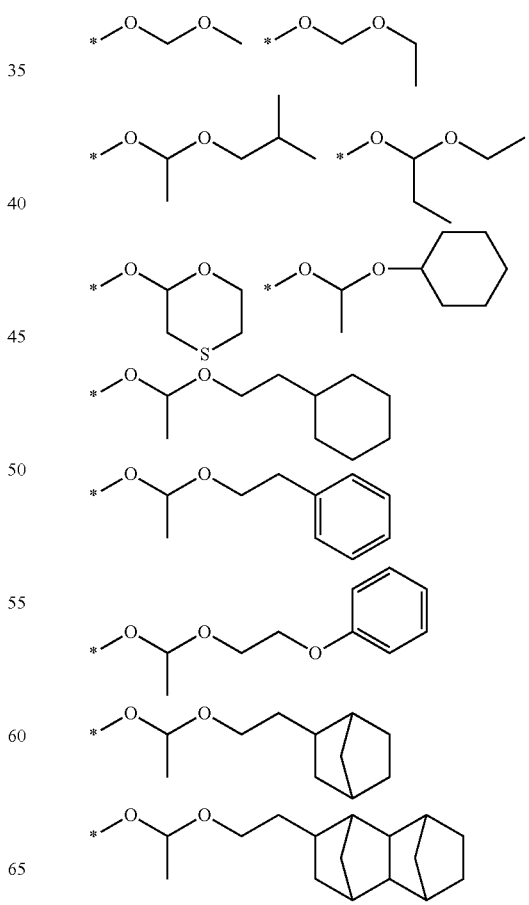

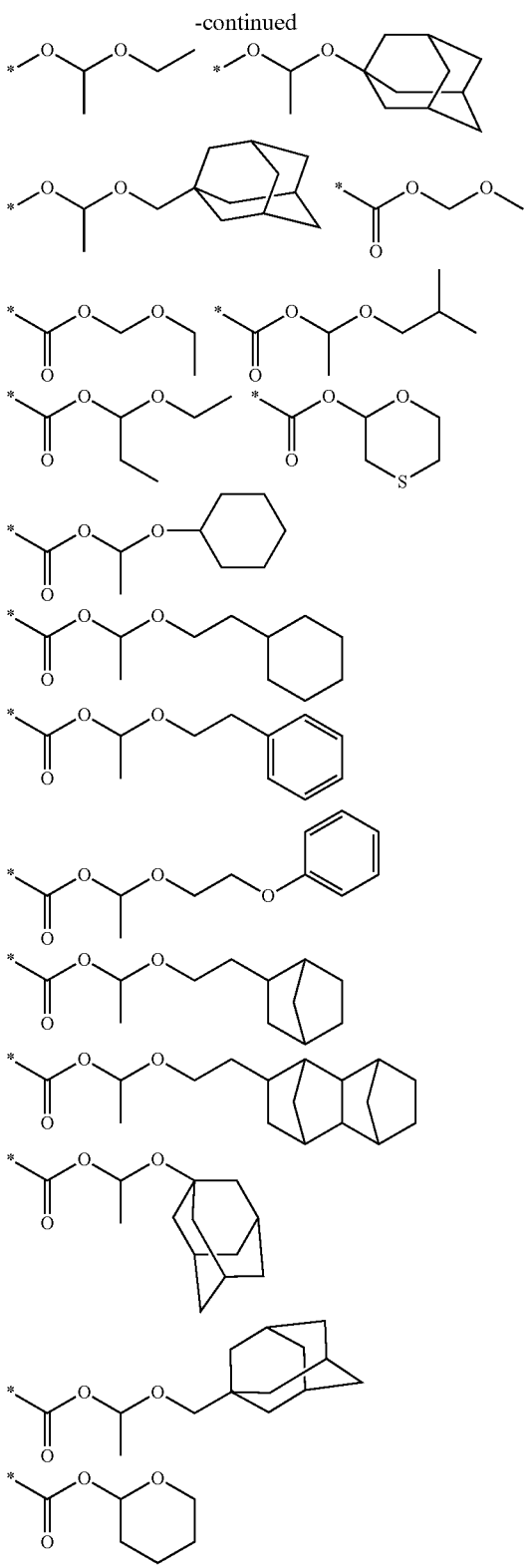

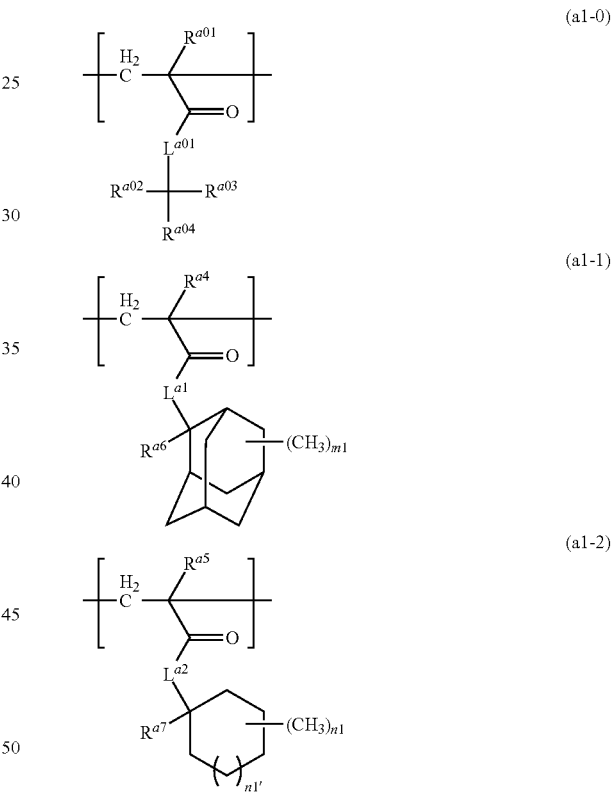

The monomer (a1) is preferably a monomer having an acid-labile group and an ethylenic unsaturated bond, and more preferably a (meth)acrylic monomer having an acid-labile group.

Of the (meth)acrylic monomers having an acid-labile group, those having an alicyclic hydrocarbon group having 5 to 20 carbon atoms are preferably exemplified. When a resin (A) including a structural unit derived from a monomer (a1) having a bulky structure such as an alicyclic hydrocarbon group is used in a resist composition, it is possible to improve the resolution of a resist pattern.

The structural unit derived from a (meth)acrylic monomer having a group (1) preferably includes a structural unit represented by formula (a1-0) (hereinafter sometimes referred to as structural unit (a1-0)), a structural unit represented by formula (a1-1) (hereinafter sometimes referred to as structural unit (a1-1)) or a structural unit represented by formula (a1-2) (hereinafter sometimes referred to as structural unit (a1-2)). More preferably, the structural unit is at least one structural unit selected from the group consisting of structural unit (a1-0), structural unit (a1-1) and structural unit (a1-2), and still more preferably at least one structural unit selected from the group consisting of structural unit (a1-1) and structural unit (a1-2). These structural units may be used alone, or two or more structural units may be used in combination.

In formula (a1-0), formula (a1-1) and formula (a1-2), $L^{a01}$, $L^{a1}$ and $L^{a2}$ each independently represent —O— or *—O—(CH$_2$)$_{k1}$—CO—O—, k1 represents an integer of 1 to 7, and * represents a bonding site to —CO—, $R^{a01}$, $R^{a4}$ and $R^{a5}$ each independently represent a hydrogen atom, a halogen atom or an alkyl group having 1 to 6 carbon atoms which may have a halogen atom, $R^{a02}$, $R^{a03}$ and $R^{a04}$ each independently represent an alkyl group having 1 to 8 carbon atoms, an alicyclic hydrocarbon group having 3 to 18 carbon atoms, an aromatic hydrocarbon group having 6 to 18 carbon atoms, or a group obtained by combining these groups, $R^{a6}$ and $R^{a7}$ each independently represent an alkyl group having 1 to 8 carbon atoms, an alkenyl group having 2 to 8 carbon atoms, an alicyclic hydrocarbon group having 3 to 18 carbon atoms, an aromatic hydrocarbon group having 6 to 18 carbon atoms, or a group obtained by combining these groups, m1 represents an integer of 0 to 14, n1 represents an integer of 0 to 10, and n1' represents an integer of 0 to 3.

$R^{a01}$, $R^{a4}$ and $R^{a5}$ are preferably a hydrogen atom or a methyl group, and more preferably a methyl group.

$L^{a01}$, $L^{a1}$ and $L^{a2}$ are preferably an oxygen atom or *—O—$(CH_2)_{k01}$—CO—O— (in which k01 is preferably an integer of 1 to 4, and more preferably 1), and more preferably an oxygen atom.

Examples of the alkyl group, the alkenyl group, the alicyclic hydrocarbon group, the aromatic hydrocarbon group, and groups obtained by combining these groups in $R^{a02}$, $R^{a03}$, $R^{a04}$, $R^{a6}$ and $R^{a7}$ include the same groups as mentioned as for $R^{a1}$, $R^{a2}$ and $R^{a3}$ of formula (1).

The alkyl group in $R^{a02}$, $R^{a03}$ and $R^{a04}$ is preferably an alkyl group having 1 to 6 carbon atoms, more preferably a methyl group or an ethyl group, and still more preferably a methyl group.

The alkyl group in $R^{a6}$ and $R^{a7}$ is preferably an alkyl group having 1 to 6 carbon atoms, more preferably a methyl group, an ethyl group, an isopropyl group or a t-butyl group, and still more preferably an ethyl group, an isopropyl group or a t-butyl group.

The alkenyl group in $R^{a6}$ and $R^{a7}$ is preferably an alkenyl group having 2 to 6 carbon atoms, and more preferably an ethenyl group, a propenyl group, an isopropenyl group or a butenyl group.

The number of carbon atoms of the alicyclic hydrocarbon group as for $R^{a02}$, $R^{a03}$, $R^{a04}$, $R^{a6}$ and $R^{a7}$ is preferably 5 to 12, and more preferably 5 to 10.

The number of carbon atoms of the aromatic hydrocarbon group of $R^{a02}$, $R^{a03}$, $R^{a04}$, $R^{a6}$ and $R^{a7}$ is preferably 6 to 12, and more preferably 6 to 10.

The total number of carbon atoms of the group obtained by combining the alkyl group with the alicyclic hydrocarbon group is preferably 18 or less.

The total number of carbon atoms of the group obtained by combining the alkyl group with the aromatic hydrocarbon group is preferably 18 or less.

$R^{a02}$ and $R^{a03}$ are preferably an alkyl group having 1 to 6 carbon atoms or an aromatic hydrocarbon group having 6 to 12 carbon atoms, and more preferably a methyl group, an ethyl group, a phenyl group or a naphthyl group.

$R^{a04}$ is preferably an alkyl group having 1 to 6 carbon atoms or an alicyclic hydrocarbon group having 5 to 12 carbon atoms, and more preferably a methyl group, an ethyl group, a cyclohexyl group or an adamantyl group.

$R^{a6}$ and $R^{a7}$ are preferably an alkyl group having 1 to 6 carbon atoms, an alkenyl group having 2 to 6 carbon atoms or an aromatic hydrocarbon group having 6 to 12 carbon atoms, more preferably a methyl group, an ethyl group, an isopropyl group, a t-butyl group, an ethenyl group, a phenyl group or a naphthyl group, and still more preferably an ethyl group, an isopropyl group, a t-butyl group, an ethenyl group or a phenyl group.

m1 is preferably an integer of 0 to 3, and more preferably 0 or 1.

n1 is preferably an integer of 0 to 3, and more preferably 0 or 1.

n1' is preferably 0 or 1.

The structural unit (a1-0) includes, for example, a structural unit represented by any one of formula (a1-0-1) to formula (a1-0-18) and a structural unit in which a methyl group corresponding to $R^{a01}$ in the structural unit (a1-0) is substituted with a hydrogen atom, a halogen atom, a haloalkyl group (alkyl group having a halogen atom) or other alkyl groups, and is preferably a structural unit represented by any one of formula (a1-0-1) to formula (a1-0-10), formula (a1-0-13) and formula (a1-0-14).

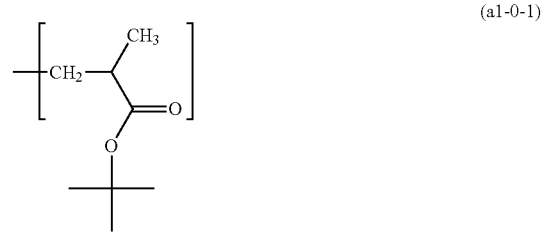

(a1-0-1)

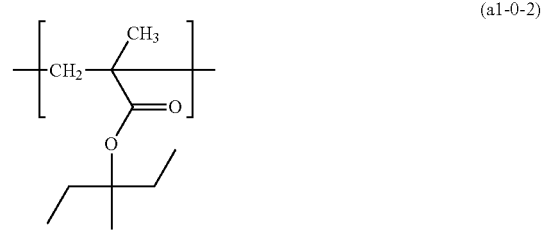

(a1-0-2)

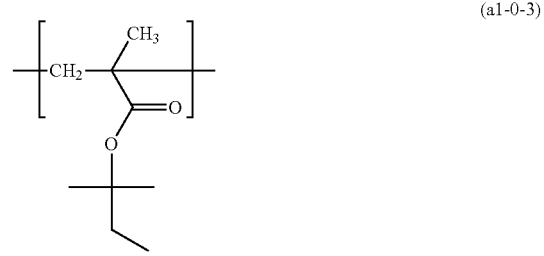

(a1-0-3)

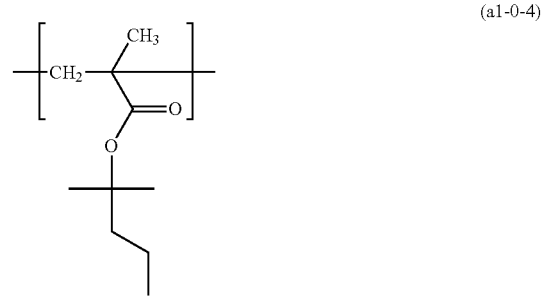

(a1-0-4)

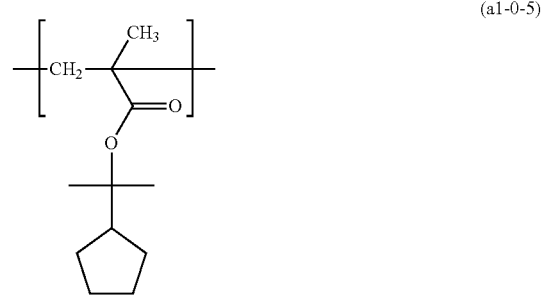

(a1-0-5)

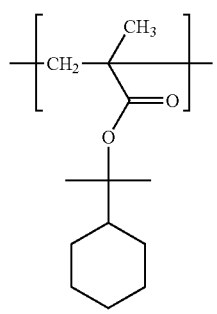 (a1-0-6)
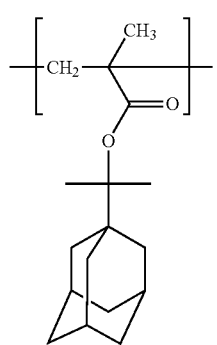 (a1-0-7)
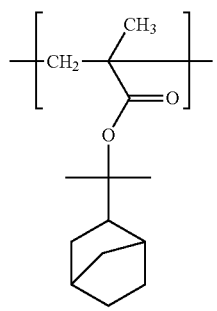 (a1-0-8)
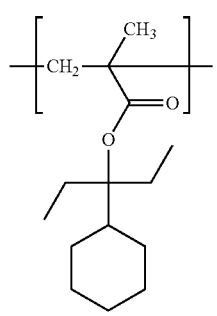 (a1-0-9)
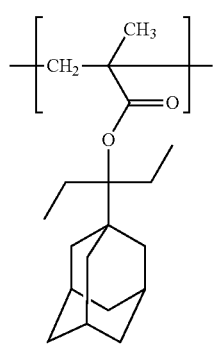 (a1-0-10)
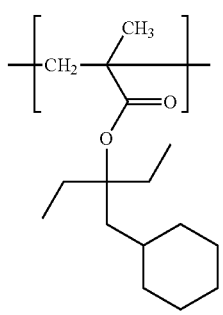 (a1-0-11)
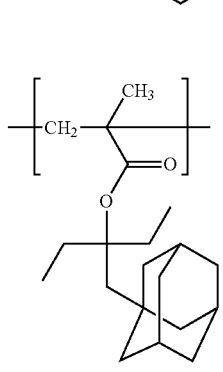 (a1-0-12)
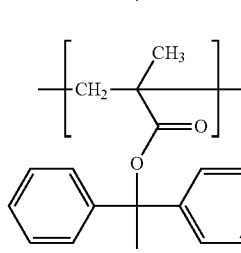 (a1-0-13)
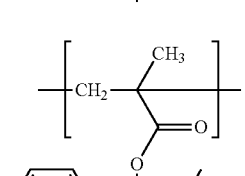 (a1-0-14)
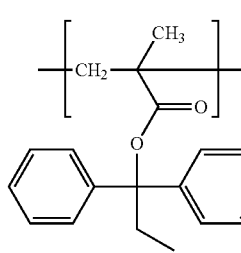 (a1-0-15)
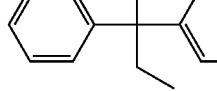 (a1-0-16)

(a1-0-17)

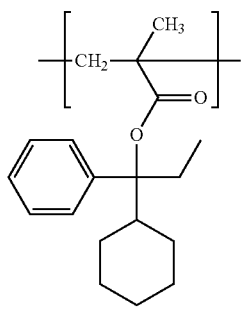

(a1-0-18)

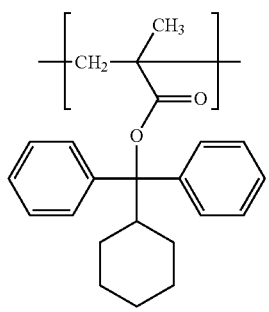

The structural unit (a1-1) includes, for example, structural units derived from the monomers mentioned in JP 2010-204646 A. Of these structural units, a structural unit represented by any one of formula (a1-1-1) to formula (a1-1-7) and a structural unit in which a methyl group corresponding to $R^{a4}$ in the structural unit (a1-1) is substituted with a hydrogen atom, a halogen atom, a haloalkyl group or other alkyl groups are preferable, and a structural unit represented by any one of formula (a1-1-1) to formula (a1-1-4) is more preferable.

(a1-1-1)

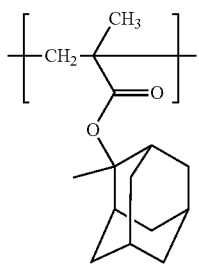

(a1-1-2)

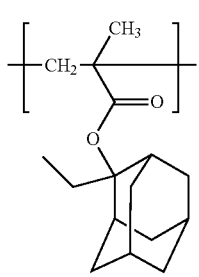

(a1-1-3)

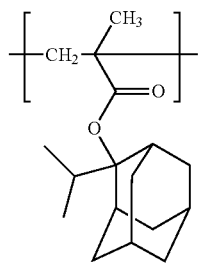

(a1-1-4)

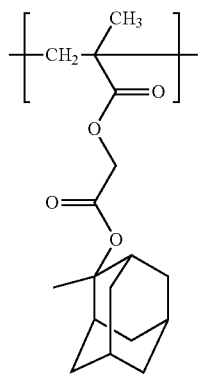

(a1-1-5)

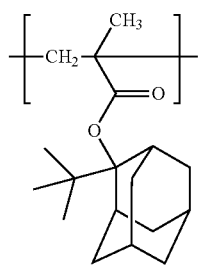

(a1-1-6)

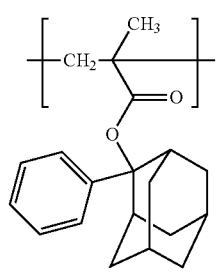

(a1-1-7)

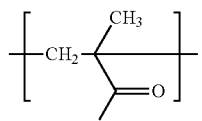

Examples of the structural unit (a1-2) include a structural unit represented by any one of formula (a1-2-1) to formula (a1-2-14), and a structural unit in which a methyl group corresponding to $R^{a5}$ in the structural unit (a1-2) is substituted with a hydrogen atom, a halogen atom, a haloalkyl group or other alkyl groups, and a structure unit represented by any one of formula (a1-2-2), formula (a1-2-5), formula (a1-2-6) and formula (a1-2-10) to formula (a1-2-14) is preferable.
(a1-2-1)
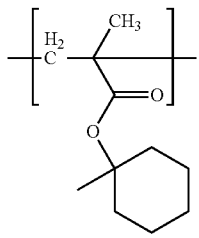
(a1-2-2)
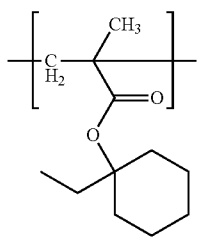
(a1-2-3)
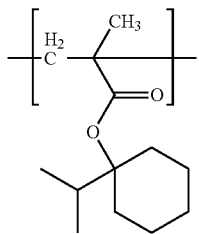
(a1-2-4)
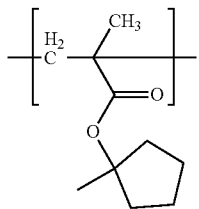
(a1-2-5)
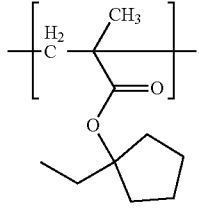
(a1-2-6)
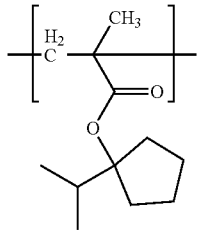
-continued
(a1-2-7)
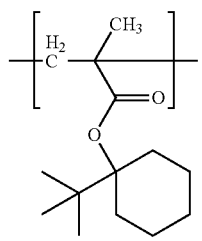
(a1-2-8)
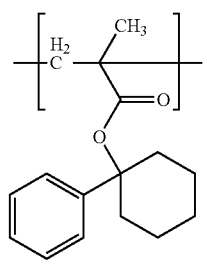
(a1-2-9)
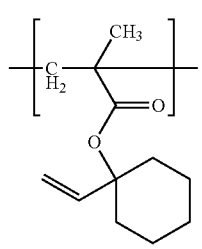
(a1-2-10)
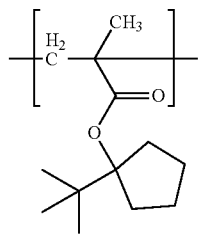
(a1-2-11)
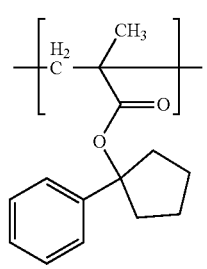
(a1-2-12)
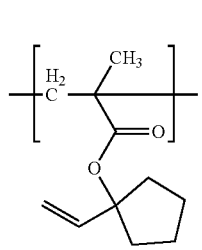

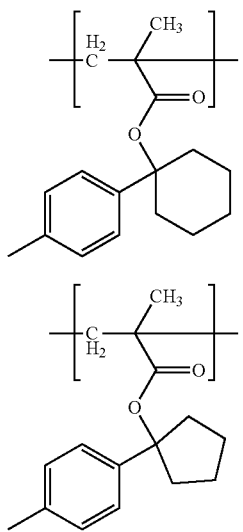

(a1-2-13)

(a1-2-14)

When the resin (A) includes a structural unit (a1-0) and/or a structural unit (a1-1) and/or a structural unit (a1-2), the total content thereof is usually 10 to 95 mol %, preferably 15 to 90 mol %, more preferably 20 to 85 mol %, still more preferably 25 to 70 mol %, and yet more preferably 30 to 70 mol %, based on all structural units of the resin (A).

In the structural unit (a1), examples of the structural unit having a group (2) include a structural unit represented by formula (a1-4) (hereinafter sometimes referred to as "structural unit (a1-4)"):

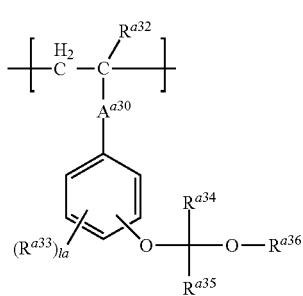

(a1-4)

wherein, in formula (a1-4), $R^{a32}$ represents a hydrogen atom, a halogen atom, or an alkyl group having 1 to 6 carbon atoms which may have a halogen atom, $R^{a33}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group, $A^{a30}$ represents a single bond or *—$X^{a31}$-($A^{a32}$-$X^{a32}$)$_{nc}$— and * represents a bonding site to carbon atoms to which —$R^{a32}$ is bonded, $A^{a32}$ represents an alkanediyl group having 1 to 6 carbon atoms, $X^{a31}$ and $X^{a32}$ each independently represent —O—, —CO—O— or —O—CO—, nc represents 0 or 1, la represents an integer of 0 to 4, and when la is an integer of 2 or more, a plurality of $R^{a33}$ may be the same or different from each other, and $R^{a34}$ and $R^{a35}$ each independently represent a hydrogen atom or a hydrocarbon group having 1 to 12 carbon atoms, $R^{a36}$ represents a hydrocarbon group having 1 to 20 carbon atoms, or $R^{a35}$ and $R^{a36}$ are bonded to each other to form a divalent hydrocarbon group having 2 to 20 carbon atoms together with —C—O— to which $R^{a35}$ and $R^{a36}$ are bonded, and —CH$_2$— included in the hydrocarbon group and the divalent hydrocarbon group may be replaced by —O— or —S—.

Examples of the halogen atom in $R^{a32}$ and $R^{a33}$ include a fluorine atom, a chlorine atom and a bromine atom.

Examples of the alkyl group having 1 to 6 carbon atoms which may have a halogen atom in $R^{a32}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

$R^{a32}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in $R^{a33}$ include a methyl group, an ethyl group, a propyl group, an isopropyl group, a butyl group, a sec-butyl group, a tert-butyl group, a pentyl group and a hexyl group. The alkyl group is preferably an alkyl group having 1 to 4 carbon atoms, more preferably a methyl group or an ethyl group, and still more preferably a methyl group.

Examples of the alkoxy group in $R^{a33}$ include a methoxy group, an ethoxy group, a propoxy group, an isopropoxy group, a butoxy group, a sec-butoxy group, a tert-butoxy group, a pentyloxy group and a hexyloxy group. The alkoxy group is preferably an alkoxy group having 1 to 4 carbon atoms, more preferably a methoxy group or an ethoxy group, and still more preferably a methoxy group.

Examples of the alkoxyalkyl group in $R^{a33}$ include a methoxymethyl group, an ethoxyethyl group, a propoxymethyl group, an isopropoxymethyl group, a butoxymethyl group, a sec-butoxymethyl group and a tert-butoxymethyl group. The alkoxyalkyl group is preferably an alkoxyalkyl group having 2 to 8 carbon atoms, more preferably a methoxymethyl group or an ethoxyethyl group, and still more preferably a methoxymethyl group.

Examples of the alkoxyalkoxy group in $R^{a33}$ include a methoxymethoxy group, a methoxyethoxy group, an ethoxymethoxy group, an ethoxyethoxy group, a propoxymethoxy group, an isopropoxymethoxy group, a butoxymethoxy group, a sec-butoxymethoxy group and a tert-butoxymethoxy group. The alkoxyalkoxy group is preferably an alkoxyalkoxy group having 2 to 8 carbon atoms, and more preferably a methoxyethoxy group or an ethoxyethoxy group.

Examples of the alkylcarbonyl group in $R^{a33}$ include an acetyl group, a propionyl group and a butyryl group. The alkylcarbonyl group is preferably an alkylcarbonyl group having 2 to 3 carbon atoms, and more preferably an acetyl group.

Examples of the alkylcarbonyloxy group in $R^{a33}$ include an acetyloxy group, a propionyloxy group and a butyryloxy group. The alkylcarbonyloxy group is preferably an alkylcarbonyloxy group having 2 to 3 carbon atoms, and more preferably an acetyloxy group.

$R^{a33}$ is preferably a halogen atom, a hydroxy group, an alkyl group having 1 to 4 carbon atoms, an alkoxy group having 1 to 4 carbon atoms or an alkoxyalkoxy group having 2 to 8 carbon atoms, more preferably a fluorine atom, an iodine atom, a hydroxy group, a methyl group, a methoxy group, an ethoxy group, an ethoxyethoxy group or an ethoxymethoxy group, and still more preferably a fluorine atom, an iodine atom, a hydroxy group, a methyl group, a methoxy group or an ethoxyethoxy group.

Examples of the *—$X^{a3}1$-$(A^{a32}$-$X^{a32})_n$— include *—O—, *—CO—O—, *—O—CO—, *—CO—O-$A^{a32}$-CO—O—, *—O—CO-$A^{a32}$-O—, *—O-$A^{a32}$-CO—O—, *—CO—O-$A^{a32}$-O—CO— and *—O—CO-$A^{a32}$-O—CO. Of these, *—CO—O—, *—CO—O-$A^{a32}$-CO—O— or *—O-$A^{a32}$-CO—O— is preferable.

Examples of the alkanediyl group in $A^{a32}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a32}$ is preferably a methylene group or an ethylene group.

$A^{a30}$ is preferably a single bond, *—CO—O— or *—CO—O-$A^{a32}$—CO—O—, more preferably a single bond, *—CO—O— or *—CO—O—CH$_2$—CO—O—, and still more preferably a single bond or *—CO—O—.

la is preferably 0, 1 or 2, more preferably 0 or 1, and still more preferably 0.

Examples of the hydrocarbon group in $R^{a34}$, $R^{a35}$ and $R^{a36}$ include an alkyl group, an alicyclic hydrocarbon group, an aromatic hydrocarbon group, and groups formed by combining these groups.

Examples of the alkyl group include a methyl group, an ethyl group, a propyl group, a butyl group, a pentyl group, a hexyl group, a heptyl group, an octyl group and the like.

The alicyclic hydrocarbon group may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group and the following groups (* represents a bonding site).

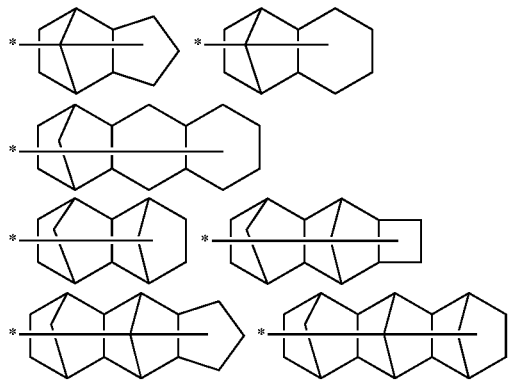

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group and the like. Particularly, examples of $R^{a36}$ include an alkyl group having 1 to 18 carbon atoms, an alicyclic hydrocarbon group having 3 to 18 carbon atoms, an aromatic hydrocarbon group having 6 to 18 carbon atoms, or a group formed by combining these groups.

$R^{a34}$ is preferably a hydrogen atom.

$R^{a35}$ is preferably a hydrogen atom, an alkyl group having 1 to 12 carbon atoms or an alicyclic hydrocarbon group having 3 to 12 carbon atoms, and more preferably a methyl group or an ethyl group.

The hydrocarbon group of $R^{a36}$ is preferably an alkyl group having 1 to 18 carbon atoms, an alicyclic hydrocarbon group having 3 to 18 carbon atoms, an aromatic hydrocarbon group having 6 to 18 carbon atoms, or a group formed by combining these groups, and more preferably an alkyl group having 1 to 18 carbon atoms, an alicyclic hydrocarbon group having 3 to 18 carbon atoms or an aralkyl group having 7 to 18 carbon atoms. The alkyl group and the alicyclic hydrocarbon group in $R^{a36}$ are preferably unsubstituted. The aromatic hydrocarbon group in $R^{a36}$ is preferably an aromatic ring having an aryloxy group having 6 to 10 carbon atoms.

—OC($R^{a34}$)($R^{a35}$)—O—$R^{a36}$ in the structural unit (a1-4) is eliminated by contacting with an acid (e.g., p-toluenesulfonic acid) to form a hydroxy group.

—OC($R^{a34}$)($R^{a35}$)—O—$R^{a36}$ is preferably bonded to the o-position or the p-position of the benzene ring, and more preferably the p-position.

The structural unit (a1-4) includes, for example, structural units derived from the monomers mentioned in JP 2010-204646 A. The structural unit preferably includes structural units represented by formula (a1-4-1) to formula (a1-4-24) and a structural unit in which a hydrogen atom corresponding to $R^{a32}$ in the structural unit (a1-4) is substituted with a halogen atom, a haloalkyl group or an alkyl group, and more preferably structural units represented by formula (a1-4-1) to formula (a1-4-5), formula (a1-4-10), formula (a1-4-13), formula (a1-4-14), formula (a1-4-19) and formula (a1-4-20).

(a1-4-1)

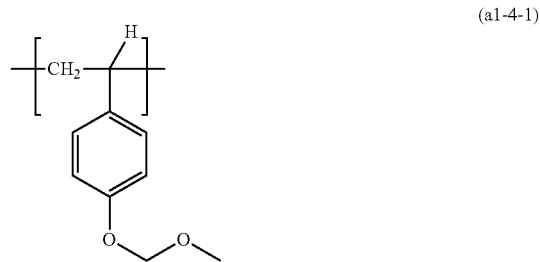

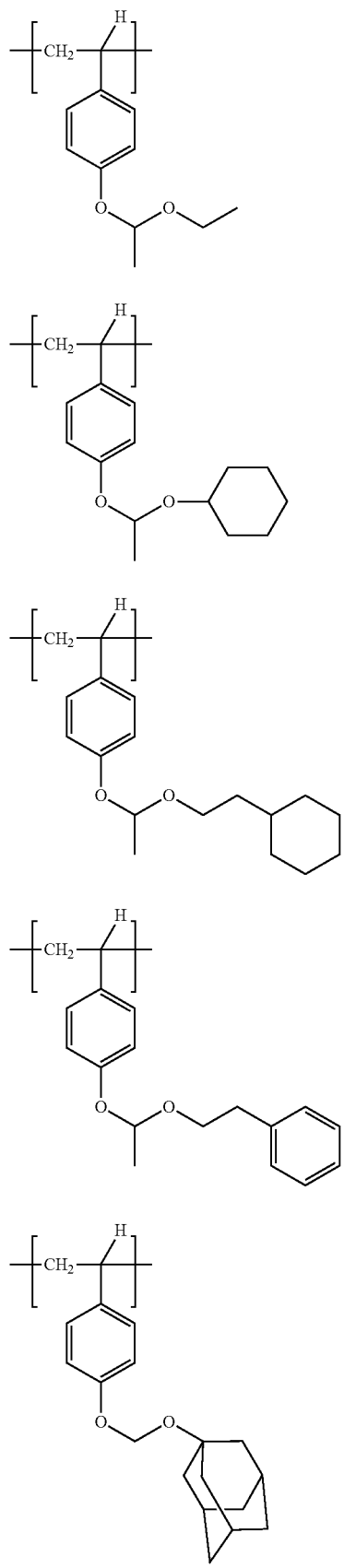
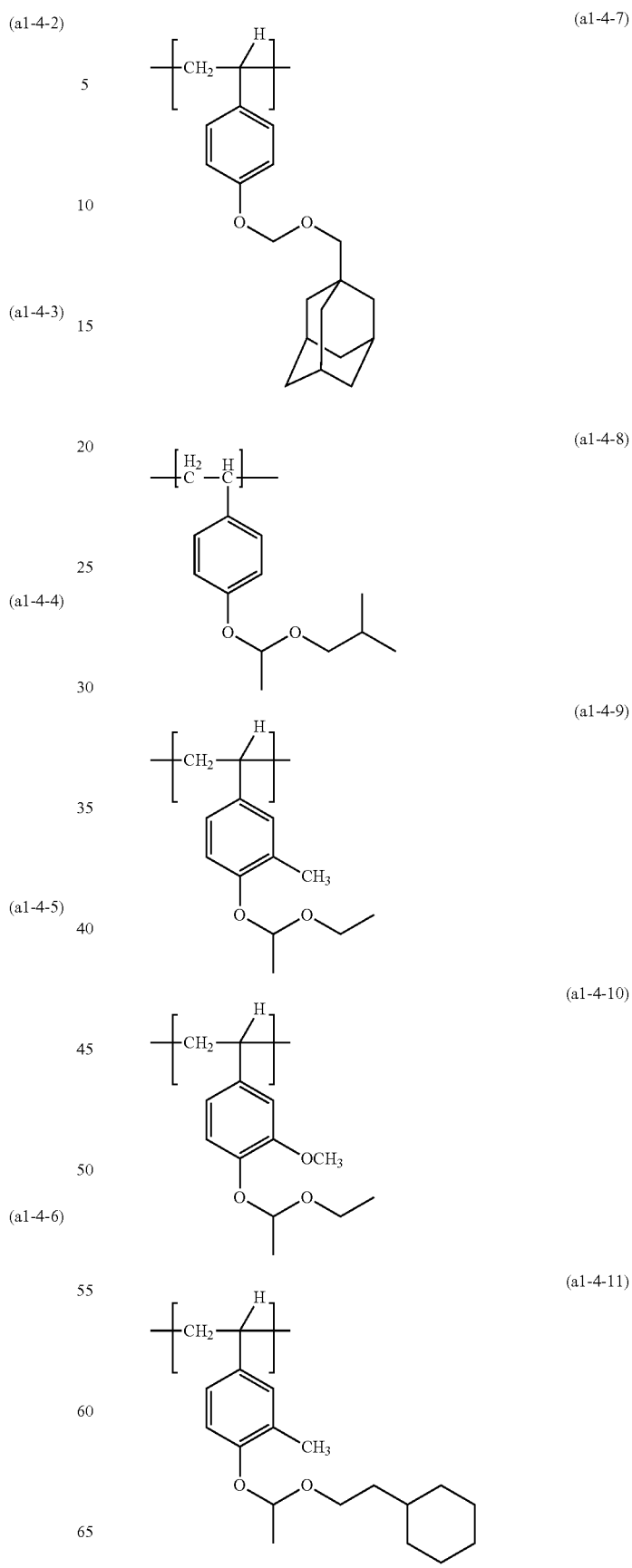

(a1-4-12)
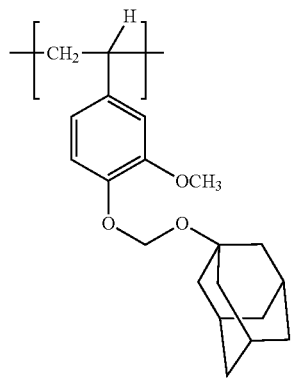
(a1-4-13)
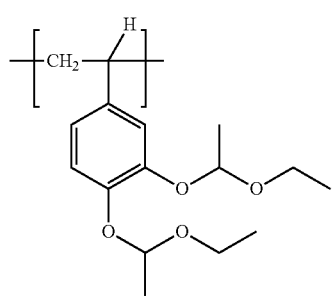
(a1-4-14)
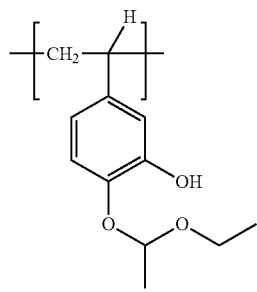
(a1-4-15)
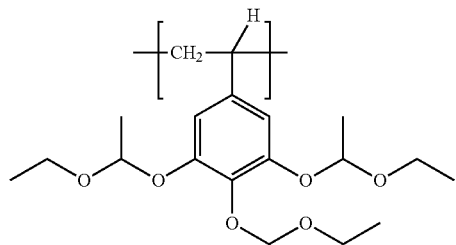
(a1-4-16)
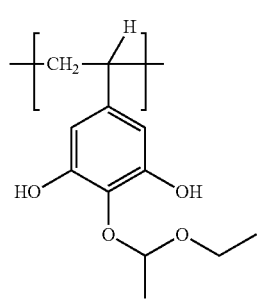
(a1-4-17)
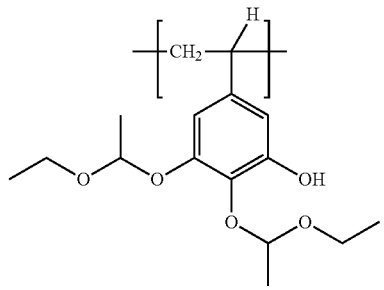
(a1-4-18)
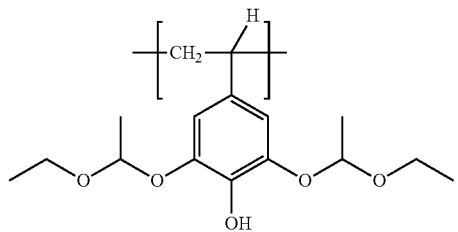
(a1-4-19)
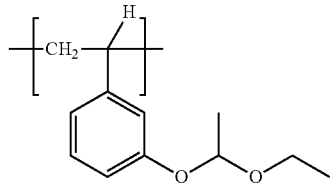
(a1-4-20)
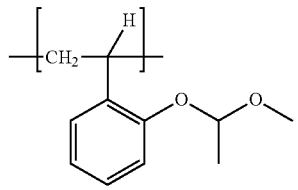
(a1-4-21)
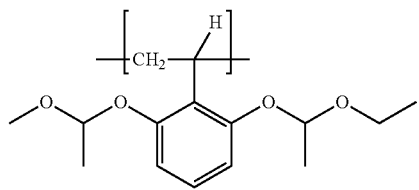
(a1-4-22)
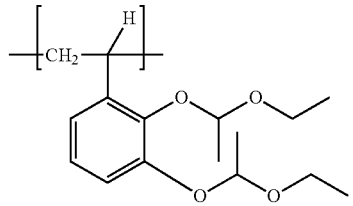

-continued

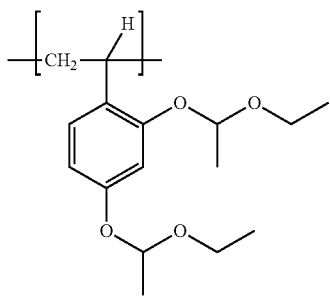
(a1-4-23)

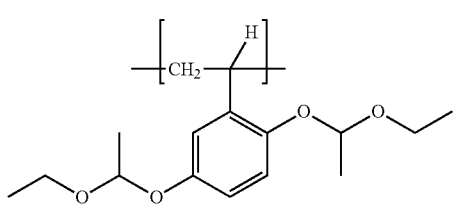
(a1-4-24)

When the resin (A) includes the structural unit (a1-4), the content is preferably 10 to 95 mol %, more preferably 15 to 90 mol %, still more preferably 20 to 85 mol %, yet more preferably 20 to 70 mol %, and particularly preferably 20 to 60 mol %, based on the total of all structural units of the resin (A).

The structural unit derived from a (meth)acrylic monomer having a group (2) also includes a structural unit represented by formula (a1-5) (hereinafter sometimes referred to as "structural unit (a1-5)").

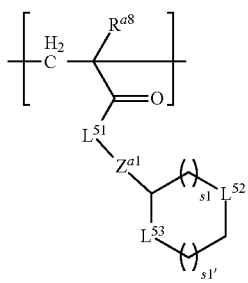
(a-5)

In formula (a1-5),
$R^{a8}$ represents an alkyl group having 1 to 6 carbon atoms which may have a halogen atom, a hydrogen atom or a halogen atom,
$Z^{a1}$ represents a single bond or *—$(CH_2)_{h3}$—CO-$L^{54}$-, h3 represents an integer of 1 to 4, and * represents a bonding site to $L^{51}$,
$L^{51}$, $L^{52}$, $L^{53}$ and $L^{54}$ each independently represent —O— or —S—,
s1 represents an integer of 1 to 3, and
s1' represents an integer of 0 to 3.

The halogen atom includes a fluorine atom and a chlorine atom and is preferably a fluorine atom.

Examples of the alkyl group having 1 to 6 carbon atoms which may have a halogen atom include a methyl group, an ethyl group, a propyl group, a butyl group, a pentyl group, a hexyl group, a heptyl group, an octyl group, a fluoromethyl group and a trifluoromethyl group.

In formula (a1-5), $R^{a8}$ is preferably a hydrogen atom, a methyl group or a trifluoromethyl group,
$L^{51}$ is preferably an oxygen atom,
one of $L^{52}$ and $L^{53}$ is preferably —O— and the other one is preferably —S—,
s1 is preferably 1,
s1' is preferably an integer of 0 to 2, and
$Z^{a1}$ is preferably a single bond or *—$CH_2$—CO—O—.

The structural unit (a1-5) includes, for example, structural units derived from the monomers mentioned in JP 2010-61117 A. Of these structural units, structural units represented by formula (a1-5-1) to formula (a1-5-4) are preferable, and structural units represented by formula (a1-5-1) or formula (a1-5-2) are more preferable.

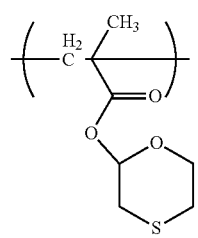
(a1-5-1)

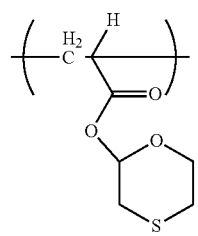
(a1-5-2)

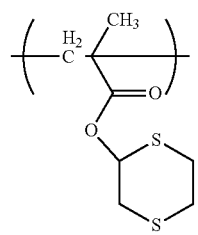
(a1-5-3)

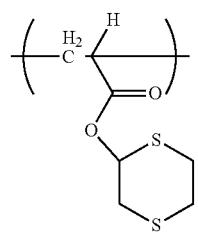
(a1-5-4)

When the resin (A) includes the structural unit (a1-5), the content is preferably 1 to 50 mol %, more preferably 3 to 45 mol %, still more preferably 5 to 40 mol %, and yet more preferably 5 to 30 mol %, based on all structural units of the resin (A).

The structural unit (a1) also includes the following structural units.

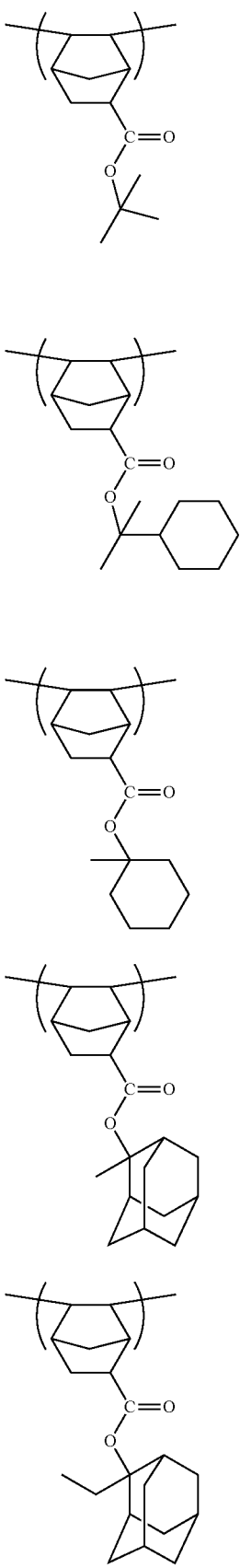

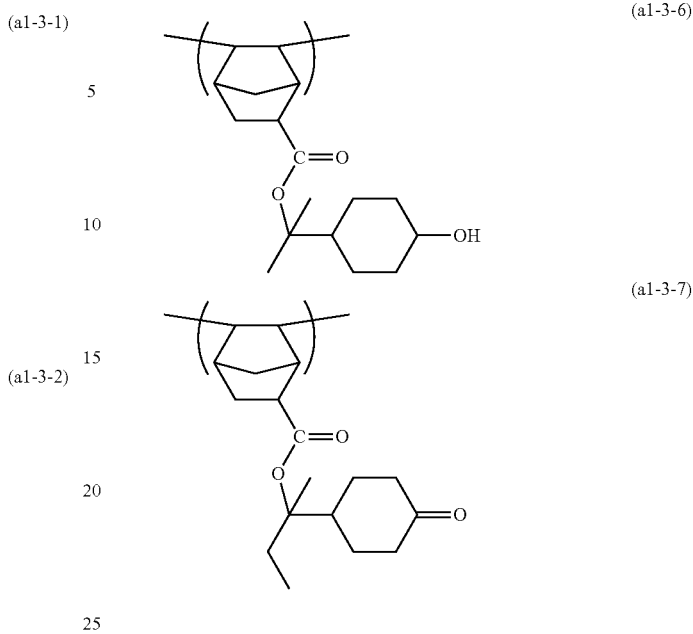

When the resin (A) includes the above-mentioned structural units such as (a1-3-1) to (a1-3-7), the content is preferably 10 to 95 mol %, more preferably 15 to 90 mol %, still more preferably 20 to 85 mol %, yet more preferably 20 to 70 mol %, and particularly preferably 20 to 60 mol %, based on all structural units of the resin (A).

<Structural Unit (s)>

The structural unit (s) is derived from a monomer having no acid-labile group (hereinafter sometimes referred to as "monomer (s)"). It is possible to use, as the monomer from which the structural unit (s) is derived, a monomer having no acid-labile group known in the resist field.

The structural unit (s) preferably has a hydroxy group or a lactone ring. When a resin including a structural unit having a hydroxy group and having no acid-labile group (hereinafter sometimes referred to as "structural unit (a2)") and/or a structural unit having a lactone ring and having no acid-labile group (hereinafter sometimes referred to as "structural unit (a3)") is used in the resist composition of the present invention, it is possible to improve the resolution of a resist pattern and the adhesion to a substrate.

<Structural Unit (a2)>

The hydroxy group possessed by the structural unit (a2) may be either an alcoholic hydroxy group or a phenolic hydroxy group.

When a resist pattern is produced from the resist composition of the present invention, in the case of using, as an exposure source, high energy rays such as KrF excimer laser (248 nm), electron beam or extreme ultraviolet light (EUV), a structural unit (a2) having a phenolic hydroxy group is preferably used, and the below-mentioned structural unit (a2-A) is more preferably used, as the structural unit (a2). When using ArF excimer laser (193 nm) or the like, a structural unit (a2) having an alcoholic hydroxy group is preferably used, and the below-mentioned structural unit (a2-1) is more preferably used, as the structural unit (a2). The structural unit (a2) may be included alone, or two or more structural units may be included.

In the structural unit (a2), examples of the structural unit having a phenolic hydroxy group include a structural unit represented by formula (a2-A) (hereinafter sometimes referred to as "structural unit (a2-A)"):

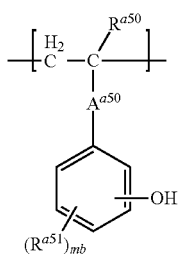

wherein, in formula (a2-A),

R$^{a50}$ represents a hydrogen atom, a halogen atom, or an alkyl group having 1 to 6 carbon atoms which may have a halogen atom, R$^{a51}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group, A$^{a50}$ represents a single bond or *—X$^{a51}$-(A$^{a52}$-X$^{a52}$)$_{nb}$—, and * represents a bonding site to carbon atoms to which —R$^{a50}$ is bonded, A$^{a52}$ represents an alkanediyl group having 1 to 6 carbon atoms, X$^{a51}$ and X$^{a52}$ each independently represent —O—, —CO—O— or —O—CO—, nb represents 0 or 1, and mb represents an integer of 0 to 4, and when mb is an integer of 2 or more, a plurality of R$^{a51}$ may be the same or different from each other.

Examples of the halogen atom in R$^{a50}$ and R$^{a51}$ include a fluorine atom, a chlorine atom and a bromine atom.

Examples of the alkyl group having 1 to 6 carbon atoms which may have a halogen atom in R$^{a50}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

R$^{a50}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in R$^{a51}$ include a methyl group, an ethyl group, a propyl group, an isopropyl group, a butyl group, a sec-butyl group, a tert-butyl group, a pentyl group and a hexyl group. The alkyl group is preferably an alkyl group having 1 to 4 carbon atoms, more preferably a methyl group or an ethyl group, and still more preferably a methyl group.

Examples of the alkoxy group in R$^{a51}$ include a methoxy group, an ethoxy group, a propoxy group, an isopropoxy group, a butoxy group, a sec-butoxy group and a tert-butoxy group. The alkoxy group is preferably an alkoxy group having 1 to 4 carbon atoms, more preferably a methoxy group or an ethoxy group, and still more preferably a methoxy group.

Examples of the alkoxyalkyl group in R$^{a51}$ include a methoxymethyl group, an ethoxyethyl group, a propoxymethyl group, an isopropoxymethyl group, a butoxymethyl group, a sec-butoxymethyl group and a tert-butoxymethyl group. The alkoxyalkyl group is preferably an alkoxyalkyl group having 2 to 8 carbon atoms, more preferably a methoxymethyl group or an ethoxyethyl group, and still more preferably a methoxymethyl group.

Examples of the alkoxyalkoxy group in R$^{a51}$ include a methoxymethoxy group, a methoxyethoxy group, an ethoxymethoxy group, an ethoxyethoxy group, a propoxymethoxy group, an isopropoxymethoxy group, a butoxymethoxy group, a sec-butoxymethoxy group and a tert-butoxymethoxy group. The alkoxyalkoxy group is preferably an alkoxyalkoxy group having 2 to 8 carbon atoms, and more preferably a methoxyethoxy group or an ethoxyethoxy group.

Examples of the alkylcarbonyl group in R$^{a51}$ include an acetyl group, a propionyl group and a butyryl group. The alkylcarbonyl group is preferably an alkylcarbonyl group having 2 to 3 carbon atoms, and more preferably an acetyl group.

Examples of the alkylcarbonyloxy group in R$^{a51}$ include an acetyloxy group, a propionyloxy group and a butyryloxy group. The alkylcarbonyloxy group is preferably an alkylcarbonyloxy group having 2 to 3 carbon atoms, and more preferably an acetyloxy group.

R$^{a51}$ is preferably a halogen atom, a hydroxy group, an alkyl group having 1 to 4 carbon atoms, an alkoxy group having 1 to 4 carbon atoms or an alkoxyalkoxy group having 2 to 8 carbon atoms, more preferably a fluorine atom, an iodine atom, a hydroxy group, a methyl group, a methoxy group, an ethoxy group, an ethoxyethoxy group or an ethoxymethoxy group, and still more preferably a fluorine atom, an iodine atom, a hydroxy group, a methyl group, a methoxy group or an ethoxyethoxy group.

Examples of *—X$^{a51}$-(A$^{a52}$-X$^{a52}$)$_{nb}$— include *—O—, *—CO—, *—O—CO—, *—CO—O-A$^{a52}$-CO—O—, *—O—CO-A$^{a52}$-O—, *—O-A$^{a52}$-CO—O—, *—CO—O-A$^{a52}$-O—CO— and *—O—CO-A$^{a52}$-O—CO—. Of these, *—CO—O—, *—CO—O-A$^{a52}$-CO—O— or *—O-A$^{a52}$-CO—O— is preferable.

Examples of the alkanediyl group in A$^{a52}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

A$^{a52}$ is preferably a methylene group or an ethylene group.

A$^{a50}$ is preferably a single bond, *—CO—O— or *—CO—O-A$^{a52}$-CO—O—, more preferably a single bond, *—CO—O— or *—CO—O—CH$_2$—CO—O—, and still more preferably a single bond or *—CO—O—.

mb is preferably 0, 1 or 2, more preferably 0 or 1, and still more preferably 0.

At least one hydroxy group is preferably bonded to the meta-position or the para-position of the benzene ring, and more preferably the meta-position. When the phenyl group has two or more hydroxy groups, two hydroxy groups are preferably bonded at the meta-position and the para-position, respectively.

Examples of the structural unit (a2-A) include structural units derived from the monomers mentioned in JP 2010-204634 A and JP 2012-12577 A.

Examples of the structural unit (a2-A) include structural units represented by formula (a2-2-1) to formula (a2-2-24), and a structural unit in which a methyl group corresponding to $R^{a50}$ in the structural unit (a2-A) is substituted with a hydrogen atom, a halogen atom, a haloalkyl group or other alkyl groups in structural units represented by formula (a2-2-1) to formula (a2-2-24). The structural unit (a2-A) is preferably structural units represented by formula (a2-2-1) to formula (a2-2-4), a structural unit represented by formula (a2-2-6), a structural unit represented by formula (a2-2-8), structural units represented by formula (a2-2-12) to formula (a2-2-18), and a structural unit in which a methyl group corresponding to $R^{a50}$ in the structural unit (a2-A) is substituted with a hydrogen atom in structural units represented by formula (a2-2-1) to formula (a2-2-4), a structural unit represented by formula (a2-2-6), a structural unit represented by formula (a2-2-8) and structural units represented by formula (a2-2-12) to formula (a2-2-18), more preferably a structural unit represented by formula (a2-2-3), a structural unit represented by formula (a2-2-4), a structural unit represented by formula (a2-2-8), structural units represented by formula (a2-2-12) to formula (a2-2-14), a structural unit represented by formula (a2-2-18), and a structural unit in which a methyl group corresponding to $R^{a50}$ in the structural unit (a2-A) is substituted with a hydrogen atom in a structural unit represented by formula (a2-2-3), a structural unit represented by formula (a2-2-4), a structural unit represented by formula (a2-2-8), structural units represented by formula (a2-2-12) to formula (a2-2-14) and a structural unit represented by formula (a2-2-18), and still more preferably a structural unit represented by formula (a2-2-3), a structural unit represented by formula (a2-2-4), a structural unit represented by formula (a2-2-8), and a structural unit in which a methyl group corresponding to $R^{a50}$ in the structural unit (a2-A) is substituted with a hydrogen atom in a structural unit represented by formula (a2-2-3), a structural unit represented by formula (a2-2-4) and a structural unit represented by formula (a2-2-8).

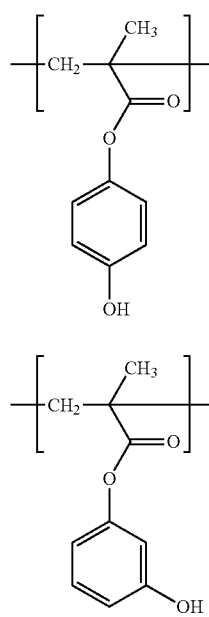

(a2-2-1)

(a2-2-2)

-continued

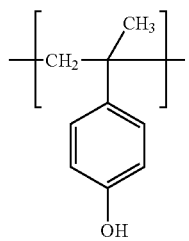

(a2-2-3)

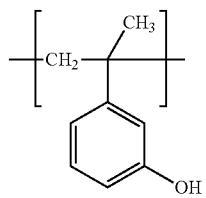

(a2-2-4)

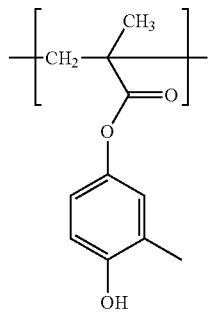

(a2-2-5)

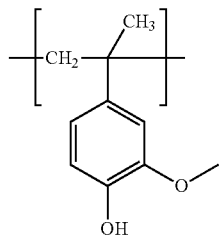

(a2-2-6)

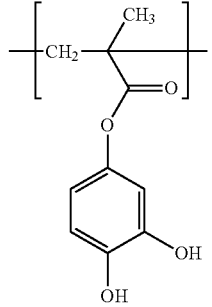

(a2-2-7)

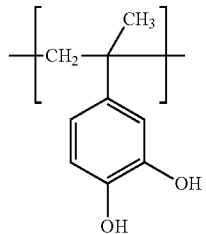

(a2-2-8)

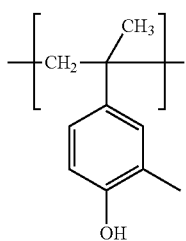 (a2-2-9)
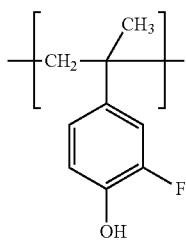 (a2-9-10)
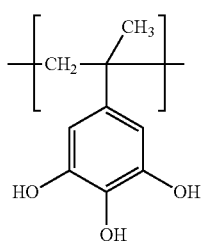 (a2-9-11)
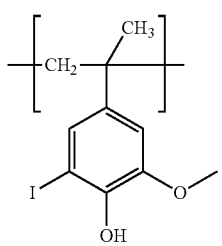 (a2-9-12)
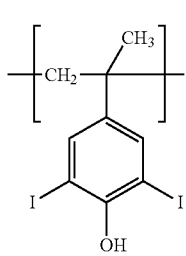 (a2-2-13)
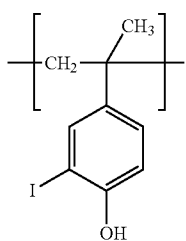 (a2-2-14)
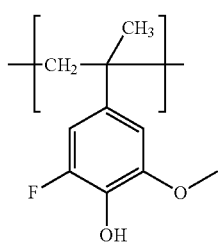 (a2-2-15)
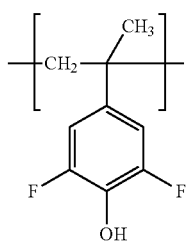 (a2-2-16)
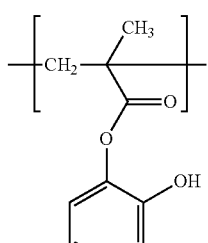 (a2-2-17)
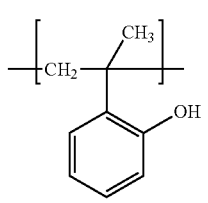 (a2-2-18)
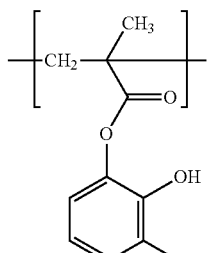 (a2-2-19)
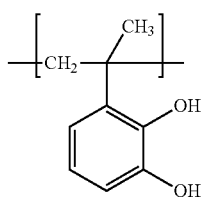 (a2-2-20)

-continued (a2-2-21)
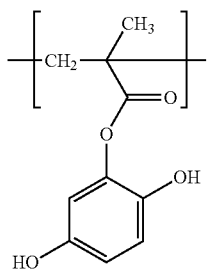

(a2-2-22)
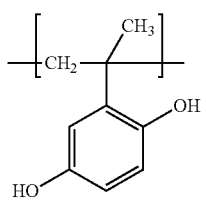

(a2-2-23)
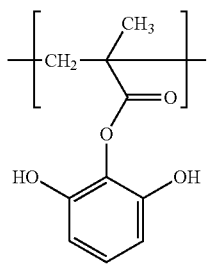

(a2-2-24)
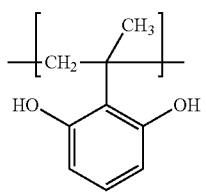

When the structural unit (a2-A) is included in the resin (A), the content of the structural unit (a2-A) is preferably 5 to 80 mol %, more preferably 10 to 70 mol %, still more preferably 15 to 65 mol %, and yet more preferably 20 to 65 mol %, based on all structural units.

The structural unit (a2-A) can be included in a resin (A) by polymerizing, for example, with a structural unit (a1-4) and treating with an acid such as p-toluenesulfonic acid. The structural unit (a2-A) can also be included in the resin (A) by polymerizing with acetoxystyrene and treating with an alkali such as tetramethylammonium hydroxide.

Examples of the structural unit having an alcoholic hydroxy group in the structural unit (a2) include a structural unit represented by formula (a2-1) (hereinafter sometimes referred to as "structural unit (a2-1)").

(a2-1)
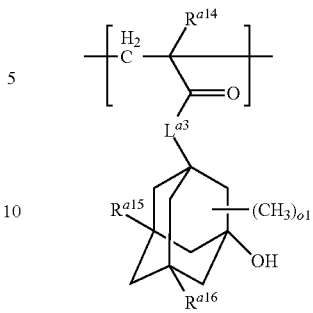

In formula (a2-1),
$L^{a3}$ represents —O— or *—O—$(CH_2)_{k2}$—CO—O—,
k2 represents an integer of 1 to 7, and * represents a bonding site to —CO—,
$R^{a14}$ represents a hydrogen atom or a methyl group,
$R^{a15}$ and $R^{a16}$ each independently represent a hydrogen atom, a methyl group or a hydroxy group, and
o1 represents an integer of 0 to 10.

In formula (a2-1), $L^{a3}$ is preferably —O— or —O—$(CH_2)_{f1}$—CO—O— (f1 represents an integer of 1 to 4), and more preferably —O—,
$R^{a14}$ is preferably a methyl group,
$R^{a15}$ is preferably a hydrogen atom,
$R^{a16}$ is preferably a hydrogen atom or a hydroxy group, and
o1 is preferably an integer of 0 to 3, and more preferably 0 or 1.

The structural unit (a2-1) includes, for example, structural units derived from the monomers mentioned in JP 2010-204646 A. A structural unit represented by any one of formula (a2-1-1) to formula (a2-1-6) is preferable, a structural unit represented by any one of formula (a2-1-1) to formula (a2-1-4) is more preferable, and a structural unit represented by formula (a2-1-1) or formula (a2-1-3) is still more preferable.

(a2-1-1)

(a2-1-2)

(a2-1-3)
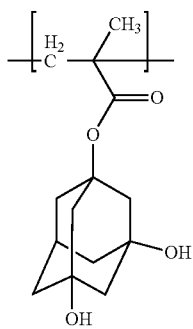

(a2-1-4)
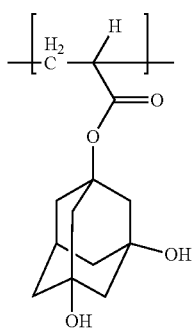

(a2-1-5)
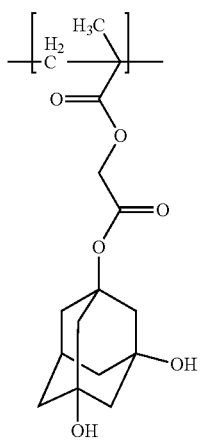

(a2-1-6)
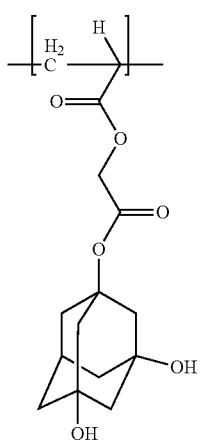

When the resin (A) includes the structural unit (a2-1), the content is usually 1 to 45 mol %, preferably 1 to 40 mol %, more preferably 1 to 35 mol %, still more preferably 1 to 20 mol %, and yet more preferably 1 to 10 mol %, based on all structural units of the resin (A).

<Structural Unit (a3)>

The lactone ring possessed by the structural unit (a3) may be a monocyclic ring such as a β-propiolactone ring, a γ-butyrolactone ring or a δ-valerolactone ring, or a condensed ring of a monocyclic lactone ring and the other ring. Preferably, a γ-butyrolactone ring, an adamantanelactone ring or a bridged ring including a γ-butyrolactone ring structure (e.g. a structural unit represented by the following formula (a3-2)) is exemplified.

The structural unit (a3) is preferably a structural unit represented by formula (a3-1), formula (a3-2), formula (a3-3) or formula (a3-4). These structural units may be included alone, or two or more structural units may be included:

(a3-1)
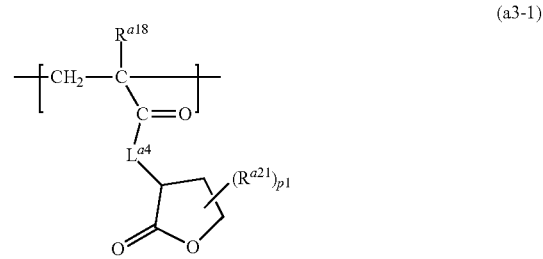

(a3-2)
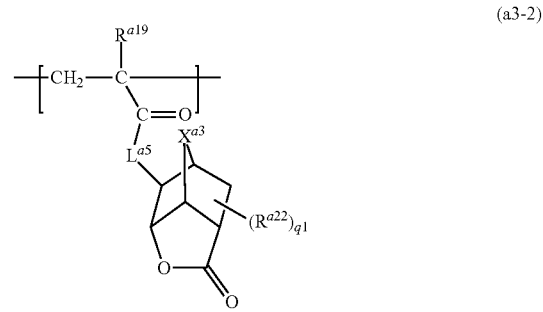

(a3-3)
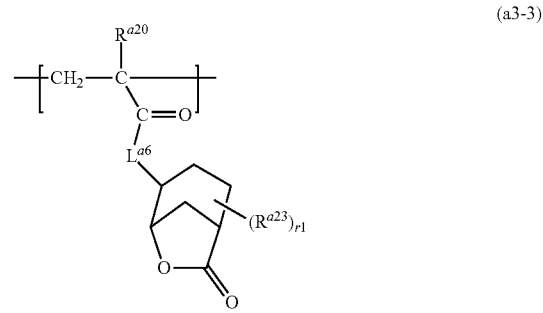

(a3-4)
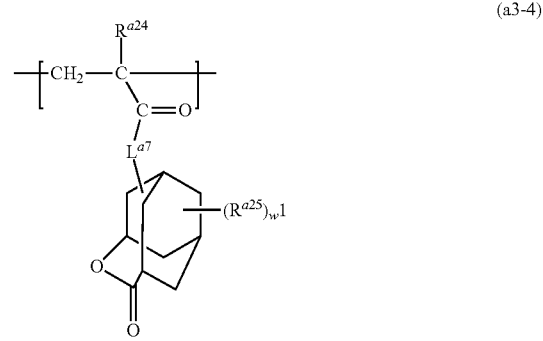

wherein, in formula (a3-1), formula (a3-2), formula (a3-3) and formula (a3-4), $L^{a4}$, Las and $L^{a6}$ each independently represent —O— or a group represented by *—O—$(CH_2)_{k3}$—CO—O— (k3 represents an integer of 1 to 7), $L^{a7}$ represents —O—, *—O-$L^{a8}$-O—, *—O-$L^{a8}$-CO—O—, *—O-$L^{a8}$-CO—O-$L^{a9}$-CO—O— or *—O-$L^{a8}$-O—CO-$L^{a9}$-O—, $L^{a8}$ and $L^{a9}$ each independently represent an alkanediyl group having 1 to 6 carbon atoms, represents a bonding site to a carbonyl group, $R^{a18}$, $R^{a19}$ and $R^{a20}$ each independently represent a hydrogen atom or a methyl group, $R^{a24}$ represents a hydrogen atom, a halogen atom, or an alkyl group having 1 to 6 carbon atoms which may have a halogen atom, $X^{a3}$ represents —$CH_2$— or an oxygen atom, $R^{a21}$ represents an aliphatic hydrocarbon group having 1 to 4 carbon atoms, $R^{a22}$, $R^{a23}$ and $R^{a25}$ each independently represent a carboxy group, a cyano group or an aliphatic hydrocarbon group having 1 to 4 carbon atoms, p1 represents an integer of 0 to 5, q1 represents an integer of 0 to 3, r1 represents an integer of 0 to 3, w1 represents an integer of 0 to 8, and when p1, q1, r1 and/or w1 is/are 2 or more, a plurality of $R^{a21}$, $R^{a22}$, $R^{a23}$ and/or $R^{a25}$ may be the same or different from each other.

Examples of the aliphatic hydrocarbon group in $R^{a21}$, $R^{a22}$, $R^{a23}$ and $R^{a25}$ include alkyl groups such as a methyl group, an ethyl group, a propyl group, an isopropyl group, a butyl group, a sec-butyl group and a tert-butyl group.

Examples of the halogen atom in $R^{a24}$ include a fluorine atom, a chlorine atom, a bromine atom and an iodine atom.

Examples of the alkyl group in $R^{a24}$ include a methyl group, an ethyl group, a propyl group, an isopropyl group, a butyl group, a sec-butyl group, a tert-butyl group, a pentyl group and a hexyl group, and the alkyl group is preferably an alkyl group having 1 to 4 carbon atoms, and more preferably a methyl group or an ethyl group.

Examples of the alkyl group having a halogen atom in $R^{a24}$ include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a trichloromethyl group, a tribromomethyl group, a triiodomethyl group and the like.

Examples of the alkanediyl group in $L^{a8}$ and $L^{a9}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

In formula (a3-1) to formula (a3-3), preferably, $L^{a4}$ to $L^{a6}$ are each independently —O— or a group in which k3 is an integer of 1 to 4 in *—O—$(CH_2)_{k3}$—CO—O—, more preferably —O— and *—O—$CH_2$—CO—O—, and still more preferably an oxygen atom, $R^{a18}$ to $R^{a21}$ are preferably a methyl group, preferably, $R^{a22}$ and $R^{a23}$ are each independently a carboxy group, a cyano group or a methyl group, and preferably, p1, q1 and r1 are each independently an integer of 0 to 2, and more preferably 0 or 1.

In formula (a3-4), $R^{a24}$ is preferably a hydrogen atom or an alkyl group having 1 to 4 carbon atoms, more preferably a hydrogen atom, a methyl group or an ethyl group, and still more preferably a hydrogen atom or a methyl group, $R^{a25}$ is preferably a carboxy group, a cyano group or a methyl group, $L^{a7}$ is preferably —O— or *—O-$L^{a8}$-CO—O—, and more preferably —O—, —O—$CH_2$—CO—O— or —O—$C_2H_4$—CO—O—, and w1 is preferably an integer of 0 to 2, and more preferably 0 or 1.

Particularly, formula (a3-4) is preferably formula (a3-4)':

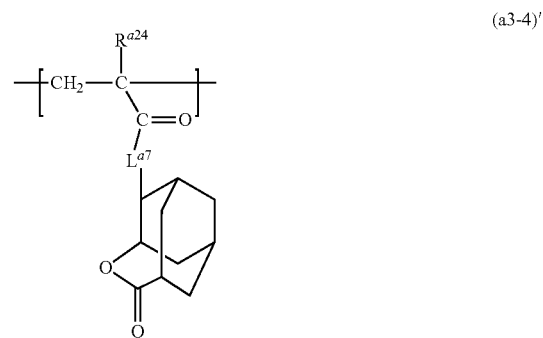

(a3-4)' wherein $R^{a24}$ and $L^{a7}$ are the same as defined above.

Examples of the structural unit (a3) include structural units derived from the monomers mentioned in JP 2010-204646 A, the monomers mentioned in JP 2000-122294 A and the monomers mentioned in JP 2012-41274 A. The structural unit (a3) is preferably a structural unit represented by any one of formula (a3-1-1), formula (a3-1-2), formula (a3-2-1), formula (a3-2-2), formula (a3-3-1), formula (a3-3-2) and formula (a3-4-1) to formula (a3-4-12), and structural units in which methyl groups corresponding to $R^{a18}$, $R^{a19}$, $R^{a20}$ and $R^{a24}$ in formula (a3-1) to formula (a3-4) are substituted with hydrogen atoms in the above structural units.

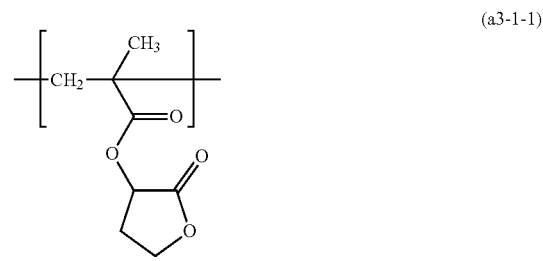

(a3-1-1)

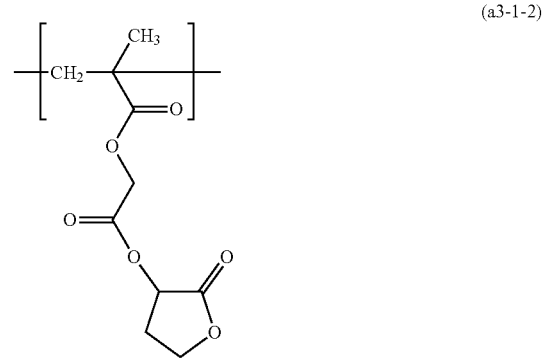

(a3-1-2)

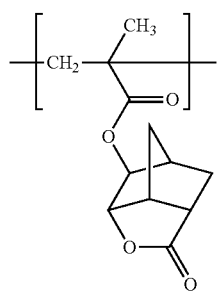
(a3-2-1)
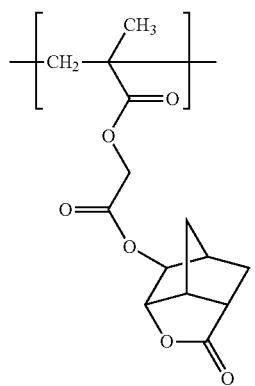
(a3-2-2)
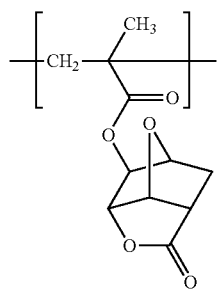
(a3-2x-1)
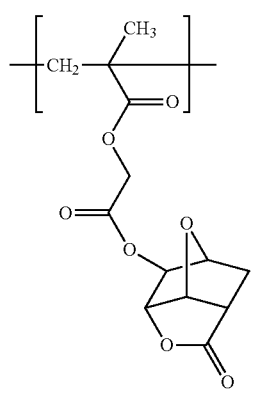
(a3-2x-2)
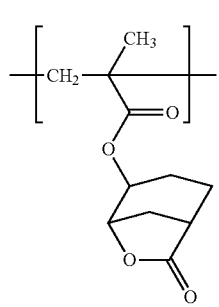
(a3-3-1)
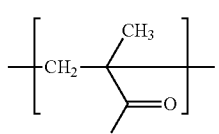
(a3-3-2)
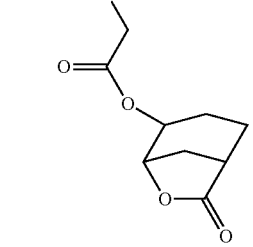
(a3-4-1)
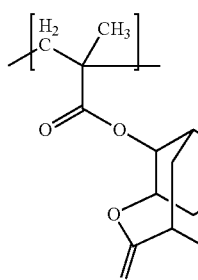
(a3-4-2)
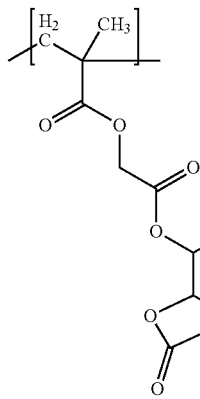
(a3-4-3)
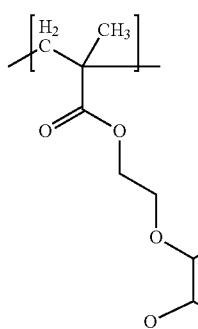

(a3-4-4)
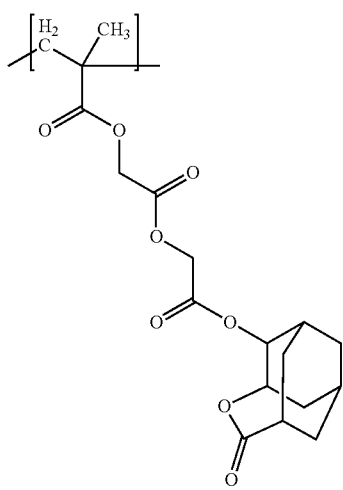
(a3-4-5)
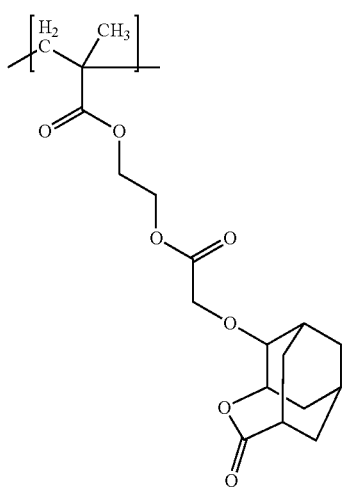
(a3-4-6)
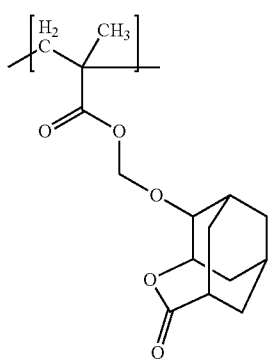
(a3-4-7)
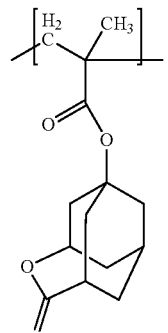
(a3-4-8)
(a3-4-9)
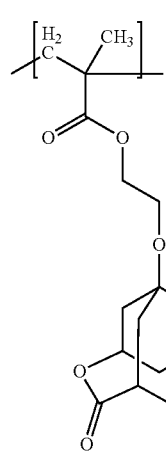

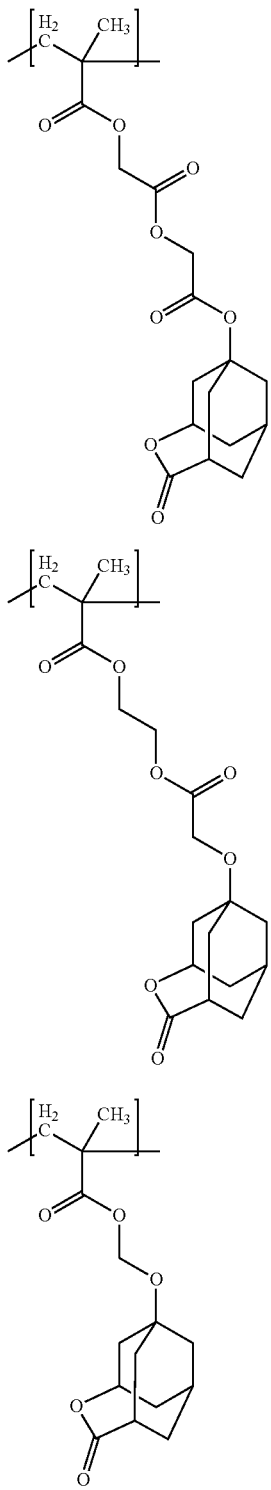

(a3-4-10)

(a3-4-11)

(a3-4-12)

When the resin (A) includes the structural unit (a3), the total content is usually 5 to 70 mol %, preferably 10 to 65 mol %, and more preferably 10 to 60 mol %, based on all structural units of the resin (A).

Each content of the structural unit (a3-1), the structural unit (a3-2), the structural unit (a3-3) or the structural unit (a3-4) is preferably 5 to 60 mol %, more preferably 5 to 50 mol %, and still more preferably 10 to 50 mol %, based on all structural units of the resin (A).

<Structural Unit (a4)>

Examples of the structural unit (a4) include the following structural unit:

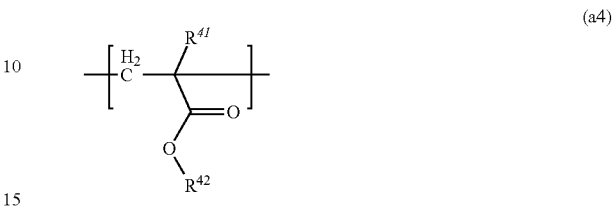

(a4)

wherein, in formula (a4), $R^{41}$ represents a hydrogen atom or a methyl group, and
$R^{42}$ represents a saturated hydrocarbon group having 1 to 24 carbon atoms which has a fluorine atom, and —$CH_2$— included in the saturated hydrocarbon group may be replaced by —O— or —CO—.

Examples of the saturated hydrocarbon group represented by $R^{42}$ include a chain hydrocarbon group and a monocyclic or polycyclic alicyclic hydrocarbon group, and groups formed by combining these groups.

Examples of the chain hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group. Examples of the monocyclic or polycyclic alicyclic hydrocarbon group include cycloalkyl groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group and the following groups (* represents a bonding site).

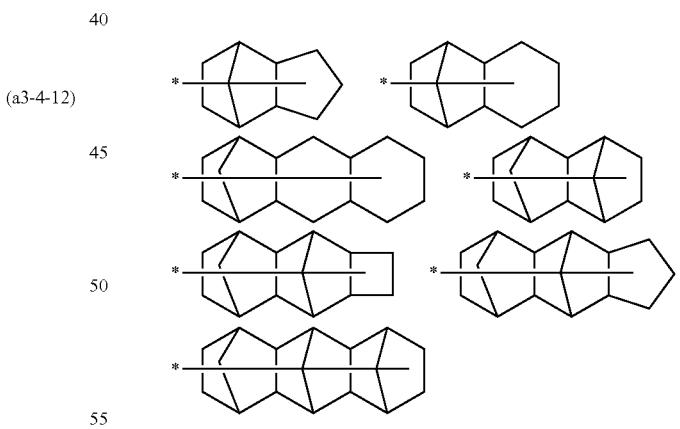

Examples of the group formed by combination include groups formed by combining one or more alkyl groups or one or more alkanediyl groups with one or more alicyclic hydrocarbon groups, for example, an -alkanediyl group-alicyclic hydrocarbon group, an -alicyclic hydrocarbon group-alkyl group, an -alkanediyl group-alicyclic hydrocarbon group-alkyl group and the like.

Examples of the structural unit (a4) include a structural unit represented by at least one selected from the group consisting of formula (a4-0), formula (a4-1), formula (a4-2), formula (a4-3) and formula (a4-4):

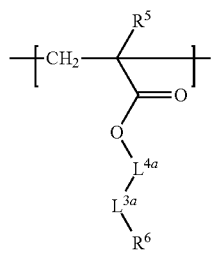
(a4-0)

wherein, in formula (a4-0), $R^5$ represents a hydrogen atom or a methyl group, $L^{4a}$ represents a single bond or a divalent aliphatic saturated hydrocarbon group having 1 to 4 carbon atoms, $L^{3a}$ represents a perfluoroalkanediyl group having 1 to 8 carbon atoms or a perfluorocycloalkanediyl group having 3 to 12 carbon atoms, and $R^6$ represents a hydrogen atom or a fluorine atom.

Examples of the divalent aliphatic saturated hydrocarbon group in $L^{4a}$ include linear alkanediyl groups such as a methylene group, an ethylene group, a propane-1,3-diyl group and a butane-1,4-diyl group; and branched alkanediyl groups such as an ethane-1,1-diyl group, a propane-1,2-diyl group, a butane-1,3-diyl group, a 2-methylpropane-1,3-diyl group and a 2-methylpropane-1,2-diyl group.

Examples of the perfluoroalkanediyl group in $L^3a$ include a difluoromethylene group, a perfluoroethylene group, a perfluoropropane-1,1-diyl group, a perfluoropropane-1,3-diyl group, a perfluoropropane-1,2-diyl group, a perfluoropropane-2,2-diyl group, a perfluorobutane-1,4-diyl group, a perfluorobutane-2,2-diyl group, a perfluorobutane-1,2-diyl group, a perfluoropentane-1,5-diyl group, a perfluoropentane-2,2-diyl group, a perfluoropentane-3,3-diyl group, a perfluorohexane-1,6-diyl group, a perfluorohexane-2,2-diyl group, a perfluorohexane-3,3-diyl group, a perfluoroheptane-1,7-diyl group, a perfluoroheptane-2,2-diyl group, a perfluoroheptane-3,4-diyl group, a perfluoroheptane-4,4-diyl group, a perfluorooctane-1,8-diyl group, a perfluorooctane-2,2-diyl group, a perfluorooctane-3,3-diyl group, a perfluorooctane-4,4-diyl group and the like.

Examples of the perfluorocycloalkanediyl group in $L^3a$ include a perfluorocyclohexanediyl group, a perfluorocyclopentanediyl group, a perfluorocycloheptanediyl group, a perfluoroadamantanediyl group and the like.

$L^{4a}$ is preferably a single bond, a methylene group or an ethylene group, and more preferably a single bond or a methylene group.

$L^{3a}$ is preferably a perfluoroalkanediyl group having 1 to 6 carbon atoms, and more preferably a perfluoroalkanediyl group having 1 to 3 carbon atoms.

Examples of the structural unit (a4-0) include the following structural units, and structural units in which a methyl group corresponding to $R^5$ in the structural unit (a4-0) in the following structural units is substituted with a hydrogen atom:

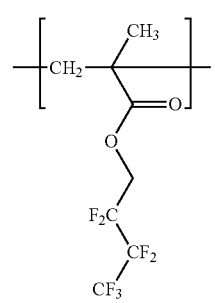
(a4-0-1)

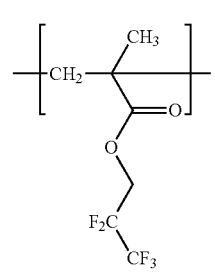
(a4-0-2)

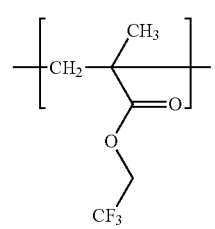
(a4-0-3)

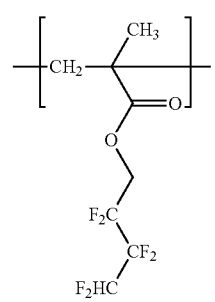
(a4-0-4)

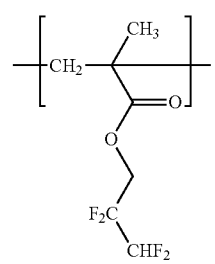
(a4-0-5)

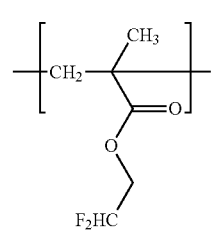
(a4-0-6)

(a4-0-7) 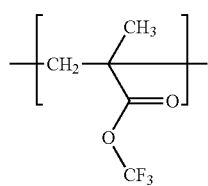
(a4-0-8) 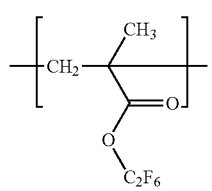
(a4-0-9) 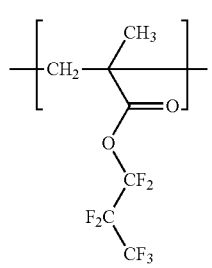
(a4-0-10) 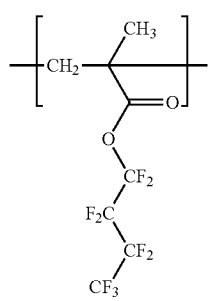
(a4-0-11) 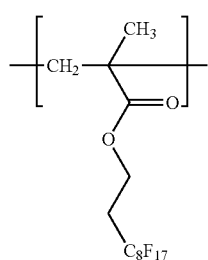
(a4-0-12) 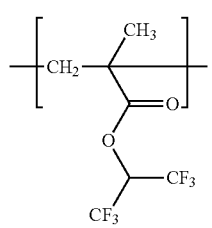
(a4-0-13) 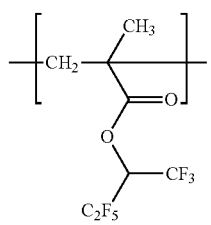
(a4-0-14) 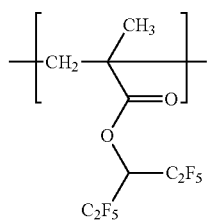
(a4-0-15) 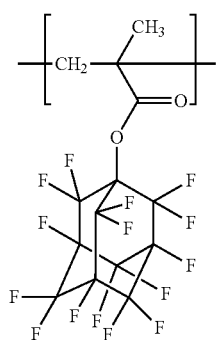
(a4-0-16) 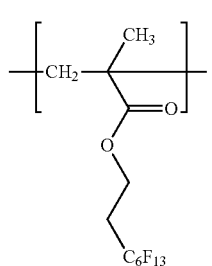
Examples of the structural unit (a4) include a structural unit represented by formula (a4-1):
(a-4-1) 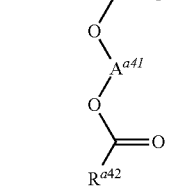
wherein, in formula (a4-1),
$R^{a41}$ represents a hydrogen atom or a methyl group,
$R^{a42}$ represents a saturated hydrocarbon group having 1 to 20 carbon atoms which may have a substituent, and —CH$_2$-included in the saturated hydrocarbon group may be replaced by —O— or —CO—, $A^{a41}$ represents an alkanediyl group having 1 to 6 carbon atoms which may have a substituent or a group represented by formula (a-g1), in which at least one of $A^{a41}$ and $R^{a42}$ has, as a substituent, a halogen atom (preferably a fluorine atom):

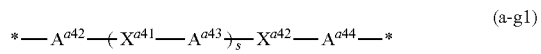

(a-g1)

[in which, in formula (a-g1),
s represents 0 or 1,
$A^{a42}$ and $A^{a44}$ each independently represent a divalent saturated hydrocarbon group having 1 to 5 carbon atoms which may have a substituent,
$A^{a43}$ represents a single bond or a divalent aliphatic hydrocarbon group having 1 to 5 carbon atoms which may have a substituent,
$X^{a41}$ and $X^{a42}$ each independently represent —O—, —CO—, —CO—O— or —O—CO—, in which the total number of carbon atoms of $A^{a42}$, $A^{a43}$, $A^{a44}$, $X^{a41}$ and $X^{a42}$ is 7 or less], and
* represents a bonding site and * at the right side represents a bonding site to —O—CO—$R^{a42}$.

Examples of the saturated hydrocarbon group in $R^{a42}$ include a chain saturated hydrocarbon group and a monocyclic or polycyclic saturated alicyclic hydrocarbon group, and groups formed by combining these groups.

Examples of the chain saturated hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the monocyclic or polycyclic alicyclic saturated hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group and the following groups (* represents a bonding site).

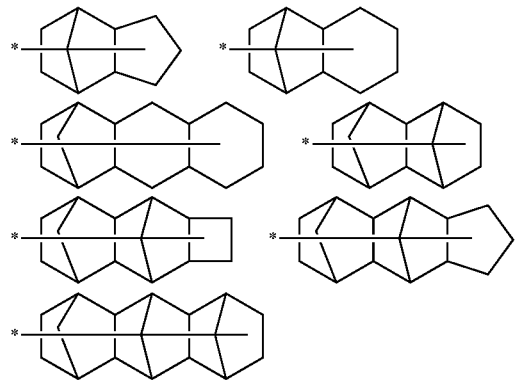

Examples of the group formed by combination include groups formed by combining one or more alkyl groups or one or more alkanediyl groups with one or more alicyclic saturated hydrocarbon groups, for example, an -alkanediyl group-alicyclic saturated hydrocarbon group, an -alicyclic saturated hydrocarbon group-alkyl group, an -alkanediyl group-alicyclic saturated hydrocarbon group-alkyl group and the like.

Examples of the substituent which may be possessed by $R^{a42}$ include at least one selected from the group consisting of a halogen atom and a group represented by formula (a-g3). Examples of the halogen atom include a fluorine atom, a chlorine atom, a bromine atom and an iodine atom, and a fluorine atom is preferable:

(a-g3)

wherein, in formula (a-g3),
$X^{a43}$ represents an oxygen atom, a carbonyl group, *—O—CO— or *—CO—O—,
$A^{a45}$ represents an aliphatic hydrocarbon group having 1 to 17 carbon atoms which may have a halogen atom, and * represents a bonding site to $R^{a42}$.

In $R^{a42}$—$X^{a43}$-$A^{a45}$, when $R^{a42}$ has no halogen atom, $A^{a45}$ represents an aliphatic hydrocarbon group having 1 to 17 carbon atoms having at least one halogen atom.

Examples of the aliphatic hydrocarbon group in $A^{a45}$ include alkyl groups such as a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group;
monocyclic alicyclic hydrocarbon groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group and the following groups (* represents a bonding site).

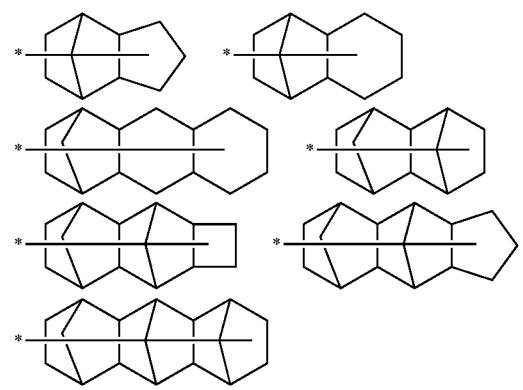

Examples of the group formed by combination include groups obtained by combining one or more alkyl groups or one or more alkanediyl groups with one or more alicyclic hydrocarbon groups, for example, an -alkanediyl group-alicyclic hydrocarbon group, an -alicyclic hydrocarbon group-alkyl group, an -alkanediyl group-alicyclic hydrocarbon group-alkyl group and the like.

$R^{a42}$ is preferably an aliphatic hydrocarbon group which may have a halogen atom, and more preferably an alkyl group having a halogen atom and/or an aliphatic hydrocarbon group having a group represented by formula (a-g3).

When $R^{a42}$ is an aliphatic hydrocarbon group having a halogen atom, an aliphatic hydrocarbon group having a fluorine atom is preferable, a perfluoroalkyl group or a perfluorocycloalkyl group is more preferable, a perfluoroalkyl group having 1 to 6 carbon atoms is still more preferable, and a perfluoroalkyl group having 1 to 3 carbon atoms is particularly preferable. Examples of the perfluoroalkyl group include a perfluoromethyl group, a perfluoroethyl group, a perfluoropropyl group, a perfluorobutyl group, a perfluoropentyl group, a perfluorohexyl group, a perfluoroheptyl group and a perfluorooctyl group. Examples of the perfluorocycloalkyl group include a perfluorocyclohexyl group and the like.

When $R^{a42}$ is an aliphatic hydrocarbon group having a group represented by formula (a-g3), the total number of carbon atoms of $R^{a42}$ is preferably 15 or less, and more preferably 12 or less, including the number of carbon atoms included in the group represented by formula (a-g3). When having the group represented by formula (a-g3) as the substituent, the number thereof is preferably 1.

When $R^{a42}$ is an aliphatic hydrocarbon group having the group represented by formula (a-g3), $R^{a42}$ is still more preferably a group represented by formula (a-g2):

$$*-A^{a46}-X^{a44}-A^{a47} \quad (a\text{-}g2)$$

wherein, in formula (a-g2),
$A^{a46}$ represents a divalent aliphatic hydrocarbon group having 1 to 17 carbon atoms which may have a halogen atom,
$X^{a44}$ represents —O—CO— or —CO—O— (** represents a bonding site to $A^{a46}$),
$A^{a47}$ represents an aliphatic hydrocarbon group having 1 to 17 carbon atoms which may have a halogen atom,
the total number of carbon atoms of $A^{a46}$, $A^{a47}$ and $X^{a44}$ is 18 or less, and at least one of $A^{a46}$ and $A^{a47}$ has at least one halogen atom, and
represents a bonding site to a carbonyl group.

The number of carbon atoms of the aliphatic hydrocarbon group as for $A^{a46}$ is preferably 1 to 6, and more preferably 1 to 3.

The number of carbon atoms of the aliphatic hydrocarbon group as for $A^{a47}$ is preferably 4 to 15, and more preferably 5 to 12, and $A^{a47}$ is still more preferably a cyclohexyl group or an adamantyl group.

Preferred structures of the group represented by formula (a-g2) are the following structures (* represents a bonding site to a carbonyl group).

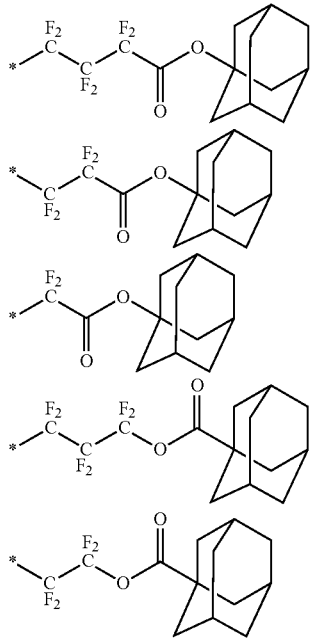

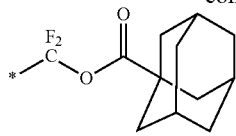

Examples of the alkanediyl group in $A^{a41}$ include linear alkanediyl groups such as a methylene group, an ethylene group, a propane-1,3-diyl group, a butane-1,4-diyl group, a pentane-1,5-diyl group and a hexane-1,6-diyl group; and branched alkanediyl groups such as a propane-1,2-diyl group, a butane-1,3-diyl group, a 2-methylpropane-1,2-diyl group, a 1-methylbutane-1,4-diyl group and a 2-methylbutane-1,4-diyl group.

Examples of the substituent in the alkanediyl group as for $A^{a41}$ include a hydroxy group and an alkoxy group having 1 to 6 carbon atoms.

$A^{a41}$ is preferably an alkanediyl group having 1 to 4 carbon atoms, more preferably an alkanediyl group having 2 to 4 carbon atoms, and still more preferably an ethylene group.

Examples of the divalent saturated hydrocarbon group represented by $A^{a42}$, $A^{a43}$ and $A^{a44}$ in the group represented by formula (a-g1) include a linear or branched alkanediyl group and a monocyclic or polycyclic divalent alicyclic hydrocarbon group, and groups formed by combining an alkanediyl group and a divalent alicyclic hydrocarbon group. Specific examples thereof include a methylene group, an ethylene group, a propane-1,3-diyl group, a propane-1,2-diyl group, a butane-1,4-diyl group, a 1-methylpropane-1,3-diyl group, a 2-methylpropane-1,3-diyl group, a 2-methylpropane-1,2-diyl group and the like.

Examples of the substituent of the divalent saturated hydrocarbon group represented by $A^{a42}$, $A^{a43}$ and $A^{a44}$ include a hydroxy group and an alkoxy group having 1 to 6 carbon atoms.

s is preferably 0.

In the group represented by formula (a-g1), examples of the group in which $X^{a42}$ is —O—, —CO—, —CO—O— or —O—CO-include the following groups. In the following exemplification, * and  each represent a bonding site, and  represents a bonding site to —O—CO—$R^{a42}$.

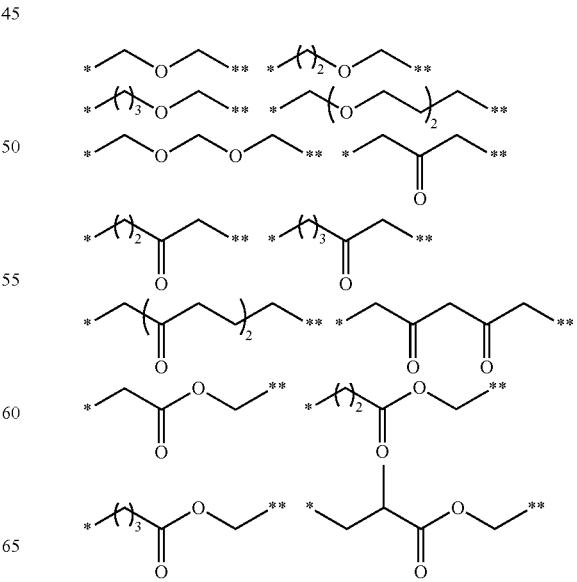

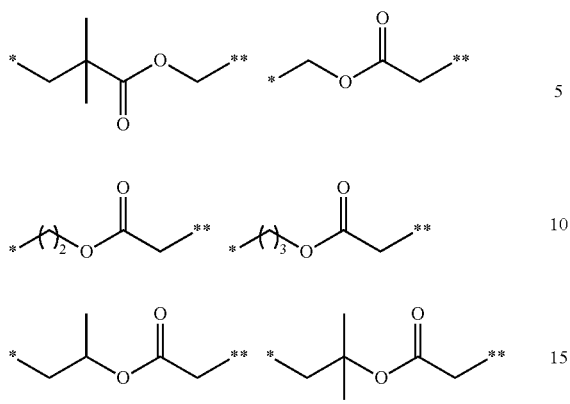
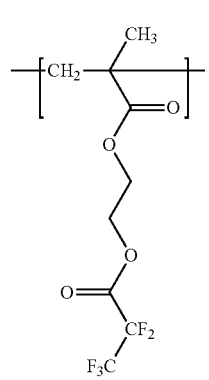
Examples of the structural unit represented by formula (a4-1) include the following structural units, and structural units in which a methyl group corresponding to $R^{a41}$ in the structural unit represented by formula (a4-1) in the following structural units is substituted with a hydrogen atom.
(a4-1-1)
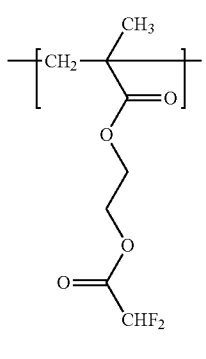
(a4-1-2)
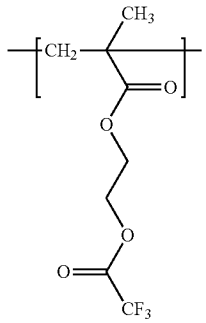
(a4-1-3)
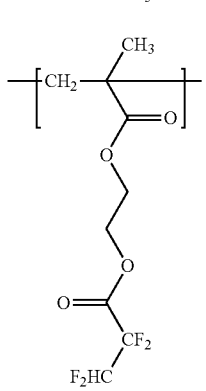
(a4-1-4)
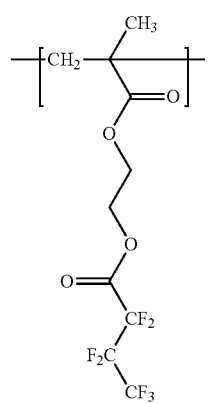
(a4-1-5)
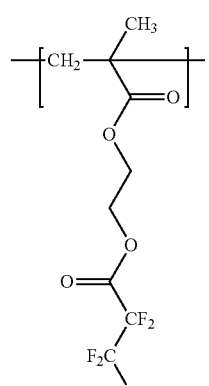
(a4-1-6)
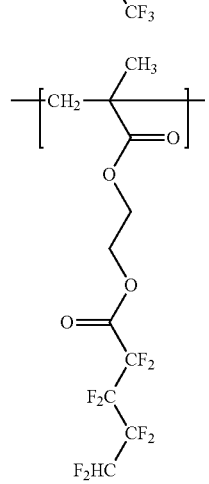
(a4-1-7)

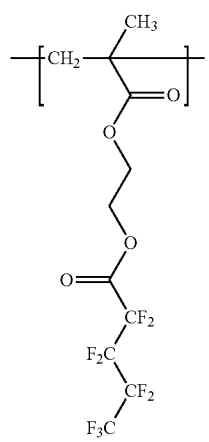 (a4-1-8)
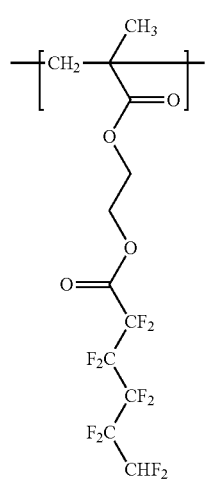 (a4-1-9)
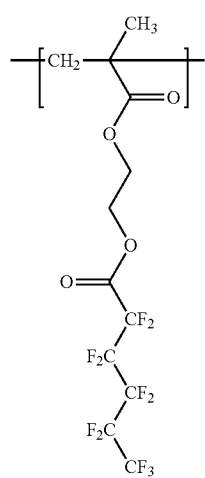 (a4-1-10)
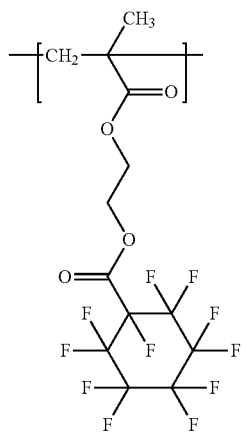 (a4-1-11)
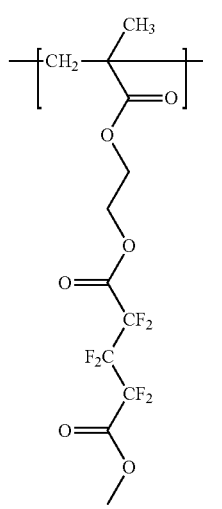 (a4-1'-1)
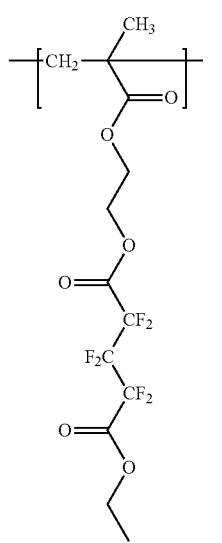 (a4-1'-2)

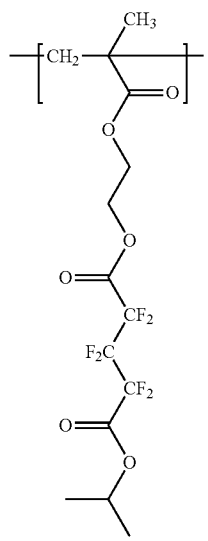
(a4-1'-3)
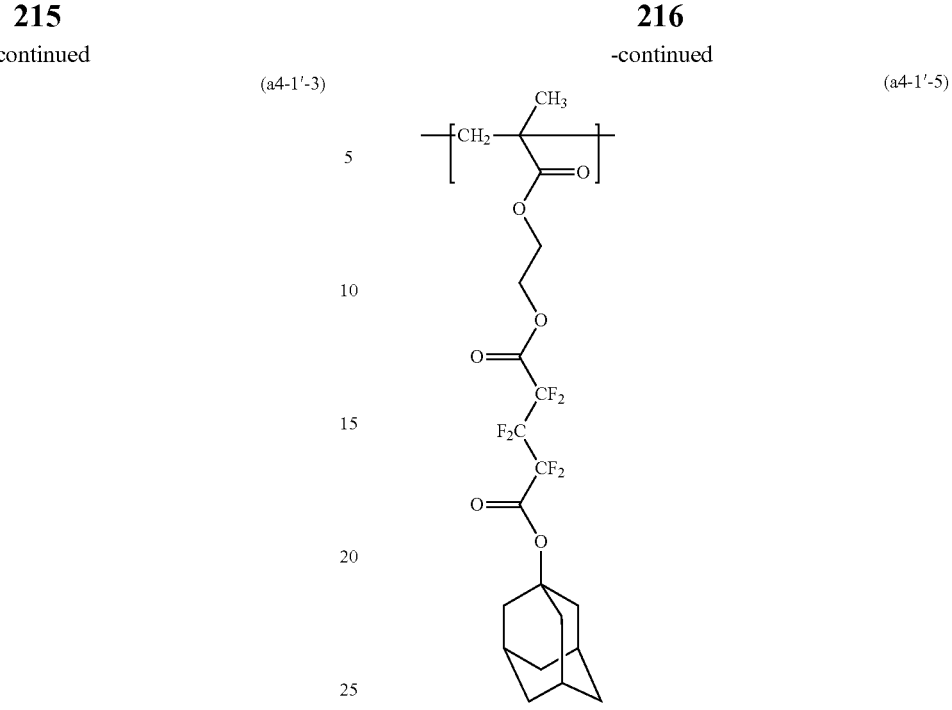
(a4-1'-5)
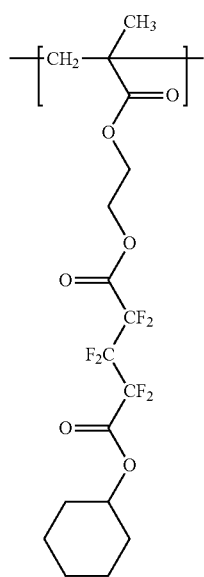
(a4-1'-4)
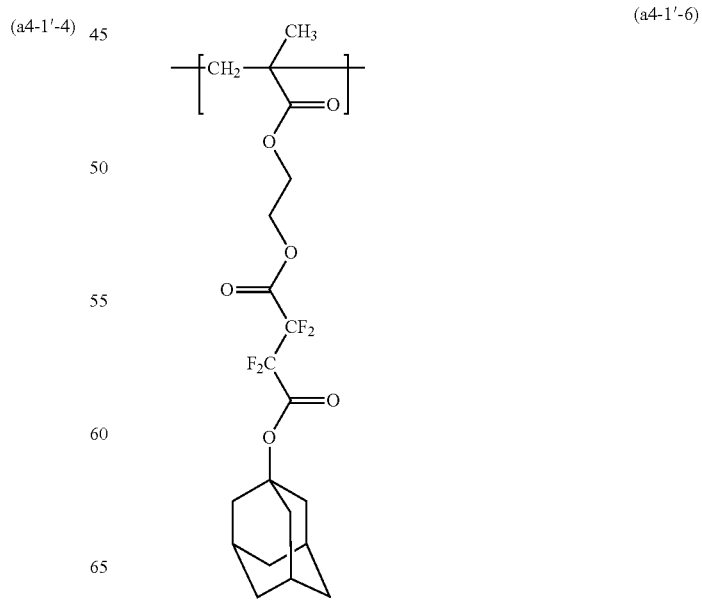
(a4-1'-6)

(a4-1'-7)
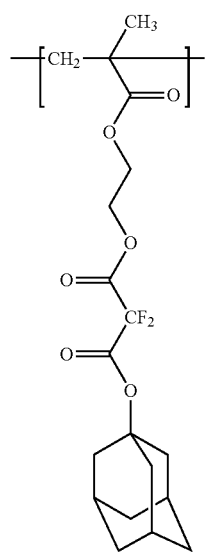
(a4-1'-8)
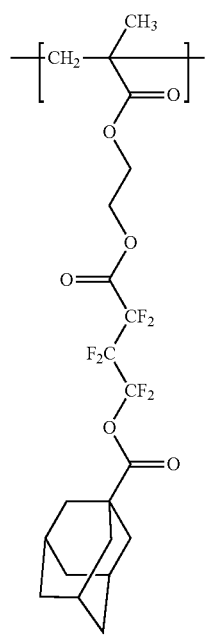
(a4-1'-9)
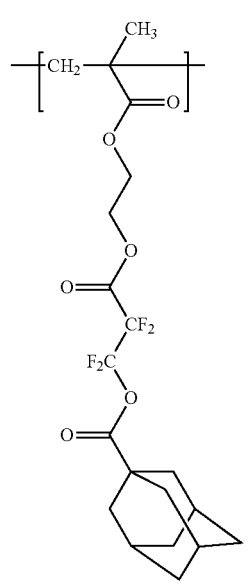
(a4-1'-10)
(a4-1'-11)
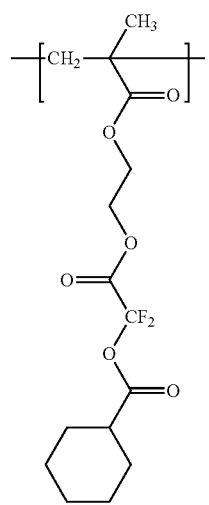

Examples of the structural unit (a4) also include a structural unit represented by formula (a4-2):

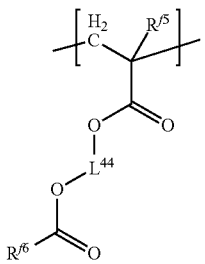

(a4-2)

wherein, in formula (a4-2),
R$^{f5}$ represents a hydrogen atom or a methyl group,
L$^{44}$ represents an alkanediyl group having 1 to 6 carbon atoms, and —CH$_2$— included in the alkanediyl group may be replaced by —O— or —CO—,
R$^{f6}$ represents a saturated hydrocarbon group having 1 to 20 carbon atoms having a fluorine atom, and the upper limit of the total number of carbon atoms of L$^{44}$ and R$^{f6}$ is 21.

Examples of the alkanediyl group having 1 to 6 carbon atoms of L$^{44}$ include those which are the same as mentioned as for the alkanediyl group in A$^{a41}$.

Examples of the saturated hydrocarbon group of R$^{f6}$ include the same groups as mentioned as for R$^{a42}$. The alkanediyl group having 1 to 6 carbon atoms in L$^{44}$ is preferably an alkanediyl group having 2 to 4 carbon atoms, and more preferably an ethylene group.

The structural unit represented by formula (a4-2) includes, for example, structural units represented by formula (a4-1-1) to formula (a4-1-11) A structural unit in which a methyl group corresponding to R$^{f5}$ in the structural unit (a4-2) is substituted with a hydrogen atom is also exemplified as the structural unit represented by formula (a4-2).

Examples of the structural unit (a4) also include a structural unit represented by formula (a4-3):

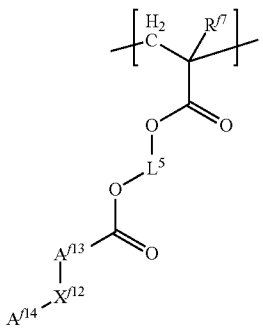

(a4-3)

wherein, in formula (a4-3),
R$^{f7}$ represents a hydrogen atom or a methyl group,
L$^{5}$ represents an alkanediyl group having 1 to 6 carbon atoms,
A$^{f13}$ represents a divalent saturated hydrocarbon group having 1 to 18 carbon atoms which may have a fluorine atom,
X$^{f12}$ represents *—O—CO— or *—CO—O— (* represents a bonding site to A$^{f13}$),
A$^{f14}$ represents a saturated hydrocarbon group having 1 to 17 carbon atoms which may have a fluorine atom, and at least one of A$^{f13}$ and A$^{f14}$ has a fluorine atom, and the upper limit of the total number of carbon atoms of L$^{5}$, A$^{f13}$ and A$^{f14}$ is 20.

Examples of the alkanediyl group in L$^{5}$ include those which are the same as mentioned as for the alkanediyl group in A$^{a41}$.

The divalent saturated hydrocarbon group which may have a fluorine atom in A$^{f13}$ is preferably a divalent chain saturated hydrocarbon group which may have a fluorine atom and a divalent alicyclic saturated hydrocarbon group which may have a fluorine atom, and more preferably a perfluoroalkanediyl group.

Examples of the divalent chain saturated hydrocarbon group which may have a fluorine atom include alkanediyl groups such as a methylene group, an ethylene group, a propanediyl group, a butanediyl group and a pentanediyl group; and perfluoroalkanediyl groups such as a difluoromethylene group, a perfluoroethylene group, a perfluoropropanediyl group, a perfluorobutanediyl group and a perfluoropentanediyl group.

The divalent alicyclic saturated hydrocarbon group which may have a fluorine atom may be either monocyclic or polycyclic. Examples of the monocyclic group include a cyclohexanediyl group and a perfluorocyclohexanediyl group. Examples of the polycyclic group include an adamantanediyl group, a norbornanediyl group, a perfluoroadamantanediyl group and the like.

Examples of the saturated hydrocarbon group and the saturated hydrocarbon group which may have a fluorine atom as for A$^{f14}$ include the same groups as mentioned as for R$^{a42}$. Of these groups, preferable are fluorinated alkyl groups such as a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group, a heptyl group, a perfluoroheptyl group, an octyl group and a perfluorooctyl group; a cyclopropylmethyl group, a cyclopropyl group, a cyclobutylmethyl group, a cyclopentyl group, a cyclohexyl group, a perfluorocyclohexyl group, an adamantyl group, an adamantylmethyl group, an adamantyldimethyl group, a norbornyl group, a norbornylmethyl group, a perfluoroadamantyl group, a perfluoroadamantylmethyl group and the like.

In formula (a4-3), L$^{5}$ is preferably an ethylene group.

The divalent saturated hydrocarbon group as for A$^{f13}$ is preferably a group including a divalent chain saturated hydrocarbon group having 1 to 6 carbon atoms and a divalent alicyclic saturated hydrocarbon group having 3 to 12 carbon atoms, and more preferably a divalent chain saturated hydrocarbon group having 2 to 3 carbon atoms.

The saturated hydrocarbon group as for A$^{f14}$ is preferably a group which has a chain saturated hydrocarbon group having 3 to 12 carbon atoms and an alicyclic saturated hydrocarbon group having 3 to 12 carbon atoms, and more preferably a group which has a chain saturated hydrocarbon group having 3 to 10 carbon atoms and an alicyclic saturated hydrocarbon group having 3 to 10 carbon atoms. Of these groups, A$^{f14}$ is preferably a group which has an alicyclic saturated hydrocarbon group having 3 to 12 carbon atoms, and more preferably a cyclopropylmethyl group, a cyclopentyl group, a cyclohexyl group, a norbornyl group and an adamantyl group.

The structural unit represented by formula (a4-3) includes, for example, structural units represented by formula (a4-1'-1) to formula (a4-1'-11). A structural unit in which a methyl group corresponding to $R^{f7}$ in the structural unit (a4-3) is substituted with a hydrogen atom is also exemplified as the structural unit represented by formula (a4-3).

It is also possible to exemplify, as the structural unit (a4), a structural unit represented by formula (a4-4):

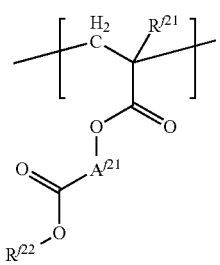

(a4-4)

wherein, in formula (a4-4),
$R^{f21}$ represents a hydrogen atom or a methyl group,
$A^{f21}$ represents $-(CH_2)_{j1}-$, $-(CH_2)_{j2}-O-(CH_2)_{j3}-$ or $-(CH_2)_{j4}-CO-O-(CH_2)_{j5}-$,
j1 to j5 each independently represent an integer of 1 to 6, and
$R^{f22}$ represents a saturated hydrocarbon group having 1 to 10 carbon atoms having a fluorine atom.

Examples of the saturated hydrocarbon group of $R^{f22}$ include those which are the same as the saturated hydrocarbon group represented by $R^{a42}$. $R^{f22}$ is preferably an alkyl group having 1 to 10 carbon atoms which has a fluorine atom or an alicyclic hydrocarbon group having 1 to 10 carbon atoms which has a fluorine atom, more preferably an alkyl group having 1 to 10 carbon atoms which has a fluorine atom, and still more preferably an alkyl group having 1 to 6 carbon atoms which has a fluorine atom.

In formula (a4-4), $A^{f21}$ is preferably $-(CH_2)_{j1}-$, more preferably an ethylene group or a methylene group, and still more preferably a methylene group.

The structural unit represented by formula (a4-4) includes, for example, the following structural units and structural units in which a methyl group corresponding to $R^{f21}$ in the structural unit (a4-4) is substituted with a hydrogen atom in structural units represented by the following formulas.

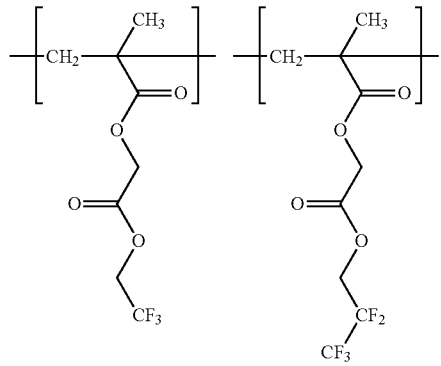

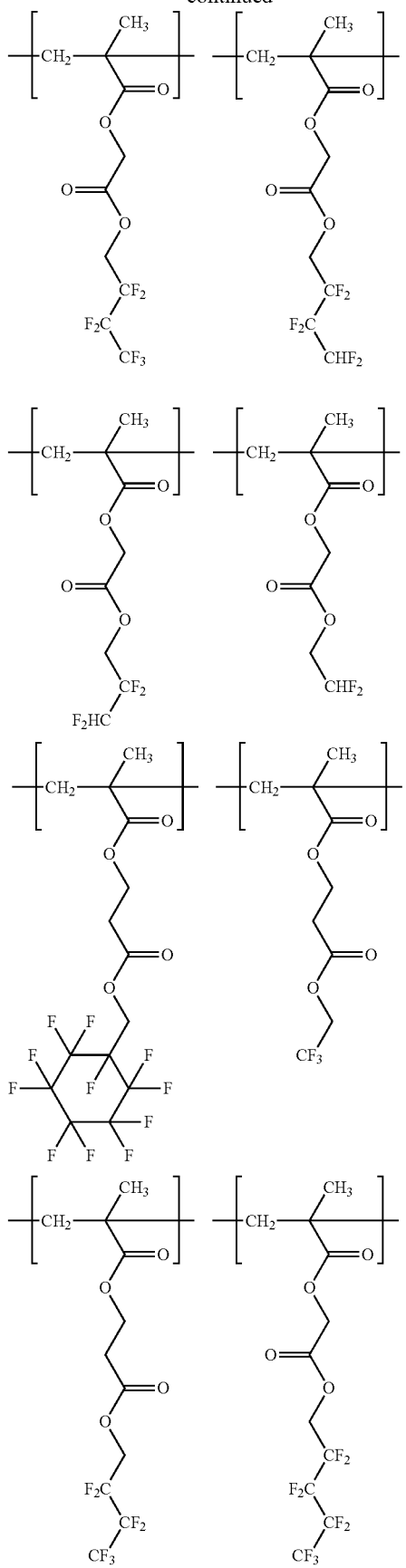

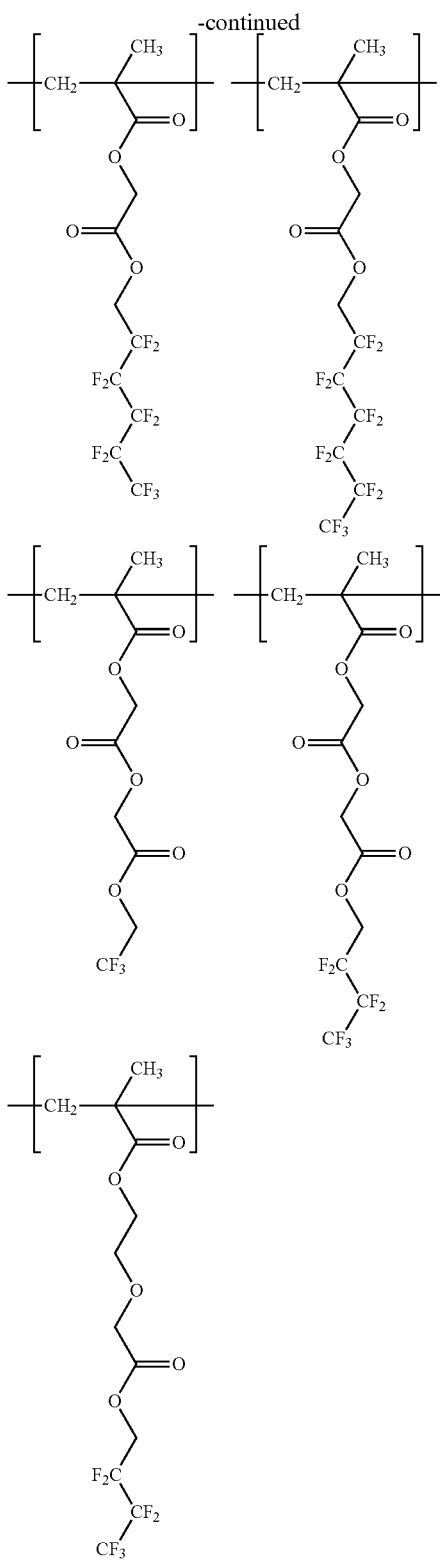

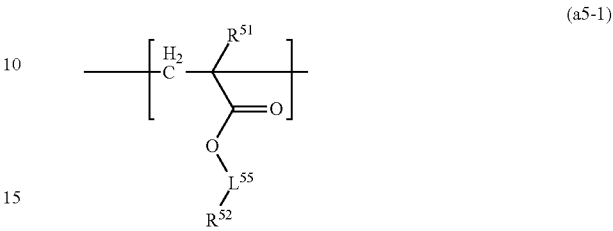

branched or cyclic hydrocarbon group. Of these, the structural unit (a5) is preferably a group having an alicyclic hydrocarbon group.

The structural unit (a5) includes, for example, a structural unit represented by formula (a5-1):

wherein, in formula (a5-1), $R^{51}$ represents a hydrogen atom or a methyl group, $R^{52}$ represents an alicyclic hydrocarbon group having 3 to 18 carbon atoms, and a hydrogen atom included in the alicyclic hydrocarbon group may be substituted with an aliphatic hydrocarbon group having 1 to 8 carbon atoms, and $L^{55}$ represents a single bond or a divalent saturated hydrocarbon group having 1 to 18 carbon atoms, and —$CH_2$— included in the saturated hydrocarbon group may be replaced by —O— or —CO—.

The alicyclic hydrocarbon group in $R^{52}$ may be either monocyclic or polycyclic. The monocyclic alicyclic hydrocarbon group includes, for example, a cyclopropyl group, a cyclobutyl group, a cyclopentyl group and a cyclohexyl group. The polycyclic alicyclic hydrocarbon group includes, for example, an adamantyl group and a norbornyl group.

The aliphatic hydrocarbon group having 1 to 8 carbon atoms includes, for example, alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Examples of the alicyclic hydrocarbon group having a substituent includes a 3-methyladamantyl group and the like.

$R^{52}$ is preferably an unsubstituted alicyclic hydrocarbon group having 3 to 18 carbon atoms, and more preferably an adamantyl group, a norbornyl group or a cyclohexyl group.

Examples of the divalent saturated hydrocarbon group in $L^{55}$ include a divalent chain saturated hydrocarbon group and a divalent alicyclic saturated hydrocarbon group, and a divalent chain saturated hydrocarbon group is preferable.

The divalent chain saturated hydrocarbon group includes, for example, alkanediyl groups such as a methylene group, an ethylene group, a propanediyl group, a butanediyl group and a pentanediyl group.

The divalent alicyclic saturated hydrocarbon group may be either monocyclic or polycyclic. Examples of the monocyclic alicyclic saturated hydrocarbon group include cycloalkanediyl groups such as a cyclopentanediyl group and a cyclohexanediyl group. Examples of the polycyclic divalent alicyclic saturated hydrocarbon group include an adamantanediyl group and a norbornanediyl group.

The group in which —$CH_2$— included in the divalent saturated hydrocarbon group represented by $L^{55}$ is replaced by —O— or —CO— includes, for example, groups represented by formula (L1-1) to formula (L1-4). In the following When the resin (A) includes the structural unit (a4), the content is preferably 1 to 20 mol %, more preferably 2 to 15 mol %, and still more preferably 3 to 10 mol %, based on all structural units of the resin (A).

<Structural Unit (a5)>

Examples of a non-leaving hydrocarbon group possessed by the structural unit (a5) include groups having a linear, formulas, * and ** each represent a bonding site, and * represents a bonding site to an oxygen atom.

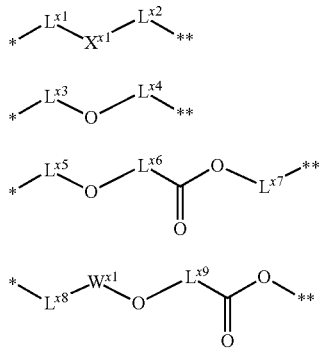

In formula (L1-1),
$X^{x1}$ represents *—O—CO— or *—CO—O— (* represents a bonding site to $L^{x1}$),
$L^{x1}$ represents a divalent aliphatic saturated hydrocarbon group having 1 to 16 carbon atoms,
$L^{x2}$ represents a single bond or a divalent aliphatic saturated hydrocarbon group having 1 to 15 carbon atoms, and the total number of carbon atoms of $L^{x1}$ and $L^{x2}$ is 16 or less.
In formula (L1-2),
$L^{x3}$ represents a divalent aliphatic saturated hydrocarbon group having 1 to 17 carbon atoms,
$L^{x4}$ represents a single bond or a divalent aliphatic saturated hydrocarbon group having 1 to 16 carbon atoms, and the total number of carbon atoms of $L^{x3}$ and $L^{x4}$ is 17 or less.
In formula (L1-3),
$L^{x5}$ represents a divalent aliphatic saturated hydrocarbon group having 1 to 15 carbon atoms,
$L^{x6}$ and $L^{x7}$ each independently represent a single bond or a divalent aliphatic saturated hydrocarbon group having 1 to 14 carbon atoms, and
the total number of carbon atoms of $L^{x5}$, $L^{x6}$ and $L^{x7}$ is 15 or less.
In formula (L1-4),
$L^{x8}$ and $L^{x9}$ represent a single bond or a divalent aliphatic saturated hydrocarbon group having 1 to 12 carbon atoms,
$W^{x1}$ represents a divalent alicyclic saturated hydrocarbon group having 3 to 15 carbon atoms, and
the total number of carbon atoms of $L^{x8}$, $L^{x9}$ and $W^{x1}$ is 15 or less.
$L^{x1}$ is preferably a divalent aliphatic saturated hydrocarbon group having 1 to 8 carbon atoms, and more preferably a methylene group or an ethylene group.
$L^{x2}$ is preferably a single bond or a divalent aliphatic saturated hydrocarbon group having 1 to 8 carbon atoms, and more preferably a single bond.
$L^{x3}$ is preferably a divalent aliphatic saturated hydrocarbon group having 1 to 8 carbon atoms.
$L^{x4}$ is preferably a single bond or a divalent aliphatic saturated hydrocarbon group having 1 to 8 carbon atoms.
$L^{x5}$ is preferably a divalent aliphatic saturated hydrocarbon group having 1 to 8 carbon atoms, and more preferably a methylene group or an ethylene group.
$L^{x6}$ is preferably a single bond or a divalent aliphatic saturated hydrocarbon group having 1 to 8 carbon atoms, and more preferably a methylene group or an ethylene group.

$L^{x7}$ is preferably a single bond or a divalent aliphatic saturated hydrocarbon group having 1 to 8 carbon atoms.
$L^{x8}$ is preferably a single bond or a divalent aliphatic saturated hydrocarbon group having 1 to 8 carbon atoms, and more preferably a single bond or a methylene group.
$L^{x9}$ is preferably a single bond or a divalent aliphatic saturated hydrocarbon group having 1 to 8 carbon atoms, and more preferably a single bond or a methylene group.
$W^{x1}$ is preferably a divalent alicyclic saturated hydrocarbon group having 3 to 10 carbon atoms, and more preferably a cyclohexanediyl group or an adamantanediyl group.

The group represented by formula (L1-1) includes, for example, the following divalent groups.

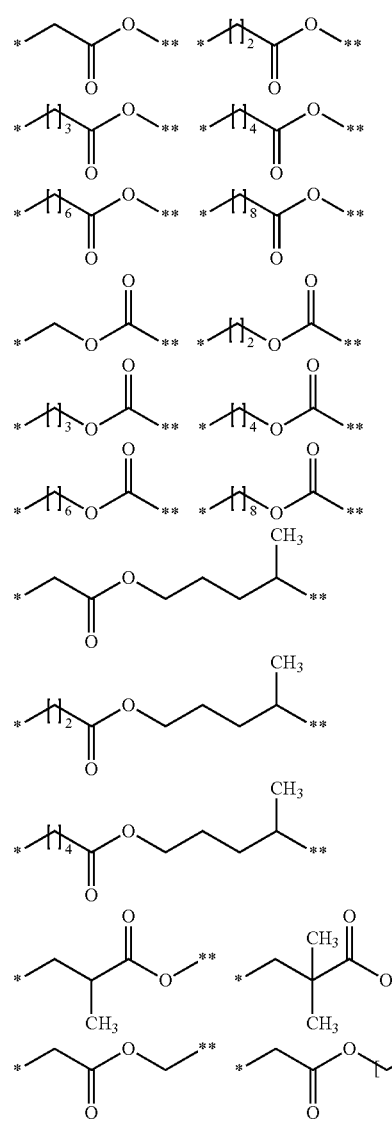

The group represented by formula (L1-2) includes, for example, the following divalent groups.

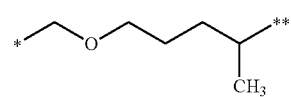

-continued

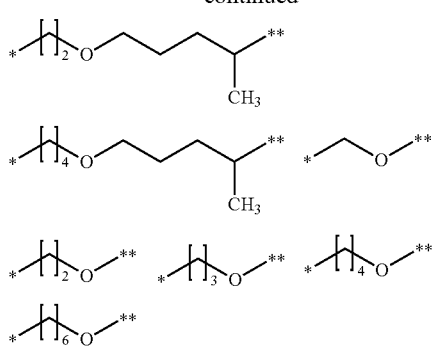

The group represented by formula (L1-3) includes, for example, the following divalent groups.

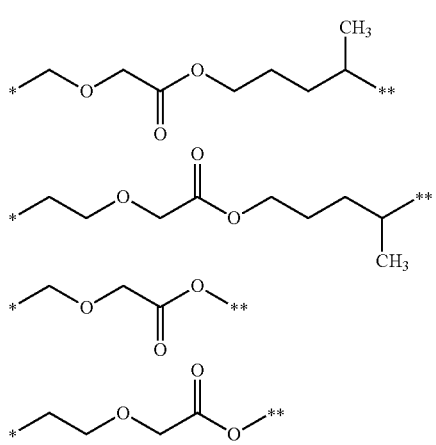

The group represented by formula (L1-4) includes, for example, the following divalent groups.

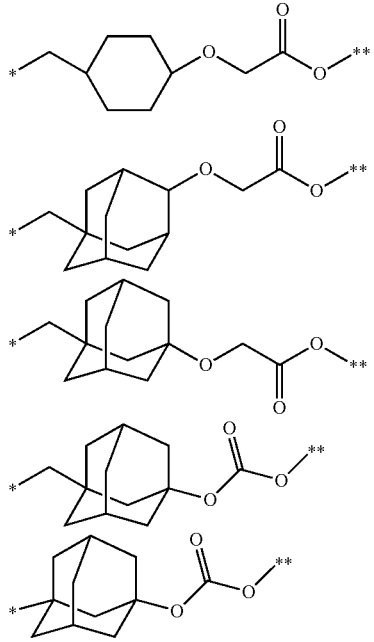

-continued

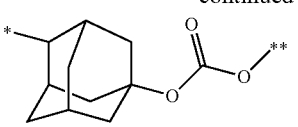

$L^{55}$ is preferably a single bond or a group represented by formula (L1-1).

Examples of the structural unit (a5-1) include the following structural units and structural units in which a methyl group corresponding to $R^{51}$ in the structural unit (a5-1) in the following structural units is substituted with a hydrogen atom.

(a5-1-1)

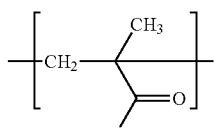

(a5-1-2)

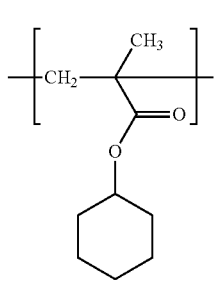

(a5-1-3)

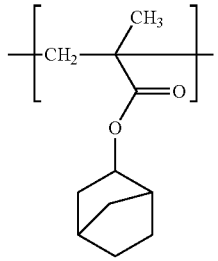

(a5-1-4)

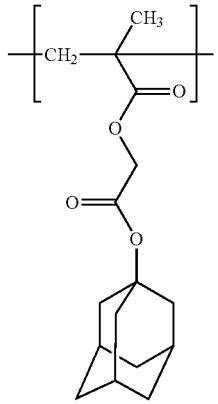

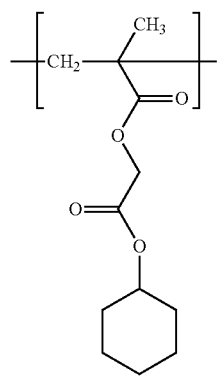
(a5-1-5)
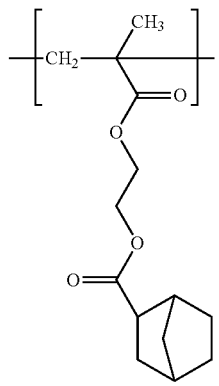
(a5-1-9)
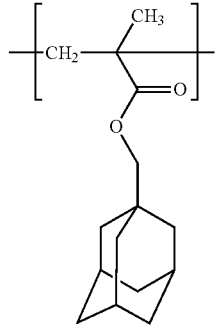
(a5-1-10)
(a5-1-6)
(a5-1-7)
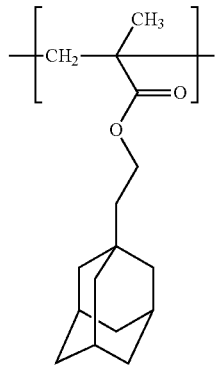
(a5-1-11)
(a5-1-8)
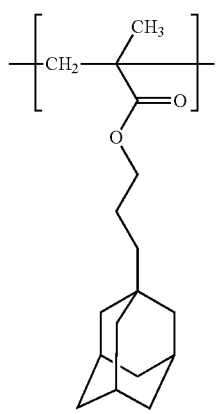
(a5-1-12)

(a5-1-13) 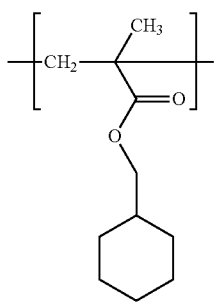

(a5-1-14) 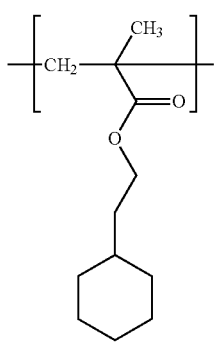

(a5-1-15) 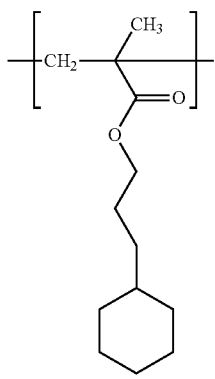

(a5-1-16) 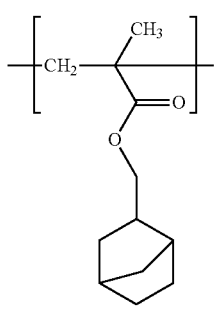

(a5-1-17) 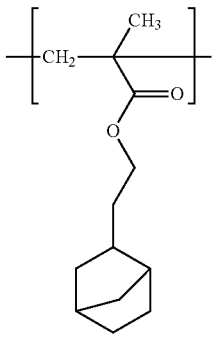

(a5-1-18) 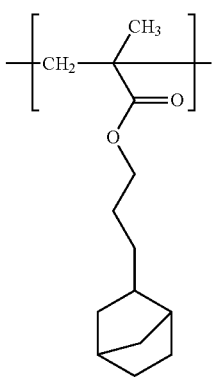

When the resin (A) includes the structural unit (a5), the content is preferably 1 to 30 mol %, more preferably 2 to 20 mol %, and still more preferably 3 to 15 mol %, based on all structural units of the resin (A).

<Structural Unit (a6)>

The structural unit (a6) is a structural unit having an —SO$_2$— group, and it is preferable to have an —SO$_2$— group in a side chain.

The structural unit having an —SO$_2$— group may have a linear structure having an —SO$_2$— group, a branched structure having an —SO$_2$— group, or a cyclic structure (monocyclic and polycyclic structure) having an —SO$_2$— group. The structural unit is preferably a structural unit which has a cyclic structure having an —SO$_2$— group, and more preferably a structural unit which has a cyclic structure (sultone ring) having —SO$_2$—O—.

Examples of the sultone ring include rings represented by the following formula (T$^1$-1), formula (T$^1$-2), formula (T$^1$-3) and formula (T$^1$-4). The bonding site can be any position. The sultone ring may be monocyclic, and is preferably polycyclic. The polycyclic sultone ring means a bridged ring which has —SO$_2$—O— as an atomic group constituting the ring, and examples thereof include rings represented by formula (T$^1$-1) and formula (T$^1$-2). The sultone ring may have, as the atomic group constituting the ring, a heteroatom, in addition to —SO$_2$—O—, like the ring represented by formula (T$^1$-2). Examples of the heteroatom include an oxygen atom, a sulfur atom or a nitrogen atom, and an oxygen atom is preferable.

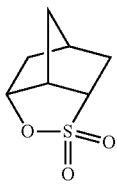

(T¹-1)

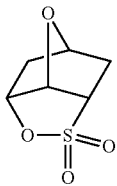

(T¹-2)

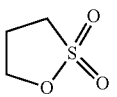

(T¹-3)

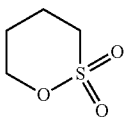

(T¹-4)

The sultone ring may have a substituent, and examples of the substituent include an alkyl group having 1 to 12 carbon atoms which may have a halogen atom or a hydroxy group, a halogen atom, a hydroxy group, a cyano group, an alkoxy group having 1 to 12 carbon atoms, an aryl group having 6 to 12 carbon atoms, an aralkyl group having 7 to 12 carbon atoms, a glycidyloxy group, an alkoxycarbonyl group having 2 to 12 carbon atoms and an alkylcarbonyl group having 2 to 4 carbon atoms.

Examples of the halogen atom include a fluorine atom, a chlorine atom, a bromine atom and an iodine atom.

Examples of the alkyl group include a methyl group, an ethyl group, a propyl group, a butyl group, a pentyl group, a hexyl group, an octyl group and a decyl group, and the alkyl group is preferably an alkyl group having 1 to 6 carbon atoms, and more preferably a methyl group.

Examples of the alkyl group having a halogen atom include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group, a trichloromethyl group, a tribromomethyl group and a triiodomethyl group, and a trifluoromethyl group is preferable.

Examples of the alkyl group having a hydroxy group include hydroxyalkyl groups such as a hydroxymethyl group and a 2-hydroxyethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aryl group include a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Examples of the aralkyl group include a benzyl group, a phenethyl group, a phenylpropyl group, a naphthylmethyl group and a naphthylethyl group.

Examples of the alkoxycarbonyl group include groups in which an alkoxy group is bonded with a carbonyl group, such as a methoxycarbonyl group or an ethoxycarbonyl group, and preferably include an alkoxycarbonyl group having 6 or less carbon atoms and more preferably include a methoxycarbonyl group.

Examples of the alkylcarbonyl group include an acetyl group, a propionyl group and a butyryl group.

From the viewpoint that it is easy to produce a monomer from which the structural unit (a6) is derived, a sultone ring having no substituent is preferable.

The sultone ring is preferably a ring represented by the following formula (T1'):

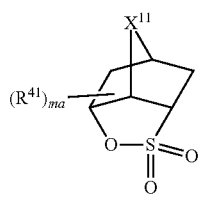

(T1')

wherein, in formula (T1'),

X$^{11}$ represents an oxygen atom, a sulfur atom or a methylene group,

R$^{41}$ represents an alkyl group having 1 to 12 carbon atoms which may have a halogen atom or a hydroxy group, a halogen atom, a hydroxy group, a cyano group, an alkoxy group having 1 to 12 carbon atoms, an aryl group having 6 to 12 carbon atoms, an aralkyl group having 7 to 12 carbon atoms, a glycidyloxy group, an alkoxycarbonyl group having 2 to 12 carbon atoms, or an alkylcarbonyl group having 2 to 4 carbon atoms, ma represents an integer of 0 to 9, and when ma is 2 or more, a plurality of R$^{41}$ may be the same or different, and the bonding site may be at any position.

X$^{11}$ is preferably an oxygen atom or a methylene group, and more preferably a methylene group.

Examples of R$^{41}$ include those which are the same as the substituent of the sultone ring, and an alkyl group having 1 to 12 carbon atoms which may have a halogen atom or a hydroxy group is preferable.

The sultone ring is more preferably a ring represented by formula (T1):

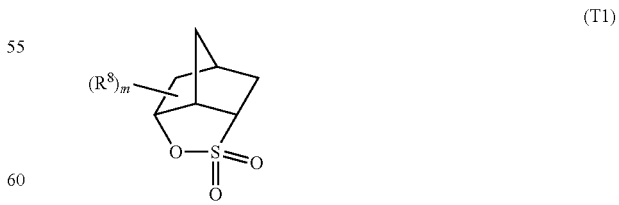

(T1)

wherein, in formula (T1),

R$^8$ represents an alkyl group having 1 to 12 carbon atoms which may have a halogen atom or a hydroxy group, a halogen atom, a hydroxy group, a cyano group, an alkoxy group having 1 to 12 carbon atoms, an aryl group having 6 to 12 carbon atoms, an aralkyl group having 7 to 12 carbon atoms, a glycidyloxy group, an alkoxycarbonyl group having 2 to 12 carbon atoms, or an alkylcarbonyl group having 2 to 4 carbon atoms, m represents an integer of 0 to 9, and when m is 2 or more, a plurality of $R^8$ may be the same or different, and the bonding site may be at any position.

Examples of $R^8$ include those which are the same as for $R^{41}$.

ma in formula (T1') and m in formula (T1) are preferably 0 or 1, and more preferably 0.

Examples of the ring represented by formula (T1') and the ring represented by formula (T1) include the following rings. The bonding site may be at any position.

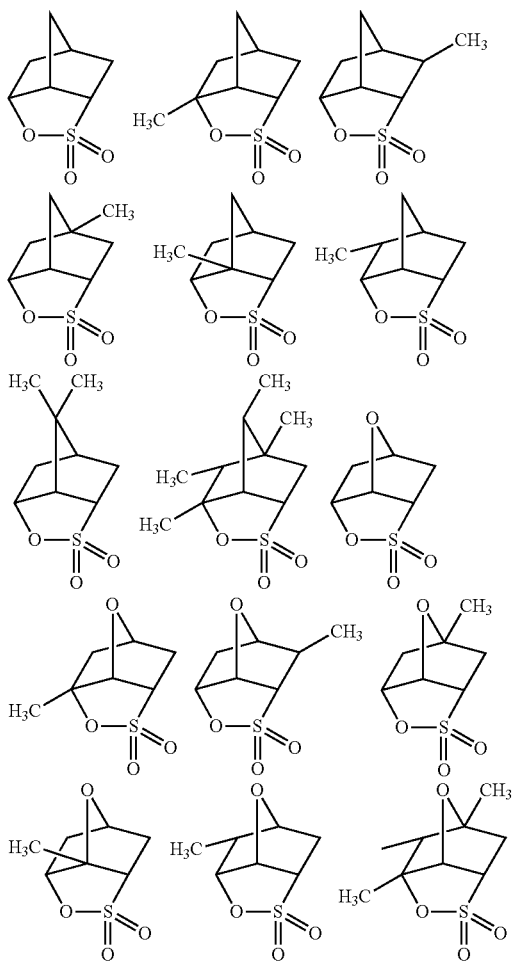

It is preferable that the structural unit having a sultone ring has the following groups. * in the following groups represents a bonding site.

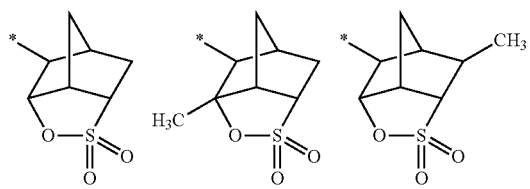

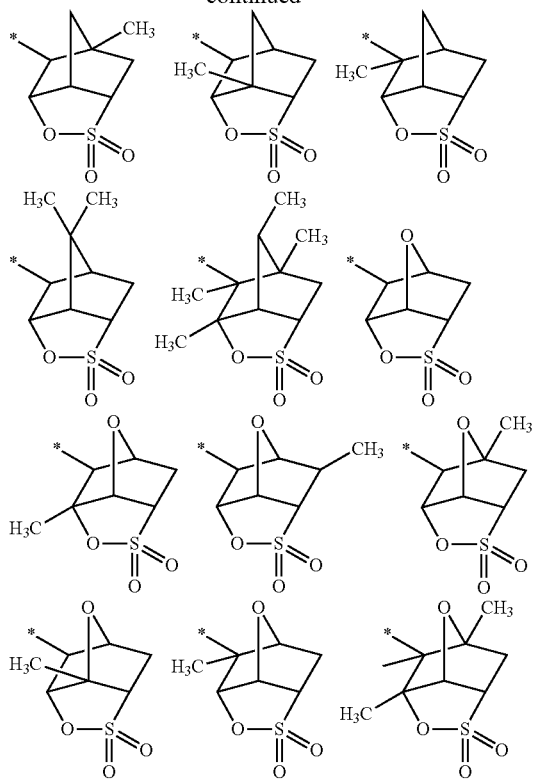

It is preferable that the structural unit having an $SO_2$— group further has a group derived from a polymerizable group. Examples of the polymerizable group include a vinyl group, an acryloyl group, a methacryloyl group, an acryloyloxy group, a methacryloyloxy group, an acryloylamino group, a methacryloylamino group, an acryloylthio group, a methacryloylthio group and the like.

Particularly, the monomer from which the structural unit (a6) is derived is preferably a monomer having an ethylenically unsaturated bond, and more preferably a (meth)acrylic monomer.

The structural unit (a6) is preferably a structural unit represented by formula (Ix):

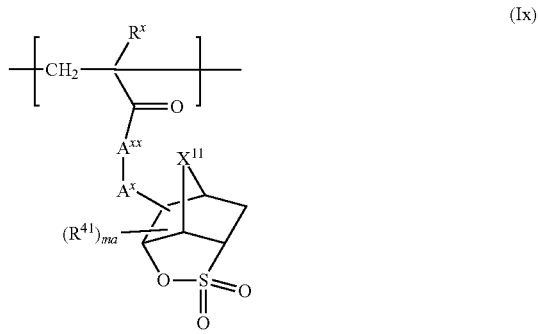

wherein, in formula (Ix), $R^x$ represents an alkyl group having 1 to 6 carbon atoms which may have a halogen atom, a hydrogen atom or a halogen atom, $A^{xx}$ represents an oxygen atom, —N($R^c$)— or a sulfur atom, $A^x$ represents a divalent saturated hydrocarbon group having 1 to 18 carbon atoms, and —$CH_2$— included in the saturated hydrocarbon group may be replaced by —O—, —CO— or —N($R^d$)—, $X^{11}$ represents an oxygen atom, a sulfur atom or a methylene group, $R^{41}$ represents an alkyl group having 1 to 12 carbon atoms which may have a halogen atom or a hydroxy group, a halogen atom, a hydroxy group, a cyano group, an alkoxy group having 1 to 12 carbon atoms, an aryl group having 6 to 12 carbon atoms, an aralkyl group having 7 to 12 carbon atoms, a glycidyloxy group, an alkoxycarbonyl group having 2 to 12 carbon atoms, or an alkylcarbonyl group having 2 to 4 carbon atoms, ma represents an integer of 0 to 9, and when ma is 2 or more, a plurality of $R^{41}$ may be the same or different, and $R^c$ and $R^d$ each independently represent a hydrogen atom or an alkyl group having 1 to 6 carbon atoms.

Examples of the halogen atom as for $R^x$ include a fluorine atom, a chlorine atom, a bromine atom and an iodine atom.

Examples of the alkyl group as for $R^x$ include a methyl group, an ethyl group, an n-propyl group, an isopropyl group, an n-butyl group, a sec-butyl group, a tert-butyl group, an n-pentyl group and an n-hexyl group, and an alkyl group having 1 to 4 carbon atoms is preferable, and a methyl group or an ethyl group is more preferable.

Examples of the alkyl group having a halogen atom as for $R^x$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group, a trichloromethyl group, a tribromomethyl group and a triiodomethyl group.

$R^x$ is preferably a hydrogen atom or an alkyl group having 1 to 4 carbon atoms, more preferably a hydrogen atom, a methyl group or an ethyl group, and still more preferably a hydrogen atom or a methyl group.

Examples of the divalent saturated hydrocarbon group as for $A^x$ include a linear alkanediyl group, a branched alkanediyl group and a monocyclic or polycyclic divalent alicyclic saturated hydrocarbon group, and the divalent saturated hydrocarbon group may be those obtained by combining two or more of these groups.

Specific examples thereof include linear alkanediyl groups such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an ethane-1,1-diyl group, a propane-1,1-diyl group and a propane-2,2-diyl group;

branched alkanediyl groups such as a butane-1,3-diyl group, a 2-methylpropane-1,3-diyl group, a 2-methylpropane-1,2-diyl group, a pentane-1,4-diyl group and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group and an adamantane-2,6-diyl group.

Examples of $R^{41}$, $X^{11}$ and ma include those which are the same as in formula (T1').

Examples of the sultone ring include those mentioned above, and of these, preferred are the above-mentioned rings in which the bonding site is specified.

Examples of the structural unit (a6) include the following structural units.

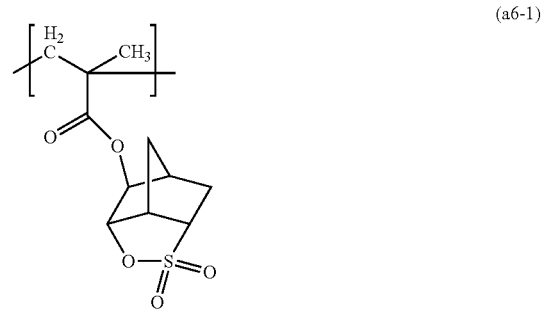

(a6-1)

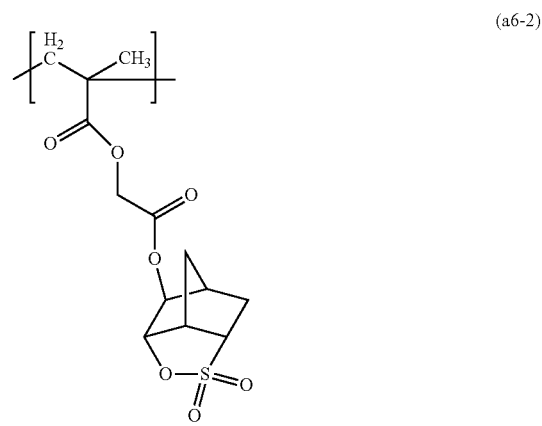

(a6-2)

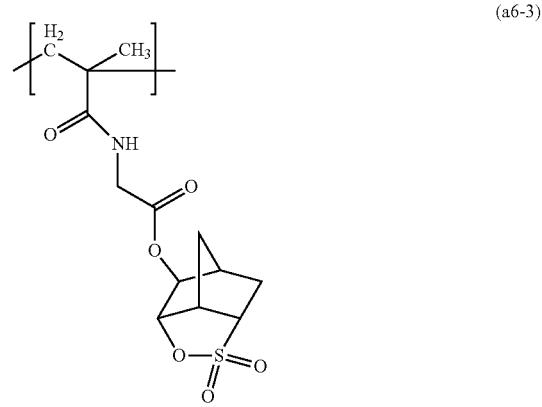

(a6-3)

(a6-4)
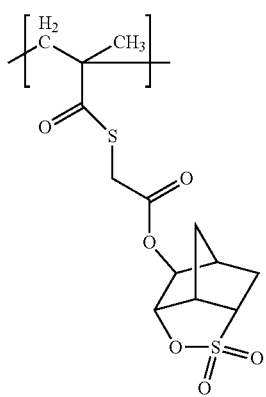
(a6-5)
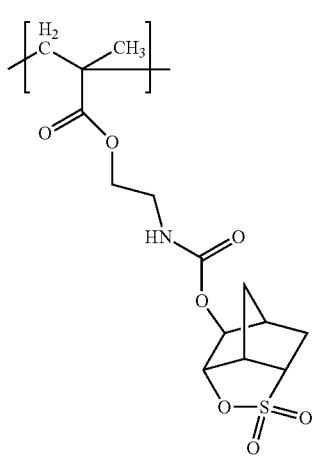
(a6-6)
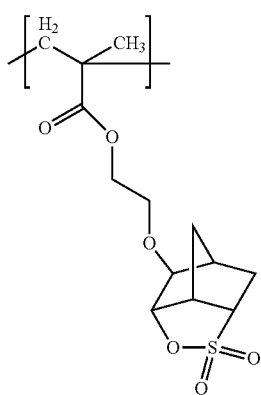
(a6-7)
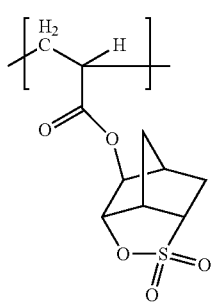
(a6-8)
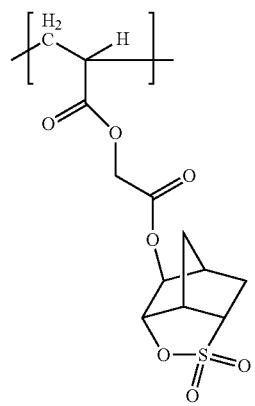
(a6-9)
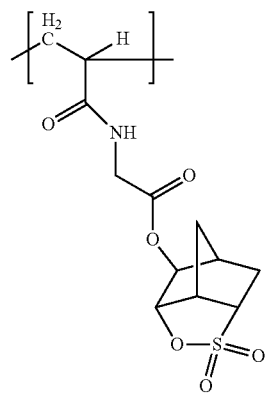
(a6-10)
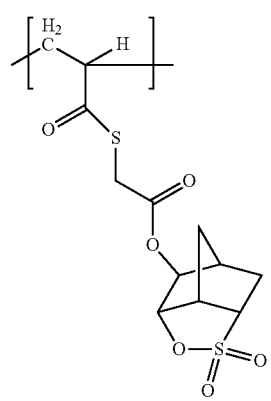
(a6-11)
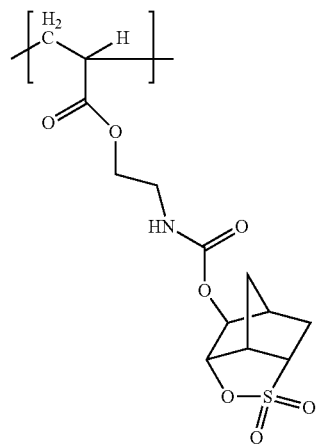

(a6-12)

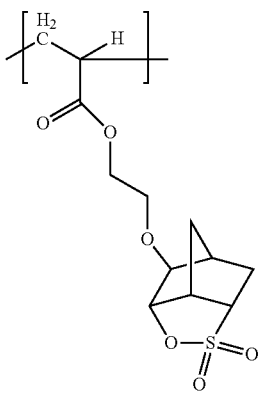

Of these, structural units represented by formula (a6-1), formula (a6-2), formula (a6-6), formula (a6-7), formula (a6-8) and formula (a6-12) are preferable, and structural units represented by formula (a6-1), formula (a6-2), formula (a6-7) and (a6-8) are more preferable.

When the resin (A) includes the structural unit (a6), the content is preferably 1 to 50 mol %, more preferably 2 to 40 mol %, and still more preferably 3 to 30 mol %, based on all structural units of the resin (A).

<Structural Unit (II)>

The resin (A) may further include a structural unit which is decomposed upon exposure to radiation to generate an acid (hereinafter sometimes referred to as "structural unit (II)"). Specific examples of the structural unit (II) include the structural units mentioned in JP 2016-79235 A, and a structural unit having a sulfonate group or a carboxylate group and an organic cation in a side chain or a structural unit having a sulfonio group and an organic anion in a side chain are preferable.

The structural unit having a sulfonate group or a carboxylate group and an organic cation in a side chain is preferably a structural unit represented by formula (II-2-A'):

(II-2-A')

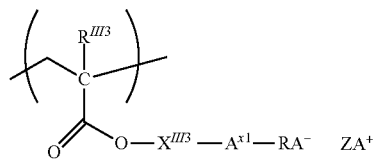

wherein, in formula (II-2-A'), $X^{III3}$ represents a divalent saturated hydrocarbon group having 1 to 18 carbon atoms, —$CH_2$— included in the saturated hydrocarbon group may be replaced by —O—, —S— or —CO—, and a hydrogen atom included in the saturated hydrocarbon group may be substituted with a halogen atom, an alkyl group having 1 to 6 carbon atoms which may have a halogen atom, or a hydroxy group, $A^{x1}$ represents an alkanediyl group having 1 to 8 carbon atoms, and a hydrogen atom included in the alkanediyl group may be substituted with a fluorine atom or a perfluoroalkyl group having 1 to 6 carbon atoms, $RA^-$ represents a sulfonate group or a carboxylate group, $R^{III3}$ represents a hydrogen atom, a halogen atom, or an alkyl group having 1 to 6 carbon atoms which may have a halogen atom, and $ZA^+$ represents an organic cation.

Examples of the halogen atom represented by $R^{III3}$ include a fluorine atom, a chlorine atom, a bromine atom and an iodine atom.

Examples of the alkyl group having 1 to 6 carbon atoms which may have a halogen atom represented by $R^{III3}$ include those which are the same as the alkyl group having 1 to 6 carbon atoms which may have a halogen atom represented by $R^{a8}$.

Examples of the alkanediyl group having 1 to 8 carbon atoms represented by $A^{x1}$ include a methylene group, an ethylene group, a propane-1,3-diyl group, a butane-1,4-diyl group, a pentane-1,5-diyl group, a hexane-1,6-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, a 2-methylbutane-1,4-diyl group and the like.

Examples of the perfluoroalkyl group having 1 to 6 carbon atoms which may be substituted in $A^{x1}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group and the like.

Examples of the divalent saturated hydrocarbon group having 1 to 18 carbon atoms represented by $X^{III3}$ include a linear or branched alkanediyl group, a monocyclic or a polycyclic divalent alicyclic saturated hydrocarbon group, or a combination thereof.

Specific examples thereof include linear alkanediyl groups such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; branched alkanediyl groups such as a butane-1,3-diyl group, a 2-methylpropane-1,3-diyl group, a 2-methylpropane-1,2-diyl group, a pentane-1,4-diyl group and a 2-methylbutane-1,4-diyl group; cycloalkanediyl groups such as a cyclobutane-1,3-diyl group, a cyclopentane-1,3-diyl group, a cyclohexane-1,4-diyl group and a cyclooctane-1,5-diyl group; and divalent polycyclic alicyclic saturated hydrocarbon groups such as a norbornane-1,4-diyl group, a norbornane-2,5-diyl group, an adamantane-1,5-diyl group and an adamantane-2,6-diyl group.

Those in which —$CH_2$— included in the saturated hydrocarbon group are replaced by —O—, —S— or —CO— include, for example, divalent groups represented by formula (X1) to formula (X53). Before replacing —$CH_2$— included in the saturated hydrocarbon group by —O—, —S— or —CO—, the number of carbon atoms is 17 or less. In the following formulas, * and ** represent a bonding site, and * represents a bonding site to $A^{x1}$.

(X1)

(X2)

(X3)

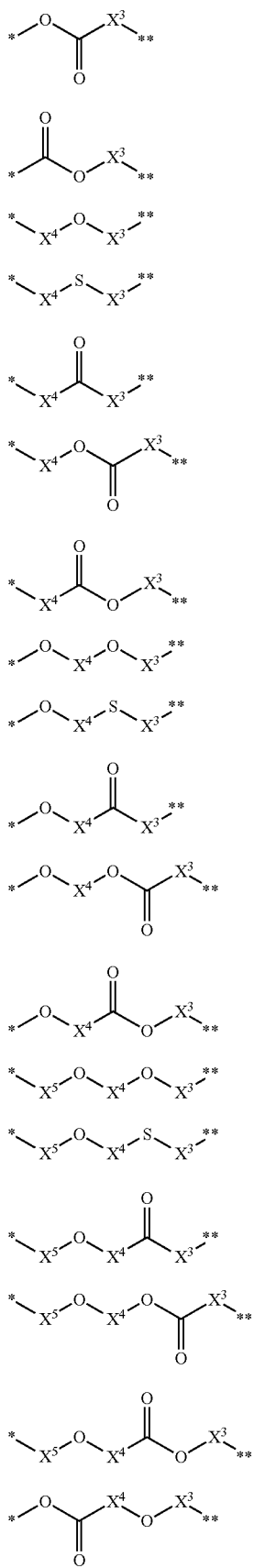
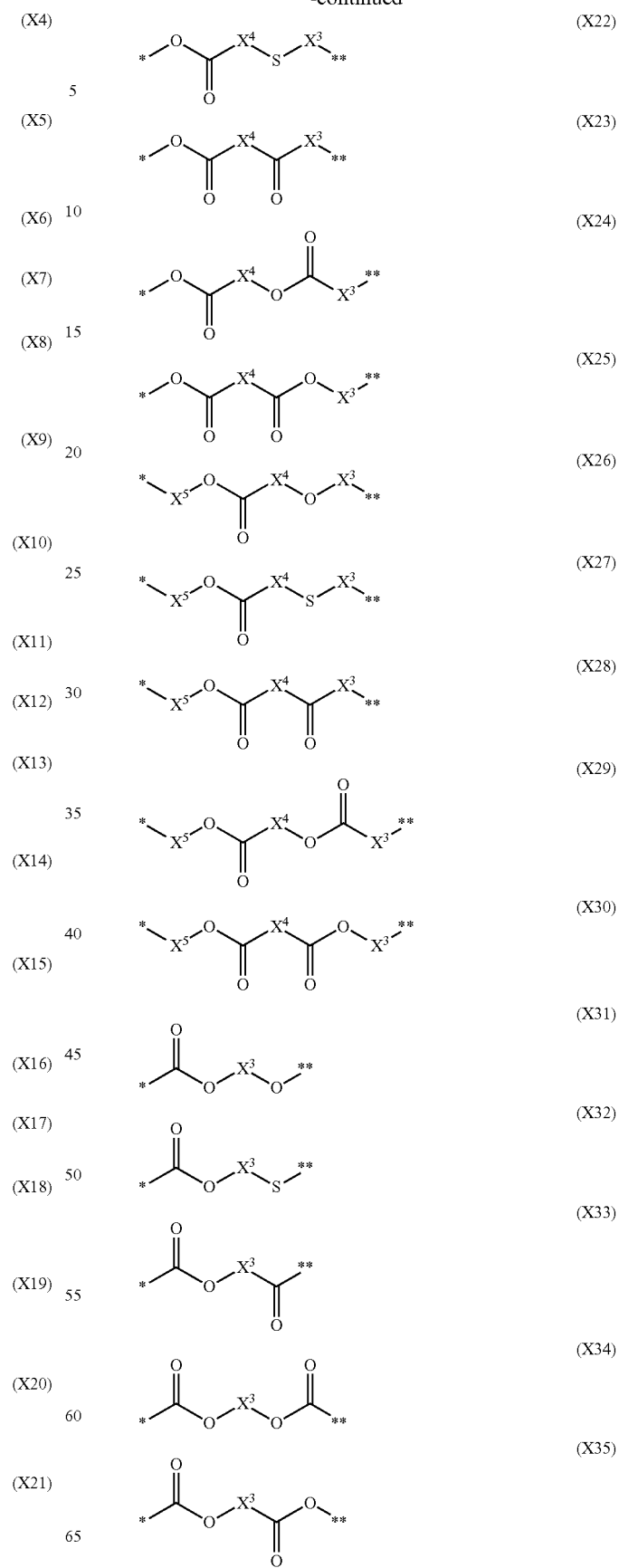

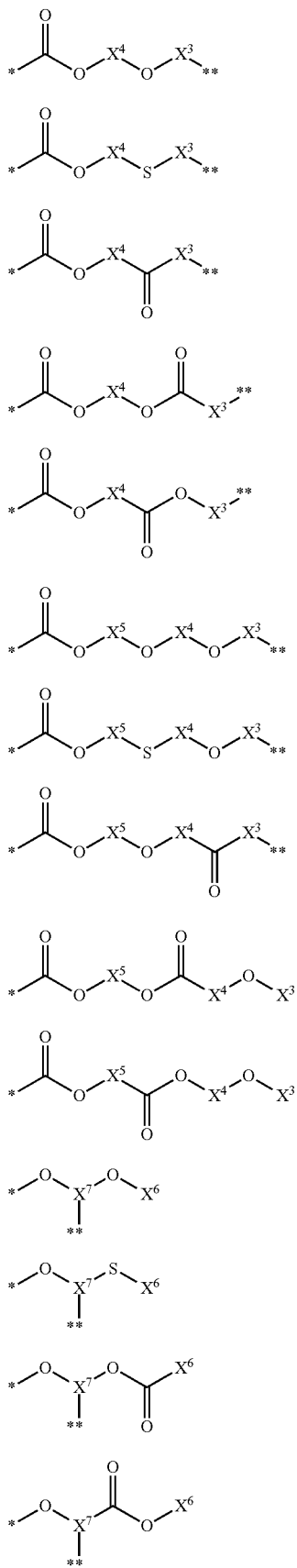

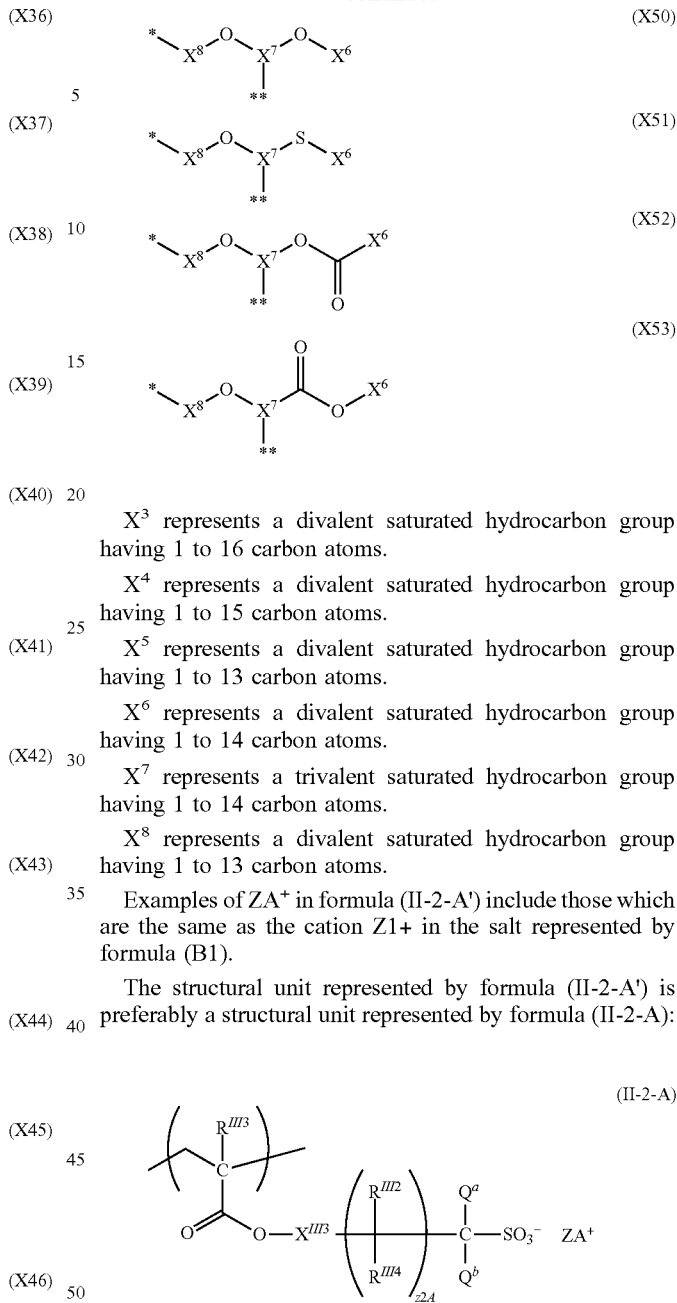

$X^3$ represents a divalent saturated hydrocarbon group having 1 to 16 carbon atoms.

$X^4$ represents a divalent saturated hydrocarbon group having 1 to 15 carbon atoms.

$X^5$ represents a divalent saturated hydrocarbon group having 1 to 13 carbon atoms.

$X^6$ represents a divalent saturated hydrocarbon group having 1 to 14 carbon atoms.

$X^7$ represents a trivalent saturated hydrocarbon group having 1 to 14 carbon atoms.

$X^8$ represents a divalent saturated hydrocarbon group having 1 to 13 carbon atoms.

Examples of $ZA^+$ in formula (II-2-A') include those which are the same as the cation Z1+ in the salt represented by formula (B1).

The structural unit represented by formula (II-2-A') is preferably a structural unit represented by formula (II-2-A):

wherein, in formula (II-2-A), $R^{III3}$, $X^{III3}$ and $ZA^+$ are the same as defined above, z2A represents an integer of 0 to 6, $R^{III2}$ and $R^{III4}$ each independently represent a hydrogen atom, a fluorine atom or a perfluoroalkyl group having 1 to 6 carbon atoms, and when z2A is 2 or more, a plurality of $R^{III2}$ and $R^{III4}$ may be the same or different form each other, and $Q^a$ and $Q^b$ each independently represent a fluorine atom or a perfluoroalkyl group having 1 to 6 carbon atoms.

Examples of the perfluoroalkyl group having 1 to 6 carbon atoms represented by $R^{III2}$, $R^{III4}$, $Q^a$ and $Q^b$ include those which are the same as the perfluoroalkyl group having 1 to 6 carbon atoms represented by $Q^{b1}$ mentioned above.

The structural unit represented by formula (II-2-A) is preferably a structural unit represented by formula (II-2-A-1):

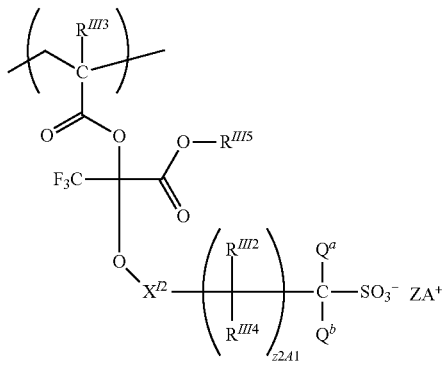

(II-2-A-1)

wherein, in formula (II-2-A-1),
$R^{III2}$, $R^{III3}$, $R^{III4}$, $Q^a$, $Q^b$ and $ZA^+$ are the same as defined above,
$R^{III5}$ represents a saturated hydrocarbon group having 1 to 12 carbon atoms,
z2A1 represents an integer of 0 to 6, and
$X^{I2}$ represents a divalent saturated hydrocarbon group having 1 to 11 carbon atoms, —$CH_2$— included in the saturated hydrocarbon group may be replaced by —O—, —S— or —CO—, and a hydrogen atom included in the saturated hydrocarbon group may be substituted with a halogen atom or a hydroxy group.

Examples of the saturated hydrocarbon group having 1 to 12 carbon atoms represented by $R^{III5}$ include linear or branched alkyl groups such as a methyl group, an ethyl group, a propyl group, an isopropyl group, a butyl group, a sec-butyl group, a tert-butyl group, a pentyl group, a hexyl group, a heptyl group, an octyl group, a nonyl group, a decyl group, an undecyl group and a dodecyl group.

Examples of the divalent saturated hydrocarbon group represented by $X^{I2}$ include those which are the same as the divalent saturated hydrocarbon group represented by $X^{III3}$.

The structural unit represented by formula (II-2-A-1) is more preferably a structural unit represented by formula (II-2-A-2):

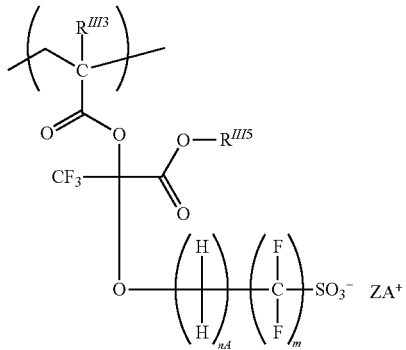

(II-2-A-2)

wherein, in formula (II-2-A-2), $R^{III3}$, $R^{III5}$ and $ZA^+$ are the same as defined above, and
m and nA each independently represent 1 or 2.

The structural unit represented by formula (II-2-A') includes, for example, the following structural units, structural units in which a group corresponding to a methyl group of $R^{III3}$ is substituted with an alkyl group having 1 to 6 carbon atoms which may have a hydrogen atom, a halogen atom (e.g., fluorine atom) or a halogen atom (e.g., trifluoromethyl group, etc.) and the structural units mentioned in WO 2012/050015 A. $ZA^+$ represents an organic cation.

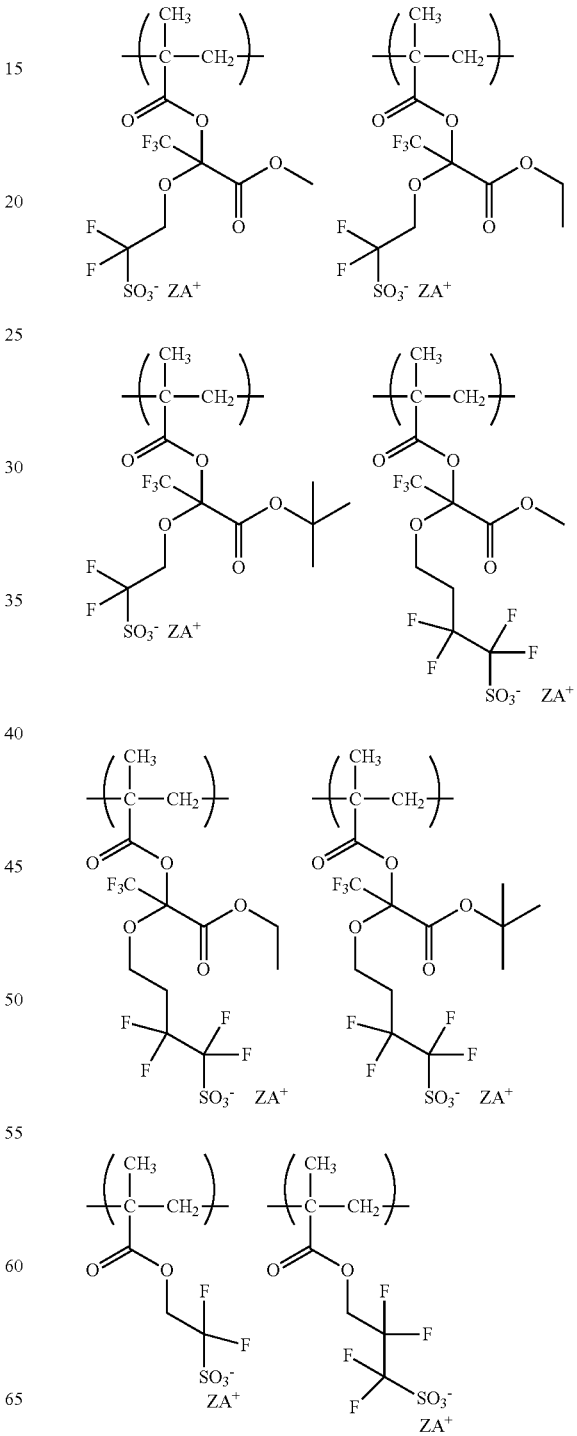

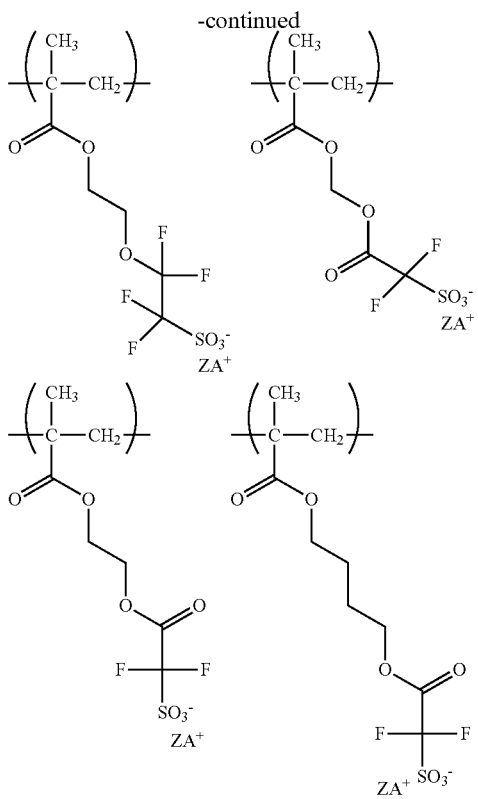

The structural unit having a sulfonio group and an organic anion in a side chain is preferably a structural unit represented by formula (II-1-1):

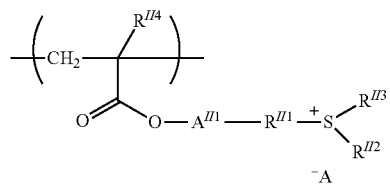

wherein, in formula (II-1-1),
$A^{II1}$ represents a single bond or a divalent linking group,
$R^{II1}$ represents a divalent aromatic hydrocarbon group having 6 to 18 carbon atoms,
$R^{II2}$ and $R^{II3}$ each independently represent a hydrocarbon group having 1 to 18 carbon atoms, and $R^{II2}$ and $R^{II3}$ may be bonded to each other to form a ring together with sulfur atoms to which $R^{II2}$ and $R^{II3}$ are bonded,
$R^{II4}$ represents a hydrogen atom, a halogen atom, or an alkyl group having 1 to 6 carbon atoms which may have a halogen atom, and
$A^-$ represents an organic anion.

Examples of the divalent aromatic hydrocarbon group having 6 to 18 carbon atoms represented by $R^{II1}$ include a phenylene group and a naphthylene group.

Examples of the hydrocarbon group represented by $R^{II2}$ and $R^{II3}$ include an alkyl group, an alicyclic hydrocarbon group, an aromatic hydrocarbon group, and groups obtained by combining these groups.

Examples of the alkyl group and the alicyclic hydrocarbon group include those which are the same as mentioned above.

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group, aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group, and the like. Examples of the halogen atom represented by $R^{II4}$ include a fluorine atom, a chlorine atom, a bromine atom and an iodine atom.

Examples of the alkyl group having 1 to 6 carbon atoms which may have a halogen atom represented by $R^{II4}$ include those which are the same as the alkyl group having 1 to 6 carbon atoms which may have a halogen atom represented by $R^{a8}$.

Examples of the divalent linking group represented by $A^{II1}$ include a divalent saturated hydrocarbon group having 1 to 18 carbon atoms, and —$CH_2$— included in the divalent saturated hydrocarbon group may be replaced by —O—, —S— or —CO—. Specific examples thereof include those which are the same as the divalent saturated hydrocarbon group having 1 to 18 carbon atoms represented by $X^{III3}$.

Examples of the structural unit including a cation in formula (II-1-1) include the following structural units and structural units in which a group corresponding to a methyl group of $R^{II4}$ is substituted with a hydrogen atom, a halogen atom (e.g., a fluorine atom, etc.) or an alkyl group having 1 to 6 carbon atoms which may have a halogen atom (e.g., a trifluoromethyl group, etc.) and the like.

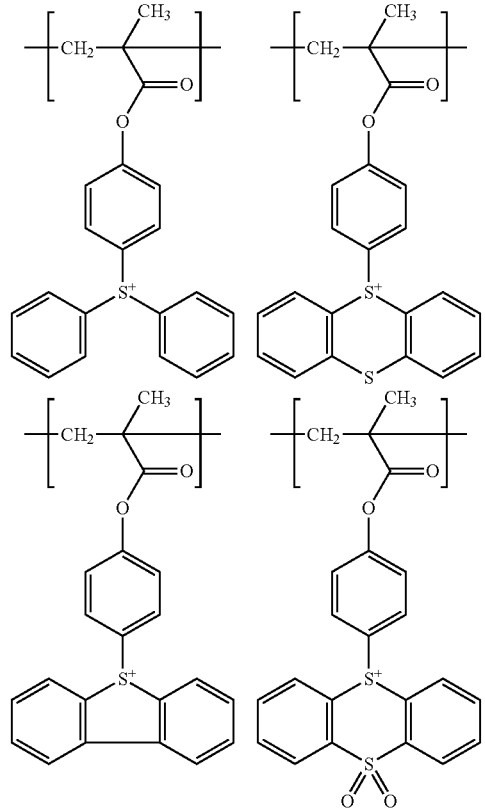

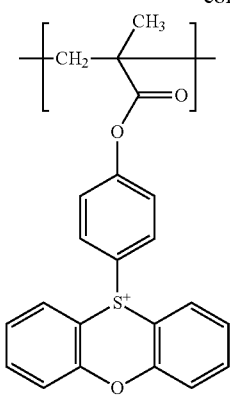
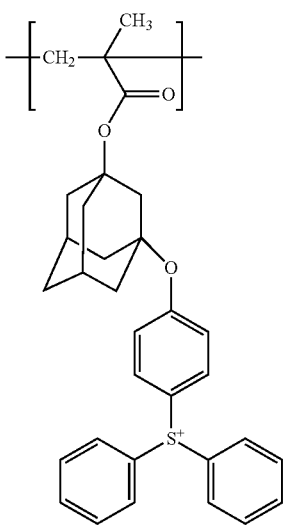
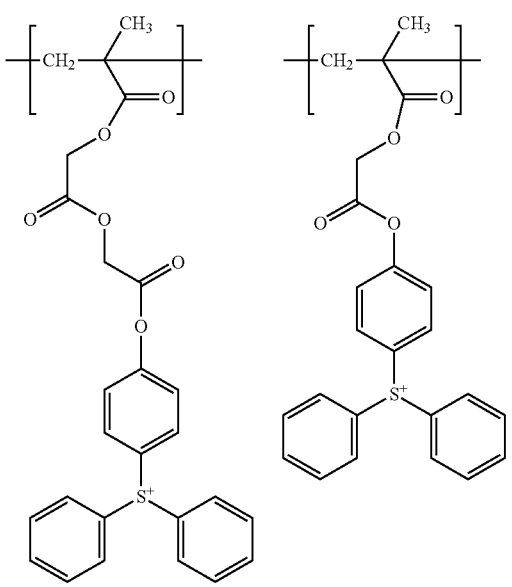
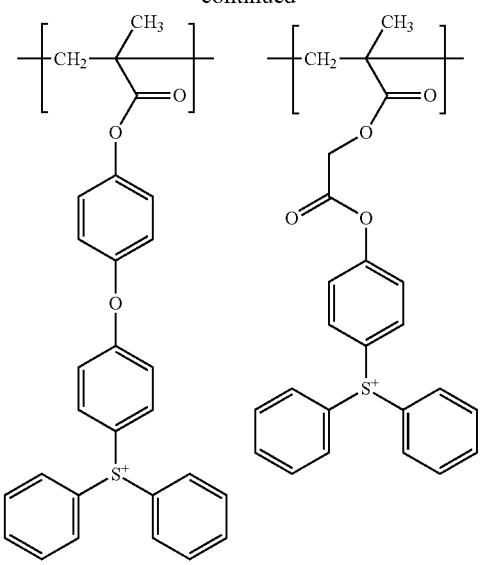
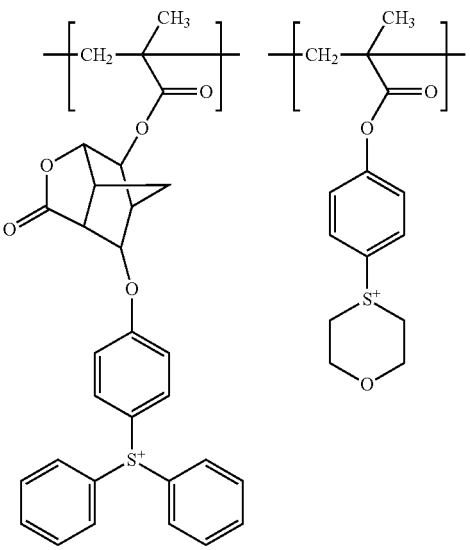

Examples of the organic anion represented by A⁻ include a sulfonic acid anion, a sulfonylimide anion, a sulfonylmethide anion and a carboxylic acid anion. The organic anion represented by A⁻ is preferably a sulfonic acid anion, and the sulfonic acid anion is more preferably an anion included in the above-mentioned salt represented by formula (B1). The sulfonylimide anion, the sulfonylmethide anion and the carboxylic acid anion are more preferably an anion Al⁻ included in the above-mentioned salt represented by formula (I).

Examples of the structural unit represented by formula (II-1-1) include the followings.

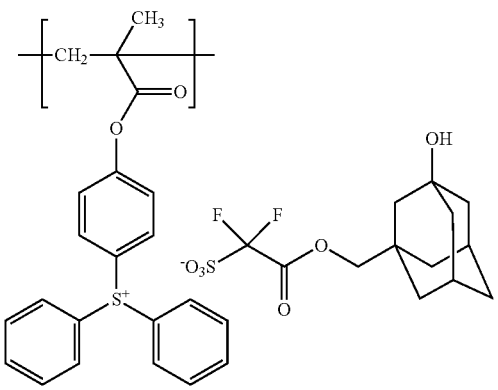

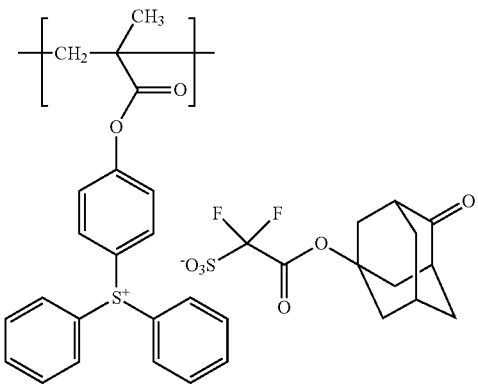

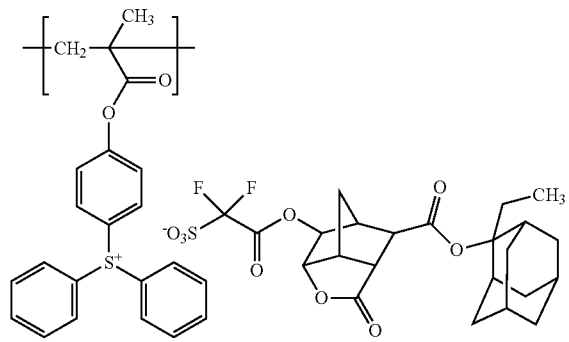

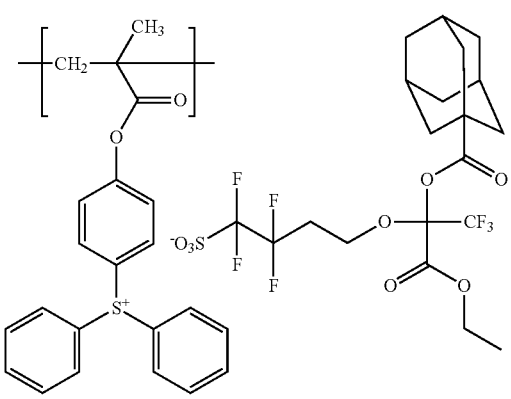

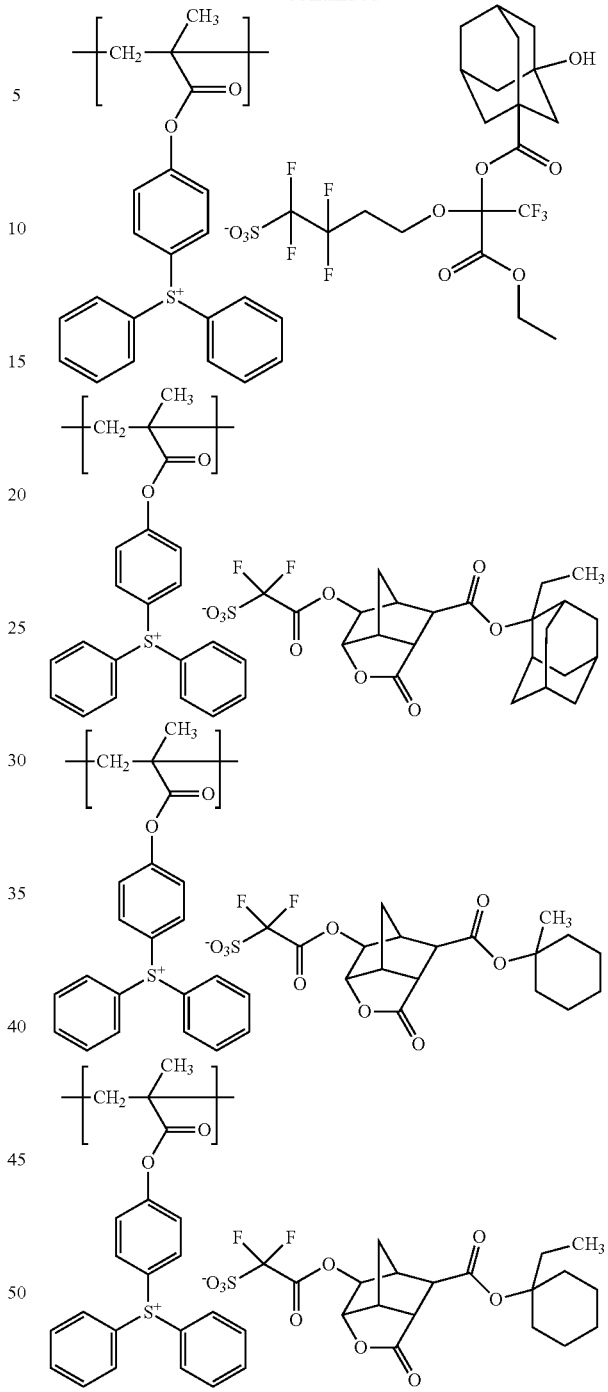

When the structural unit (II) is included in the resin (A), the content of the structural unit (II) is preferably 1 to 20 mol %, more preferably 2 to 15 mol %, and still more preferably 3 to 10 mol %, based on all structural units of the resin (A).

The resin (A) may include structural units other than the structural units mentioned above, and examples of such structural unit include structural units well-known in the art.

The resin (A) is preferably a resin composed of a structural unit (a1) and a structural unit (s), namely, a copolymer of a monomer (a1) and a monomer (s).

The structural unit (a1) is preferably at least one selected from the group consisting of a structural unit (a1-0), a structural unit (a1-1) and a structural unit (a1-2) (preferably the structural unit having a cyclohexyl group or a cyclopentyl group), more preferably at least two, and still more preferably at least two selected from the group consisting of a structural unit (a1-1) and a structural unit (a1-2).

The structural unit (s) is preferably at least one selected from the group consisting of a structural unit (a2) and a structural unit (a3). The structural unit (a2) is preferably a structural unit (a2-1) or a structural unit (a2-A). The structural unit (a3) is preferably at least one selected from the group consisting of a structural unit represented by formula (a3-1), a structural unit represented by formula (a3-2) and a structural unit represented by formula (a3-4).

The respective structural units constituting the resin (A) may be used alone, or two or more structural units may be used in combination. Using a monomer from which these structural units are derived, it is possible to produce by a known polymerization method (e.g. radical polymerization method). The content of the respective structural units included in the resin (A) can be adjusted according to the amount of the monomer used in the polymerization.

The weight-average molecular weight of the resin (A) is preferably 2,000 or more (more preferably 2,500 or more, and still more preferably 3,000 or more), and 50,000 or less (more preferably 30,000 or less, and still more preferably 15,000 or less). In the present specification, the weight-average molecular weight is a value determined by gel permeation chromatography under the conditions mentioned in Examples.

<Resin Other than Resin (A)>

The resist composition of the present invention may use the resin other than the resin (A) in combination.

The resin other than the resin (A) includes, for example, a resin including a structural unit (a4) or a structural unit (a5) (hereinafter sometimes referred to as resin (X)).

The resin (X) is preferably a resin including a structural unit (a4), particularly.

In the resin (X), the content of the structural unit (a4) is preferably 30 mol % or more, more preferably 40 mol % or more, and still more preferably 45 mol % or more, based on the total of all structural units of the resin (X).

Examples of the structural unit, which may be further included in the resin (X), include a structural unit (a1), a structural unit (a2), a structural unit (a3) and structural units derived from other known monomers. Particularly, the resin (X) is preferably a resin composed only of a structural unit (a4) and/or a structural unit (a5).

The respective structural unit constituting the resin (X) may be used alone, or two or more structural units may be used in combination. Using a monomer from which these structural units are derived, it is possible to produce by a known polymerization method (e.g. radical polymerization method). The content of the respective structural units included in the resin (X) can be adjusted according to the amount of the monomer used in the polymerization.

The weight-average molecular weight of the resin (X) is preferably 6,000 or more (more preferably 7,000 or more) and 80,000 or less (more preferably 60,000 or less). The measurement means of the weight-average molecular weight of the resin (X) is the same as in the case of the resin (A).

When the resist composition of the present invention includes the resin (X), the content is preferably 1 to 60 parts by mass, more preferably 1 to 50 parts by mass, still more preferably 1 to 40 parts by mass, yet more preferably 1 to 30 parts by mass, and further preferably 1 to 8 parts by mass, based on 100 parts by mass of the resin (A).

The content of the resin (A) in the resist composition is preferably 80% by mass or more and 99% by mass or less, and more preferably 90% by mass or more and 99% by mass or less, based on the solid component of the resist composition. When including resins other than the resin (A), the total content of the resin (A) and resins other than the resin (A) is preferably 80% by mass or more and 99% by mass or less, and more preferably 90% by mass or more and 99% by mass or less, based on the solid component of the resist composition. In the present specification, "solid content of resist composition" means the total of contents in which the below-mentioned solvent (E) is removed from the total amount of the resist composition. The solid content of the resist composition and the content of the resin thereto can be measured by a known analysis means such as liquid chromatography or gas chromatography.

<Solvent (E)>

The content of the solvent (E) in the resist composition is usually 90% by mass or more and 99.9% by mass or less, preferably 92% by mass or more and 99% by mass or less, and more preferably 94% by mass or more and 99% by mass or less. The content of the solvent (E) can be measured, for example, by a known analysis means such as liquid chromatography or gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. The solvent (E) may be used alone, or two or more solvents may be used.

<Quencher (C)>

Examples of the quencher (C) include a basic nitrogen-containing organic compound, and a salt generating an acid having an acidity lower than that of an acid generated from an acid generator. When the resist composition includes the quencher (C), the content of the quencher (C) is preferably about 0.01 to 15% by mass, more preferably about 0.01 to 10% by mass, still more preferably about 0.1 to 8% by mass, and yet more preferably about 0.1 to 7% by mass, based on the amount of the solid component of the resist composition.

Examples of the basic nitrogen-containing organic compound include amine and an ammonium salt. Examples of the amine include an aliphatic amine and an aromatic amine. Examples of the aliphatic amine include a primary amine, a secondary amine and a tertiary amine.

Examples of the amine include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'- diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine, bipyridine and the like, preferably diisopropylaniline, and more preferably 2,6-diisopropylaniline.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, 3-(trifluoromethyl)phenyltrimethylammonium hydroxide, tetra-n-butylammonium salicylate and choline.

The acidity in a salt generating an acid having an acidity lower than that of an acid generated from the acid generator is indicated by the acid dissociation constant (pKa). Regarding the salt generating an acid having an acidity lower than that of an acid generated from the acid generator, the acid dissociation constant of an acid generated from the salt usually meets the following inequality: −3<pKa, preferably −1<pKa<7, and more preferably 0<pKa<5.

Examples of the salt generating an acid having an acidity lower than that of an acid generated from the acid generator include salts represented by the following formulas, a salt represented by formula (D) mentioned in JP 2015-147926 A (hereinafter sometimes referred to as "weak acid inner salt (D)"), and salts mentioned in JP 2012-229206 A, JP 2012-6908 A, JP 2012-72109 A, JP 2011-39502 A and JP 2011-191745 A. The salt generating an acid having an acidity lower than that of an acid generated from the acid generator is preferably a salt generating a carboxylic acid having an acidity lower than that of an acid generated from the acid generator (salt having a carboxylic acid anion), more preferably a weak acid inner salt (D), and still more preferably a diphenyliodonium salt containing a phenyl group substituted with a carboxylic acid anion among the weak acid inner salt (D).

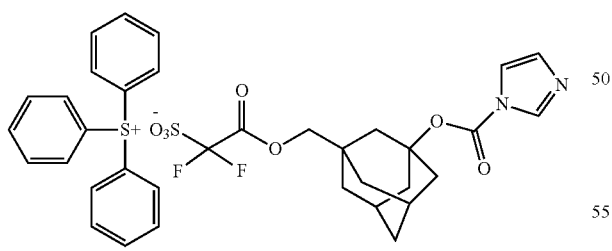

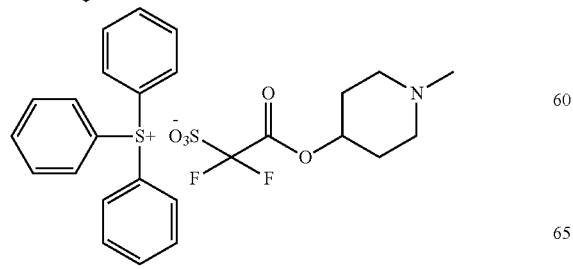

-continued

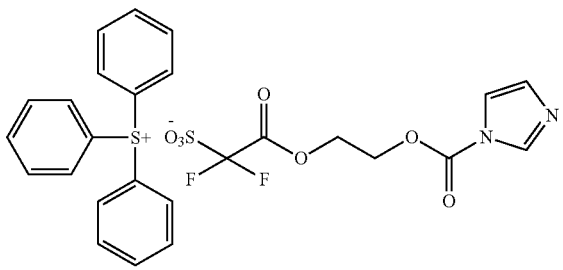

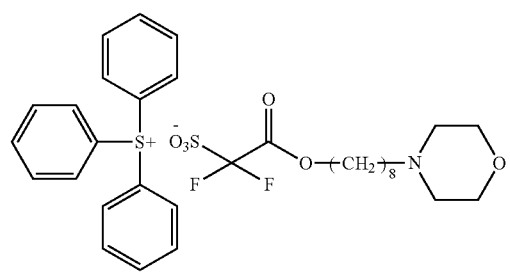

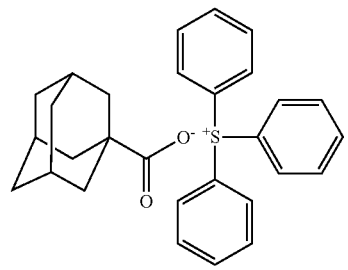

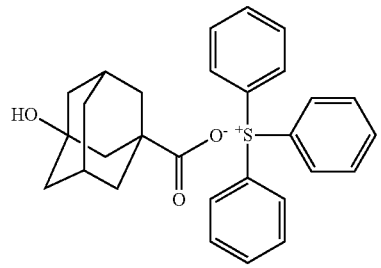

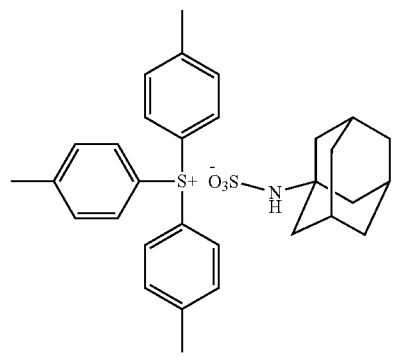

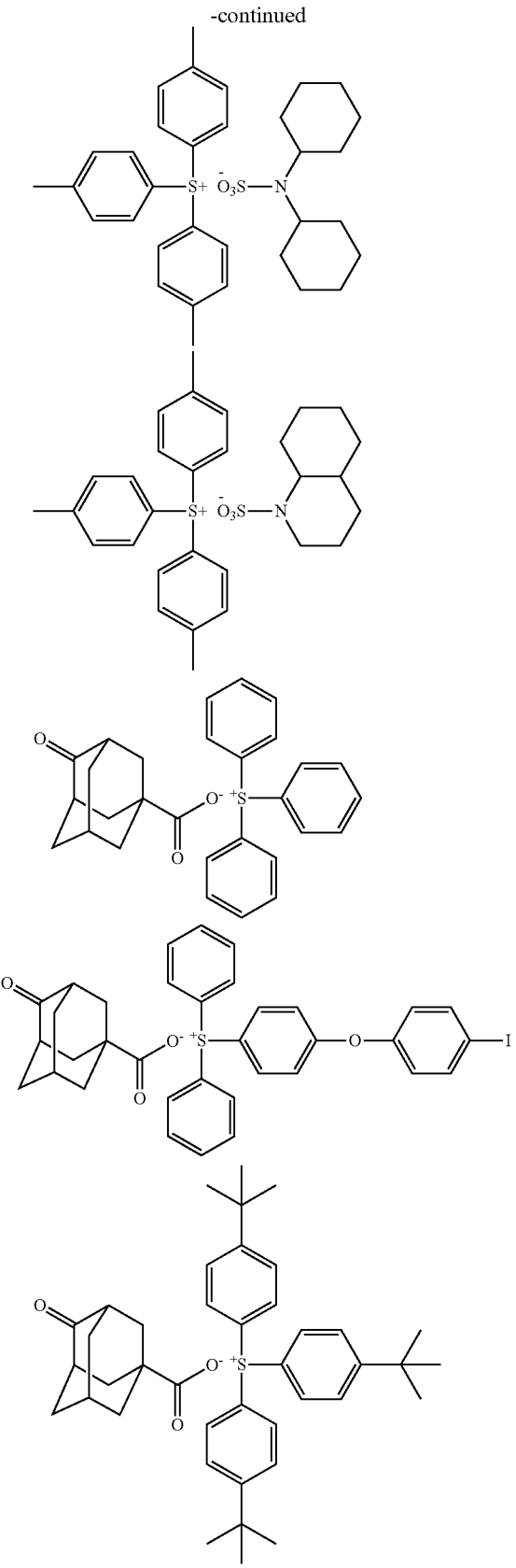

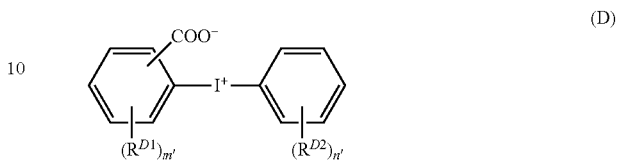

two phenyl groups are bonded, and a carboxylic acid anion substituted with at least one phenyl group of two phenyl groups bonded to the iodonium cation, and specific examples thereof include a salt represented by the following formula:

wherein, in formula (D), $R^{D1}$ and $R^{D2}$ each independently represent a hydrocarbon group having 1 to 12 carbon atoms, an alkoxy group having 1 to 6 carbon atoms, an acyl group having 2 to 7 carbon atoms, an acyloxy group having 2 to 7 carbon atoms, an alkoxycarbonyl group having 2 to 7 carbon atoms, a nitro group or a halogen atom, and m' and n' each independently represent an integer of 0 to 4, and when m' is 2 or more, a plurality of $R^{D1}$ may be the same or different, and when n' is 2 or more, a plurality of $R^{D2}$ may be the same or different.

Examples of the hydrocarbon group as for $R^{D1}$ and $R^{D2}$ include a chain hydrocarbon group, an alicyclic hydrocarbon group, an aromatic hydrocarbon group, and a group formed by combining these groups.

Examples of the chain hydrocarbon group include alkyl groups such as a methyl group, an ethyl group, a propyl group, an isopropyl group, a butyl group, an isobutyl group, a tert-butyl group, a pentyl group, a hexyl group, a nonyl group and the like.

The alicyclic hydrocarbon group may be either monocyclic or polycyclic, or may be either saturated or unsaturated. Examples thereof include cycloalkyl groups such as a cyclopropyl group, a cyclobutyl group, a cyclopentyl group, a cyclohexyl group, a cyclononyl group and a cyclododecyl group, a norbornyl group, an adamantyl group and the like.

Examples of the aromatic hydrocarbon group include aryl groups such as a phenyl group, a 1-naphthyl group, a 2-naphthyl group, a 2-methylphenyl group, a 3-methylphenyl group, a 4-methylphenyl group, a 4-ethylphenyl group, a 4-propylphenyl group, a 4-isopropylphenyl group, a 4-butylphenyl group, a 4-t-butylphenyl group, a 4-hexylphenyl group, a 4-cyclohexylphenyl group, an anthryl group, a p-adamantylphenyl group, a tolyl group, a xylyl group, a cumenyl group, a mesityl group, a biphenyl group, a phenanthryl group, a 2,6-diethylphenyl group, a 2-methyl-6-ethylphenyl group and the like.

Examples of the group formed by combining these groups include an alkyl-cycloalkyl group, a cycloalkyl-alkyl group, an aralkyl group (e.g., a phenylmethyl group, a 1-phenylethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl group, a 5-phenyl-1-pentyl group, a 6-phenyl-1-hexyl group, etc.) and the like.

Examples of the alkoxy group include a methoxy group, an ethoxy group and the like.

Examples of the acyl group include an acetyl group, a propanoyl group, a benzoyl group, a cyclohexanecarbonyl group and the like.

Examples of the acyloxy group include a group obtained by bonding an oxy group (—O—) to the above acyl group.

Examples of the weak acid inner salt (D) is preferably a diphenyliodonium salt having an iodonium cation to which Examples of the alkoxycarbonyl group include a group obtained by bonding a carbonyl group (—CO—) to the above alkoxy group.

Examples of the halogen atom include a fluorine atom, a chlorine atom, a bromine atom and the like.

Preferably, $R^{D1}$ and $R^{D2}$ each independently represent an alkyl group having 1 to 8 carbon atoms, a cycloalkyl group having 3 to 10 carbon atoms, an alkoxy group having 1 to 6 carbon atoms, an acyl group having 2 to 4 carbon atoms, an acyloxy group having 2 to 4 carbon atoms, an alkoxycarbonyl group having 2 to 4 carbon atoms, a nitro group or a halogen atom.

Preferably, m' and n' are each independently an integer of 0 to 2, and more preferably 0, and when m' is 2 or more, a plurality of $R^{D}1$ may be the same or different, and when n' is 2 or more, a plurality of $R^{D2}$ may be the same or different.

More specifically, the following salts are exemplified.

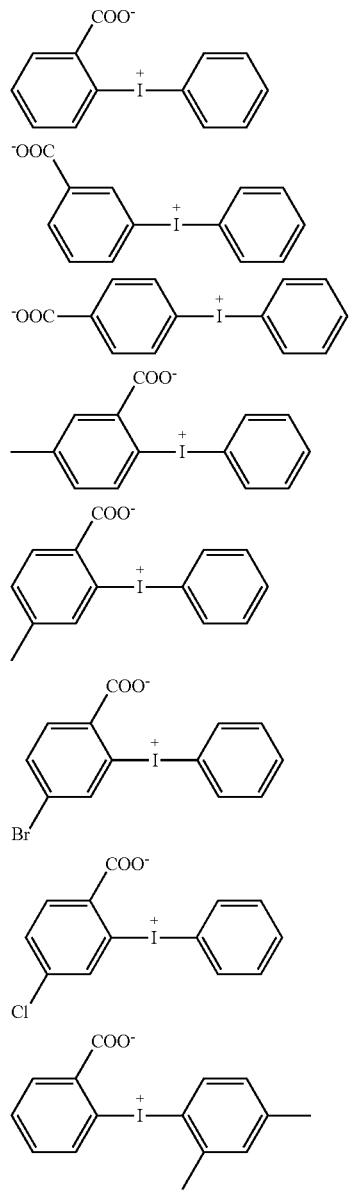

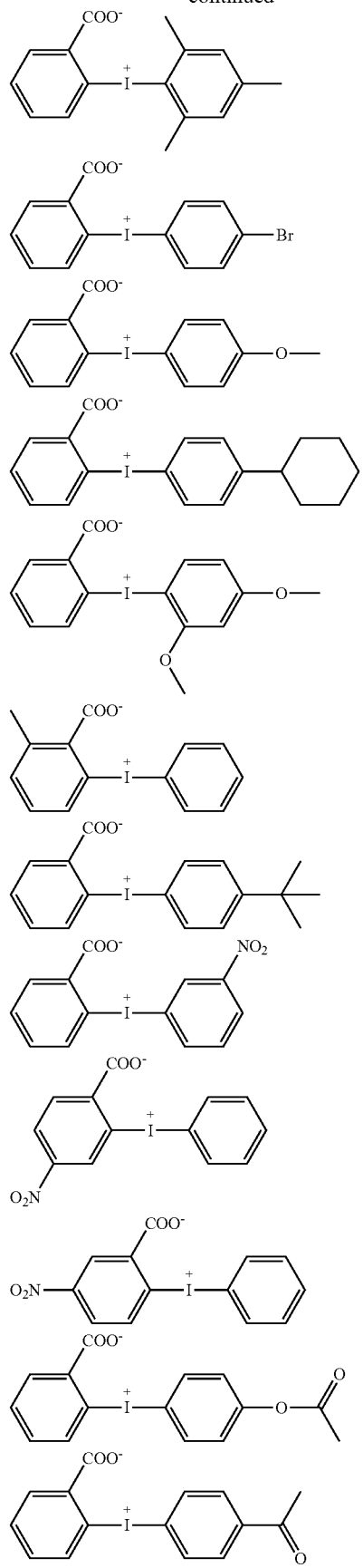

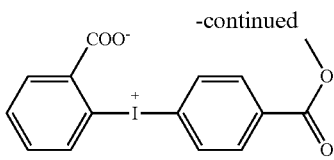

<Other Components>

The resist composition of the present invention may also include components other than the components mentioned above (hereinafter sometimes referred to as "other components (F)"). The other components (F) are not particularly limited and it is possible to use various additives known in the resist field, for example, sensitizers, dissolution inhibitors, surfactants, stabilizers and dyes.

<Preparation of Resist Composition>

The resist composition of the present invention can be prepared by mixing a salt (I) and a resin (A), and if necessary, an acid generator (B), resins other than the resin (A), a solvent (E), a quencher (C) and other components (F). The order of mixing these components is any order and is not particularly limited. It is possible to select, as the temperature during mixing, appropriate temperature from 10 to 40° C., according to the type of the resin, the solubility in the solvent (E) of the resin and the like. It is possible to select, as the mixing time, appropriate time from 0.5 to 24 hours according to the mixing temperature. The mixing means is not particularly limited and it is possible to use mixing with stirring.

After mixing the respective components, the mixture is preferably filtered through a filter having a pore diameter of about 0.003 to 0.2 μm.

(Method for Producing Resist Pattern)

The method for producing a resist pattern of the present invention include:

(1) a step of applying the resist composition of the present invention on a substrate,
(2) a step of drying the applied composition to form a composition layer,
(3) a step of exposing the composition layer,
(4) a step of heating the exposed composition layer, and
(5) a step of developing the heated composition layer.

The resist composition can be usually applied on a substrate using a conventionally used apparatus, such as a spin coater. Examples of the substrate include inorganic substrates such as a silicon wafer, and organic substrates in which a resist film is formed on the surface. Before applying the resist composition, the substrate may be washed, and an organic antireflection film may be formed on the substrate.

The solvent is removed by drying the applied composition to form a composition layer. Drying is performed by evaporating the solvent using a heating device such as a hot plate (so-called "prebake"), or a decompression device. The heating temperature is preferably 50 to 200° C. and the heating time is preferably 10 to 180 seconds. The pressure during drying under reduced pressure is preferably about 1 to $1.0 \times 10^5$ Pa.

The composition layer thus obtained is usually exposed using an aligner. The aligner may be a liquid immersion aligner. It is possible to use, as an exposure source, various exposure sources, for example, exposure sources capable of emitting laser beam in an ultraviolet region such as KrF excimer laser (wavelength of 248 nm), ArF excimer laser (wavelength of 193 nm) and F2 excimer laser (wavelength of 157 nm), an exposure source capable of emitting harmonic laser beam in a far-ultraviolet or vacuum ultra violet region by wavelength-converting laser beam from a solid-state laser source (YAG or semiconductor laser), an exposure source capable of emitting electron beam or extreme ultraviolet light (EUV) and the like. In the present specification, such exposure to radiation is sometimes collectively referred to as "exposure". The exposure is usually performed through a mask corresponding to a pattern to be required. When electron beam is used as the exposure source, exposure may be performed by direct writing without using the mask.

The exposed composition layer is subjected to a heat treatment (so-called "post-exposure bake") to promote the deprotection reaction in an acid-labile group. The heating temperature is usually about 50 to 200° C., and preferably about 70 to 150° C. It is also possible to perform a chemical treatment (silylation) which adjusts the hydrophilicity or hydrophobicity of the resin on a surface side of the composition after heating. Before performing the development, the steps of application of the resist composition, drying, exposure and heating may be repeatedly performed on the exposed composition layer.

The heated composition layer is usually developed with a developing solution using a development apparatus. Examples of the developing method include a dipping method, a paddle method, a spraying method, a dynamic dispensing method and the like. The developing temperature is preferably, for example, 5 to 60° C. and the developing time is preferably, for example, 5 to 300 seconds. It is possible to produce a positive resist pattern or negative resist pattern by selecting the type of the developing solution as follows.

When the positive resist pattern is produced from the resist composition of the present invention, an alkaline developing solution is used as the developing solution. The alkaline developing solution may be various aqueous alkaline solutions used in this field. Examples thereof include aqueous solutions of tetramethylammonium hydroxide and (2-hydroxyethyl)trimethylammonium hydroxide (commonly known as choline). The surfactant may be contained in the alkaline developing solution.

It is preferable that the developed resist pattern is washed with ultrapure water and then water remaining on the substrate and the pattern is removed.

When the negative resist pattern is produced from the resist composition of the present invention, a developing solution containing an organic solvent (hereinafter sometimes referred to as "organic developing solution") is used as the developing solution.

Examples of the organic solvent contained in the organic developing solution include ketone solvents such as 2-hexanone and 2-heptanone; glycol ether ester solvents such as propylene glycol monomethyl ether acetate; ester solvents such as butyl acetate; glycol ether solvents such as propylene glycol monomethyl ether; amide solvents such as N,N-dimethylacetamide; and aromatic hydrocarbon solvents such as anisole.

The content of the organic solvent in the organic developing solution is preferably 90% by mass or more and 100% by mass or less, more preferably 95% by mass or more and 100% by mass or less, and still more preferably the organic developing solution is substantially composed of the organic solvent.

Particularly, the organic developing solution is preferably a developing solution containing butyl acetate and/or 2-heptanone. The total content of butyl acetate and 2-heptanone in the organic developing solution is preferably 50% by mass or more and 100% by mass or less, more preferably 90% by mass or more and 100% by mass or less, and still more preferably the organic developing solution is substantially composed of butyl acetate and/or 2-heptanone.

The surfactant may be contained in the organic developing solution. A trace amount of water may be contained in the organic developing solution.

During development, the development may be stopped by replacing by a solvent with the type different from that of the organic developing solution.

The developed resist pattern is preferably washed with a rinsing solution. The rinsing solution is not particularly limited as long as it does not dissolve the resist pattern, and it is possible to use a solution containing an ordinary organic solvent which is preferably an alcohol solvent or an ester solvent.

After washing, the rinsing solution remaining on the substrate and the pattern is preferably removed.

<Applications>

The resist composition of the present invention is suitable as a resist composition for exposure of KrF excimer laser, a resist composition for exposure of ArF excimer laser, a resist composition for exposure of electron beam (EB) or a resist composition for exposure of EUV, particularly a resist composition for exposure of electron beam (EB) or a resist composition for exposure of EUV, and the resist composition is useful for fine processing of semiconductors.

EXAMPLES

The present invention will be described more specifically by way of Examples. Percentages and parts expressing the contents or amounts used in the Examples are by mass unless otherwise specified.

The weight-average molecular weight is a value determined by gel permeation chromatography. Analysis conditions of gel permeation chromatography are as follows.

Column: TSKgel Multipore HXL-M×3+guardcolumn (manufactured by TOSOH CORPORATION)
Eluent: tetrahydrofuran
Flow rate: 1.0 mL/min
Detector: RI detector
Column temperature: 40° C.
Injection amount: 100 μl
Molecular weight standards: polystyrene standard (manufactured by TOSOH CORPORATION)

Structures of compounds were confirmed by measuring a molecular ion peak using mass spectrometry (Liquid Chromatography: Model 1100, manufactured by Agilent Technologies, Inc., and Mass Spectrometry: Model LC/MSD, manufactured by Agilent Technologies, Inc.). The value of this molecular ion peak in the following Examples is indicated by "MASS".

Example 1: Synthesis of Salt Represented by Formula (I-1224)

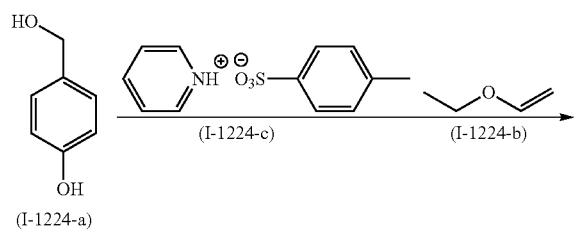

(I-1224-a)    (I-1224-c)    (I-1224-b)

-continued

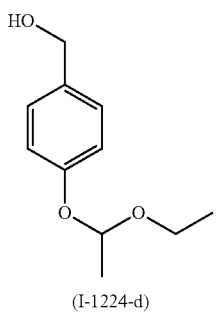

(I-1224-d)

22.55 Parts of a compound represented by formula (I-1224-a), 4.56 parts of a compound represented by formula (I-1224-c), 150 parts of ethyl acetate and 15 parts of tetrahydrofuran were mixed, followed by stirring at 23° C. for 30 minutes. To the mixed solution thus obtained, 13.10 parts of a compound represented by formula (I-1224-b) was added, followed by stirring at 23° C. for 18 hours. To the reaction mass thus obtained, 50 parts of n-heptane and 70 parts of ion-exchanged water were added, and after stirring at 23° C. for 30 minutes, the organic layer was isolated through separation. To the organic layer thus recovered, 70 parts of ion-exchanged water was added, and after stirring at 23° C. for 30 minutes, the organic layer was isolated through separation. This water washing operation was repeated four times. The organic layer thus obtained was concentrated and then the concentrated mass was isolated using a column (silica gel 60N (spherical, neutral) 100-210 μm; manufactured by Kanto Chemical Co., Inc., developing solvent: n-heptane/ethyl acetate=1/1) to obtain 8.91 parts of a compound represented by formula (I-1224-d).

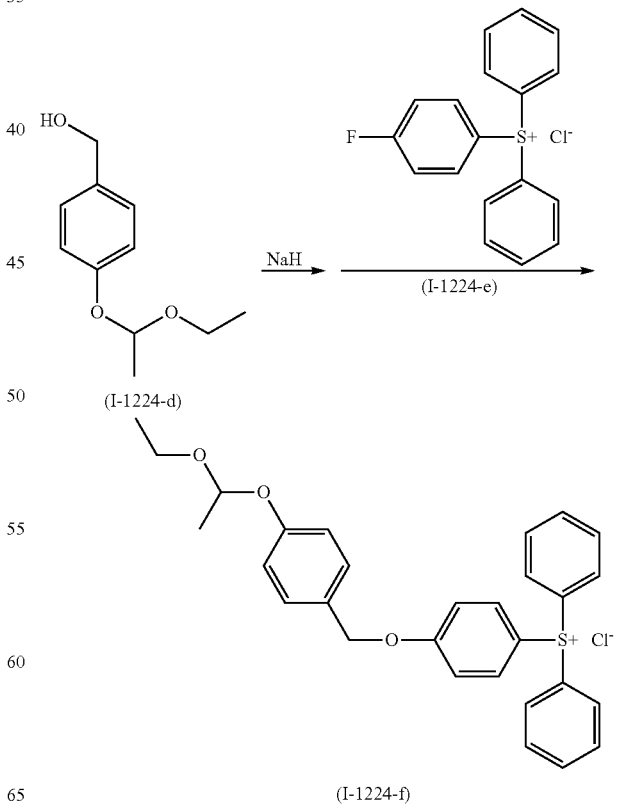

(I-1224-d)

(I-1224-f)

1.02 Parts of a compound represented by formula (I-1224-d) and 10 parts of tetrahydrofuran were mixed, and after stirring at 23° C. for 30 minutes and cooling to 5° C., 0.14 part of sodium hydride was added. To the mixture thus obtained, 1.82 parts of a salt represented by formula (I-1224-e) was added, followed by stirring at 5° C. for 3 hours and further stirring at 23° C. for 1 hour. To the mixture thus obtained, 30 parts of chloroform and 15 parts of ion-exchanged water were added, and after stirring at 23° C. for 30 minutes, the organic layer was isolated through separation. The organic layer thus obtained was concentrated and 30 parts of tert-butyl methyl ether was added to the concentrated residue. After stirring at 23° C. for 30 minutes, the supernatant was removed, followed by concentration to obtain 1.95 parts of a salt represented by formula (I-1224-f).

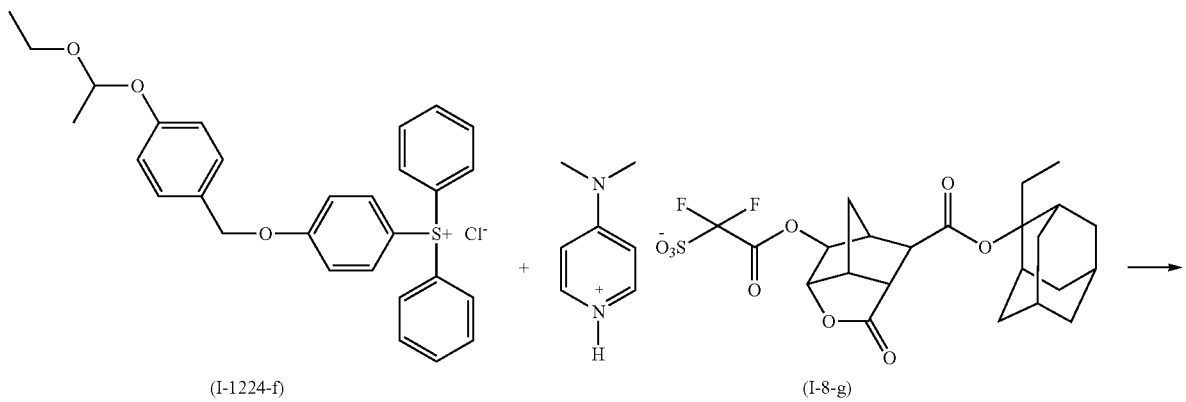

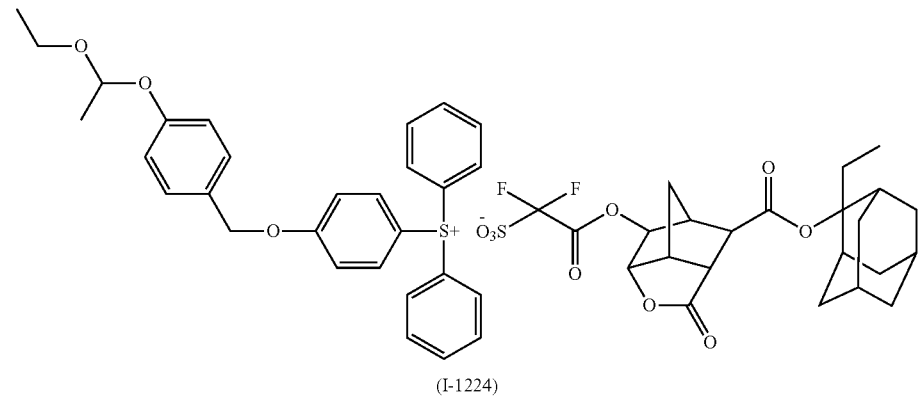

0.78 Part of a salt represented by formula (I-1224-f), 1.02 parts of a salt represented by formula (I-8-g), 30 parts of chloroform and 15 parts of ethyl acetate were mixed, followed by stirring at 23° C. for 2 hours. To the mixture thus obtained, 20 parts of ion-exchanged water was added, and after stirring at 23° C. for 30 minutes, the organic layer was isolated through separation. This water washing operation was repeated five times. The organic layer thus obtained was concentrated and 30 parts of tert-butyl methyl ether was added to the concentrated residue, followed by stirring at 23° C. for 30 minutes and further filtration to obtain 1.21 parts of a salt represented by formula (I-1224).

MASS (ESI (+) Spectrum): $M^+$ 457.2

MASS (ESI (−) Spectrum): $M^-$ 517.1

Example 2: Synthesis of Salt Represented by Formula (I-1232)

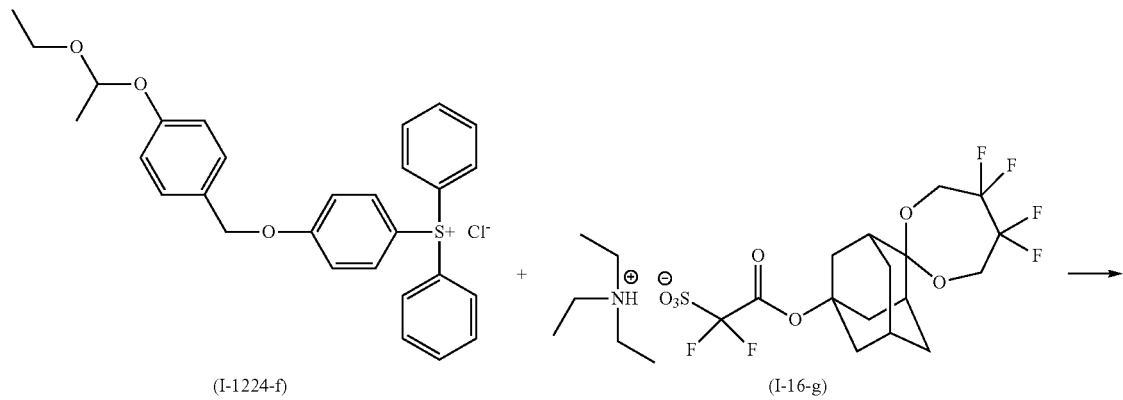

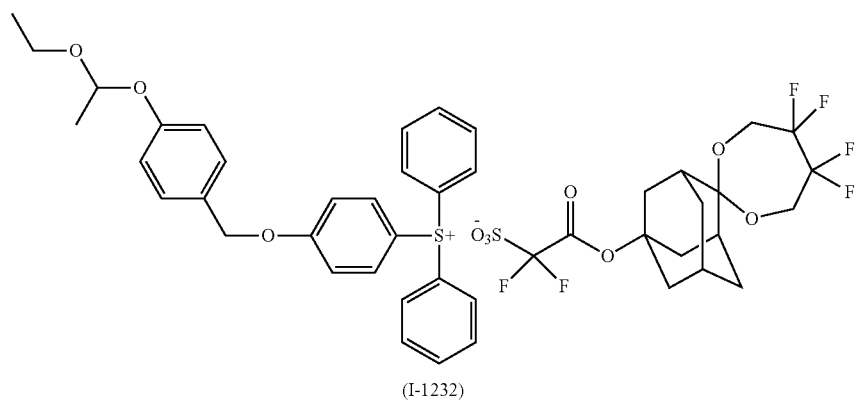

0.78 Part of a salt represented by formula (I-1224-f), 0.91 part of a salt represented by formula (I-16-g), 30 parts of chloroform and 15 parts of ethyl acetate were mixed, followed by stirring at 23° C. for 2 hours. To the mixture thus obtained, 20 parts of ion-exchanged water was added, and after stirring at 23° C. for 30 minutes, the organic layer was isolated through separation. This water washing operation was repeated five times. The organic layer thus obtained was concentrated and 30 parts of tert-butyl methyl ether was added to the concentrated residue, followed by stirring at 23° C. for 30 minutes and further filtration to obtain 1.23 parts of a salt represented by formula (I-1232).

MASS (ESI (+) Spectrum): $M^+$ 457.2
MASS (ESI (−) Spectrum): $M^-$ 467.1

Example 3: Synthesis of Salt Represented by Formula (I-8)

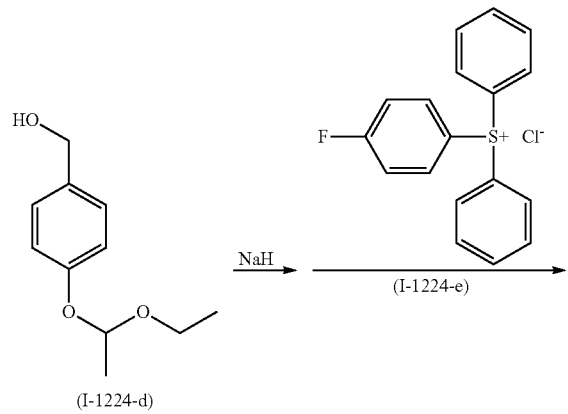

(I-1224-d)

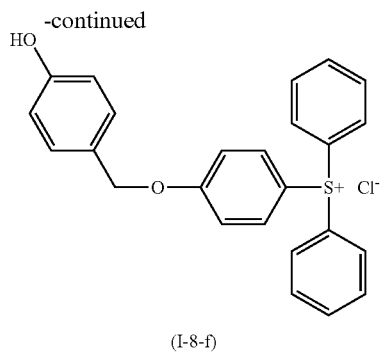

(I-1224-e)

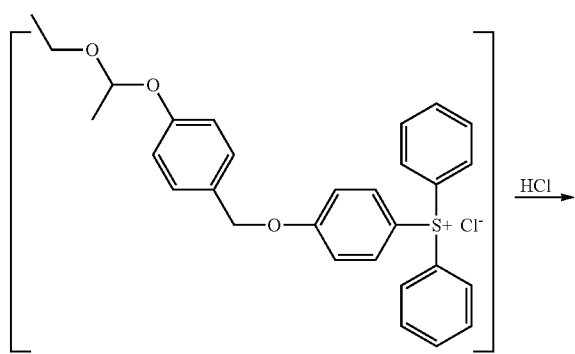

HCl →

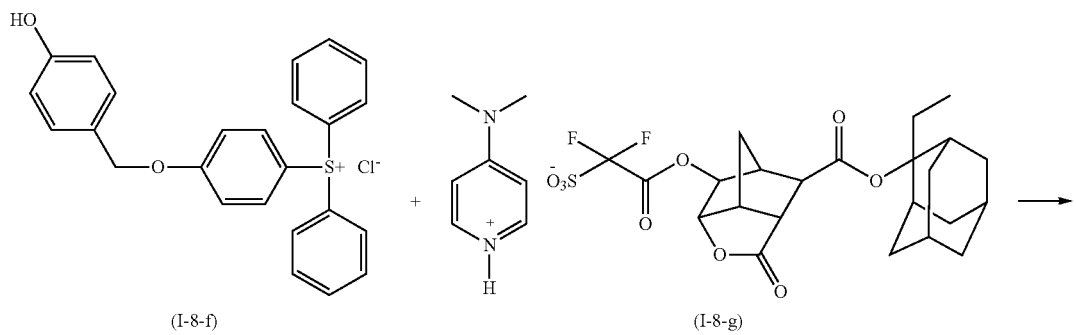

(I-8-f)

1.02 Parts of a compound represented by formula (I-1224-d) and 10 parts of tetrahydrofuran were mixed, and after stirring at 23° C. for 30 minutes and further cooling to 5° C., 0.14 part of sodium hydride was added. To the mixture thus obtained, 1.82 parts of a salt represented by formula (I-1224-e) was added, followed by stirring at 5° C. for 3 hours. To the mixture thus obtained, 6.30 parts of 1N hydrochloric acid was added, followed by raising the temperature to 23° C. and further stirring at 23° C. for 6 hours. To the mixture thus obtained, 30 parts of chloroform and 15 parts of ion-exchanged water were added, and after stirring at 23° C. for 30 minutes, the organic layer was isolated through separation. The organic layer thus obtained was concentrated, and 1 part of acetonitrile and 30 parts of tert-butyl methyl ether were added to the concentrated residue. After stirring at 23° C. for 30 minutes, the supernatant was removed, followed by concentration to obtain 1.55 parts of a salt represented by formula (I-8-f).

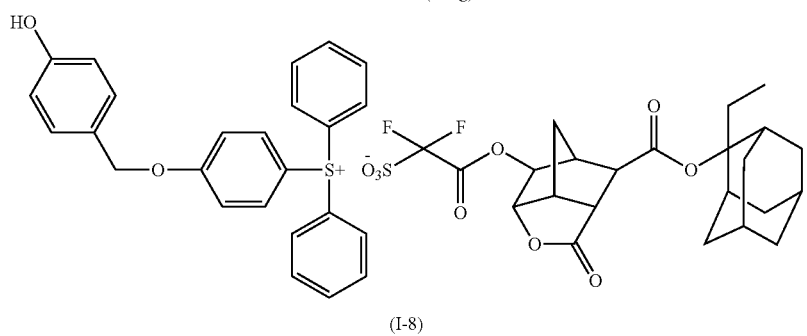

(I-8)

0.79 Part of a salt represented by formula (I-8-f), 1.20 parts of a salt represented by formula (I-8-g) and 20 parts of chloroform were added, followed by stirring at 23° C. for 3 hours. To the reaction product thus obtained, 15 parts of ion-exchanged water was added, and after stirring at 23° C. for 30 minutes, the organic layer was isolated through separation. To the organic layer thus obtained, 15 parts of ion-exchanged water was added, and after stirring at 23° C. for 30 minutes, the organic layer was isolated through separation. This water washing operation was repeated five times. The organic layer thus obtained was concentrated, and 1.5 parts of acetonitrile and 30 parts of tert-butyl methyl ether were added to the concentrated residue. After stirring at 23° C. for 30 minutes, the supernatant was removed, followed by concentration to obtain 1.25 parts of a salt represented by formula (I-8).

MASS (ESI (+) Spectrum): M⁺ 385.1
MASS (ESI (−) Spectrum): M⁻ 517.1

Example 4: Synthesis of Salt Represented by Formula (I-16)

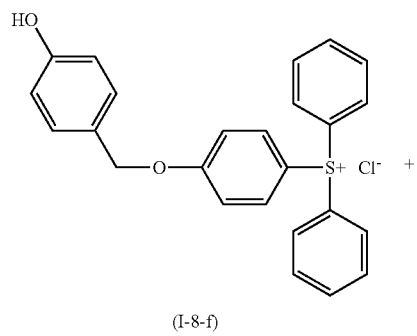

(I-8-f)

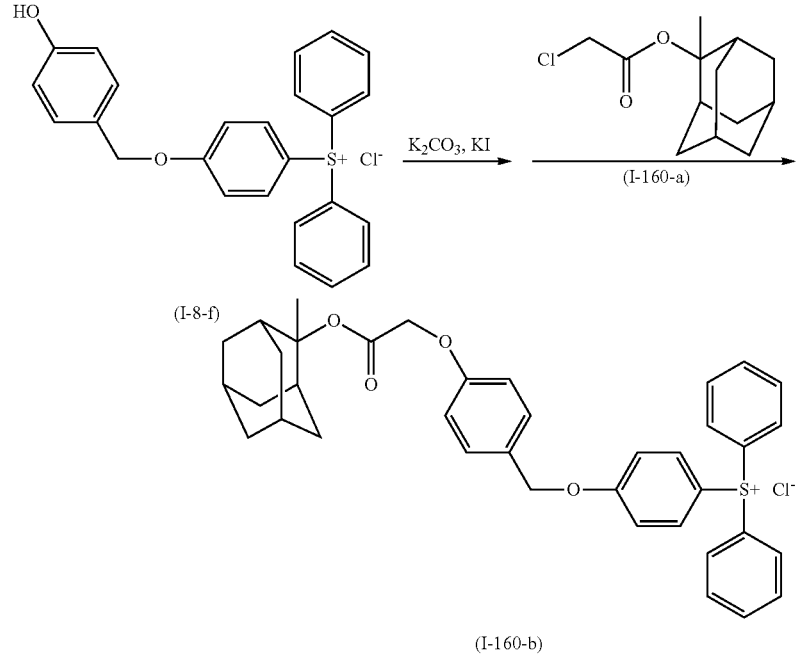

0.79 Part of a salt represented by formula (I-8-f), 1.07 parts of a salt represented by formula (I-16-g) and 20 parts of chloroform were added, followed by stirring at 23° C. for 3 hours. To the reaction product thus obtained, 15 parts of ion-exchanged water was added, and after stirring at 23° C. for 30 minutes, the organic layer was isolated through separation. To the organic layer thus obtained, 15 parts of ion-exchanged water was added, and after stirring at 23° C. for 30 minutes, the organic layer was isolated through separation. This water washing operation was repeated five times. The organic layer thus obtained was concentrated, and 1.5 parts of acetonitrile and 30 parts of tert-butyl methyl ether were added to the concentrated residue. After stirring at 23° C. for 30 minutes, the supernatant was removed, followed by concentration to obtain 1.29 parts of a salt represented by formula (I-16).

MASS (ESI (+) Spectrum): M⁺ 385.1 MASS (ESI (−) Spectrum): M⁻ 467.1

Example 5: Synthesis of Salt Represented by Formula (I-160)

0.98 Part of a salt represented by formula (I-8-f) and 30 parts of dimethylformamide were mixed, and after stirring at 23° C. for 30 minutes, 0.16 part of potassium carbonate and 0.05 part of potassium iodide were added and the temperature was raised to 75° C. To the mixture thus obtained, 1.13 parts of a compound represented by formula (I-160-a) was added, followed by stirring at 75° C. for 5 hours and further cooling to 23° C. To the mixture thus obtained, 50 parts of chloroform and 20 parts of an aqueous 5% oxalic acid solution were added, and after stirring at 23° C. for 30 minutes, the organic layer was isolated through separation. To the organic layer thus obtained, 20 parts of ion-exchanged water was added, and after stirring at 23° C. for 30 minutes, the organic layer was isolated through separation. This water washing operation was repeated five times. The organic layer thus obtained was concentrated to obtain 1.31 parts of a salt represented by formula (I-160-b).

1.00 Part of a salt represented by formula (I-160-b), 1.02 parts of a salt represented by formula (I-8-g), 30 parts of chloroform and 15 parts of ethyl acetate were mixed, followed by stirring at 23° C. for 2 hours. To the mixture thus obtained, 20 parts of ion-exchanged water was added, and after stirring at 23° C. for 30 minutes, the organic layer was isolated through separation. This water washing operation was repeated five times. The organic layer thus obtained was concentrated and 30 parts of tert-butyl methyl ether was added to the concentrated residue, followed by stirring at 23° C. for 30 minutes and further filtration to obtain 1.36 parts of a salt represented by formula (I-160).

MASS (ESI (+) Spectrum): M⁺ 591.3
MASS (ESI (−) Spectrum): M⁻ 517.1

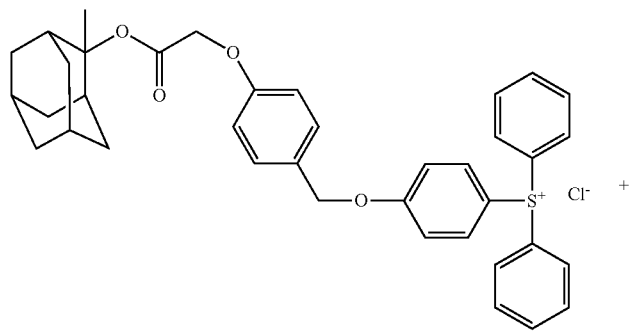

(I-160-b)

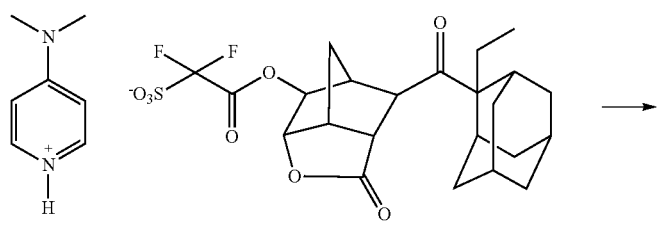

(I-8-g)

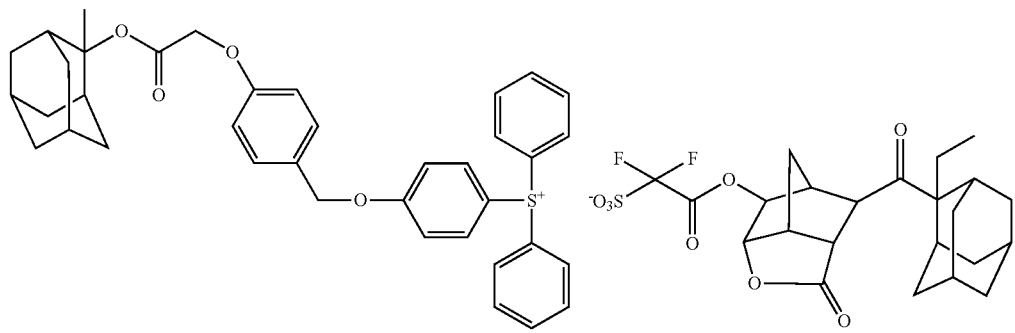

(I-160)

Example 6: Synthesis of Salt Represented by Formula (I-168)

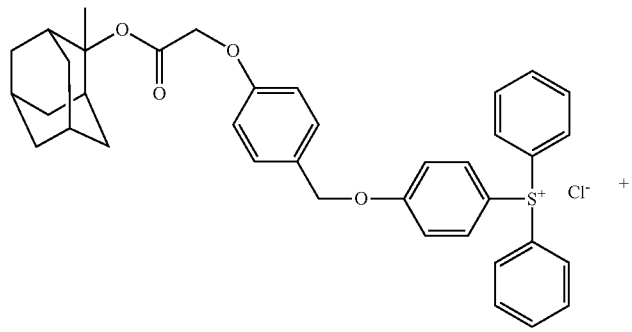

(I-160-b)

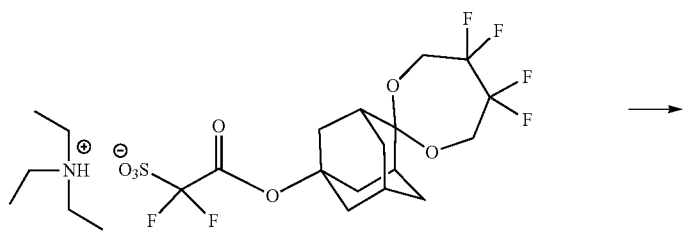

(I-16-g)

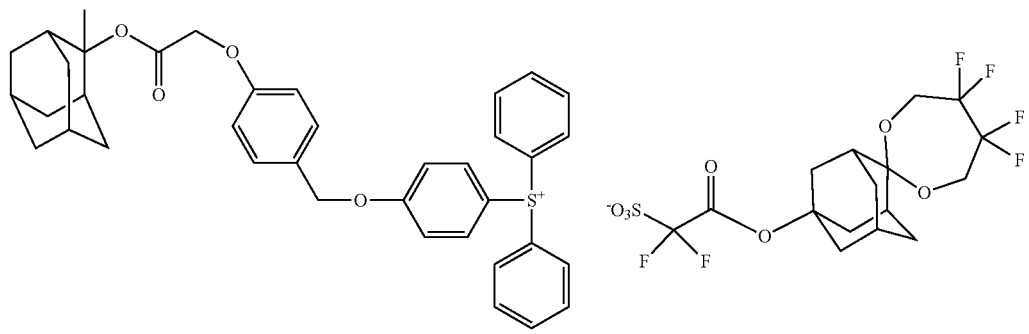

(I-168)

1.00 Part of a salt represented by formula (I-160-b), 0.91 part of a salt represented by formula (I-16-g), 30 parts of chloroform and 15 parts of ethyl acetate were mixed, followed by stirring at 2300 for 2 hours. To the mixture thus obtained, 20 parts of ion-exchanged water was added, and after stirring at 23° C. for 30 minutes, the organic layer was isolated through separation. This water washing operation was repeated five times. The organic layer thus obtained was concentrated and 30 parts of tert-butyl methyl ether was added to the concentrated residue, followed by stirring at 23° C. for 30 minutes and further filtration to obtain 1.29 parts of a salt represented by formula (I-168).

MASS (ESI (+) Spectrum): $M^+$ 591.3
MASS (ESI (−) Spectrum): $M^-$ 467.1

Example 7: Synthesis of Salt Represented by Formula (I-156)

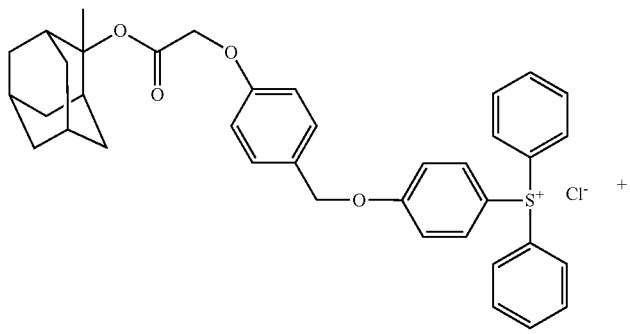

(I-160-b)

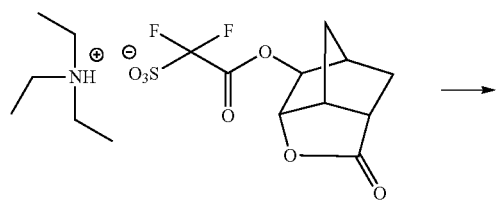

(I-4-g)

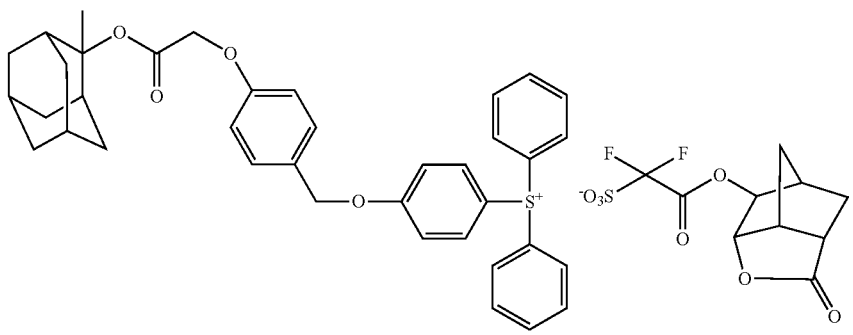

(I-156)

1.00 Part of a salt represented by formula (I-160-b), 0.66 part of a salt represented by formula (I-4-g), 30 parts of chloroform and 15 parts of ethyl acetate were mixed, followed by stirring at 23° C. for 2 hours. To the mixture thus obtained, 20 parts of ion-exchanged water was added, and after stirring at 23° C. for 30 minutes, the organic layer was isolated through separation. This water washing operation was repeated five times. The organic layer thus obtained was concentrated, and 1 part of acetonitrile and 30 parts of tert-butyl methyl ether were added to the concentrated residue. After stirring at 23° C. for 30 minutes, the supernatant was removed, followed by concentration to obtain 1.03 parts of a salt represented by formula (I-156).

MASS (ESI (+) Spectrum): M$^+$ 591.3
MASS (ESI (−) Spectrum): M$^-$ 311.0

Example 8: Synthesis of Salt Represented by Formula (I-1346)

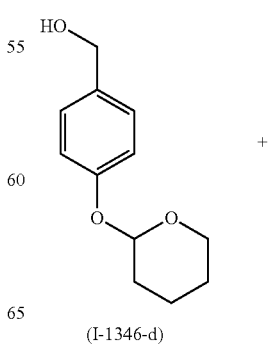

(I-1346-d)

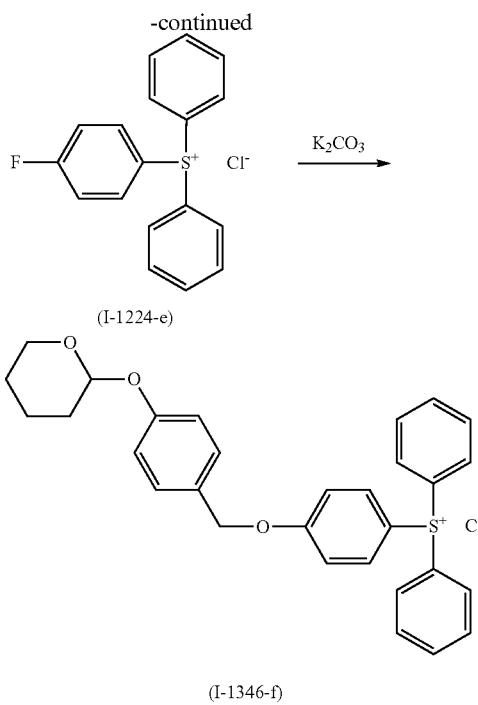

10.85 Parts of a compound represented by formula (I-1346-d), 13.97 parts of a salt represented by formula (I-1224-e) and 90 parts of dimethylformamide were mixed, and after stirring at 23° C. for 30 minutes, the temperature was raised to 90° C. To the mixture thus obtained, 14.41 parts of potassium carbonate was added, followed by stirring at 90° C. for 3 hours and further cooling to 23° C. To the mixture thus obtained, 200 parts of chloroform and 150 parts of ion-exchanged water were added, and after stirring at 23° C. for 30 minutes, the organic layer was isolated through separation. To the organic layer thus obtained, 150 parts of ion-exchanged water was added, and after stirring at 23° C. for 30 minutes, the organic layer was isolated through separation. This water washing operation was repeated three times. The organic layer thus obtained was concentrated, and 10 parts of acetonitrile and 210 parts of tert-butyl methyl ether were added to the concentrated residue. After stirring at 23° C. for 30 minutes, the supernatant was removed, followed by concentration to obtain 24.66 parts of a salt represented by formula (I-1346-f).

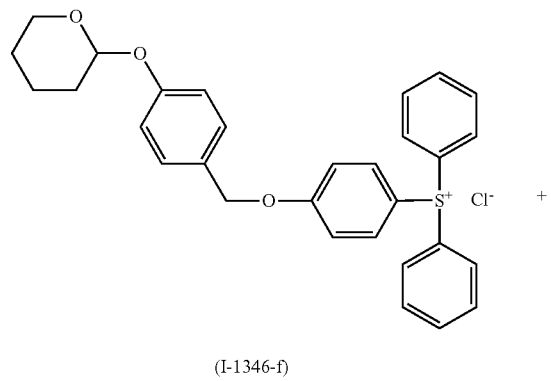

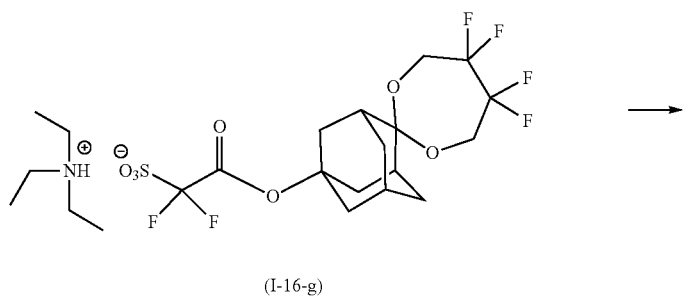

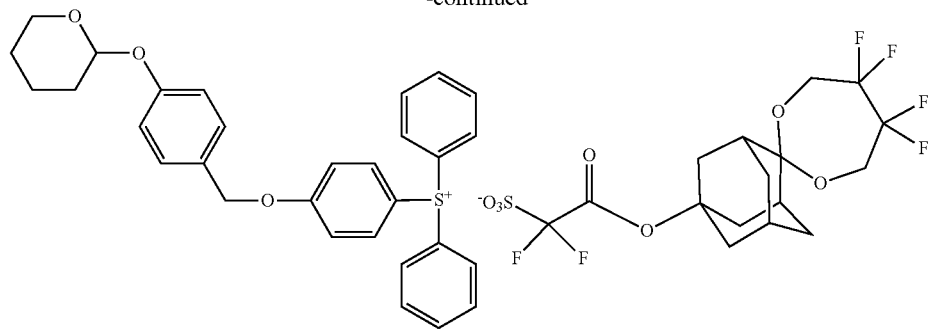

(I-1346)

0.80 Part of a salt represented by formula (I-1346-f), 0.91 part of a salt represented by formula (I-16-g), 30 parts of chloroform and 15 parts of ethyl acetate were mixed, followed by stirring at 23° C. for 2 hours. To the mixture thus obtained, 20 parts of ion-exchanged water was added, and after stirring at 23° C. for 30 minutes, the organic layer was isolated through separation. This water washing operation was repeated five times. The organic layer thus obtained was concentrated and 30 parts of tert-butyl methyl ether was added to the concentrated residue, followed by stirring at 23° C. for 30 minutes and further filtration to obtain 1.21 parts of a salt represented by formula (I-1346).

MASS (ESI (+) Spectrum): M⁺ 469.2
MASS (ESI (−) Spectrum): M⁻ 467.1

Example 9: Synthesis of Salt Represented by Formula (I-282)

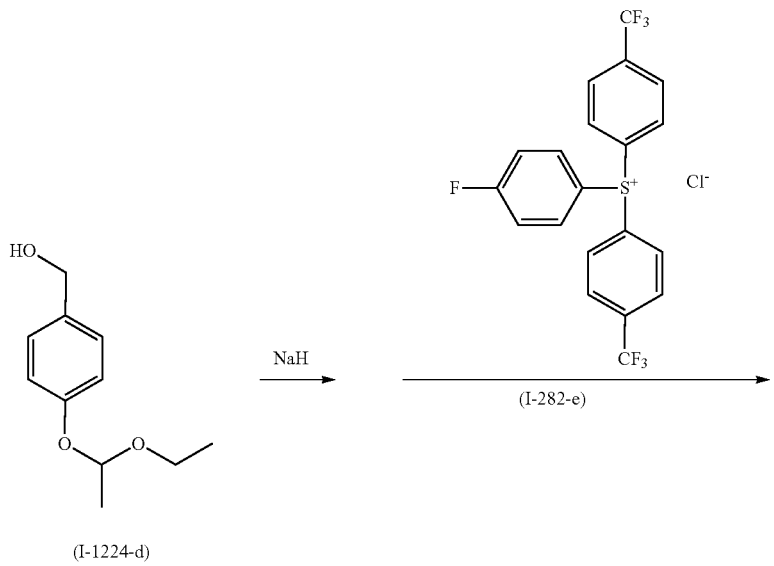

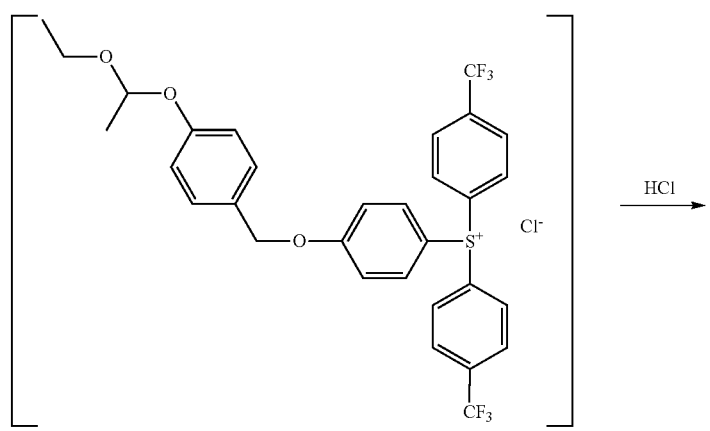

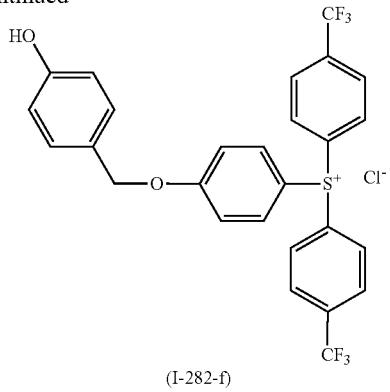

(I-282-f)

1.02 Parts of a compound represented by formula (I-1224-d) and 20 parts of tetrahydrofuran were mixed, and after stirring at 23° C. for 30 minutes and cooling to 5° C., 0.14 part of sodium hydride was added. To the mixture thus obtained, 2.60 parts of a salt represented by formula (I-282-e) was added, followed by stirring at 5° C. for 3 hours. To the mixture thus obtained, 6.30 parts of 1N hydrochloric acid was added, followed by temperature rising to 23° C. and further stirring at 23° C. for 6 hours. To the mixture thus obtained, 30 parts of chloroform and 15 parts of ion-exchanged water were added, and after stirring at 23° C. for 30 minutes, the organic layer was isolated through separation. The organic layer thus obtained was concentrated, and 1 part of acetonitrile and 30 parts of tert-butyl methyl ether were added to the concentrated residue. After stirring at 23° C. for 30 minutes, the supernatant was removed, followed by concentration to obtain 1.95 parts of a salt represented by formula (I-282-f).

1.30 Parts of a salt represented by formula (I-282-f) and 30 parts of dimethylformamide were mixed, and after stirring at 23° C. for 30 minutes, 0.16 part of potassium carbonate and 0.05 part of potassium iodide were added, and then the temperature was raised to 75° C. To the mixture thus obtained, 1.13 parts of a compound represented by formula (I-160-a) was added, followed by stirring at 75° C. for 5 hours and further cooling to 23° C. To the mixture thus obtained, 50 parts of chloroform and 20 parts of an aqueous 5% oxalic acid solution were added, and after stirring at 23°

C. for 30 minutes, the organic layer was isolated through separation. To the organic layer thus obtained, 20 parts of ion-exchanged water was added, and after stirring at 23° C. for 30 minutes, the organic layer was isolated through separation. This water washing operation was repeated five times. The organic layer thus obtained was concentrated to obtain 1.53 parts of a compound represented by formula (I-282-g).

chloroform and 15 parts of ethyl acetate were mixed, followed by stirring at 23° C. for 2 hours. To the mixture thus obtained, 20 parts of ion-exchanged water was added, and after stirring at 23° C. for 30 minutes, the organic layer was isolated through separation. This water washing operation was repeated five times. The organic layer thus obtained was concentrated and 30 parts of tert-butyl methyl ether was added to the concentrated residue, followed by stirring at 23° C. for 30 minutes and further filtration to obtain 1.53 parts of a salt represented by formula (I-282).

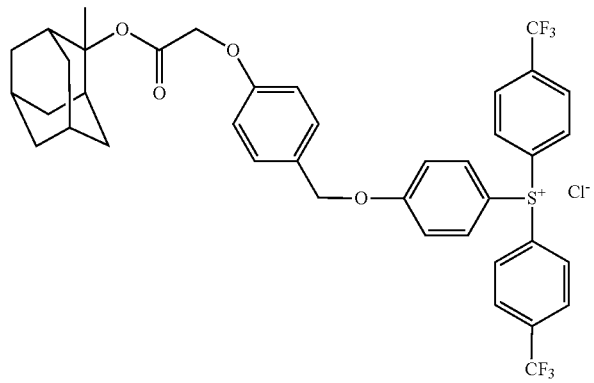

(I-282-g)

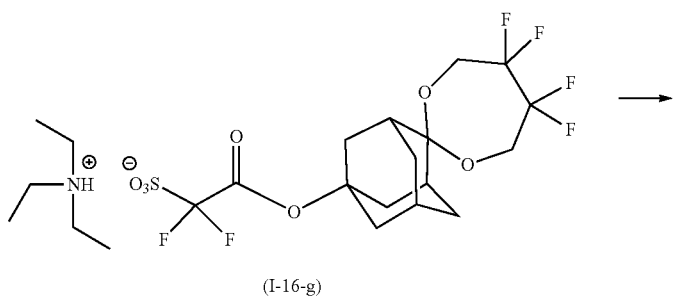

(I-16-g)

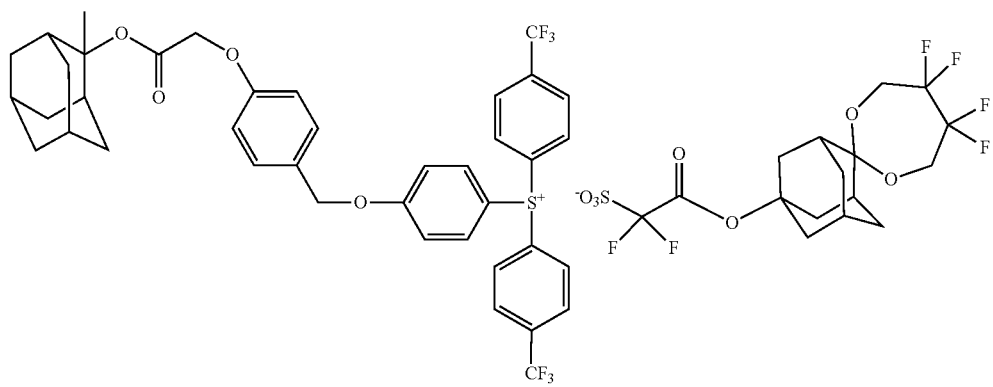

(I-282)

1.21 Parts of a salt represented by formula (I-282-g), 0.91 part of a salt represented by formula (I-16-g), 30 parts of MASS (ESI (+) Spectrum): $M^+$ 727.2
MASS (ESI (−) Spectrum): $M^-$ 467.1

Example 10: Synthesis of Salt Represented by Formula (I-1878)
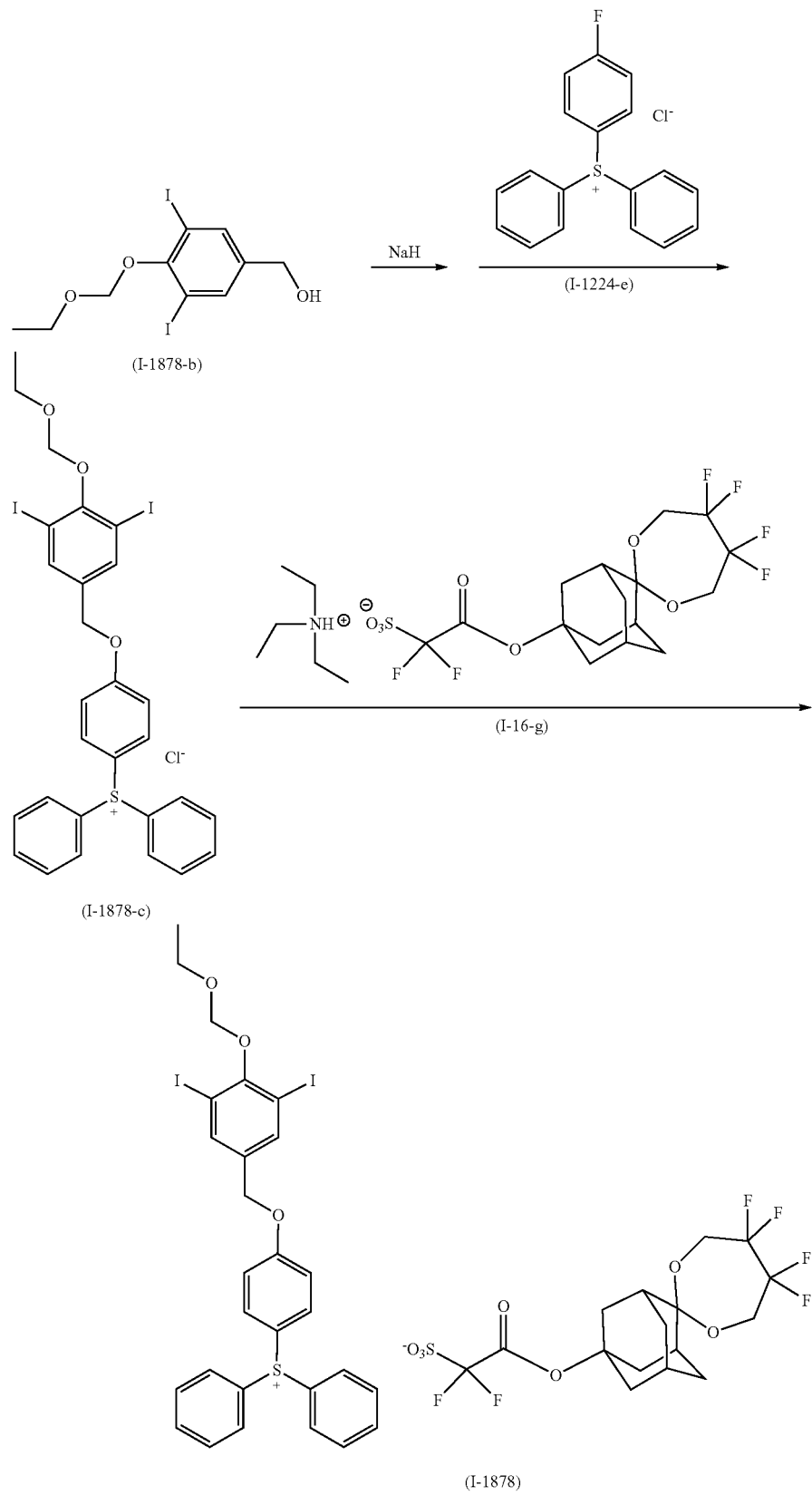

4.34 Parts of a compound represented by formula (I-1878-b) and 30 parts of dimethylformamide were mixed, followed by stirring at 23° C. for 30 minutes. The mixture thus obtained was cooled to 0° C. and then mixed with 0.30 part of sodium hydride, followed by stirring at 0° C. for 4 hours. To the mixture thus obtained, 3.17 parts of a salt represented by formula (I-1224-e) was added at 0° C., followed by stirring at 0° C. for 3 hours to obtain a mixture containing a salt represented by formula (I-1878-c). The temperature of the mixture thus obtained was raised to 23° C. and 11 parts of an aqueous 5% oxalic acid solution was added, and after stirring at 23° C. for 30 minutes, 5.70 parts of a salt represented by formula (I-16-g) was added, followed by stirring at 23° C. for 7 hours. To the reaction product thus obtained, 60 parts of chloroform and 30 parts of ion-exchanged water were added, and after stirring at 23° C. for 30 minutes, the organic layer was isolated through separation. To the organic layer thus recovered, 30 parts of ion-exchanged water was added, and after stirring at 23° C. for 30 minutes, the organic layer was isolated through separation. This water washing operation was repeated seven times. The organic layer thus obtained was concentrated and 30 parts of tert-butyl methyl ether was added to the concentrated residue. After stirring at 23° C. for 30 minutes, the supernatant was removed, followed by concentration to obtain 9.49 parts of a salt represented by formula (I-1878).

MASS (ESI (+) Spectrum): M+ 695.0
MASS (ESI (−) Spectrum): M− 467.1

Example 11: Synthesis of Salt Represented by Formula (I-1992)

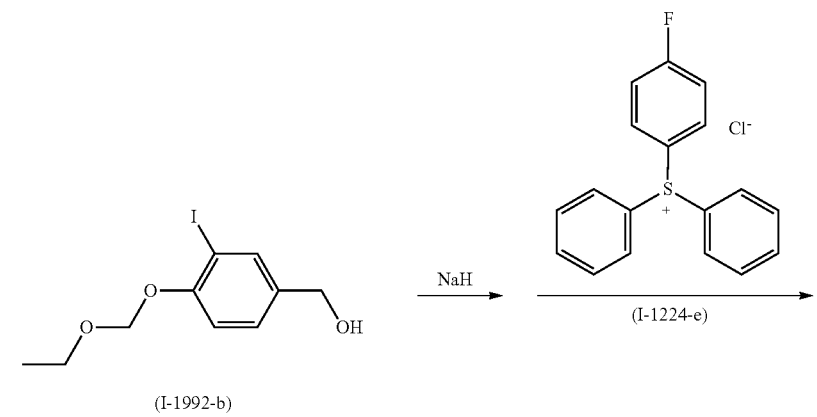

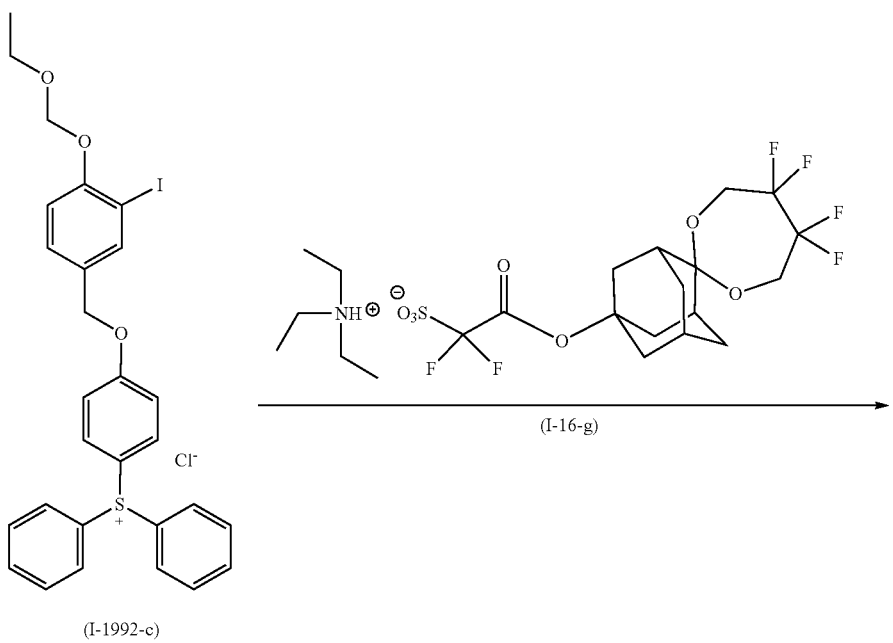

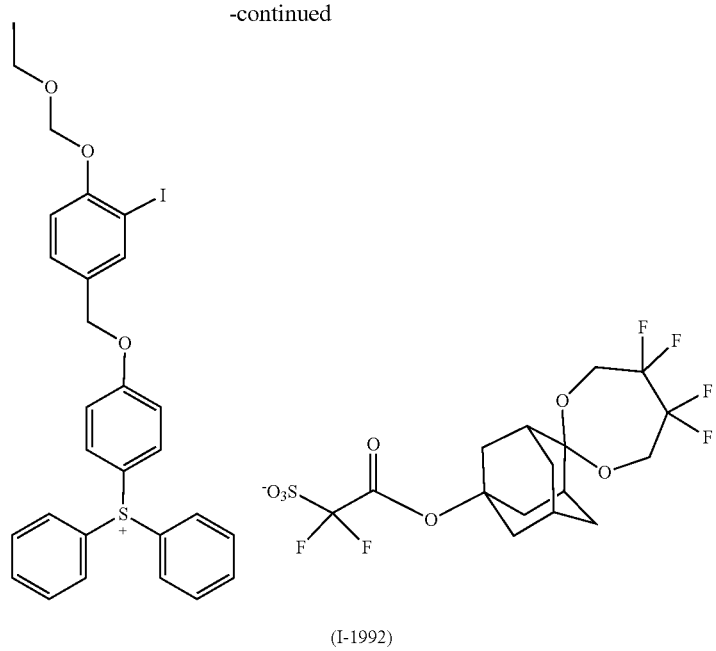

(I-1992)

3.08 Parts of a salt represented by formula (I-1992-b) and 30 parts of dimethylformamide were mixed, followed by stirring at 23° C. for 30 minutes. The mixture thus obtained was cooled to 0° C. and then mixed with 0.30 part of sodium hydride, followed by stirring at 0° C. for 4 hours. To the mixture thus obtained, 3.17 parts of a salt represented by formula (1-1224-e) was added at 0° C., followed by stirring at 0° C. for 3 hours to obtain a mixture containing a salt represented by formula (I-1992-c). The temperature of the mixture thus obtained was raised to 23° C. and then 11 parts of an aqueous 5% oxalic acid solution was added, followed by stirring at 23° C. for 30 minutes, addition of 5.70 parts of a salt represented by formula (I-16-g) and further stirring at 23° C. for 7 hours. To the reaction product thus obtained, 60 parts of chloroform and 30 parts of ion-exchanged water were added, and after stirring at 23° C. for 30 minutes, the organic layer was isolated through separation. To the organic layer thus recovered, 30 parts of ion-exchanged water was added, and after stirring at 23° C. for 30 minutes, the organic layer was isolated through separation. This water washing operation was repeated seven times. The organic layer thus obtained was concentrated and then 30 parts of tert-butyl methyl ether was added to the concentrated residue and, after stirring at 23° C. for 30 minutes, the supernatant was removed, followed by concentration to obtain 8.66 parts of a salt represented by formula (I-1992).

MASS (ESI (+) Spectrum): M$^+$ 569.1
MASS (ESI (−) Spectrum): M$^-$ 467.1

Example 12: Synthesis of Salt Represented by Formula (I-2106)

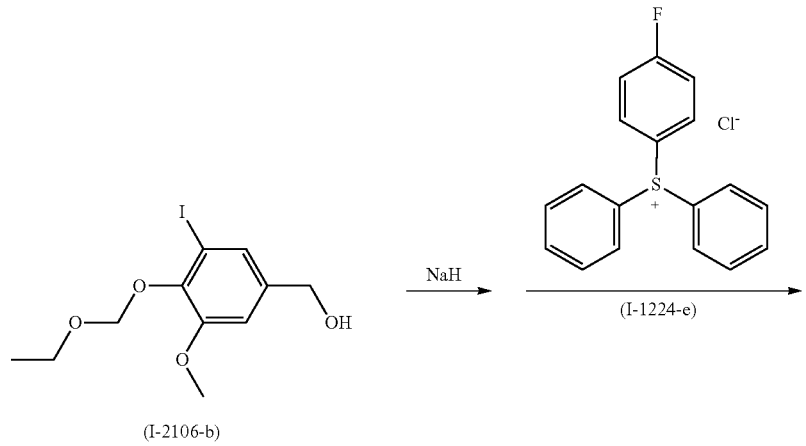

(I-2106-b)

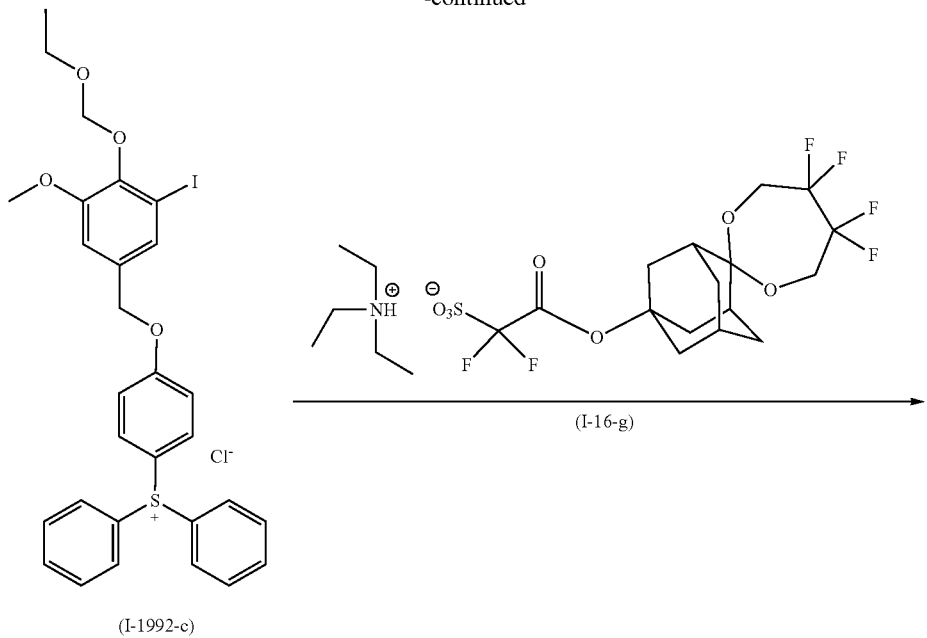

(I-1992-c) (I-16-g)

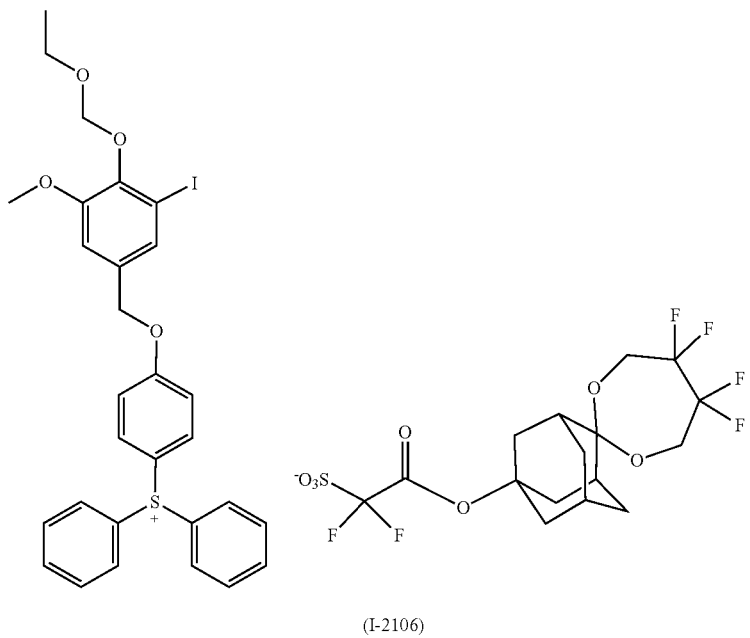

(I-2106)

3.38 Parts of a salt represented by formula (I-2106-b) and 30 parts of dimethylformamide were mixed, followed by stirring at 23° C. for 30 minutes. The mixture thus obtained was cooled to 0° C. and then 0.30 part of sodium hydride was added, followed by stirring at 0° C. for 4 hours. To the mixture thus obtained, 3.17 parts of a salt represented by formula (I-1224-e) was added at 0° C., followed by stirring at 0° C. for 3 hours to obtain a mixture containing a salt represented by formula (I-2106-c). The temperature of the mixture thus obtained was raised to 23° C. and then 11 parts of an aqueous 5% oxalic acid solution was added, followed by stirring at 23° C. for 30 minutes, addition of 5.70 parts of a salt represented by formula (I-16-g) and further stirring at 23° C. for 7 hours. To the reaction product thus obtained, 60 parts of chloroform and 30 parts of ion-exchanged water were added, and after stirring at 23° C. for 30 minutes, the organic layer was isolated through separation. To the organic layer thus recovered, 30 parts of ion-exchanged water was added, and after stirring at 23° C. for 30 minutes, the organic layer was isolated through separation. This water washing operation was repeated seven times. The organic layer thus obtained was concentrated and then 30 parts of tert-butyl methyl ether was added and, after stirring at 23° C. for 30 minutes, the supernatant was removed, followed by concentration to obtain 9.13 parts of a salt represented by formula (I-2106).

MASS (ESI (+) Spectrum): $M^+$ 599.1
MASS (ESI (−) Spectrum): $M^-$ 467.1

Example 13: Synthesis of Salt Represented by Formula (I-2220)

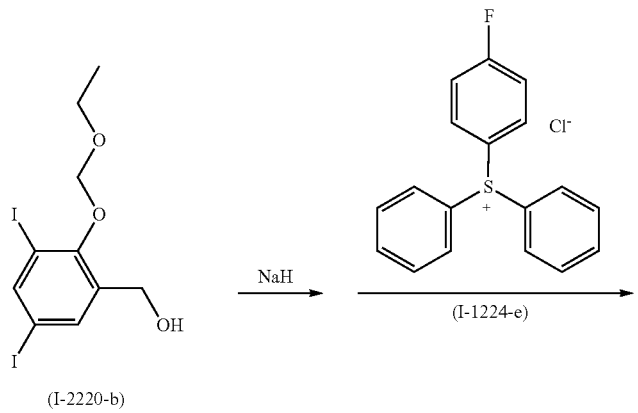

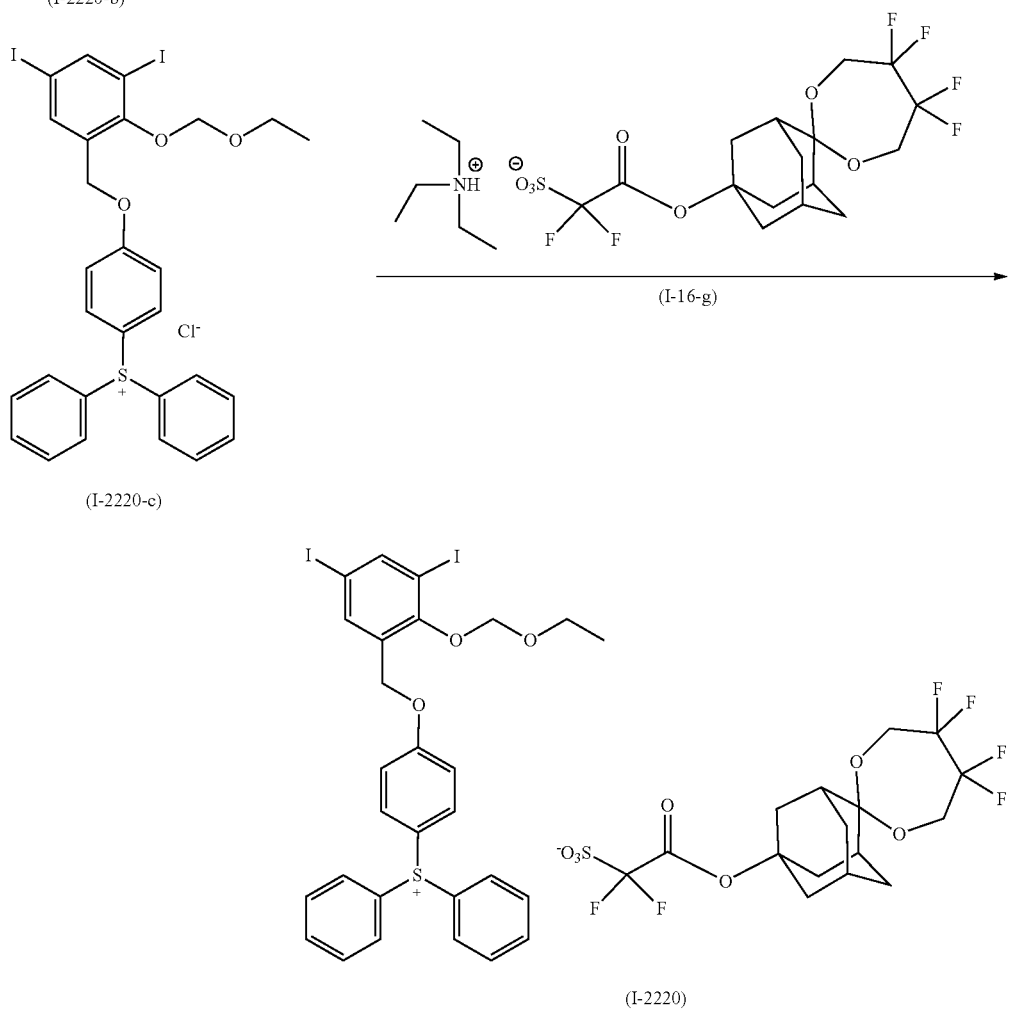

4.34 Parts of a compound represented by formula (I-2220-b) and 30 parts of dimethylformamide were mixed, followed by stirring at 23° C. for 30 minutes. The mixture thus obtained was cooled to 0° C. and then 0.30 part of sodium hydride was mixed, followed by stirring at 0° C. for 4 hours. To the mixture thus obtained, 3.17 parts of a salt represented by formula (I-1224-e) was added at 0° C., followed by stirring at 0° C. for 3 hours to obtain a mixture containing a salt represented by formula (I-2220-c). The temperature of the mixture thus obtained was raised to 23° C. and then 11 parts of an aqueous 5% oxalic acid solution was added, followed by stirring at 23° C. for 30 minutes, addition of 5.70 parts of a salt represented by formula (I-16-g) and further stirring at 23° C. for 7 hours. To the reaction product thus obtained, 60 parts of chloroform and 30 parts of ion-exchanged water were added, and after stirring at 23° C. for 30 minutes, the organic layer was isolated through separation. To the organic layer thus recovered, 30 parts of ion-exchanged water was added, and after stirring at 23° C. for 30 minutes, the organic layer was isolated through separation. This water washing operation was repeated seven times. The organic layer thus obtained was concentrated and then 30 parts of tert-butyl methyl ether was added and, after stirring at 23° C. for 30 minutes, the supernatant was removed, followed by concentration to obtain 7.12 parts of a salt represented by formula (I-2220).

MASS (ESI (+) Spectrum): M⁺ 695.0
MASS (ESI (−) Spectrum): M⁻ 467.1

Example 14: Synthesis of Salt Represented by Formula (I-2486)

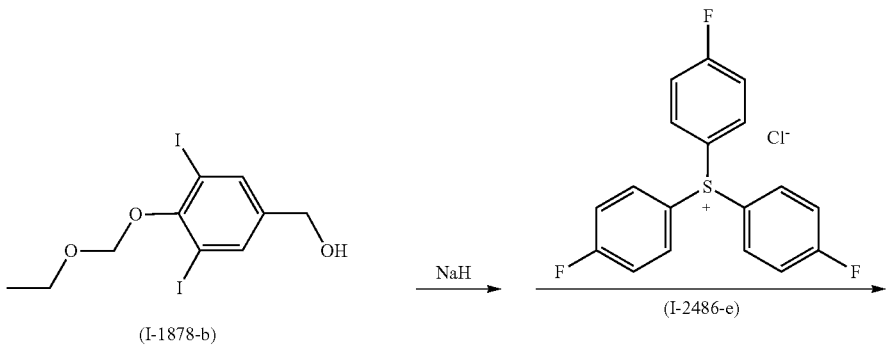

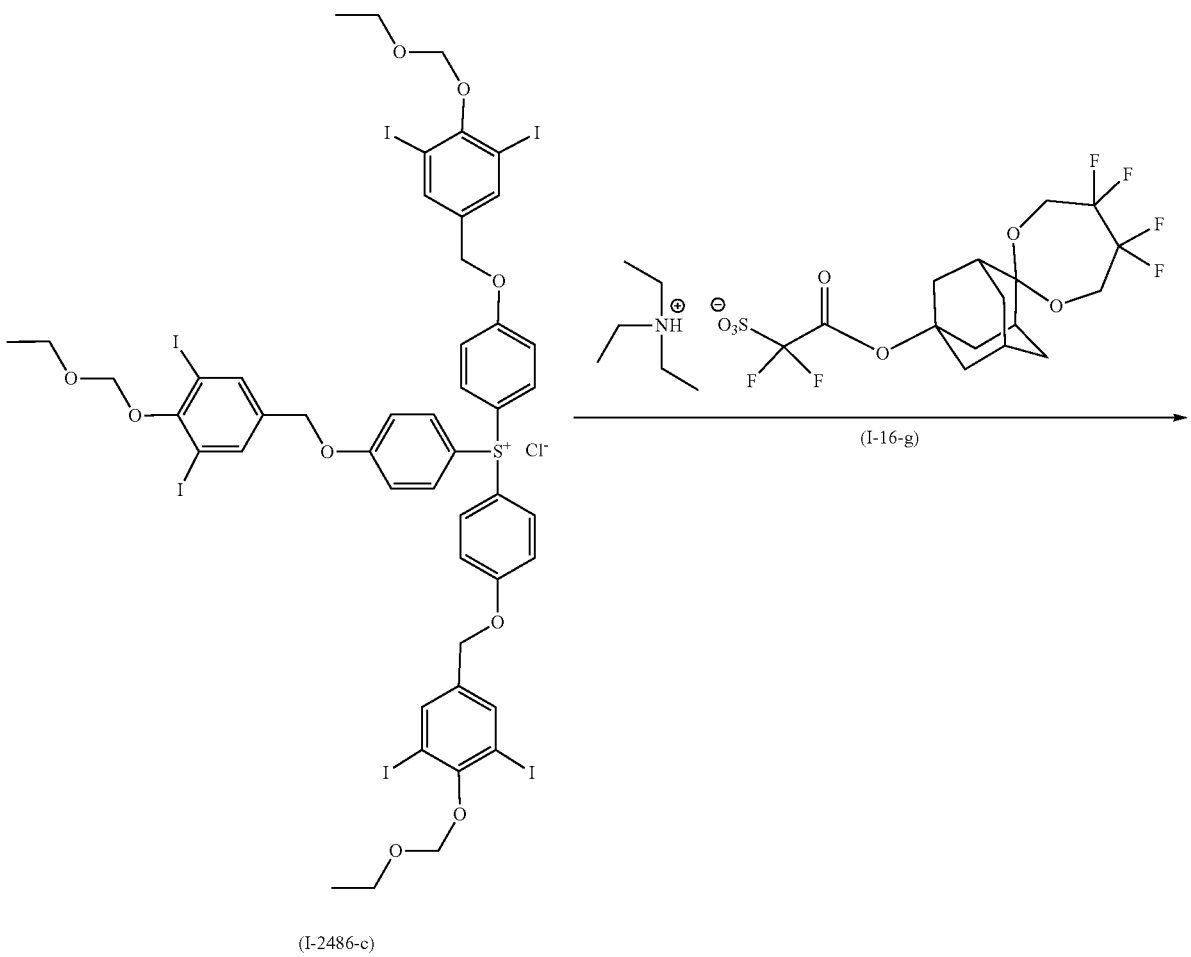

-continued

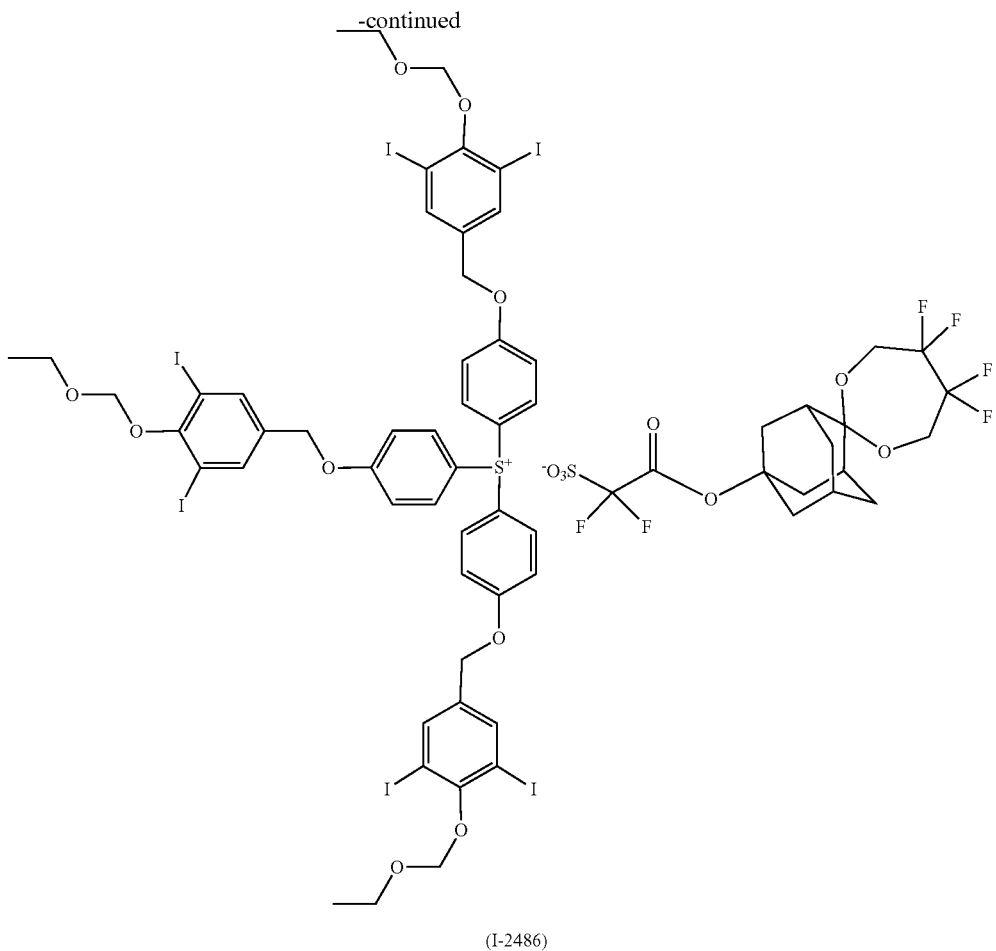

(I-2486)

13.02 Parts of a compound represented by formula (I-1878-b) and 50 parts of dimethylformamide were mixed, followed by stirring at 2300 for 30 minutes. The mixture thus obtained was cooled to 000 and then 0.90 part of sodium hydride was mixed, followed by stirring at 000 for 4 hours. To the mixture thus obtained, 3.53 parts of a salt represented by formula (I-2486-e) was added at 0°, followed by stirring at 000 for 3 hours to obtain a mixture containing a salt represented by formula (I-2486-c). The temperature of the mixture thus obtained was raised to 23° C. and then 11 parts of an aqueous 5% oxalic acid solution was added, followed by stirring at 23° C. for 30 minutes, addition of 5.70 parts of a salt represented by formula (I-16-g) and further stirring at 23° C. for 7 hours. To the reaction product thus obtained, 100 parts of chloroform and 50 parts of ion-exchanged water were added, and after stirring at 23° C. for 30 minutes, the organic layer was isolated through separation. To the organic layer thus recovered, 30 parts of ion-exchanged water was added, and after stirring at 23° C. for 30 minutes, the organic layer was isolated through separation. This water washing operation was repeated seven times. The organic layer thus obtained was concentrated and then 30 parts of tert-butyl methyl ether was added and, after stirring at 23° C. for 30 minutes, the supernatant was removed, followed by concentration to obtain 13.98 parts of a salt represented by formula (I-2486).

MASS (ESI (+) Spectrum): M$^+$ 1558.7
MASS (ESI (−) Spectrum): M$^−$ 467.1

Synthesis Example 1: Synthesis of Salt Represented by Formula (IX-5)

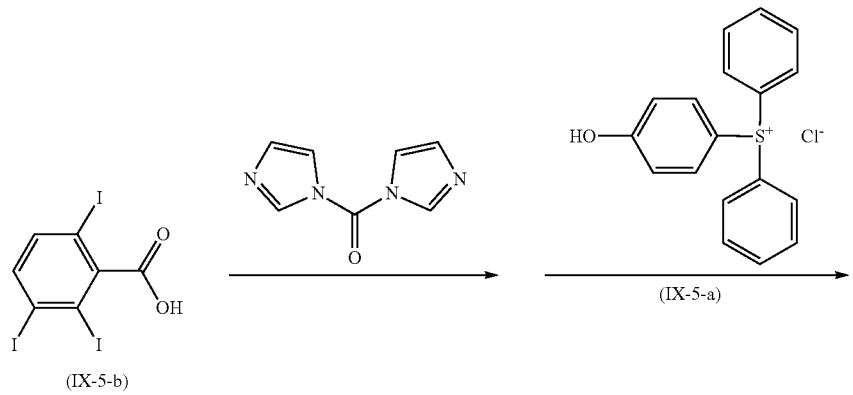

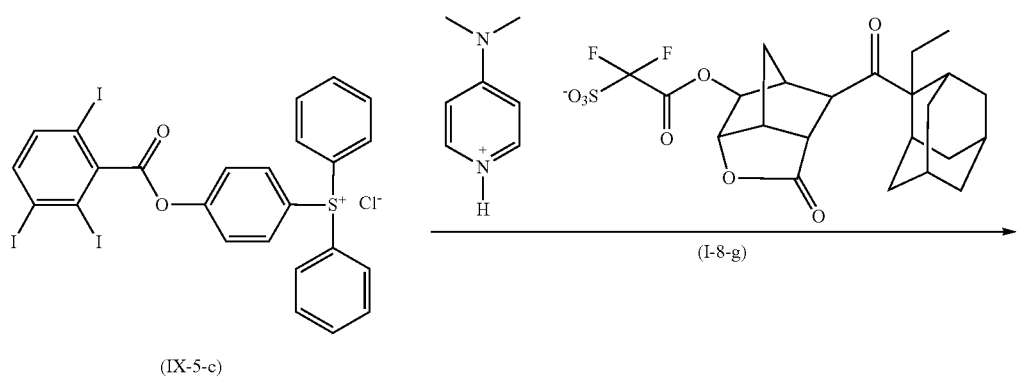

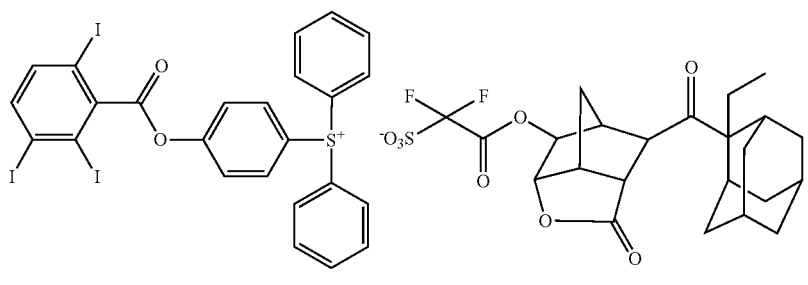

2.25 Parts of a compound represented by formula (IX-5-b) and 30 parts of chloroform were mixed, followed by stirring at 23° C. for 30 minutes. To the mixed solution thus obtained, 0.73 part of carbonyldiimidazole was added, followed by stirring at 50° C. for 2 hours. To the mixed solution thus obtained, 1.42 parts of a salt represented by formula (IX-5-a) was added, followed by stirring at 50° C. for 3 hours and further cooling to 23° C. To the mixture thus obtained, 15 parts of an aqueous 5% oxalic acid solution was added, and after stirring at 23° C. for 30 minutes, the organic layer was isolated through separation. To the organic layer thus obtained, 15 parts of ion-exchanged water was added, and after stirring at 23° C. for 30 minutes, the organic layer was isolated through separation. To the organic layer thus obtained, 2.63 parts of a salt represented by formula (I-8-g) was added, followed by stirring at 23° C. for 2 hours. To the reaction product thus obtained, 30 parts of chloroform and 30 parts of ion-exchanged water were added, and after stirring at 23° C. for 30 minutes, the organic layer was isolated through separation. To the organic layer thus recovered, 30 parts of ion-exchanged water was added, and after stirring at 23° C. for 30 minutes, the organic layer was isolated through separation. This water washing operation was repeated seven times. The organic layer thus obtained was concentrated and then 30 parts of tert-butyl methyl ether were added to the concentrated residue and, after stirring at 23° C. for 30 minutes, the supernatant was removed, followed by concentration to obtain 2.18 parts of a salt represented by formula (IX-5).

MASS (ESI (+) Spectrum): $M^+$ 760.8

MASS (ESI (−) Spectrum): $M^-$ 517.1

Synthesis Example 2: Synthesis of Salt Represented by Formula (IX-6)

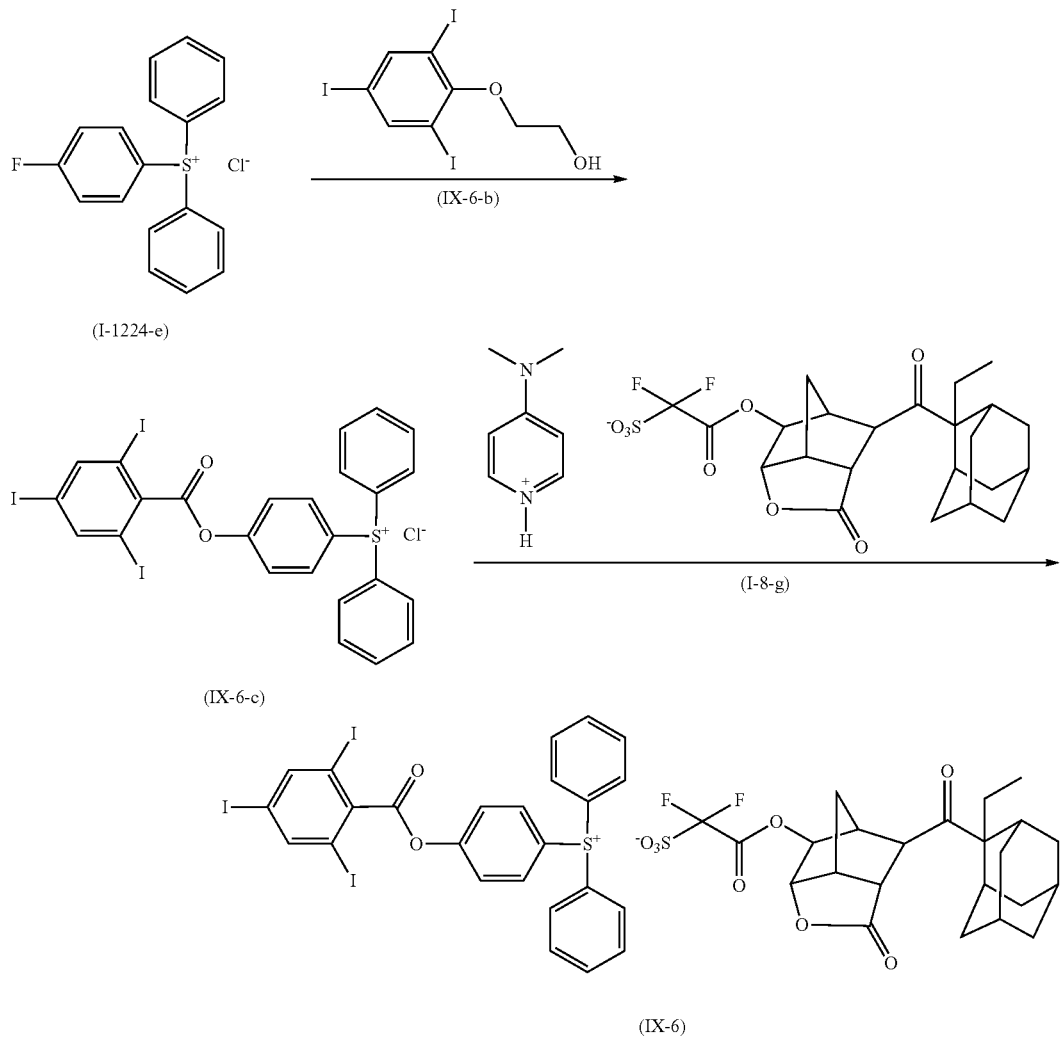

1.43 Parts of a salt represented by formula (I-1224-e), 2.11 parts of a compound represented by formula (IX-6-b) and 10 parts of dimethylformamide were mixed, followed by stirring at 23° C. for 30 minutes. To the mixture thus obtained, 0.40 part of potassium carbonate was added, followed by stirring at 23° C. for 30 minutes and further stirring at 90° C. for 20 hours to obtain a mixture containing a salt represented by formula (IX-6-c). The mixture thus obtained was cooled to 23° C. and then 11 parts of an aqueous 5% oxalic acid solution was added, followed by stirring at 23° C. for 30 minutes, addition of 2.63 parts of a salt represented by formula (I-8-g) and further stirring at 23° C. for 7 hours. To the reaction product thus obtained, 30 parts of chloroform and 30 parts of ion-exchanged water were added, and after stirring at 23° C. for 30 minutes, the organic layer was isolated through separation. To the organic layer thus recovered, 30 parts of ion-exchanged water was added, and after stirring at 23° C. for 30 minutes, the organic layer was isolated through separation. This water washing operation was repeated seven times. The organic layer thus obtained was concentrated and then the concentrated mixture was isolated using a column (silica gel 60N (spherical, neutral) 100-210 µm; manufactured by Kanto Chemical Co., Inc., developing solvent: methanol/chloroform=1/1) to obtain 0.44 part of a salt represented by formula (IX-6).

MASS (ESI (+) Spectrum): $M^+$ 776.8
MASS (ESI (−) Spectrum): $M^−$ 517.1

Synthesis of Resin

Compounds (monomers) used in synthesis of a resin (A) are shown below. Hereinafter, these compounds are referred to as "monomer (a1-1-3)" according to the formula number.

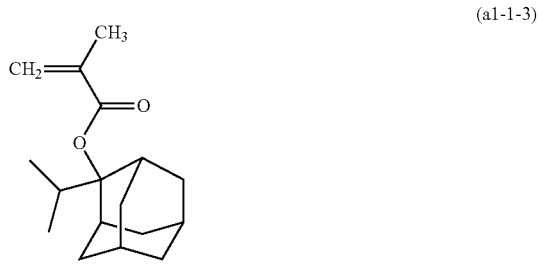

(a1-1-3)

(a1-2-5)
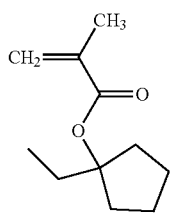

(a1-2-6)
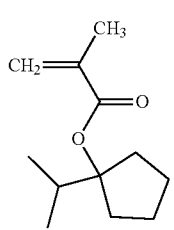

(a1-4-2)
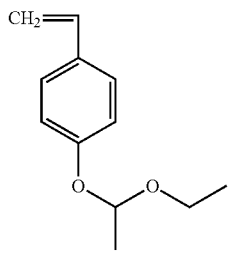

(a1-4-13)
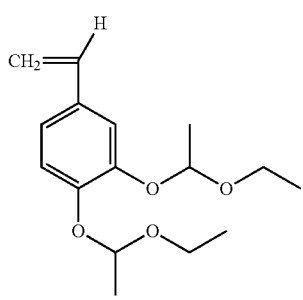

(a2-1-3)
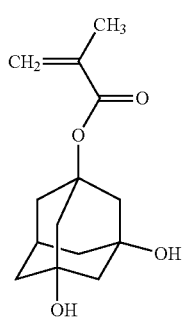

(a3-4-2)
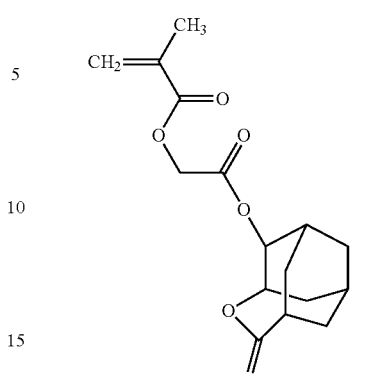

(a1-4-19)
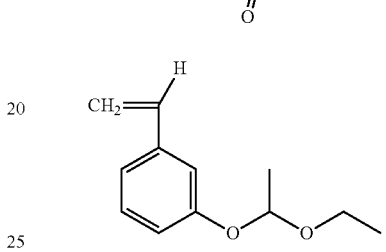

Synthesis Example 3 [Synthesis of Resin A1]

Using a monomer (a1-1-3), a monomer (a1-2-6), a monomer (a2-1-3), a monomer (a3-4-2) and a monomer (a1-4-2) as monomers, these monomers were mixed in a molar ratio of 20:35:3:15:27 [monomer (a1-1-3):monomer (a1-2-6):monomer (a2-1-3):monomer (a3-4-2):monomer (a1-4-2)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1.2 mol % and 3.6 mol % based on the total molar number of all monomers, followed by heating at 73° C. for about 5 hours. Thereafter, to the polymerization reaction solution thus obtained, an aqueous p-toluenesulfonic acid solution (2.5% by weight) was added in the amount of 2.0 mass times the total mass of all monomers, followed by stirring for 12 hours and further isolation through separation. The organic layer thus recovered was poured into a large amount of n-heptane to precipitate a resin, followed by filtration and recovery to obtain a resin A1 having a weight-average molecular weight of about $5.3 \times 10^3$ in a yield of 63%. This resin A1 has the following structural units.

A1
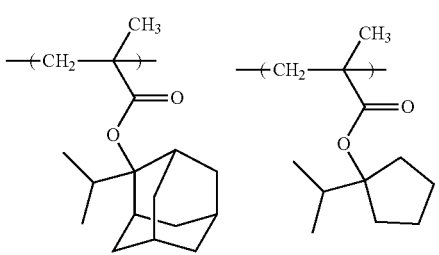

-continued

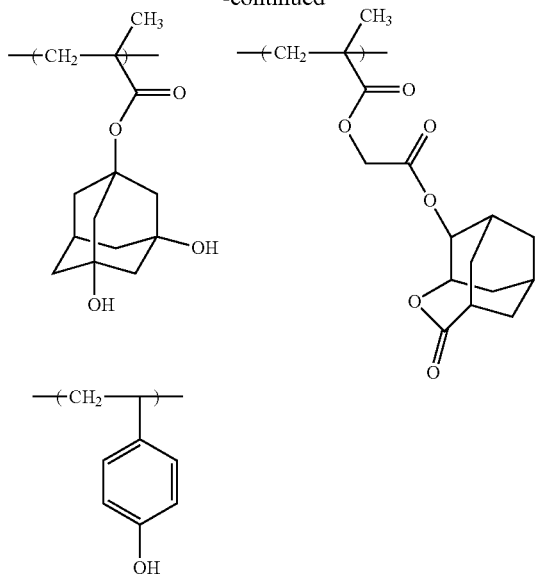

Synthesis Example 4 [Synthesis of Resin A2]

Using a monomer (a1-1-3), a monomer (a1-2-6), a monomer (a2-1-3), a monomer (a3-4-2) and a monomer (a1-4-13) as monomers, these monomers were mixed in a molar ratio of 20:35:3:15:27 [monomer (a1-1-3):monomer (a1-2-6):monomer (a2-1-3):monomer (a3-4-2):monomer (a1-4-13)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1.2 mol % and 3.6 mol % based on the total molar number of all monomers, followed by heating at 73° C. for about 5 hours. Thereafter, to the polymerization reaction solution thus obtained, an aqueous p-toluenesulfonic acid solution (2.5% by weight) was added in the amount of 2.0 mass times the total mass of all monomers, followed by stirring for 12 hours and further isolation through separation. The organic layer thus recovered was poured into a large amount of n-heptane to precipitate a resin, followed by filtration and recovery to obtain a resin A2 having a weight-average molecular weight of about $5.1 \times 10^3$ in a yield of 61%. This resin A2 has the following structural units.

-continued

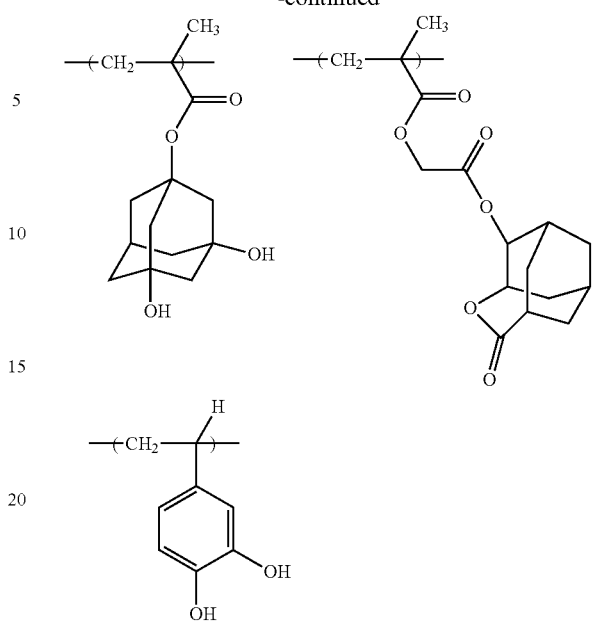

Synthesis Example 5 [Synthesis of Resin A3]

Using a monomer (a1-2-6), a monomer (a2-1-3), a monomer (a3-4-2) and a monomer (a1-4-19) as monomers, these monomers were mixed in a molar ratio of 53:3:12:32 [monomer (a1-2-6):monomer (a2-1-3):monomer (a3-4-2):monomer (a1-4-19)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1.2 mol % and 3.6 mol % based on the total molar number of all monomers, followed by heating at 73° C. for about 5 hours. Thereafter, to the polymerization reaction solution thus obtained, an aqueous p-toluenesulfonic acid solution (2.5% by weight) was added in the amount of 2.0 mass times the total mass of all monomers, followed by stirring for 12 hours and further isolation through separation. The organic layer thus recovered was poured into a large amount of n-heptane to precipitate a resin, followed by filtration and recovery to obtain a resin A3 having a weight-average molecular weight of about $5.5 \times 10^3$ in a yield of 74%. This resin A3 has the following structural units.

A2

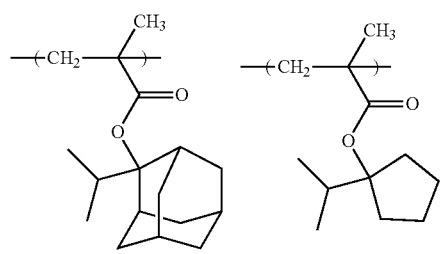

A3

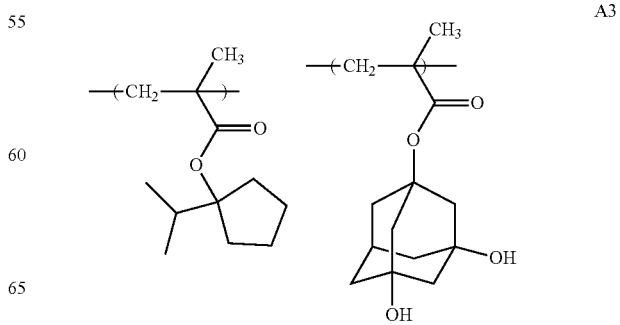

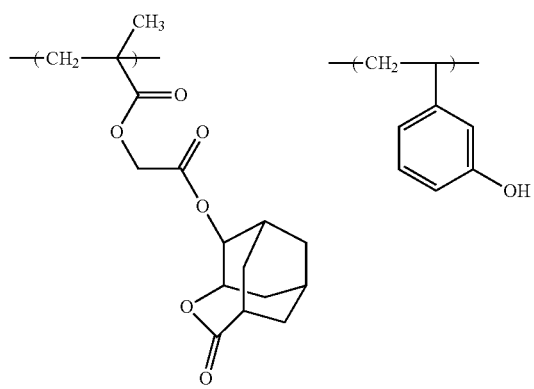

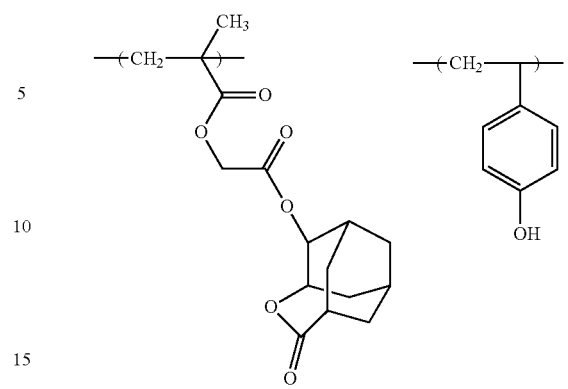

Synthesis Example 6 [Synthesis of Resin A4]

Using a monomer (a1-2-6), a monomer (a2-1-3), a monomer (a3-4-2) and a monomer (a1-4-2) as monomers, these monomers were mixed in a molar ratio of 53:3:12:32 [monomer (a1-2-6):monomer (a2-1-3):monomer (a3-4-2): monomer (a1-4-2)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1.2 mol % and 3.6 mol % based on the total molar number of all monomers, followed by heating at 73° C. for about 5 hours. Thereafter, to the polymerization reaction solution thus obtained, an aqueous p-toluenesulfonic acid solution (2.5% by weight) was added in the amount of 2.0 mass times the total mass of all monomers, followed by stirring for 12 hours and further isolation through separation. The organic layer thus recovered was poured into a large amount of n-heptane to precipitate a resin, followed by filtration and recovery to obtain a resin A4 having a weight-average molecular weight of about $5.3 \times 10^3$ in a yield of 88%. This resin A4 has the following structural units.

Synthesis Example 7 [Synthesis of Resin A5]

Using a monomer (a1-2-6), a monomer (a2-1-3), a monomer (a3-4-2) and a monomer (a1-4-13) as monomers, these monomers were mixed in a molar ratio of 53:3:12:32 [monomer (a1-2-6):monomer (a2-1-3):monomer (a3-4-2): monomer (a1-4-13)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1.2 mol % and 3.6 mol % based on the total molar number of all monomers, followed by heating at 73° C. for about 5 hours. Thereafter, to the polymerization reaction solution thus obtained, an aqueous p-toluenesulfonic acid solution (2.5% by weight) was added in the amount of 2.0 mass times the total mass of all monomers, followed by stirring for 12 hours and further isolation through separation. The organic layer thus recovered was poured into a large amount of n-heptane to precipitate a resin, followed by filtration and recovery to obtain a resin A5 having a weight-average molecular weight of about $5.1 \times 10^3$ in a yield of 79%. This resin A5 has the following structural units.

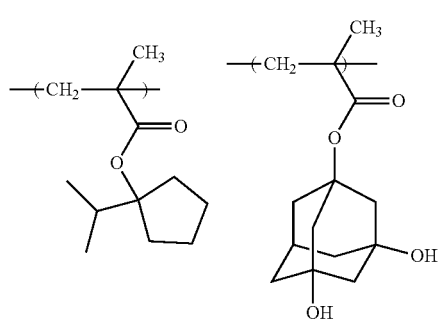

A4

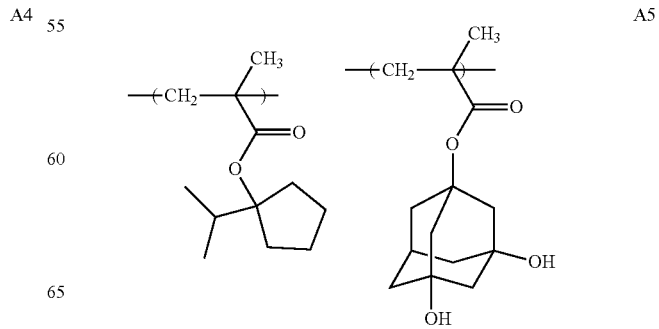

A5

-continued

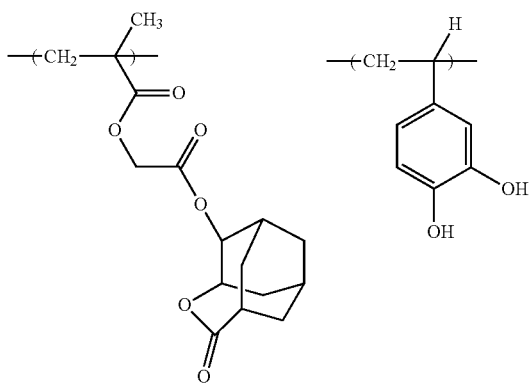

<Preparation of Resist Composition>

As shown in Table 2, the following components were mixed and the mixture thus obtained was filtered through a fluororesin filter having a pore diameter of 0.2 μm to prepare resist compositions.

TABLE 2

| Resist composition | Resin | Acid generator | Salt (I) | Quencher (C) | PB/PEB |
|---|---|---|---|---|---|
| Composition 1 | A2 = 10 parts | — | I-160 = 1.5 parts | C1 = 0.35 part | 100° C./130° C. |
| Composition 2 | A1 = 10 parts | — | I-160 = 1.5 parts | C1 = 0.35 part | 100° C./130° C. |
| Composition 3 | A1 = 10 parts | — | I-168 = 1.5 parts | C1 = 0.35 part | 100° C./130° C. |
| Composition 4 | A1 = 10 parts | — | I-156 = 1.5 parts | C1 = 0.35 part | 100° C./130° C. |
| Composition 5 | A1 = 10 parts | — | I-1224 = 1.5 parts | C1 = 0.35 part | 100° C./130° C. |
| Composition 6 | A1 = 10 parts | — | I-1232 = 1.5 parts | C1 = 0.35 part | 100° C./130° C. |
| Composition 7 | A1 = 10 parts | — | I-8 = 1.5 parts | C1 = 0.35 part | 100° C./130° C. |
| Composition 8 | A1 = 10 parts | — | I-16 = 1.5 parts | C1 = 0.35 part | 100° C./130° C. |
| Composition 9 | A1 = 10 parts | — | I-1346 = 1.5 parts | C1 = 0.35 part | 100° C./130° C. |
| Composition 10 | A1 = 10 parts | — | I-282 = 1.5 parts | C1 = 0.35 part | 100° C./130° C. |
| Composition 11 | A1 = 10 parts | — | I-1878 = 1.5 parts | C1 = 0.35 part | 100° C./130° C. |
| Composition 12 | A1 = 10 parts | — | I-1992 = 1.5 parts | C1 = 0.35 part | 100° C./130° C. |
| Composition 13 | A1 = 10 parts | — | I-2106 = 1.5 parts | C1 = 0.35 part | 100° C./130° C. |
| Composition 14 | A1 = 10 parts | — | I-2220 = 1.5 parts | C1 = 0.35 part | 100° C./130° C. |

TABLE 2-continued

| Resist composition | Resin | Acid generator | Salt (I) | Quencher (C) | PB/PEB |
|---|---|---|---|---|---|
| Composition 15 | A2 = 10 parts | — | I-1878 = 1.5 parts | C1 = 0.35 part | 100° C./130° C. |
| Composition 16 | A3 = 10 parts | — | I-1878 = 1.5 parts | C1 = 0.35 part | 100° C./130° C. |
| Composition 17 | A4 = 10 parts | — | I-1878 = 1.5 parts | C1 = 0.35 part | 100° C./130° C. |
| Composition 18 | A5 = 10 parts | — | I-1878 = 1.5 parts | C1 = 0.35 part | 100° C./130° C. |
| Composition 19 | A1 = 10 parts | — | I-2486 = 1.5 parts | C1 = 0.35 part | 100° C./130° C. |
| Comparative Composition 1 | A1 = 10 parts | IX-1 = 1.5 parts | — | C1 = 0.35 part | 100° C./130° C. |
| Comparative Composition 2 | A1 = 10 parts | IX-2 = 1.5 parts | — | C1 = 0.35 part | 100° C./130° C. |
| Comparative Composition 3 | A1 = 10 parts | IX-3 = 1.5 parts | — | C1 = 0.35 part | 100° C./130° C. |
| Comparative Composition 4 | A1 = 10 parts | IX-4 = 1.5 parts | — | C1 = 0.35 part | 100° C./130° C. |
| Comparative Composition 5 | A1 = 10 parts | IX-5 = 1.5 parts | — | C1 = 0.35 part | 100° C./130° C. |
| Comparative Composition 6 | A1 = 10 parts | IX-6 = 1.5 parts | — | C1 = 0.35 part | 100° C./130° C. |

<Resin>

A1 to A5: Resin A1 to Resin A5

<Salt (I)>

I-8: salt represented by formula (I-8)

I-16: salt represented by formula (I-16)

I-156: salt represented by formula (I-156)

I-160: salt represented by formula (I-160)

I-168: Salt represented by formula (I-168)

I-282: Salt represented by formula (I-282)

I-1224: Salt represented by formula (I-1224)

I-1232: Salt represented by formula (I-1232)

I-1346: Salt represented by formula (I-1346)

I-1878: Salt represented by formula (I-1878)

I-1992: Salt represented by formula (I-1992)

I-2106: Salt represented by formula (I-2106)

I-2220: Salt represented by formula (I-2220)

I-2486: Salt represented by formula (I-2486)

<Acid Generator>

IX-1

IX-2

IX-3

IX-4

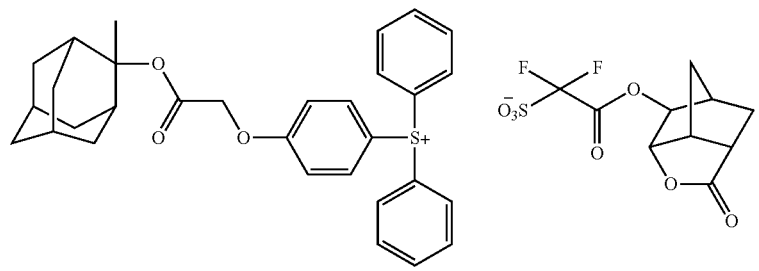

(IX-1)

-continued

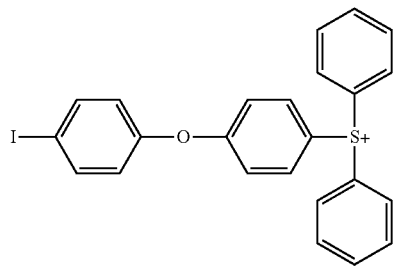 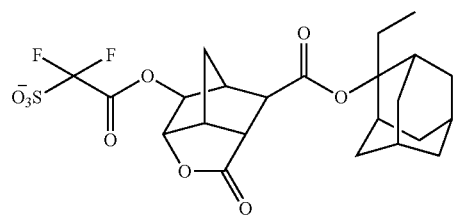

(IX-2)

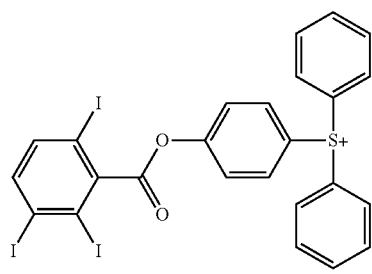 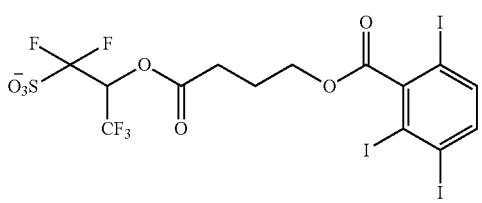

(IX-3)

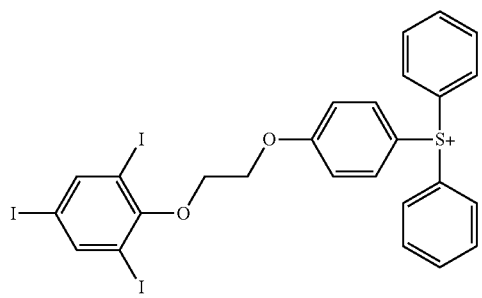

(IX-4)

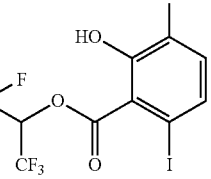

IX-5: Salt represented by formula (IX-5)
IX-6: Salt represented by formula (IX-6)
<Quencher (C)>
C1: synthesized by the method mentioned in JP 2011-39502 A

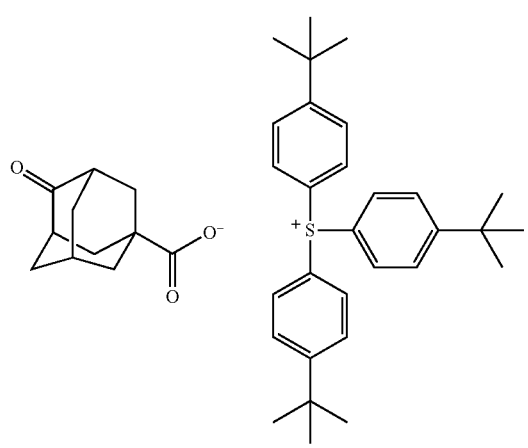

<Solvent>

| | |
|---|---|
| Propylene glycol monomethyl ether acetate | 400 parts |
| Propylene glycol monomethyl ether | 100 parts |
| γ-Butyrolactone | 5 parts |

(Evaluation of Exposure of Resist Composition with Electron Beam, Organic Solvent Development)

Each 6 inch-diameter silicon wafer was treated with hexamethyldisilazane on a direct hot plate at 90° C. for 60 seconds. A resist composition was spin-coated on the silicon wafer in such a manner that the thickness of the composition layer became 0.04 μm. Then, the coated silicon wafer was prebaked on the direct hot plate at the temperature shown in the column "PB" of Table 2 for 60 seconds to form a composition layer. Using an electron-beam direct-write system ("ELS-F125 125 keV", manufactured by ELIONIX INC.), contact hole patterns (hole pitch of 40 nm/hole diameter of 17 nm) were directly written on the composition layer formed on the wafer while changing the exposure dose stepwise.

After exposure, post-exposure baking was performed on the hot plate at the temperature shown in the column "PEB" of Table 2 for 60 seconds. Next, the composition layer on this silicon wafer was developed with butyl acetate (manufactured by Tokyo Chemical Industry Co., Ltd.) as a developer at 23° C. for 20 seconds using the dynamic dispensing method to obtain resist patterns.

In the resist pattern obtained after development, the exposure dose at which the diameter of holes formed became 17 nm was regarded as effective sensitivity.

<Evaluation of CD Uniformity (CDU)>

In the effective sensitivity, the hole diameter of the pattern formed with a hole dimeter of 17 nm was determined by measuring 24 times per one hole and the average of the measured values was regarded as the average hole diameter. The standard deviation was determined under the conditions that the average diameter of 400 holes about the patterns formed with a hole dimeter of 17 nm in the same wafer was regarded to as population.

The results are shown in Table 3. The numerical value in the table represents the standard deviation (nm).

TABLE 3

|  | Resist composition | CDU |
|---|---|---|
| Example 15 | Composition 1 | 2.51 |
| Example 16 | Composition 2 | 2.58 |
| Example 17 | Composition 3 | 2.52 |
| Example 18 | Composition 4 | 2.69 |
| Example 19 | Composition 5 | 2.62 |
| Example 20 | Composition 6 | 2.55 |
| Example 21 | Composition 7 | 2.68 |
| Example 22 | Composition 8 | 2.62 |
| Example 23 | Composition 9 | 2.53 |
| Example 24 | Composition 10 | 2.42 |
| Example 25 | Composition 11 | 2.33 |
| Example 26 | Composition 12 | 2.38 |
| Example 27 | Composition 13 | 2.32 |
| Example 28 | Composition 14 | 2.35 |
| Example 29 | Composition 15 | 2.24 |
| Example 30 | Composition 16 | 2.28 |
| Example 31 | Composition 17 | 2.35 |
| Example 32 | Composition 18 | 2.26 |
| Example 33 | Composition 19 | 2.24 |
| Comparative Example 1 | Comparative Composition 1 | 2.89 |
| Comparative Example 2 | Comparative Composition 2 | 2.92 |
| Comparative Example 3 | Comparative Composition 3 | 2.99 |
| Comparative Example 4 | Comparative Composition 4 | 2.88 |
| Comparative Example 5 | Comparative Composition 5 | 2.89 |
| Comparative Example 6 | Comparative Composition 6 | 2.83 |

As compared with Comparative Compositions 1 to 6, Compositions 1 to 19 exhibited satisfactory evaluation of CD uniformity (CDU).

A resist composition including a salt of the present invention is capable of obtaining a resist pattern with satisfactory CD uniformity (CDU), and is therefore useful for fine processing of semiconductors and is industrially extremely useful.

What is claimed is:
1. A salt represented by formula (I):

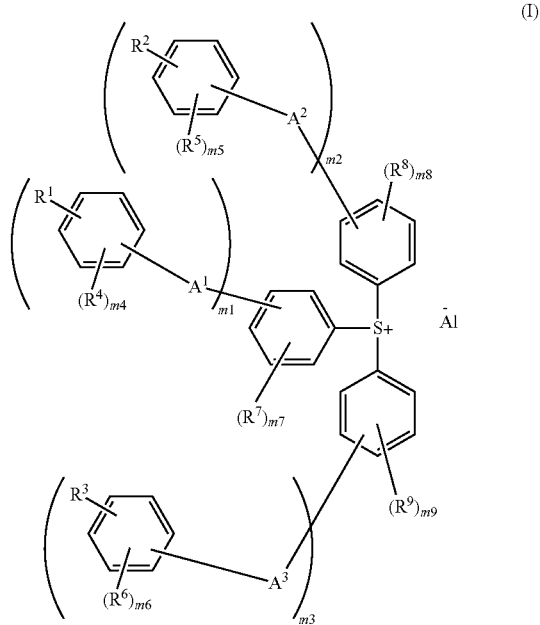

wherein, in formula (I),
$R^1$, $R^2$ and $R^3$ each independently represent a hydroxy group, *—O—$R^{10}$, *—O—CO—O—$R^{10}$ or *—O-$L^{10}$-CO—O—$R^{10}$, and * represents a bonding site to the benzene ring,
$L^{10}$ represents an alkanediyl group having 1 to 6 carbon atoms,
$R^{10}$ represents an acid-labile group,
$R^4$, $R^5$, $R^6$, $R^7$, $R^8$ and $R^9$ each independently represent a halogen atom, a haloalkyl group having 1 to 12 carbon atoms or a hydrocarbon group having 1 to 18 carbon atoms, the hydrocarbon group may have a substituent, and —$CH_2$— included in the haloalkyl group and the hydrocarbon group may be replaced by —O—, —S—, —CO— or —$SO_2$—,
$A^1$, $A^2$ and $A^3$ each independently represent a hydrocarbon group having 2 to 20 carbon atoms, the hydrocarbon group may have a substituent, and —$CH_2$— included in the hydrocarbon group may be replaced by —O—, —CO—, —S— or —$SO_2$—,
m1 represents an integer of 1 to 5, and when m1 is 2 or more, a plurality of groups in parentheses may be the same or different from each other,
m2 represents an integer of 0 to 5, and when m2 is 2 or more, a plurality of groups in parentheses may be the same or different from each other,
m3 represents an integer of 0 to 5, and when m3 is 2 or more, a plurality of groups in parentheses may be the same or different from each other,
m4 represents an integer of 0 to 4, and when m4 is 2 or more, a plurality of $R^4$ may be the same or different from each other,
m5 represents an integer of 0 to 4, and when m5 is 2 or more, a plurality of $R^5$ may be the same or different from each other,
m6 represents an integer of 0 to 4, and when m6 is 2 or more, a plurality of $R^6$ may be the same or different from each other, m7 represents an integer of 0 to 4, and when m7 is 2 or more, a plurality of $R^7$ may be the same or different from each other, m8 represents an integer of 0 to 5, and when m8 is 2 or more, a plurality of $R^8$ may be the same or different from each other, m9 represents an integer of 0 to 5, and when m9 is 2 or more, a plurality of $R^9$ may be the same or different from each other, in which 1≤m1+m7≤5, 0≤m2+m8≤5, 0≤m3+m9≤5, and AI⁻ represents a sulfonic acid anion, a sulfonylimide anion, a sulfonylmethide anion or a carboxylic acid anion, provided that the sulfonic acid anion does not comprise a structure represented by —C(H)(F)—C(F)(F)—SO₃⁻.

2. The salt according to claim 1, wherein $A^1$ is *—$X^{01}$-$L^{01}$- or *-$L^{01}$-$X^{01}$—, $A^2$ is *—$X^{02}$-$L^{02}$- or *-$L^{02}$-$X^{02}$— and $A^3$ is *—$X^{03}$-$L^{03}$- or *-$L^{03}$-$X^{03}$—, wherein $X^{01}$, $X^{02}$ and $X^{03}$ each independently represent —O—, —CO—, —S— or —SO₂—, $L^{01}$, $L^{02}$ and $L^{03}$ each independently represent a hydrocarbon group having 1 to 19 carbon atoms, the hydrocarbon group may have a substituent, —CH₂— included in the hydrocarbon group may be replaced by —O—, —CO—, —S— or —SO₂—, and * represents a bonding site to the benzene ring to which $R^1$, $R^2$ or $R^3$ is bonded.

3. The salt according to claim 2, wherein $X^{01}$, $X^{02}$ and $X^{03}$ are each independently —O— or —S—.

4. The salt according to claim 2, wherein $L^{01}$, $L^{02}$ and $L^{03}$ are each independently an alkanediyl group having 1 to 6 carbon atoms and —CH₂— included in the alkanediyl group may be replaced by —O— or —CO—.

5. The salt according to claim 1, wherein $R^1$, $R^2$ and $R^3$ are each independently a hydroxy group, *—O—$R^{10}$ or *—O-$L^{10}$-CO—O—$R^{10}$ and * represents a bonding site to the benzene ring.

6. The salt according to claim 1, wherein the acid-labile group as for $R^{10}$ is a group represented by formula (1a) or a group represented by formula (2a):

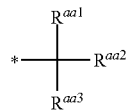

(1a)

wherein, in formula (1a), Raa1, $R^{aa1}$, $R^{aa2}$ and $R^{aa3}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or a group obtained by combining these groups, or $R^{aa1}$ and $R^{aa2}$ may be bonded to each other to form an alicyclic hydrocarbon group having 3 to 20 carbon atoms together with carbon atoms to which $R^{aa1}$ and $R^{aa2}$ are bonded, and

* represents a bonding site:

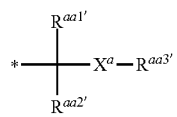

(2a)

wherein, in formula (2a), $R^{aa1'}$ and $R^{aa2'}$ each independently represent a hydrogen atom or a hydrocarbon group having 1 to 12 carbon atoms, $R^{aa3'}$ represents a hydrocarbon group having 1 to 20 carbon atoms, or $R^{aa2'}$ and $R^{aa3'}$ may be bonded to each other to form a heterocyclic group having 3 to 20 carbon atoms together with —C—$X^a$— to which $R^{aa2'}$ and $R^{aa3'}$ are bonded, and —CH₂— included in the hydrocarbon group and the heterocyclic group may be replaced by —O— or —S—, $X^a$ represents an oxygen atom or a sulfur atom, and

* represents a bonding site.

7. The salt according to claim 1, wherein when m4, m5 or m6 is an integer of 1 or more, $R^4$, $R^5$ and $R^6$ are each independently a fluorine atom, an iodine atom, a perfluoroalkyl group having 1 to 4 carbon atoms or an alkyl group having 1 to 4 carbon atoms and —CH₂— included in the alkyl group may be replaced by —O— or —CO—.

8. The salt according to claim 1, wherein when m7, m8 or m9 is an integer of 1 or more, $R^7$, $R^8$ and $R^9$ are each independently a fluorine atom, an iodine atom, a perfluoroalkyl group having 1 to 4 carbon atoms or an alkyl group having 1 to 4 carbon atoms and —CH₂— included in the alkyl group may be replaced by —O— or —CO—.

9. The salt according to claim 1, wherein AI⁻ is a sulfonic acid anion, and the sulfonic acid anion is an anion represented by formula (I-A):

(I-A)

wherein, in formula (I-A), $Q^1$ and $Q^2$ each independently represent a hydrogen atom, a fluorine atom, an alkyl group having 1 to 6 carbon atoms or a perfluoroalkyl group having 1 to 6 carbon atoms, $L^1$ represents a saturated hydrocarbon group having 1 to 24 carbon atoms, —CH₂— included in the saturated hydrocarbon group may be replaced by —O— or —CO—, and a hydrogen atom included in the saturated hydrocarbon group may be substituted with a fluorine atom or a hydroxy group, provided that when $Q^1$ and $Q^2$ are fluorine atoms, the group directly attached to —C($Q^1$)($Q^2$)- is not —C(H)(F)—, and $Y^1$ represents a methyl group which may have a substituent, or an alicyclic hydrocarbon group having 3 to 24 carbon atoms which may have a substituent, and —CH₂— included in the alicyclic hydrocarbon group may be replaced by —O—, —S—, —SO₂— or —CO—.

10. An acid generator comprising the salt according to claim 1.

11. A resist composition comprising the acid generator according to claim 10 and a resin having an acid-labile group.

12. The resist composition according to claim 11, wherein the resin having an acid-labile group includes at least one selected from the group consisting of a structural unit represented by formula (a1-0), a structural unit represented by formula (a1-1) and a structural unit represented by formula (a1-2):

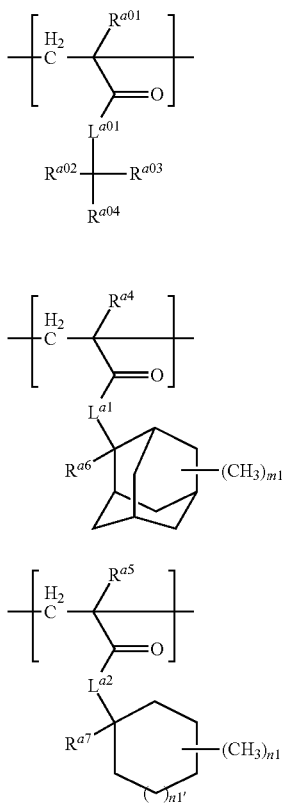

(a1-0)

(a1-1)

(a1-2)

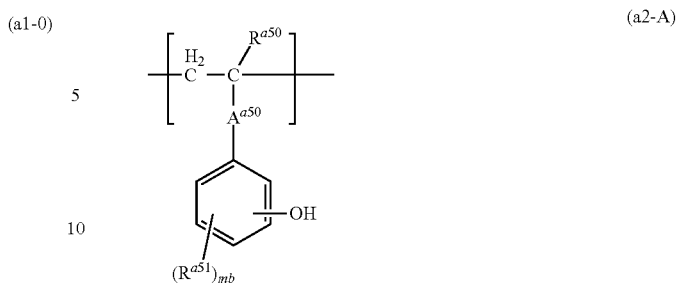

(a2-A)

wherein, in formula (a2-A),
- $R^{a50}$ represents a hydrogen atom, a halogen atom, or an alkyl group having 1 to 6 carbon atoms which may have a halogen atom,
- $R^{a51}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group,
- $A^{a50}$ represents a single bond or $*-X^{a5}-(A^{a52}-X^{a52})_{nb}-$, and * represents a bonding site to carbon atoms to which $-R^{a50}$ is bonded,
- $A^{a52}$ represents an alkanediyl group having 1 to 6 carbon atoms,
- $X^{a51}$ and $X^{a52}$ each independently represent $-O-$, $-CO-O-$ or $-O-CO-$,
- nb represents 0 or 1, and
- mb represents an integer of 0 to 4, and when mb is an integer of 2 or more, a plurality of $R^{a51}$ may be the same or different from each other, wherein, in formula (a1-0), formula (a1-1) and formula (a1-2),
- $L^{a01}$, $L^{a1}$ and $L^{a2}$ each independently represent $-O-$ or $*-O-(CH_2)_{k1}-CO-O-$, k1 represents an integer of 1 to 7, and * represents a bonding site to $-CO-$,
- $R^{a01}$, $R^{a4}$ and $R^{a5}$ each independently represent a hydrogen atom, a halogen atom, or an alkyl group having 1 to 6 carbon atoms which may have a halogen atom,
- $R^{a02}$, $R^{a03}$ and $R^{a04}$ each independently represent an alkyl group having 1 to 8 carbon atoms, an alicyclic hydrocarbon group having 3 to 18 carbon atoms, an aromatic hydrocarbon group having 6 to 18 carbon atoms, or a group obtained by combining these groups,
- $R^{a6}$ and $R^{a7}$ each independently represent an alkyl group having 1 to 8 carbon atoms, an alkenyl group having 2 to 8 carbon atoms, an alicyclic hydrocarbon group having 3 to 18 carbon atoms, an aromatic hydrocarbon group having 6 to 18 carbon atoms, or a group formed by combining these groups,
- m1 represents an integer of 0 to 14,
- n1 represents an integer of 0 to 10, and
- n1' represents an integer of 0 to 3.

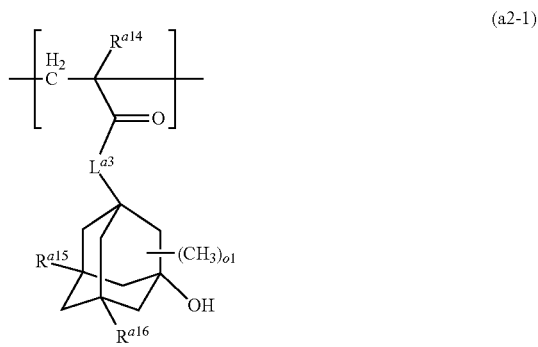

(a2-1)

wherein, in formula (a2-1),
- $L^{a3}$ represents $-O-$ or $*-O-(CH_2)_{k2}-CO-O-$, k2 represents an integer of 1 to 7, and * represents a bonding site to $-CO-$,
- $R^{a14}$ represents a hydrogen atom or a methyl group,
- $R^{a15}$ and $R^{a16}$ each independently represent a hydrogen atom, a methyl group or a hydroxy group, and
- o1 represents an integer of 0 to 10.

13. The resist composition according to claim 11, wherein the resin having an acid-labile group includes a structural unit represented by formula (a2-A) or a structural unit represented by formula (a2-1):

14. The resist composition according to claim 11, further comprising a salt generating an acid having an acidity lower than that of an acid generated from the acid generator.

15. A method for producing a resist pattern, which comprises:
   (1) a step of applying the resist composition according to claim 11 on a substrate,
   (2) a step of drying the applied resist composition to form a composition layer,
   (3) a step of exposing the composition layer,
   (4) a step of heating the exposed composition layer, and
   (5) a step of developing the heated composition layer.

16. The salt according to claim 9, wherein when $Q^1$ and $Q^2$ are fluorine atoms, a hydrogen atom included in —$CH_2$— in the saturated hydrocarbon group directly attached to —$CQ^1Q^2$- is not substituted with a fluorine atom.

17. The salt according to claim 6, wherein when $R^1$ is *—O-$L^{10}$-CO—O—$R^{10}$ and $R^{10}$ is a group represented by formula (1a), m4 is an integer of 1 to 4.

18. The acid generator according to claim 10, which is not a salt comprising a sulfonic acid anion comprising a structure represented by —C(H)(F)—C(F)(F)—$SO_3^-$.

* * * * *